(12) United States Patent
Speckbacher et al.

(10) Patent No.: US 11,904,042 B2
(45) Date of Patent: Feb. 20, 2024

(54) HAIR COLORING COMPOSITION AND METHODS FOR ITS APPLICATION AND REMOVAL

(71) Applicant: HFC Prestige International Holding Switzerland S.a.r.l, Petit-Lancy (CH)

(72) Inventors: Markus Speckbacher, Mettenheim-Hart (DE); Ingo Weber, Basel (CH); Petra Braun, Hessen (DE); Malte Afflerbach, Darmstadt (DE); Corinne Mohr, Lorsch (DE); Simon Paul Godfrey, Oberursel (DE); Mathias Kurt Herrlein, Kronberg (DE); Matija Crne, Wiesbaden (DE); Graham Mckelvey, Schwalbach (DE); Andrej Gross, Schwalbach am Taunus (DE); Tatjana Schaefer, Schwalbach (DE); Yan Wang, Parsippany, NJ (US)

(73) Assignee: HFC Prestige International Holding Switzerland S.a.r.l., Petit-Lancy (CH)

( * ) Notice: Subject to any disclaimer, the term of this patent is extended or adjusted under 35 U.S.C. 154(b) by 553 days.

(21) Appl. No.: 15/733,837

(22) PCT Filed: Jul. 5, 2019

(86) PCT No.: PCT/EP2019/068187
§ 371 (c)(1),
(2) Date: Nov. 30, 2020

(87) PCT Pub. No.: WO2020/008074
PCT Pub. Date: Jan. 9, 2020

(65) Prior Publication Data
US 2021/0220251 A1    Jul. 22, 2021

Related U.S. Application Data

(60) Provisional application No. 62/694,570, filed on Jul. 6, 2018, provisional application No. 62/694,781, filed
(Continued)

(30) Foreign Application Priority Data

Mar. 27, 2019  (WO) ................. PCT/EP2019/057813
Mar. 27, 2019  (WO) ................. PCT/EP2019/057814

(51) Int. Cl.
*A61Q 5/10* (2006.01)
*A61K 8/89* (2006.01)
(Continued)

(52) U.S. Cl.
CPC ............. *A61K 8/89* (2013.01); *A61K 8/8152* (2013.01); *A61Q 5/065* (2013.01);
(Continued)

(58) Field of Classification Search
CPC .. A61K 8/89; A61K 8/8152; A61K 2800/412; A61K 2800/4324;
(Continued)

(56) References Cited

U.S. PATENT DOCUMENTS 4,559,057 A    12/1985  Bogaty et al.
5,258,481 A    11/1993  Tesselmans et al.
(Continued)

FOREIGN PATENT DOCUMENTS

CA          2643107 A1 *  9/2007  ............. C07D 47/06
CN       111432887 A     7/2020
(Continued)

OTHER PUBLICATIONS

STIC Search Report dated Jul. 20, 2023.*
(Continued)

*Primary Examiner* — Eisa B Elhilo
(74) *Attorney, Agent, or Firm* — Dennemeyer & Associates LLC; Victoria Friedman

(57) ABSTRACT

The instant disclosure generally relates to a coloring composition for coloring mammalian or synthetic keratin fibers
(Continued)

or keratinous surfaces. The composition comprising a medium, optionally pigment microparticles and at least one dye, in particular at least one peri-arylene dye dissolved in the medium. Methods of using such compositions are also described herein.

15 Claims, 1 Drawing Sheet

Related U.S. Application Data on Jul. 6, 2018, provisional application No. 62/694,799, filed on Jul. 6, 2018, provisional application No. 62/694,734, filed on Jul. 6, 2018, provisional application No. 62/694,847, filed on Jul. 6, 2018, provisional application No. 62/694,808, filed on Jul. 6, 2018, provisional application No. 62/694,869, filed on Jul. 6, 2018, provisional application No. 62/694,739, filed on Jul. 6, 2018, provisional application No. 62/696,301, filed on Jul. 10, 2018, provisional application No. 62/739,592, filed on Oct. 1, 2018, provisional application No. 62/739,672, filed on Oct. 1, 2018, provisional application No. 62/739,556, filed on Oct. 1, 2018, provisional application No. 62/740,027, filed on Oct. 2, 2018, provisional application No. 62/769,239, filed on Nov. 19, 2018, provisional application No. 62/774,627, filed on Dec. 3, 2018.

(51) Int. Cl.
*A61K 8/81* (2006.01)
*A61Q 5/06* (2006.01)

(52) U.S. Cl.
CPC .......... *A61K 2800/412* (2013.01); *A61K 2800/4324* (2013.01); *A61K 2800/594* (2013.01); *A61K 2800/884* (2013.01); *A61K 2800/95* (2013.01)

(58) Field of Classification Search
CPC ........ A61K 2800/594; A61K 2800/884; A61K 2800/95; A61K 2800/43; A61K 2800/882; A61K 8/84; A61K 8/898; A61Q 5/065; C09B 3/14; C09B 5/62; C09B 67/0083; C09B 67/009
USPC .......................................................... 8/405
See application file for complete search history.

(56) References Cited

U.S. PATENT DOCUMENTS

| | | | |
|---|---|---|---|
| 5,567,428 A | 10/1996 | Hugehes | |
| 5,990,479 A | 11/1999 | Weiss et al. | |
| 6,225,198 B1 | 5/2001 | Alivisatos et al. | |
| 6,451,747 B1 | 9/2002 | Decoster | |
| 6,492,484 B2 | 12/2002 | Misumi et al. | |
| 9,546,301 B2 | 1/2017 | Derksen et al. | |
| 10,011,677 B2 | 7/2018 | Yamashita et al. | |
| 10,959,919 B2 | 3/2021 | Dahne et al. | |
| 10,973,754 B2 | 4/2021 | Herrlein et al. | |
| 11,324,688 B2 | 5/2022 | Herrlein et al. | |
| 11,478,415 B2 | 10/2022 | Herrlein et al. | |
| 2003/0203978 A1 | 10/2003 | Obrien et al. | |
| 2004/0010863 A1 | 1/2004 | Gawtrey et al. | |
| 2005/0226838 A1 | 10/2005 | Krause et al. | |
| 2006/0041026 A1 | 2/2006 | Mahr et al. | |
| 2007/0134180 A1 | 6/2007 | Simard et al. | |
| 2007/0180630 A1* | 8/2007 | Javet | A61Q 5/065 8/405 |
| 2008/0108740 A1 | 5/2008 | Evers | |
| 2008/0184496 A1 | 8/2008 | Brun et al. | |
| 2008/0241090 A1* | 10/2008 | Speckbacher | C09B 5/62 546/34 |
| 2009/0233062 A1 | 9/2009 | Nakamura et al. | |
| 2010/0083446 A1 | 4/2010 | Brun et al. | |
| 2010/0088036 A1 | 4/2010 | Goddard-Clark et al. | |
| 2011/0061179 A1 | 3/2011 | Cremer et al. | |
| 2011/0083284 A1 | 4/2011 | Suddaby et al. | |
| 2014/0242281 A1 | 8/2014 | Swarup et al. | |
| 2014/0336093 A1 | 11/2014 | Koellnberger | |
| 2015/0174051 A1 | 6/2015 | Teboul | |
| 2016/0120284 A1 | 5/2016 | Crne et al. | |
| 2016/0120285 A1 | 5/2016 | Crne et al. | |
| 2016/0175212 A1 | 6/2016 | Zhou et al. | |
| 2016/0235655 A1 | 8/2016 | Herrlein et al. | |
| 2016/0271049 A1 | 9/2016 | Schulze et al. | |
| 2017/0001045 A1 | 1/2017 | Aubert et al. | |
| 2017/0158888 A1 | 6/2017 | Kang et al. | |
| 2017/0189312 A1 | 7/2017 | Van Nguyen et al. | |
| 2017/0189314 A1 | 7/2017 | Elsen-wahrer et al. | |
| 2018/0105718 A1 | 4/2018 | Swarup et al. | |
| 2018/0263353 A1 | 9/2018 | Crne et al. | |
| 2018/0263354 A1 | 9/2018 | Crne et al. | |
| 2021/0220251 A1 | 7/2021 | Speckbacher et al. | |
| 2021/0401713 A1 | 12/2021 | Herrlein et al. | |
| 2022/0054392 A1 | 2/2022 | Herrlein et al. | |

FOREIGN PATENT DOCUMENTS

| | | |
|---|---|---|
| CN | 111432888 A | 7/2020 |
| DE | 19913625 A1 | 9/2000 |
| DE | 102006011271 A1 | 9/2007 |
| EP | 132960 A2 | 2/1985 |
| EP | 1184426 A2 | 3/2002 |
| EP | 1600148 A1 | 11/2005 |
| EP | 1600149 A1 | 11/2005 |
| EP | 1825883 A1 | 8/2007 |
| EP | 3015134 A1 | 5/2016 |
| EP | 3015135 A1 | 5/2016 |
| EP | 3058934 A1 | 8/2016 |
| EP | 3058989 A1 | 8/2016 |
| EP | 3397346 A1 | 11/2018 |
| FR | 2899795 A1 | 10/2007 |
| FR | 2992559 A1 | 1/2014 |
| JP | S 50-034400 A | 4/1975 |
| JP | S 60-105608 A | 6/1985 |
| JP | 2005-350460 A | 12/2005 |
| JP | 2007-084510 A | 4/2007 |
| JP | 2008-502613 A | 1/2008 |
| JP | 2009-520002 A | 5/2009 |
| JP | 2010-530842 A | 9/2010 |
| JP | 2012-515219 A | 7/2012 |
| JP | 2012-530841 A | 12/2012 |
| JP | 2015-521646 A | 7/2015 |
| JP | 2017-533224 A | 11/2017 |
| KR | 101603845 B1 | 3/2016 |
| KR | 2019-0028636 A | 3/2019 |
| KR | 20190028636 A | 3/2019 |
| WO | 2005065632 A1 | 7/2005 |
| WO | WO-2007071706 A2 | 6/2007 |
| WO | WO-2009073759 A1 | 6/2009 |
| WO | WO-2011128255 A1 | 10/2011 |
| WO | WO-2015097308 A1 | 7/2015 |
| WO | WO-2016066747 A1 | 5/2016 |
| WO | WO-2017108599 A1 | 6/2017 |
| WO | WO-2017117543 A1 | 7/2017 |
| WO | 2017189585 A1 | 11/2017 |
| WO | WO-2017220781 A1 | 12/2017 |
| WO | WO-2018039314 A1 | 3/2018 |
| WO | WO-2018130912 A1 | 7/2018 |
| WO | WO-2018185345 A1 | 10/2018 |
| WO | 2018234530 A1 | 12/2018 |
| WO | 2019071204 A1 | 4/2019 |
| WO | 2019071207 A1 | 4/2019 |
| WO | WO-2019211050 A1 | 11/2019 |
| WO | WO-2020007511 A1 | 1/2020 |
| WO | WO-2020008073 A2 | 1/2020 |
| WO | WO-2020008074 A1 | 1/2020 |
| WO | 2020035362 A1 | 2/2020 |
| WO | WO-2020008073 A3 | 3/2020 |

(56) References Cited

FOREIGN PATENT DOCUMENTS

| WO | WO-2020114647 A1 | 6/2020 |
|---|---|---|
| WO | 2021032837 A1 | 2/2021 |
| WO | 2021032873 A1 | 2/2021 |

OTHER PUBLICATIONS

International Search Report issued in connection with PCT Application No. PCT/EP2019/057811 dated Sep. 4, 2019.
International Search Report and written opinion received in PCT Patent Application No. PCT/EP2021/057812, dated Jan. 7, 2019.
Campiglio Chiara Emma et al., "Coss-Linking Strategies for Electrospun Gelatin Scaffolds", Materials, vol. 1, No. 15, Aug. 4, 2019.
International Search Report and written opinion received in PCT Patent Application No. PCT/EP2021/067924, dated Nov. 26, 2021.
International Search Report and written opinion received in PCT Patent Application No. PCT/EP2021/067925, dated Nov. 22, 2021.
International Search Report and written opinion received in PCT Patent Application No. PCT/EP2021/067928, dated Dec. 22, 2021.
European Search Report received for EP Patent Application No. 17195273.2, Extended European Search Report dated Jan. 11, 2018.
International Search Report and Written Opinion received for PCT Patent Application No. PCT/US2018/054717, dated Dec. 20, 2018.
International Search Report and Written Opinion received for PCT Patent Application No. PCT/US2018/054724, dated Feb. 26, 2019.
International Search Report and Written Opinion received for PCT Patent Application No. PCT/US2019/057812, dated Jan. 7, 2019.
International Search Report and Written Opinion received for PCT Patent Application No. PCT/EP2019/057811, dated Sep. 4, 2019.
International Search Report and written opinion received in PCT Patent Application No. PCT/EP2021/067927, dated Dec. 6, 2021.
International Search Report and written opinion received in PCT Patent Application No. PCT/EP2021/067926, dated Dec. 7, 2021.
Cansu et al., "Atmospheric Pressure Plasma Jet Treatment of Human Hair Fibers", Journal of Bio- and Tribo- Corrosion, vol. 1:7, No. 1, Feb. 4, 2015.
Zheng et al, "Adhesion of aqueous polyurethane adhesive to human hair", International Journal of Adhesion and Adhesives, Elsevier, Amsterdam, NL, vol. 48, Sep. 30, 2013, pp. 14-19.
Shima et al, "The effect of nitrogen plasma on the skin and hair follicles : a possible promising future for the treatment of alopecia", Archives of Dermatological Research, Springer Berlin Heidelberg, Berlin/Heidelberg, vol. 312, No. 5, Dec. 6, 2019 , pp. 361-371.
Shao et al.: "Surface Treatment of Wool to Achieve Hydrophilic Fibre and the Effect on Subsequent Dyeing and Protease Treatment", Advanced Materials Research; ISSN 1662-8985; Eco-Dyeing, Finishing and Green Chemistry : Selected, Peer Reviewed Papers From the 2011 International Conference on Eco-Dyeing, Finishing and Green Chemistry (EDFGC 2011), Jun. 8-12, 2011, Hangzhou, China, vol. 441, Jan. 1, 2012 (Jan. 1, 2012), pp. 249-254.
"U.S. Appl. No. 17/052,431, Preliminary Amendment filed Nov. 2, 2020".
"International Application Serial No. PCT/EP2019/057813, International Search Report dated Jul. 11, 2019", 5 pgs.
"International Application Serial No. PCT/EP2019/057813, Written Opinion dated Jul. 11, 2019", 9 pgs.
"International Application Serial No. PCT/EP2019/057814, International Preliminary Report on Patentability dated Nov. 12, 2020", 19 pgs.
"International Application Serial No. PCT/EP2019/057814, International Search Report dated Sep. 16, 2019", 8 pgs.
"International Application Serial No. PCT/EP2019/057814, Invitation to Pay Additional Fees mailed Jul. 26, 2019", 10 pgs.
"International Application Serial No. PCT/EP2019/057814, Written Opinion dated Sep. 16, 2019", 17 pgs.
"International Application Serial No. PCT/EP2019/068186, International Search Report dated Feb. 3, 2020", 7 pgs.
"International Application Serial No. PCT/EP2019/068186, Invitation to Pay Additional Fees mailed Dec. 2, 2019", 14 pgs.
"International Application Serial No. PCT/EP2019/068186, Written Opinion dated Feb. 3, 2020", 12 pgs.
"International Application Serial No. PCT/EP2019/068187, International Search Report dated Dec. 4, 2019", 5 pgs.
"International Application Serial No. PCT/EP2019/068187, Written Opinion dated Dec. 4, 2019", 12 pgs.
"International Application Serial No. PCT/EP2019/076647, International Search Report dated Jan. 9, 2020", 7 pgs.
"International Application Serial No. PCT/EP2019/076647, Written Opinion dated Jan. 9, 2020", 13 pgs.
Bordes, C, et al., "Determination of poly(epsilon-caprolactone) solubility parameters: Application to solvent substitution in a microencapsulation process", International journal of pharmaceutics, 383(1-2), (Jan. 4, 2010), 236-243.

* cited by examiner

HAIR COLORING COMPOSITION AND METHODS FOR ITS APPLICATION AND REMOVAL

CROSS-REFERENCE TO RELATED APPLICATION

This application is a U.S. National Stage Filing under 35 U.S.C. 371 from International Application No. PCT/EP2019/068187, filed on Jul. 5, 2019, and published as WO 2020/008074 on Jan. 9, 2020, which application claims the benefit of priority to U.S. Application Ser. No. 62/694,570, filed Jul. 6, 2018, U.S. Application Ser. No. 62/694,781, filed Jul. 6, 2018, U.S. Application Ser. No. 62/694,799, filed Jul. 6, 2018, U.S. Application Ser. No. 62/694,734, filed Jul. 6, 2018, U.S. Application Ser. No. 92/694,847, filed Jul. 6, 2018, U.S. Application Ser. No. 62/694,808, filed Jul. 6, 2018, U.S. Application Ser. No. 62/694,869, filed Jul. 6, 2018, U.S. Application Ser. No. 62/694,739, filed Jul. 6, 2018, U.S. Application Ser. No. 62/696,301, filed Jul. 10, 2018, U.S. Application Ser. No. 62/739,592, filed Oct. 1, 2018, U.S. Application Ser. No. 62/739,672, filed. Oct. 1, 2018, U.S. Application Ser. No. 62/739,556, filed Oct. 1, 2019, U.S. Application Ser. No. 62/740,027, filed Oct. 2, 2018, U.S. Application Ser. No. 62/769,239, filed Nov. 19, 2018, PCT Application Ser. No. PCT/EP2019/057814, filed Mar. 27, 2019, and PCT Application Ser. No. PCT/EP2019/057813, all of which are incorporated by reference herein in their entirety.

BACKGROUND

Treatments to mammalian or synthetic keratin fibers are known. Mammalian keratin fibers (natural hair) is structured as a cuticle or outer surface layer, a cortex which is an internal mid layer containing melanin or color bodies and keratin bundles, and an central core termed medulla. Typical dye treatments focus on changes of the cortex. Of particular note are cortex treatments that alter the appearance of the hair, for example by changing the color or reflective properties of hair. This can be achieved through treating hair cortex with a formulation containing dye molecules (so call direct dyes) which diffuse into or are absorbed through the cuticle of the hair fibers. Alternatively, so called oxidative dyes may be employed wherein the dye precursors diffuse into the cortex and then react to from colored species within the cortex of the hair. Often the oxidative dye products are designed to also lighten the hair, decolorizing some of the melanin of the cortex to enable a wider range of colors to be achieved. Over time the color imparted to the hair is removed during washing. This can happen rapidly for so called direct dyes, and leads to a shorter term change in hair appearance, typically lasting for a few washes. The so called oxidative dyes may last considerably longer, and indeed removing the color can be hard to achieve, even after a considerable number of washes. When oxidative dyes are eventually removed by washing out, the melanin has also been decolorized by bleaching so that it will not return to its original color but to a lighter color. Unfortunately, the process of decolorizing hair leads not only to a lightening of the hair but also to a change in the perceived tone of the hair, leading to what is often described as an off tone or brassy result where the hair looks more orange than untreated hair of a similar lightness. Alternatively pigments can be adhered to the hair surface to alter the perceived color, however this approach normally only lasts until the hair is next washed.

One drawback of the known oxidation based technologies in this area is that the methods for applying dye based coloring materials involves compositions that can irritate the scalp, for example such compositions may contain ammonia (often as ammonium hydroxide) or monoethanolamine combined with hydrogen peroxide. This prevents the hair coloration experience from being pleasant or a so called wellness experience. Such coloring compositions also alter the hair structure itself, leading to oxidation of the hair surface, and partial degradation to the keratinous proteins from which the hair structure is constructed. With repeated coloring, these changes in hair structure become more pronounced. The color obtained when coloring with such composition is hard to predict, and even highly experienced users can still be surprised with the results that are obtained. Yet another drawback to known technologies is that, once the color is on the hair, the dye based coloring material is difficult to remove and/or cannot be completely removed. A drawback of pigment based coloring approaches is the low adherent fastness of the pigment or colored material to the keratin fibers. This results in the pigment based color effectively being removed after a single hair wash. Another drawback for both dye and pigment based approaches is that the application of hair coloration materials often yields uneven results as (1) adherence and or penetration of hair coloration materials to the hair surface or within the hair can vary with hair type for example due to changes in porosity, changes in surface composition due to proximity to scalp and/or age of the user; and (2) even when material is adhered or penetrated into the hair, differences in coloration of the underlying hair, including presence of pheomelanin and eumelanin, may yield different color results, even when the same color pigments or dyes are applied across hair types/colors having different native characteristics. There is therefore a need for compositions and methods that not only make the hair coloring experience a beauty/wellness experience, but also address, among other things, the foregoing drawbacks of known technologies.

SUMMARY

According to aspects of the invention, the hair coloring composition, method and coated hair embodiments provide a surface coloration of hair strands that may be substantially uniform to significantly varied, may give strands an appearance of a muted, brilliant, shiny or reflective nature. These aspects provide color fastness during a series of washes with shampoo or soap yet with appropriate formulations can be readily removed to leave the natural shade of the hair. These aspects significantly lessen and/or avoid treatment of hair that may cause breakage of keratin protein intermolecular bonds.

The aspect of the invention concerning the hair coloring composition provides embodiments comprising a medium with one or more dyes. The dyes are soluble in the medium. The composition optionally further comprises pigment microparticles. The pigment microparticles may comprise irregular shapes of at least one pigment color and have at least one dimension of less than one micron. In some embodiments, the medium may be a non-aqueous solvent or a mixture of non-aqueous solvents with polar protic or aprotic polar organic solvent. In other embodiments, the medium may be water or a mixture of water and a polar, protic or aprotic organic solvent.

The hair coloring composition further may comprise a film former. Suitable film formers are, for example, carboxylic acid polymers, a copolymer comprising repeating units of at least one (meth)acrylate monomer, at least one olefin monomer and (meth)acrylic acid monomer, and polar functional silicone polymers. Further suitable film formers are multicomponent compositions, in particular multicomponent compositions according to the present disclosure. The film former preferably is soluble in the medium. The carboxylic acid polymer may comprise a (meth)acrylic acid homopolymer, copolymer or terpolymer. The polar functional silicone polymer may comprise any pendant, terminal or polymer chain block group that provides a polar dipolar or polar ionic character to the polar functional silicone polymer. Exemplary polar groups of a dipolar or ionic character include but are not limited to carboxylic acid groups, sulfonic or sulfuric acid groups, hydroxyl groups, amide groups, amine functional groups, polyol, polyamido, polyether and polyglycol groups. A multicomponent composition may comprise a first component comprising a linear and/or branched first silicone polymer with functional groups, and a second component comprising a second linear or branched silicone polymer with functional groups, a third component comprising a base compound. A multicomponent in situ linkable composition may comprise a first component comprising an organic polymer having pendant or terminal or pendant and terminal first functional groups, a second component comprising an in situ linking material having second functional groups, and a third component comprising a base compound having third functional groups.

Embodiments of the optional carboxylic acid polymer component of the hair coloring composition may comprise homopolymers, copolymers and/or terpolymers with an acid value ranging from about 0.01 to about 700, about 3 to about 500, more preferably about 3 to about 200, especially more preferably about 25 to 175, most preferably about 40 to about 200, with a favored upper range of up to about 170 In addition to the (meth)acrylic acid monomer, the copolymer and terpolymer may include neutral olefinic monomers. Embodiments of the carboxylic acid polymer component may be neutralized with a base to provide enhanced solubility of the carboxylic acid polymer in the medium. The homopolymers, copolymer and/or terpolymers may have a weight average molecular weight ranged from about 500 Da to about 1 MDa, preferably about 500 Da to about 500 kDa, more preferably about 1 kDa to about 200 kDa and most preferably about 1 KDa to about 200 kDa.

Embodiments of the (meth)acrylate copolymer component of the coloring composition may comprise the polymerization product of a (meth)acrylate ester of such alkyl groups as methyl, ethyl, propyl, butyl, pentyl, hexyl, heptyl, ethylhexyl, octyl, decyl, and lauryl as well as olefins such as ethylene, propene, butene, pentene, hexene, octene, decene, dodecane, styrene, o, m or p-methyl, ethyl, propyl, butyl, pentyl or hexyl styrene, o, m, or p-carboxy or carboxamido styrene, or similar aromatic or aliphatic olefins. The (meth)acrylate copolymer has an acid value ranging from about 1 to about 200. Embodiments of the (meth)acrylate copolymer component may be at least partially neutralized with a base to provide enhanced dispersibility of the (meth)acrylate copolymer in the medium and the neutralization may provide increased solubility. The copolymer may have a weight average molecular weight ranged from about 2 kDa to about 10 MDa, preferably about 5 kDa to about 500 kDa.

Embodiments of the polar functional silicone polymer component of the hair coloring composition may comprise any pendant, terminal or polymer chain block group that provides a polar, dipolar or polar ionic character to the polar functional silicone polymer and enables the polymer to adhere moderately to strongly to strands of hair. Exemplary polar groups of a dipolar or ionic character include but are not limited to amine groups, carboxylic acid groups, sulfonic or sulfuric acid groups, hydroxyl groups, amide groups, sulfonamide groups, polyol, polyamido, polyether and polyglycol groups. Of these, the amine groups is especially most preferred. The carboxylic acid, sulfonic acid, sulfuric acid groups are especially more preferred. The hydroxyl, polyol, amide, sulfonamide and polyamide groups are preferred. The polyether and poly glycol (polyethylene glycol and polypropylene glycol) groups can function as polar groups in appropriate circumstances.

A preferred polar functional silicone polymer is one having amine functional groups (hereinafter an aminosilicone polymer). The molar ratio of siloxane monomeric units with at least one pendant organic amine group (hereinafter SiA moieties) to siloxane monomeric units having silicon bonded to a substituent selected from the group consisting of oxygen, hydroxyl, alkoxy (C1 to C6), alkyl (C1 to C6), amidoalkyl (C1 to C6), alkylamide (C1 to C6), sulfonamidoalkyl (C1 to C6) and alkylsulfonamide (C1 to C6) and any combination thereof (hereinafter SiC moieties) of the aminosilicone polymer is in the range of from about 1:1000 to 1:10 (ratio of SiA units to SiC units), preferably 1:1000 to 1:25, more preferably 1:600 to 1:50, most preferably 1:400 to 1:75 or 1:300 to 1:200. An SiA moiety may contain more than one amine group in which case it counts as just one SiA moiety. An SiC moiety may contain any number of other pendant groups as long as a primary, secondary, tertiary or quaternary amine group is not present. The aminosilicone polymer may have a weight average molecular weight ranged from about 10 kDa to about 150 kDa, preferably about 18 kDa to about 130 kDa, more preferably about 22 kDa to about 120 kDa.

The amine functional groups of the aminosilicone polymer may be primary, secondary, tertiary amine groups or quaternary ammonium groups or any combination thereof. The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—Si(R')$_2$—O— wherein each R' is independently selected from a pendant organic amine group and an alkyl group of 1 to 6 carbons and at least one R' group is a pendant organic amine group. The organic amine group may be a linear alkyl group of 1 to 16 carbons or a branched or cyclic alkyl group of 3 to 16 carbons. The alkyl group may contain one or more heteroatoms and/or hetero-groups in the chain including such groups as —NH—, —O—, —S—, —CONH— or —NHCO—, —SO$_2$NH— or —NHSO$_2$—. Typical pendant amine groups include such arrangements as:
—(CH$_2$)$_3$—NH—(CH$_2$)$_3$NH$_2$, —CH$_2$—CH(CH$_3$)—CH$_2$—NH—(CH$_2$)$_3$NH$_2$
—(CH$_2$)$_3$—CONH—(CH$_2$)$_3$NH$_2$, —(CH$_2$)$_3$—NHCO—(CH$_2$)$_3$NH$_2$ and
single amine groups such as —(CH$_2$)$_n$—NH$_2$ wherein n is 2 to 6, preferably 3 or 4 or branched chain versions thereof such as —CH$_2$—CH(CH$_3$)—CH$_2$—NH$_2$.

The amine functional group or groups may be pendant to the silicone chain at uniform or random locations along and within the silicone chain. The amine functional group may also terminate the ends of the silicone chain but an aminosilcone polymer having terminal amine groups preferably will also have pendant amine groups along the silicone chain. If the aminosilicone polymer contains only terminal amine groups, its weight average molecular weight preferably will be low so that its SiA:SiC ratio will conform to the foregoing values. Preferably, such a terminal aminosilicone polymer will also contain cross-linking groups (as described below) so that when applied to hair strands, it will preferably cross-link to become larger molecules.

The silicone chain of the aminosilicone polymer may be linear, branched or crosslinked. In addition to the SiA moieties shown below as formula E, the chain is constructed of SiC moieties of the formulas A, B, C and D wherein R is defined as given above:

A) —O(R)2Si—O— (known as a D siloxane unit)
B) —O(R)SI(—O—)2 or —O—Si(—O—)2-O— (known as T siloxane unit and Q sesquisilicate unit respectively)
C) (R)3SI—O— (known as M siloxane unit)
D) X—Si(R)2-O with X as —OH or —OR
E) —O—SI(R')2-O— with each R' independently being alkyl or an organic amine group and at least one R' being an organic amine group.

For this embodiment of the aminosilicone polymer component of the hair coloring composition, the A), B), C) and D) groups constitute together the SiC moieties defined above. The A) group provides a linear silicone chain link, the B) group provides a branched or crosslinked silicone chain link, the C and D groups provide a silicone chain termination. The E group constitutes the SiA moiety defined above. The R groups of the SiC moieties may be any organic group except an amine group as defined above. Preferably the R groups are alkyl groups of 1 to 6 carbons, preferably methyl or ethyl, more preferably methyl. The distribution of the SiA moiety and the A), B), C), and D) groups of the SiC moiety follows ordered or random arrangement and the SiA to SiC ratios and weight average molecular weight ranges given above. The silicone chain of the aminosilicone polymer component of the hair coloring composition may also include an additional unit to form an organosilicone block copolymer. This organo block unit is an organic oligomer chain formed from oligomerization of an alkylenyl group, a diester group, an hydroxy acid group, a diamide group, a diurethane or diurea group. The blocks are formed by linkage of the terminal group of the organic block to the terminal silicone of a silicone block through carbon-silicon bonds.

The aminosilicone polymer may be formulated into the hair coloring composition as a neutral polymer which may in part be protonated, or preferably as a cationic polymer by combination with an appropriate amount or concentration of a protonating agent such as an organic or inorganic acid, or as a permanently positively charged polymer through use of quaternary ammonium groups as at least a portion of the amine functional group. Preferably the formulation of the hair coloring composition will provide at least in part a medium that protonates at least some of the aminosilicone polymer and preferably protonates a majority or all of the aminosilicone polymer.

Embodiments of the pigment microparticles optionally used on the hair coloring formulation described herein may comprise organic pigment microparticles, which imparts color to the hair, having a given D50[vol], and pigment microparticles, for providing light scattering properties to the colored hair, having a D50[vol] which is larger than the D50[vol] value of the organic pigment microparticles. Embodiments optionally include a mixture of organic pigment microparticles having a D50[vol] of about 0.02 micron to about 0.18 micron, preferably of about 0.08 micron to about 0.15 micron, and light-scattering pigment microparticles having a D50[vol] of about 0.15 micron to about 0.3 micron, preferably of about 0.16 micron to about 0.25 micron.

Embodiments of the pigment microparticles optionally used on the hair coloring formulation described herein may comprise organic pigment microparticles, which imparts color to the hair, having a given D50[vol], and pigment microparticles, for providing light reflecting properties to the colored hair, which are effectively two dimensional particles with two axis considerably larger than the third axis, wherein the two considerably larger axes of the two dimensional particles are larger than the D50[vol] value of the organic pigment microparticles. Embodiments optionally include a mixture of organic pigment microparticles having a D50[vol] of about 0.06 micron to about 0.18 micron, preferably of about 0.08 micron to about 0.15 micron, and light-reflecting pigment microparticles wherein the two considerably larger axes of the two-dimensional particles have length of about 1.0 micron to about 50 micron, preferably of about 2 micron to about 15 micron.

The aspect of the invention concerning the method for combining the hair coloring composition with hair strands comprises applying the hair coloring composition to the hair and setting the hair to remove and/or eliminate the medium. The resulting colored hair strands comprise one or more dyes optionally in combination with a film former. Irrespective of whether or not the applied hair coloring composition comprises a film former, the method may further comprise a step of separately applying a film former composition to the hair. Applying film former in a separate step may be done prior to applying the hair coloring composition to the hair, but usually will be done after having applied the hair coloring composition to the hair. Typically, applying film former in a separate step will be done prior to setting the hair to remove and/or eliminate the medium.

The method furthermore may comprise as an initial step of the method a pretreatment of the hair. Pretreatment modifies the surface of the hair. A primer composition applied upon pretreatment to the hair can serve as an "activating agent" of the hair surface and may convert the native hair surface from a hydrophobic entity with low surface charge to a more hydrophilic, thus to a more polar, to a more negatively and/or to a positively charged surface.

In embodiments without film former, the one or more dyes form an at least partial color coating on the surface of hair. The embodiments with film former have a coating thickness of from about 50 nm to 3 microns, preferably 150 nm to 5 microns. In embodiments with film former, the dyes may be substantially uniformly dissolved in the film former.

In addition to the dyes dissolved in the medium, optionally pigment microparticles in mixture with the medium, optionally in mixture with a film former such as carboxylic acid polymer or polar functional silicone polymer, the hair coloring composition may optionally contain additional components in this mixture. These additional components include but not limited to one or more of plasticizers, conditioners, thickening agents, adjuvants, moisturizers, surfactants, fatty substances, waxes, fatty amids, and soluble organic dyes of colors different from the dyes. The hair coloring composition consequently may contain a number of components that add to the total solids content of the composition. Generally, for application to human hair, the hair coloring composition may have a total solids content ranging from about 1 wt % to about 40 wt %, preferably about 2 wt % to about 30 wt %, more preferably about 4 wt % to about 20 wt % relative to the total weight of the composition. The solids content in this context will include at least the carboxylic acid polymer and the dyes. Any additional component that is ordinarily a solid is also to be included in the total solids content of the composition. While components that are liquids at room temperature, such as ethylene glycol, ethylene diamine and similar compounds, would not ordinarily be considered solids, they can be included in the solids content of the hair coloring composition if they will remain on the hair strands following application and setting of the hair coloring composition on human hair. Components such as ethylene glycol, for example, are cross linking agents for acrylate film formers and will remain in an optional film former coating following application and setting.

The aspect of the invention concerning the fastness of the color on the hair strands comprises the ability of the color to somewhat to substantially resist dissolution by ordinary cleaning of the hair. Ordinary cleaning of the hair may involve washing with soap and water, washing with an aqueous dilution of shampoo and washing with water.

The aspect of the invention concerning removal of the color on the hair strands comprises application of a de-coloring medium in which the one or more dyes are soluble. In some embodiments with film former, the coating of the optional film former is essentially inert with the de-coloring medium so that the film former coating substantially remains on the hair while the color substantially is removed. In other embodiments with film former, it may be desirable to remove the film former together with the one or more dyes.

Removing the film former may be done by applying to the hair a medium of a trigger formulation designed to remove the coating.

Trigger formulation embodiments for removing a carboxylic acid polymer film former comprise a medium with a base. Embodiments of the base include organic and inorganic compounds that provide a stronger basic medium than does a dilute aqueous mixture of soap or a shampoo containing an anionic surfactant. Included are aqueous solutions or mixtures of ammonia, trialkyl amine of from one to four carbons in each alkyl group, dialkylamino alkyl alcohols of from one to four carbons in each of the dialkyl groups and two to four carbons in the alkyl group, alkanolamines such as monoethanolamine, diethanolamine and triethanolamine, bicarbonate or carbonate of alkali or alkaline earth metal salts, acetaldehyde ammonia trimer, alkali or alkaline earth metal hydroxides and/or alkaline earth metal halide complexes with trialkyl amine described above.

Trigger formulation embodiments for removing a polar functional silicone polymer film former comprise one of the following pairs:

I) a medium containing a base, which medium is to be used with a polar functional silicone polymer having cationic or positive polar groups such as protonated and quaternary amines;

II) a medium containing an acid, which medium is to be used with a polar functional silicone polymer having negative polar groups such as carboxylate salt groups; or, III) a medium containing an aqueous or non-aqueous solution of a volatile, cosmetically acceptable alcohol and a nonionic surfactant. This medium (III) is to be used with a polar functional silicone polymer having only dipolar functional groups such as hydroxyls, polyglycols, amides or esters which are not charged or ionic.

iv) a medium comprising a solvent with a Hansen Solubility parameter of $0<H_p<15$, $10<H_d<20$, $0<H_h<22$.

With each of these media, the trigger formulation is believed to interact with the complex of the polar functional silicone polymer and the surfaces of hair strands. For example, it is believed that positively charged protonated amine groups and quaternary ammonium groups bind with the negative groups of the keratin protein on the surfaces of the strands of hair. The strong positive-negative couple binds the polymer to the hair strand. Addition of a base that has a stronger negativity than does the keratin protein competitively displaces the keratin protein from the couple and renders the polymer soluble in the medium due to the salt formation of the base-protonated amine or quaternary ammonium salt.

Embodiments of the acid medium include organic and inorganic compounds that provide a stronger acidic medium than does a dilute aqueous mixture of for example orange or lemon juice (citric acid). Embodiments of the base medium include organic and inorganic compounds that provide a stronger basic medium than does a dilute aqueous mixture of soap or a shampoo containing an anionic surfactant. Included are aqueous solutions or mixtures of ammonia, trialkyl amine of from one to four carbons in each alkyl group, dialkylamino alkyl alcohols of from one to four carbons in each of the dialkyl groups and two to four carbons in the alkyl group, alkanolamines such as monoethanolamine, diethanolamine and triethanolamine, bicarbonate or carbonate of alkali or alkaline earth metal salts, acetaldehyde ammonia trimer, alkali or alkaline earth metal hydroxides and/or alkaline earth metal halide complexes with trialkyl amine described above.

The medium for all four arrangements above (I, II III and IV) will also include appropriate selections of compatible organic solvent, surfactant and solubilization adjuncts such as ionic strengtheners and builders, complexing agents, soap, and similar hair cleansing substances.

An additional aspect of the invention concerns the application of the hair coloring composition to keratin tissue such as brows, lashes, nails and skin as well as to hair on the scalp. For such applications to keratin tissue, the hair coloring composition becomes a coloring composition. The coloring composition may be applied to the hair of eyebrows and eye lashes with appropriate adjustments of the composition parameters within the parameters described for hair on the scalp. Typically, the eyebrow hair may be treated with the coloring composition using parameters similar to or the same as those of the hair coloring composition for hair on the scalp. The hair of eyelashes typically can be similarly treated with the coloring composition for eyebrows and the viscosity adjusted to provide a somewhat more viscous coloring composition for application to the eye lashes. For nails and skin, the parameters of the coloring composition may be similar to those of the hair coloring composition and viscosity adjusted to provide embodiments that will not readily drip or otherwise flow off the nail or skin surface to which the coloring composition is applied. The coloring composition for nails and skin may also be at least moderately cross-linked to provide a durable coating or covering on the keratin nail and skin substrate.

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise The term "may" in the context of this application means "is permitted to" or "is able to" and is a synonym for the term "can." The term "may" as used herein does not mean possibility or chance.

The term and/or in the context of this application means one or the other or both. For example an aqueous solution of A and/or B means an aqueous solution of A alone, an aqueous solution of B alone and an aqueous solution of a combination of A and B.

The terms (meth)acrylic acid and (meth)acrylate mean herein both of the acrylic acid and methacrylic acid and both of the acrylate methacrylate esters. The parenthesis surrounding the prefix "meth" means that the term (meth) acrylic encompasses both of the methacrylic acid and acrylic acid monomers. This term has the same meaning when used with polymers. Without a parenthesis, the term "methacryl." means only the methacrylic acid and esters, and does not include acrylic acid and esters. The suffix "ate" means that the term (meth)acrylate is an ester formed by combination of a monoalcohol or diol with methacrylic acid or acrylic acid.

Acid value or acid number used according to the invention means the mass of potassium hydroxide (56 g per mole) in milligrams that is required to neutralize one gram of the substance being investigated. The formula is X mg KOH=AV wherein X mg is the amount of KOH needed to neutralize 1 gram of test substance. Because the calculation is always based upon 1 gram of the test substance, if it is assumed that the test substance contains a mole of acid per mole of test substance, the number of moles of test substance in this 1 gram decreases as the molecular weight increases. Hence the AV decreases for this kind of acid material as its molecular weight increases. For example, the AV of benzoic acid (mw of 122) (1 g/122 g per mole×56 g per mole×1000 mg/g) is 459 while the AV of naphthoic acid (mw of 178) (56/178×1000 mg/g) is 315. For acidic polymers, an acid value will not usually provide its molecular weight because the polymer usually will be composed of units other than acid. Nevertheless, molecular weight calculation of an acidic polymer can be made if it is composed only of acid monomers. For example, the acid number of acrylic acid (mw of acrylic acid is 72 g/mol) is determined by the formula (1 g/72 g mol$^{-1}$×56 g mol$^{-1}$)=0.778 gm of KOH. This number in milligrams is 778 mg which provides the acid number of 778. With a dimer of acrylic acid this acid number is halved (1 g/144×56 g m$^{-1}$)=389. This demonstration shows that the acid value (AV) of polyacrylic acid will decrease as the weight average molecular weight of the polyacrylic acid increases. At an acid number of 97.2 for a polyacrylic acid, the apparent mw would be 56/0.0972 or 576 g per mole. This would provide an oligomer of 8 acrylic acid monomers per mol.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as daltons (Da), kiloDaltons (kDa) and megaDaltons, which is million daltons or (MDa). The acronym Mw stands for weight average molecular weight, Mn is the number average molecular weight of a given polymer. Polydispersity is a unit-less number and indicates the breadth of the distribution of the polymer molecular weights and is defined as the Mw/Mn.

The term "about" is understood to mean±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

The term "hydrogen bonding" is understood to mean a compound or group that contain a hydroxyl group or a hydrogen that is part of a polar group, such as but not limited to an amine, a carboxylic acid, a urethane group, a urea group and other similar groups and that can form molecule to molecule interaction through electrostatic or ionic interaction between positive and negative dipolar or ionic groups.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

Hair and hair strands mean natural or synthetic keratin fibers. Hair, hair strands and keratin fibers are used interchangeably in this document. Natural keratin fibers include those from mammals and/or on mammals including human, primate, ruminant, camelid, equine, rodent and neovison including but not limited to cow, sheep, deer, goat, buffalo, *lama*, alpaca, camel, guanaco, vicuna, horse, antelope, moose, elk, rat, mouse, beaver, rabbit, mink, monkey, ape and similar species. Synthetic keratin fibers include polyamides, polyacrylic and polyester fibers, especially polyamide fibers which are used for artificial hair implantation.

Homopolymer, copolymer and terpolymer mean polymers having carbon-carbon backbones with side chains of various classes of groups. The homopolymer has side chains of carboxylic acid and optionally some carboxylic acid derivative groups wherein the derivative is an acyl group bound to a leaving group. The homopolymer may be a single monomeric unit structure such as acrylic acid or may be several monomeric unit structures wherein each unit contains at least a carboxylic acid side chain. The copolymer and terpolymer have side chains of carboxylic acid as described above for the homopolymer and also have side chains of esters, amides and side chains such as alkyl groups or aromatic groups or similar groups which not derived from carboxylic acid groups. The copolymer may contain two different monomeric units and may contain one or two additional different monomeric units. The terpolymer may contain at least three different monomeric units and may contain multiple different monomeric units.

As used herein, the term "transfer resistance" generally refers to the quality exhibited by compositions that are not readily removed by contact with another material, such as, for example, an item of clothing or the skin. Transfer resistance can be evaluated by any method known in the art for evaluating such. For example, transfer resistance of a composition can be evaluated by the amount of product transferred from a wearer to any other substrate after the expiration of a certain amount of time following application of the composition to the hair. The amount of composition transferred to the substrate can then be evaluated and compared. For example, a composition can be transfer resistant if a majority of the product is left on the wearer's hair. Preferably little or no composition is transferred to the substrate from the hair.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched hydrocarbon chain radical consisting solely of carbon and hydrogen atoms, unless otherwise specifically described as having additional heteroatoms or heterogroups. The alkyl group contains no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

"Alkylenyl" refers to a straight or branched divalent hydrocarbon chain consisting solely of carbon and hydrogen atoms, unless otherwise specifically described as having additional heteroatoms or heterogroups. The alkylenyl group contains no unsaturation has a valence bond at either end of the chain and has a numerical range of carbon atoms of 1 to 10, which numerical range includes each integen in the range. An example of a divalent hydrocarbon chain designated as an alkylenyl group is —$CH_2$—$CH_2$—$CH_2$—$CH_2$— which is butylenyl.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_5$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

"Alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl is an alkyl group which encompasses both straight and branched chain alkyls of from 1 to 4 carbon atoms.

"Amino" or "amine" refers to an —$N(R^a)_2$ radical group, where each $R^a$ is independently hydrogen or linear, branched or cyclic alkyl of 1 to 6 carbons. When an —$N(R^a)_2$ group has two Ra other than hydrogen they can be combined with the nitrogen atom to form a 4-, 5-, 6-, or 7-membered ring.

"Aryl" refers to a conjugated pi radical with six or ten ring atoms which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or monocyclic-ring polycyclic (i.e., rings which share adjacent pairs of ring atoms) groups.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the rest of the molecule may be through either a heteroatom or a carbon in the heteroalkyl chain.

"Heteroaryl" or heteroaromatic refers to a 5, 6 or 10-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

"Heterocyclic" refers to any monocyclic or polycyclic moiety comprising at least one heteroatom selected from nitrogen, oxygen and sulfur. As used herein, heterocyclyl moieties can be aromatic or nonaromatic. The moieties heteroaryl and heterocyclyl alkyl are members of the heterocyclic group.

As used herein, the term "minimally alters the keratin fibers, upon application" generally means that after removal of the coloring composition the hair fibers are returned to a substantially unaltered state. The state of the hair can be assessed for example using ATR FT-IR for oxidative damage as described later or through tensile testing methods known to those skilled in the art for assessing hair strength for example using equipment such as those designed and sold by Dia-Stron™.

As used herein, the term "color fastness" means substantial color lastingness or color fastness when the color of the colored hair fibers change less than 50%, less than 40%, less than 30%, less than 20%, less than 10% after the colored hair fibers are processed through a multi-cycle rinse study. One kind of protocol for determining color fastness is described in the section below titled "Removal of Color".

As used herein, the term "setting" means converting the Hair Coloring Composition to a solid micro coating through the application of means designed to remove or otherwise separate the medium from the other components of the Hair Coloring Composition.

As used herein, the term "soluble" in the context of the dyes disclosed herein refers to a solubility in the medium of the hair coloring composition in an amount sufficient to provide a colored solution. Typically, the dyes disclosed herein are soluble in an appropriate medium in amounts of 100 mg/Liter or higher. The dyes of the present invention are soluble, and present in dissolved form in the hair coloring composition. Being soluble represents a distinction from pigments, which per definition are non-dissolved solids.

As used herein, the term "minimally alters the keratin fibers, upon application" generally means that after removal of the coloring composition the hair fibers are returned to a substantially unaltered state.

FIGURES

FIG. 1 shows hair strands treated according to the present invention. The hair strands show (from bottom to top):
(2): Dye S-19 as applied without washing
(without marking): Dye S-19 remaining after 5 times washing
(OFF): Dye S-19 remaining after oil treatment
(R): untreated control

DETAILED DESCRIPTION

The instant invention generally relates to addressing drawbacks of known technology for treating mammalian or synthetic keratin fibers by limiting damage to keratin proteins within the fibers, particularly after repeated drying events; facilitating the quantitative or substantially quantitative on demand removal of the color; limiting quick or inconsistent wash-out of the coloring means; limiting irritation of the scalp upon applying known compositions (e.g., containing hydrogen peroxide with either ammonia or monoethanolamine at and an elevated pH); and shortening at least one of the treatment process and post-treatment processes, including drying time. In sum, the present invention is directed to compositions for treating mammalian or synthetic keratin fibers in such a way that the color can be applied and remain on the hair until it is desired to remove the color. This makes the treatment process a wellness experience. It is also desired that the results are predictable, enabling the user to achieve their target hair color result.

The composition and method aspects of the invention are directed to embodiments of a hair coloring composition that are adapted to provide colored embodiments on the surfaces of hair strands. The colored embodiments have "color fastness" that enables them to remain in somewhat to substantial to essential original composition on the keratin fibers (hair) through at least a series of washings with diluted aqueous media containing soap and/or shampoo. Yet, the color can be removed from the hair to leave the hair in its substantially to essentially natural state before application of the hair coloring composition to the hair. The hair coloring composition embodiments minimally alter keratin fibers upon their application to hair strands and the embodiments of the method of application may be accomplished in short times.

The embodiments of the hair coloring composition according to the invention comprise a medium and at least one dye in the medium. The embodiments of the hair coloring composition according to the invention further may comprise a film former. The embodiments of the method of application according to the invention comprise application of the hair coloring composition to the hair followed by removal and/or elimination of the medium. The embodiments of the method of removal according to the invention comprise application of a de-coloring medium which acts as a solvent for the one or more dyes.

1 THE DYES

According to an embodiment, the dyes envisaged by the present invention are aromatic dyes or dyes comprising an aromatic moiety.

According to an embodiment, an aromatic dye according to the present invention may be selected from rylene dyes, nitro dyes, aryl and heteroaryl azo dyes, chinon/chinonimine/chinondiimine dyes, methin dyes, azomethine-like hydrazone and imine dyes, and porphyrin dyes. In particular, the dye or an aromatic ring of the dye may be substituted with one or more hydrophobic moieties having a linear or non-linear structure. Optionally, the dye is substituted with a reactive moiety R20, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkyl)OSO2(aryl), (C0-C6 alkyl)SO2Cl, (C0-C6 alkyl)Si(O—(C1-C3 alkyl))3, (aryl)SO2Cl, aryl(C0-C4)OH, aryl(C0-C4)NH2, wherein aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, and formula (30),

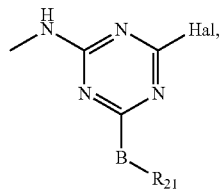

(30)

wherein B is selected from NH and O; Hal is F, Cl or Br; and R21 is linear or branched (C1-C6 alkyl).

According to an embodiment, the dye may show a particular partition pattern between polar/unpolar solvents. For example, the dye may have an octanol/water partition coefficient (log $P_{ow}$) of at least 20, wherein log $P_{ow}$ is calculated based on the GALAS algorithm using ACD/Labs software.

The one or more hydrophobic moieties with which the dyes may be substituted usually will be long-chain alkyl structures. According to an embodiment, each of the one or more hydrophobic moieties comprises 14-28 carbon atoms, and is selected from:

—(CH2)m-CH(C3-24 alkyl)2 or —(CH2)m-C(C3-24 alkyl)3, wherein m=0-5, wherein alkyl is linear and is optionally substituted with one or more substituents selected from halogen, C1-C6 alkyl, C1-C6 alkoxy, NH(C1-C6 alkyl), and N(C1-C6 alkyl)2, —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and —(CH2)o-phenyl, wherein o=1-3 which may be substituted with up to 3 substituents selected from C1-C6 alkyl and C1-C6 alkoxy, in particular isopropyl and/or tert-butyl, —(CH2)n-naphthyl, wherein n=0-3 which may be substituted with up to 3 substituents selected from C1-C6 alkyl and C1-C6 alkoxy, in particular isopropyl and/or tert-butyl The moieties may be unsymmetrical in that the alkyl chains have different chain lengths. Alternatively, the moieties may be symmetrical.

According to an embodiment, the dye is a peri-arylene dye comprising a perylene, terrylene or quarterrylene core or higher rylene core, wherein the dye is soluble in a medium having an octanol/water partition coefficient (log $P_{ow}$) of at least 12, wherein log $P_{ow}$ is calculated based on the GALAS algorithm using ACD/Labs software.

According to an embodiment, the dye is a peri-arylene dye comprising a perylene, terrylene or quarterrylene core or higher rylene core, having an octanol/water partition coefficient (log $P_{ow}$) of at least 20, wherein log $P_{ow}$ is calculated based on the GALAS algorithm using ACD/Labs software.

According to a particular embodiment, the dye may have an octanol/water partition coefficient (log $P_{ow}$) of at least 21, in particular at least 22, wherein log $P_{ow}$ is calculated based on the GALAS algorithm.

According to an embodiment, the dye may have an octanol/water partition coefficient (log $P_{ow}$) of at least 5.2, wherein log $P_{ow}$ is calculated based on the conventional algorithm using ACD/Labs software.

According to an embodiment, the dye is a peri-arylene dye comprising a perylene, terrylene or quarterrylene core or higher rylene core, wherein the dye is substituted with one or more hydrophobic moieties having a non-linear structure and comprising at least 14 carbon atoms. Optionally, the dye is substituted with a reactive moiety R20, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkyl)OSO2(aryl), (C0-C6 alkyl)SO2Cl, (C0-C6 alkyl)Si(O—(C1-C3 alkyl))3, (aryl)SO2Cl, aryl(C0-C4)OH, aryl(C0-C4)NH2, wherein aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, and formula (30),

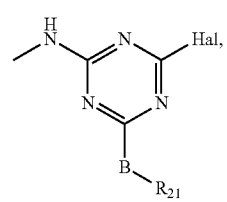

(30)

wherein B is selected from NH and O; Hal is F, Cl or Br; and R21 is linear or branched (C1-C6 alkyl).

According to an embodiment, the rylene core is substituted at the positions corresponding to positions 3,4 and/or 9,10 of the perylene core with a bridging group. According to a particular embodiment, the bridging group at the positions corresponding to positions 3,4 of the perylene core is substituted with a hydrophobic moiety having a non-linear structure and comprising at least 14 carbon atoms. According to another particular embodiment, bridging groups are present both at the positions corresponding to positions 3,4 and 9,10 of the perylene core, and both bridging groups are substituted with a hydrophobic moiety having a non-linear structure and comprising at least 14 carbon atoms.

According to a particular example, the at least one hydrophobic moiety may comprise at least 15 carbon atoms, at least 17 carbon atoms, at least 19 carbon atoms or at least 21 carbon atoms.

According to an embodiment, the dye may be substituted with two or more of said hydrophobic moieties. According to a particular embodiment, the dye is substituted with two of said hydrophobic moieties. According to an embodiment, the dye may be substituted with at least one reactive moiety R20. For example the dye may be substituted with one reactive moiety R20. According to another embodiment, the dye may be free of a reactive moiety R20.

2 THE PERI-ARYLENE DYES

According to an embodiment, the dye according to the present invention is a peri-arylene dye according to formula (1)

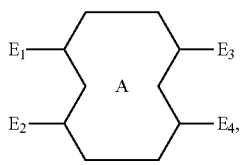
(1)

wherein structure A

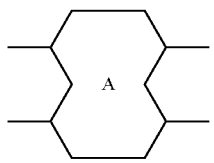

is selected from formulae (2) through (4)

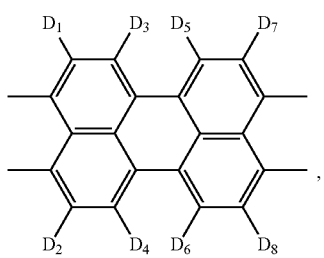
(2)

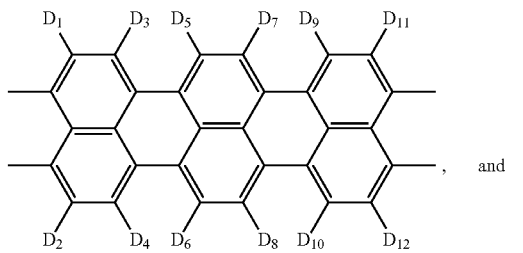
(3)

and

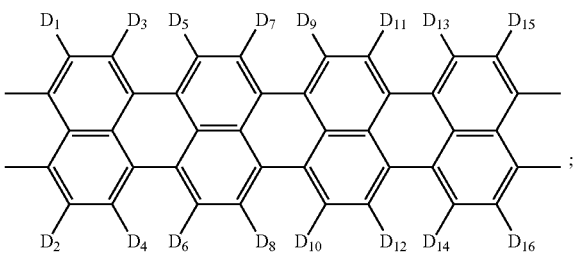
(4)

wherein each of D1 through D16 independently may be selected from hydrogen, C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl.

In addition, an even number of the moieties D1 through D16 may form one or more divalent moieties and/or one or more condensed ring structures.

In particular, one or more of the pairs of D3/D5, D4/D6, D7/D9, D8/D10, D11/D13 and D12/D14 may be a divalent moiety selected from —O—, —S—, -(secondary amine)-, or -(tertiary amine)-. When one of the said pairs forms a divalent moiety being a tertiary amine, an example for such structure is —N(C1-C24 alkyl)-, wherein alkyl optionally may be substituted with one or more substituents selected from C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester.

Furthermore, one or more of the pairs of D3/D5, D4/D6, D7/D9, D8/D10, D11/D13 and D12/D14 may form a condensed ring structure selected from formulae (5) through (8):

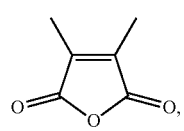
(5)

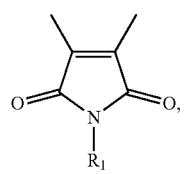
(6)

wherein R1 is hydrogen, linear or branched (C1-C5)alkyl, cyclohexyl, a reactive moiety R20, or —(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2;

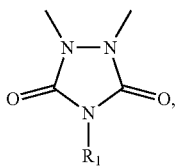

(7)

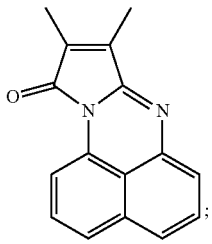

(8)

optionally substituted with up to 3 substituents selected from hydroxyl, nitro, halogen, C1-C6 alkyl, C1-C6 alkoxy, NH(C1-C6 alkyl), N(C1-C6 alkyl)2, and a reactive moiety R20.

According to an embodiment, E1 and E2 in Formula (1) each may be a monovalent moiety independently selected from hydrogen, C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl. If E1 and E2 in Formula (1) are monovalent moieties, the pair of moieties E3/E4 is a divalent moiety according to formula (9) or (10):

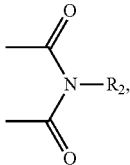

(9)

wherein R2 is a hydrophobic moiety comprising at least 6 carbon atoms, or a reactive moiety R20;

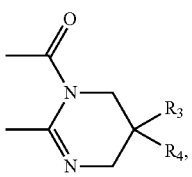

(10)

and wherein R3 is a hydrophobic moiety comprising at least 3 carbon atoms, or a reactive moiety R20;

and wherein R4 is hydrogen, methyl, ethyl, methoxy, ethoxy, a reactive moiety R20, or a hydrophobic moiety R3.

According to an embodiment, the pair of moieties E1/E2 and the pair of moieties E3/E4 both are a divalent moiety. If both E1/E2 and E3/E4 are divalent moieties, E1/E2 is selected from formulae (11) and (12) and E3/E4 is independently selected from formulae (11) through (15):

(11)

wherein R5 is hydrogen, linear or branched (C1-C5)alkyl, cyclohexyl, amino, NH(C1-C4 alkyl), N(C1-C4 alkyl)2, a reactive moiety R20, or a hydrophobic moiety R2;

(12)

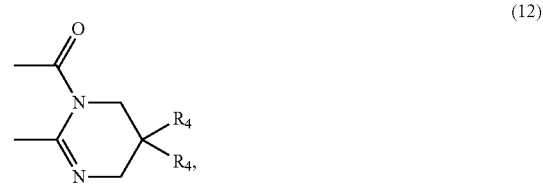

(13)

wherein R6 is hydrogen, methyl, ethyl, methoxy, ethoxy, a reactive moiety R20, or a hydrophobic moiety;

(14)

optionally substituted with up to 3 substituents selected from hydroxyl, nitro, halogen, C1-C6 alkyl, C1-C6 alkoxy, NH(C1-C6 alkyl), N(C1-C6 alkyl)2, a reactive moiety R20; and

(15)

optionally substituted with up to 3 substituents selected from hydroxyl, nitro, halogen, C1-C6 alkyl, C1-C6 alkoxy, NH(C1-C6 alkyl), N(C1-C6 alkyl)2, a reactive moiety R20.

When the pair E1/E2 is a divalent moiety according to formula (11) or (13) and the pair E3/E4 is a divalent moiety according to formula (11), (12) or (13), at least one R4, R5 or R6 is a hydrophobic moiety. When both pairs E1/E2 and E3/E4 are divalent moieties according to formula (12), all moieties R4 may be hydrogen.

According to an embodiment, one of the pairs D3/D5, D7/D9 and D11/D13 is a divalent moiety selected from —O—, —S—, —NH—, -(tertiary amine)- (such as —N(C1-C24 alkyl)-), or a condensed ring structure selected from formulae (5) through (8).

According to another embodiment, one of the pairs D3/D5, D7/D9 and D11/D13 and one of the pairs D4/D6, D8/D10 and D12/D14 is a divalent moiety selected from —O—, —S—, —NH—, -(tertiary amine)- (such as —N(C1-C24 alkyl)-), or a condensed ring structure selected from formulae (5) through (8).

According to a particular embodiment, D3/D5 and D4/D6, or D7/D9 and D8/D10, or D11/D13 and D12/D14 are divalent moieties selected from —O—, —S—, —NH—, -(tertiary amine)- (such as —N(C1-C24 alkyl)-), or a condensed ring structure selected from formulae (5) through (8). According to an embodiment, D3/D5 and D4/D6, or D7/D9 and D8/D10, or D11/D13 and D12/D14 form identical divalent moieties or condensed ring structures.

According to an embodiment, structure A is the perylene core according to Formula (2), and the resulting dye accordingly is a perylene dye.

As mentioned above, R2 may be a hydrophobic moiety. According to an embodiment, R2 is a hydrophobic moiety comprising 6-28 carbon atoms. In particular, R2 may be a hydrophobic moiety comprising 6-28 carbon atoms, selected from:

—(CH2)m-C(R2a)(R2b)(R2b), wherein m=0-5, R2a is linear C3-24 alkyl and each R2b independently is hydrogen or linear C3-24 alkyl, wherein alkyl is optionally substituted with one or more substituents selected from halogen, C1-C6 alkyl, C1-C6 alkoxy, NH(C1-C6 alkyl), and N(C1-C6 alkyl)2, —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3 or, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and —(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, in particular isopropyl and/or tert-butyl.

According to a particular embodiment, R2 may be a moiety comprising 14-28 carbon atoms, selected from:

—(CH2)m-CH(C3-24 alkyl)2 or —(CH2)m-C(C3-24 alkyl)3, wherein m=0-5, wherein alkyl is linear and is optionally substituted with one or more substituents selected from halogen, C1-C6 alkyl, C1-C6 alkoxy, NH(C1-C6 alkyl), and N(C1-C6 alkyl)2, —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3 or, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and —(CH2)o-phenyl, wherein o=1-3 which may be substituted with up to 3 substituents selected from C1-C6 alkyl and C1-C6 alkoxy, in particular isopropyl and/or tert-butyl, —(CH2)n-naphthyl, wherein n=0-3 which may be substituted with up to 3 substituents selected from C1-C6 alkyl and C1-C6 alkoxy, in particular isopropyl and/or tert-butyl.

According to a further particular embodiment, R2 may be a moiety, in particular a moiety comprising 14-28 carbon atoms, selected from:

—(CH2)m-CH(C7-16 alkyl)2 or —(CH2)m-C(C7-16 alkyl)3, wherein n=0-3, wherein alkyl is linear and is optionally substituted with one or more substituents selected from halogen, methyl, ethyl, propyl, isopropyl, or —(CH2)n-N(C7-C16 alkyl)2 or —(CH2)n-NH—(CH2)n-C(C5-C10 alkyl)3, wherein n=0-3 and alkyl is linear and is optionally substituted with one or more substituents selected from halogen, methyl, ethyl, propyl, isopropyl.

According to a further particular embodiment, R2 may be a moiety, in particular a moiety comprising 14-28 carbon atoms, selected from —(CH2)m-CH(C9-16 alkyl)2 or —(CH2)m-C(C9-16 alkyl)3, wherein alkyl is linear, or —N(C8-C16 alkyl)2 or —NH—CH2-C(C6-C8 alkyl)3, wherein alkyl is linear.

In embodiments comprising the moiety R3, R3 may be a hydrophobic moiety —(CH2)m-C(R3a)(R3b)(R3b), wherein m=0-5, R3a is C3-24 alkyl and each R3b independently is hydrogen or C3-24 alkyl, wherein alkyl is linear and is optionally substituted with one or more substituents selected from halogen, C1-C6 alkyl, C1-C6 alkoxy, NH(C1-C6 alkyl), N(C1-C6 alkyl)2. According to a particular embodiment, R3a and at least one R3b may be optionally substituted C3-24 alkyl, for example optionally substituted C6-20 alkyl.

In embodiments comprising the moiety R6, R6 may be a hydrophobic moiety R6a selected from:

—(CH2)m-C(R6b)(R6c)(R6c), wherein m=0-5, R6b is linear C3-24 alkyl and each R6c independently is hydrogen or linear C3-24 alkyl, wherein alkyl is optionally substituted with one or more substituents selected from halogen, C1-C6 alkyl, C1-C6 alkoxy, NH(C1-C6 alkyl), and N(C1-C6 alkyl)2, —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2.

According to a particular embodiment, R6b and at least one R6c may be optionally substituted C3-24 alkyl, for example optionally substituted C6-20 alkyl. According to another embodiment, R6a may be —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted.

According to an embodiment, the peri-arylene dye is a compound according to formula (16), (17), (18) or (19):

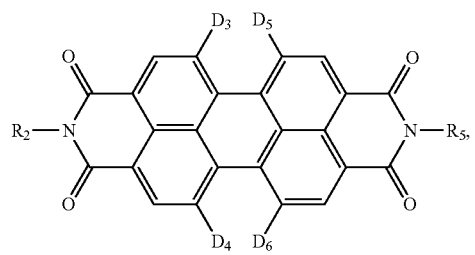
(16)

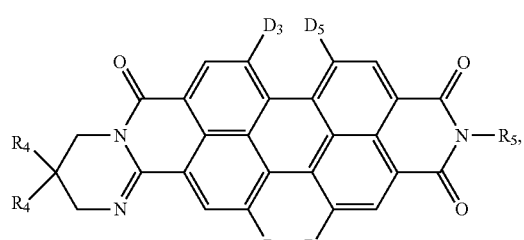
(17)

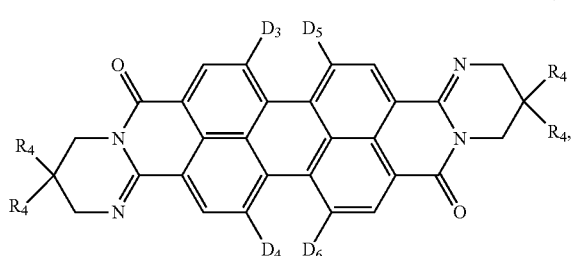
(18)

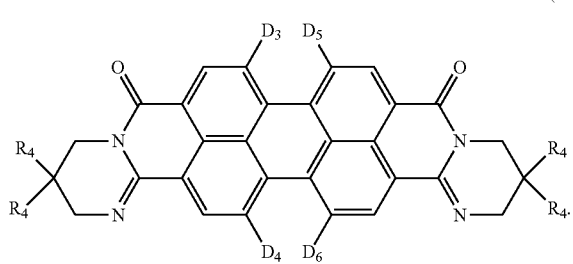
(19)

According to embodiments of the peri-arylene dyes of formulae (16) to (19), D3 is hydrogen, D5 is selected from hydroxyl, amino, N(C1-C24 alkyl)2, NH(C1-C24 alkyl), nitro and halogen, and the pair D4/D6 is a divalent moiety selected from —O—, —S—, —NH—, or formulae (5) through (8).

According to embodiments of the peri-arylene dyes of formulae (16) to (19), D3 and D5 each is hydrogen, and the pair D4/D6 is a divalent moiety selected from —O—, —S—, —NH—, or formulae (5) through (8).

According to embodiments of the peri-arylene dyes of formulae (16) to (19), the pair D4/D6 is a divalent moiety according to formula (5).

According to embodiments of the peri-arylene dyes of formulae (16) to (19), D3, D4 and D6 each is hydrogen, and D5 is selected from hydroxyl, amino, N(C1-C24 alkyl)2, NH(C1-C24 alkyl), nitro and halogen. According to particular embodiments, D5 is selected from amino, nitro, N(C1-C6 alkyl)2, and NH(C1-C6 alkyl).

According to embodiments of the peri-arylene dye of formula (16), R5 is amino, NH(C1-C4 alkyl) or N(C1-C4 alkyl)2.

According to embodiments of the peri-arylene dyes of formulae (16) to (19), each R5 is R2 and wherein each R4 is R3.

As mentioned above, the peri-arylene dye may comprise at least one hydrophobic moiety. For example, the peri-arylene dye may comprise at least two of said hydrophobic moieties. According to embodiments, the dye may be substituted with at least one reactive moiety R20. For example the dye may be substituted with one reactive moiety R20. According to embodiments, the dye may be free of a reactive moiety R20.

According to embodiments, the peri-arylene dye may have a molecular weight of more than 500 g/mol, in particular more than 760 g/mol. For example the molecular weight may be more than 860 g/mol, such as more than 960 g/mol.

According to a specific embodiment, the peri-arylene dye is a compound according to formula (20):

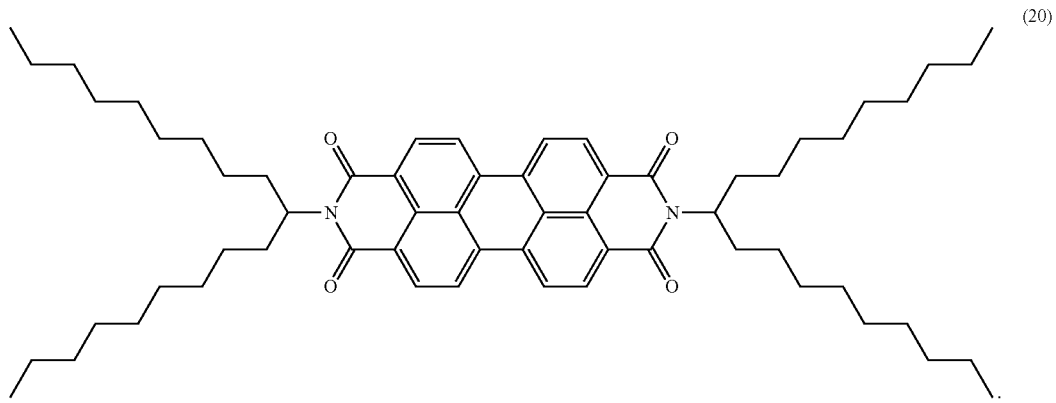
(20)

According to a specific embodiment, the peri-arylene dye is a compound according to formula (21):
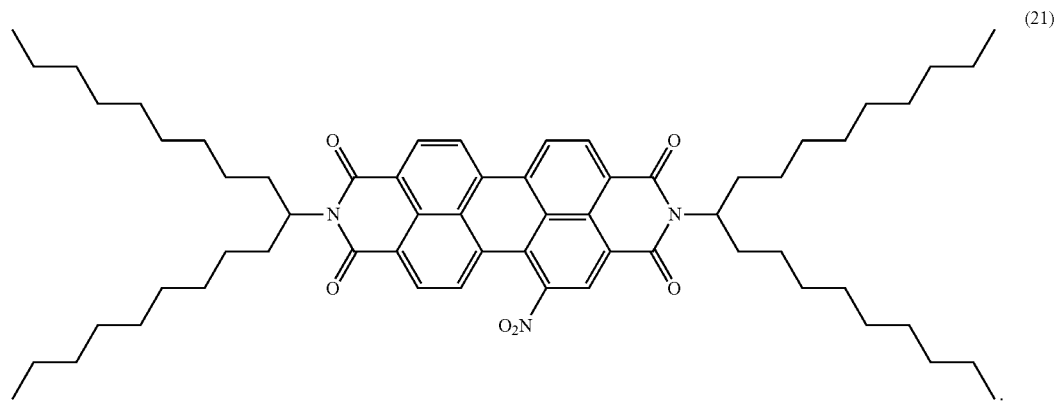 [SMILES: CCCCCCCCCC(CCCCCCCCC)N1C(=O)c2ccc3c4ccc5c6c(cc([N+](=O)[O-])c(c7ccc(c2c37)C1=O)c64)C(=O)N(C(CCCCCCCCC)CCCCCCCCC)C5=O]
According to a specific embodiment, the peri-arylene dye is a compound according to formula (22):
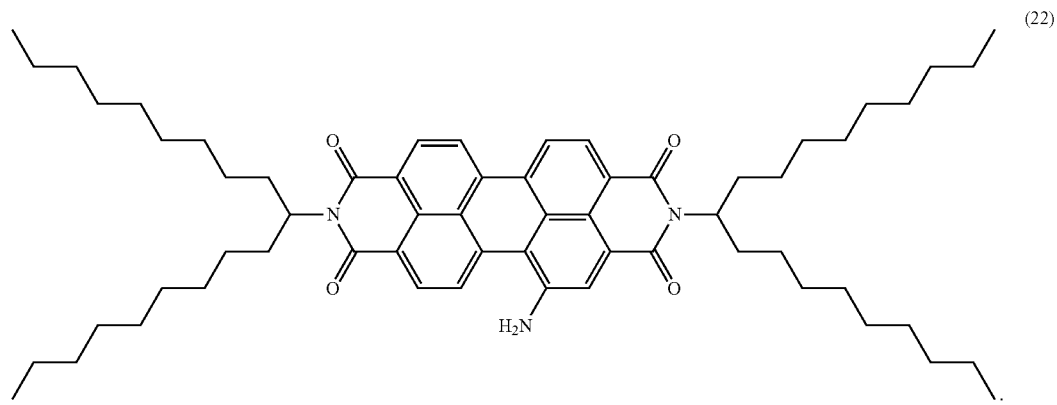 [SMILES: CCCCCCCCCC(CCCCCCCCC)N1C(=O)c2ccc3c4ccc5c6c(cc(N)c(c7ccc(c2c37)C1=O)c64)C(=O)N(C(CCCCCCCCC)CCCCCCCCC)C5=O]
According to a specific embodiment, the peri-arylene dye is a compound according to formula (23):
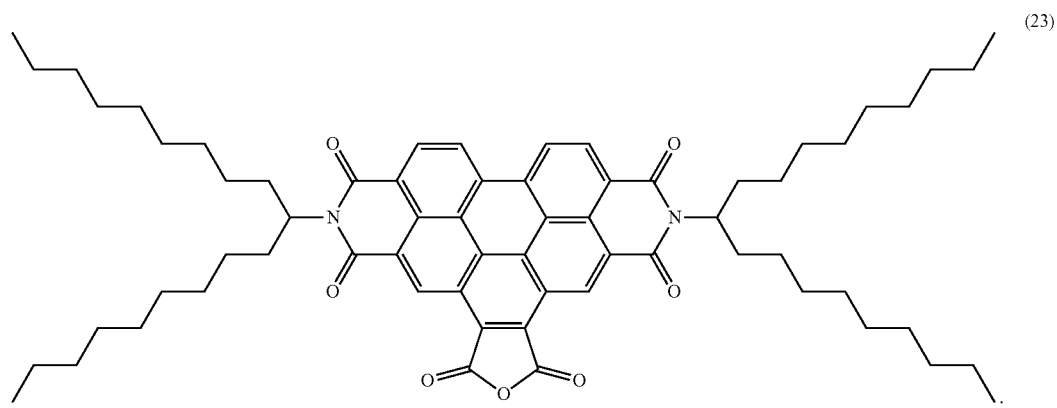 [SMILES: CCCCCCCCCC(CCCCCCCCC)n1c(=O)c2ccc3c4ccc5c(=O)n(C(CCCCCCCCC)CCCCCCCCC)c(=O)c6cc7c8c(=O)oc(=O)c8c8cc(c1=O)c2c3c8c7c4c56]

According to a specific embodiment, the peri-arylene dye is a compound according to formula (31):

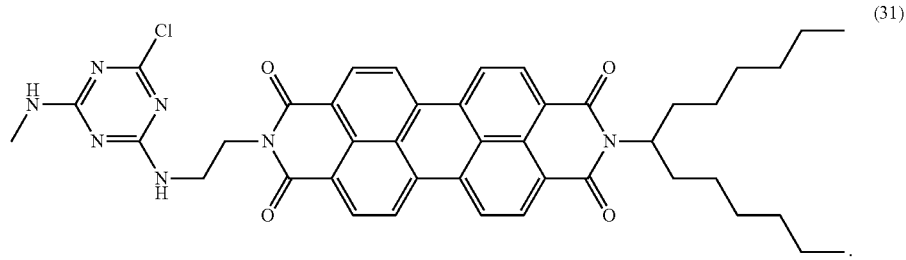 [SMILES: CCCCCCC(CCCCCC)N1C(=O)c2ccc3c4ccc5c6c(ccc(c7ccc(c2c37)C1=O)c64)C(=O)N(CCNc1nc(Cl)nc(NC)n1)C5=O]

According to a specific embodiment, the peri-arylene dye is a compound according to formula (32):

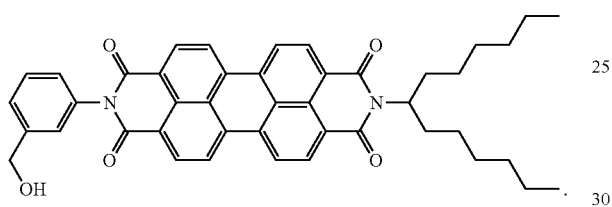

According to a specific embodiment, the peri-arylene dye is a compound according to formula (33):

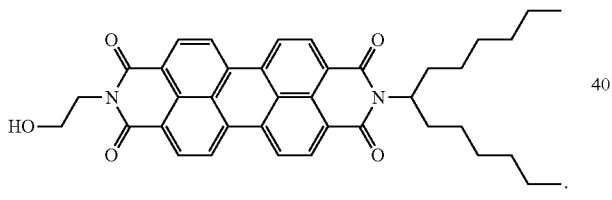

According to a specific embodiment, the peri-arylene dye is a compound according to formula (34):

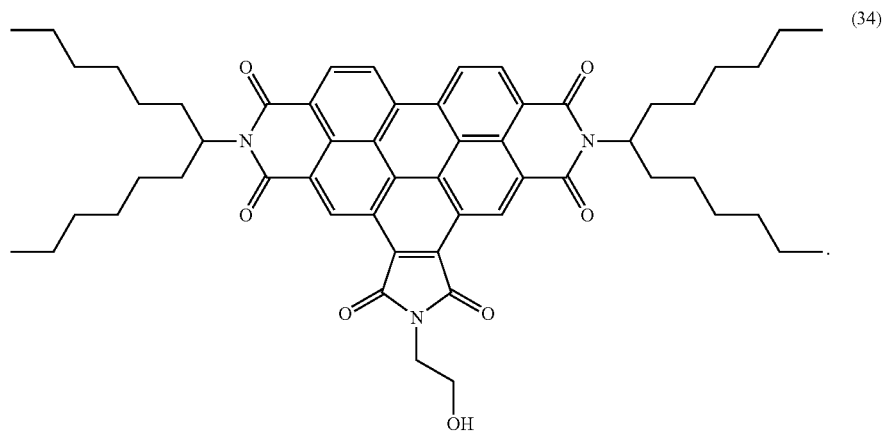 [SMILES: CCCCCCC(CCCCCC)n1c(=O)c2ccc3c4ccc5c(=O)n(C(CCCCCC)CCCCCC)c(=O)c6cc7c8c(=O)n(CCO)c(=O)c8c8cc(c1=O)c2c3c8c7c4c56]

According to specific embodiments, the peri-arylene dye is a compound according to one of the formulae below:

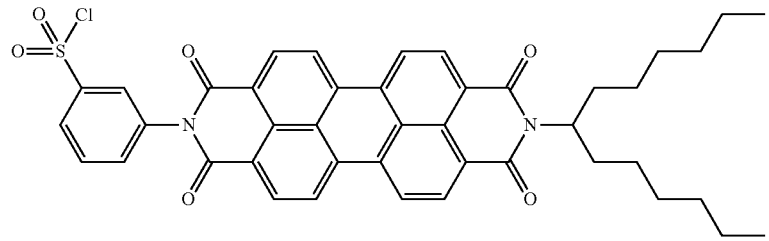

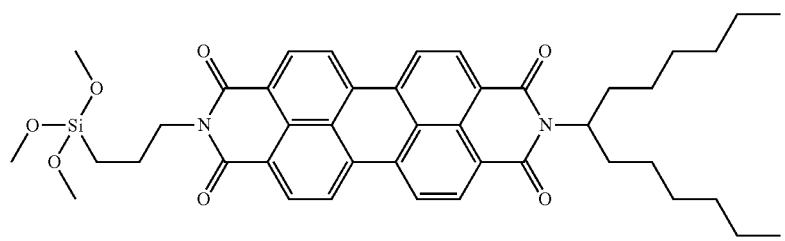

The peri-arylene dyes of the present invention have at least one absorption maximum in the visible spectrum. Typically, they have at least one absorption maximum within the 400-700 nm range. The maximum absorption coefficient at the at least one absorption maximum typically is at least 20,000 L/mol·cm, for example at least 30,000 L/mol·cm, such as at least 50,000 L/mol·cm.

The peri-arylene dyes of the present invention furthermore may be photoluminescent. If so, the fluorescence quantum yield may be 15% or higher for absorptions in the range of 560-590 nm. For absorptions in the range of 490-530 nm, the fluorescence quantum yield may be 80% or higher, such as at least 90% or 95%.

Peri-arylene dyes of the present invention may have an octanol/water partition coefficient (log $P_{ow}$) of at least 20, wherein log $P_{ow}$ is calculated based on the GALAS algorithm using ACD/Labs software.

According to embodiments, peri-arylene dyes of the present invention may have may have an octanol/water partition coefficient (log $P_{ow}$) of at least 21, in particular at least 22, wherein log $P_{ow}$ is calculated based on the GALAS algorithm.

Stated differently, peri-arylene dyes of the present invention may be soluble in a medium having an octanol/water partition coefficient (log $P_{ow}$) of at least 12, wherein log $P_{ow}$ is calculated based on the GALAS algorithm using ACD/Labs software.

With respect to the solubility, the peri-arylene dyes of the present invention described above may be soluble in a medium comprising a linear or branched C2-C8 alcohol. The medium optionally may comprise water in an amount below the solubility limit. According to embodiments, the medium may comprise (iso)propanol, butanol or a mixture thereof. According to particular embodiments, the peri-arylene dyes of the present invention are soluble in (iso)propanol, (iso)butanol or t-tert butanol, typically in amounts of at least 0.1% by weight, or at least 0.5% by weight, such as at least 1% by weight. The prefix (iso) in this context denotes both the linear n-alcohol as well as the iso-form.

3 THE HYDROPHILIC PERI-ARYLENE DYES

According to an embodiment, the dye according to the present invention is a peri-arylene dye according to formula (24):

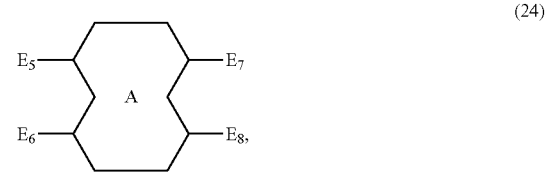

(24)

wherein structure A

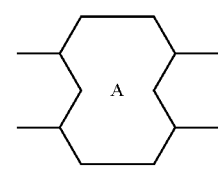

is selected from formulae (2) through (4)

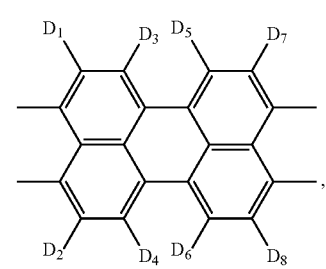

(2)

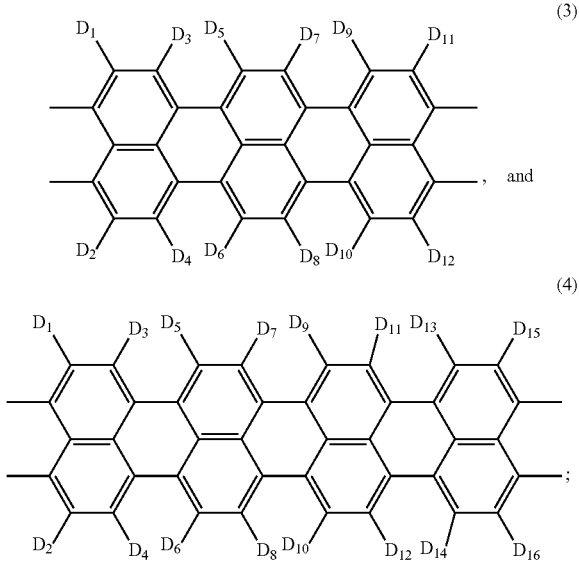

(3)

(4)

wherein each of D1 through D16 independently may be selected from hydrogen, C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl.

In addition, an even number of the moieties D1 through D16 may form one or more divalent moieties and/or one or more condensed ring structures.

In particular, one or more of the pairs of D3/D5, D4/D6, D7/D9, D8/D10, D11/D13 and D12/D14 may be a divalent moiety selected from —O—, —S—, -(secondary amine)-, or -(tertiary amine)-. When one of the said pairs forms a divalent moiety being a tertiary amine, an example for such structure is —N(C1-C24 alkyl)-, wherein alkyl optionally may be substituted with one or more substituents selected from C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester.

Furthermore, one or more of the pairs of D3/D5, D4/D6, D7/D9, D8/D10, D11/D13 and D12/D14 may form a condensed ring structure selected from formulae (5) through (8):

(5)

(6)

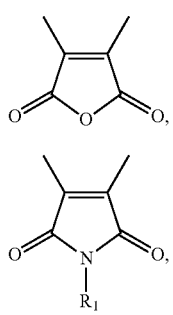

wherein R1 is hydrogen, linear or branched (C1-C5)alkyl, cyclohexyl, or —(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2;

(7)

(8)

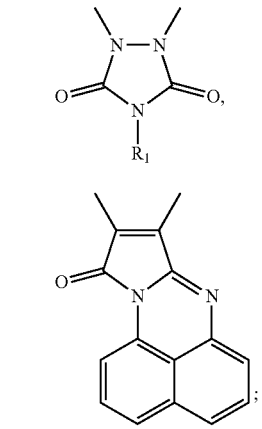

optionally substituted with up to 3 substituents selected from hydroxyl, nitro, halogen, C1-C6 alkyl, C1-C6 alkoxy, NH(C1-C6 alkyl), N(C1-C6 alkyl)2.

According to an embodiment, E5 and E6 in Formula (24) each may be a monovalent moiety independently selected from hydrogen, C1-C6 alkyl, (C0-C4 alkyl)hydroxy, C1-C4 alkoxy, amino, N(C1-C24 alkyl)2, —NH(C1-C24 alkyl), carboxylic acid, sulfonic acid, nitro, halogen, C1-C3 carboxyl ester, phenoxy optionally substituted with up to 3 (C1-C6)alkyl. If E5 and E6 in Formula (24) are monovalent moieties, the pair of moieties E7/E8 is a divalent moiety according to formula (25) or (26), below.

According to an embodiment, the pair of moieties E5/E6 and the pair of moieties E7/E8 both are a divalent moiety independently selected from formulae (25) and (26).

Formula (25) is (25)

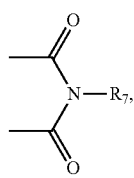

wherein R7 is hydrogen or a hydrophilic moiety R9.
Formula (26) is (26)

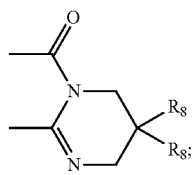

wherein each R8 independently is hydrogen or a hydrophilic moiety R9.

When E5 and E6 are monovalent moieties and the pair E7/E8 is a divalent moiety according to formula (25) or (26), at least one R7 or R8 is a hydrophilic moiety R9. Similarly, when the pair E5/E6 and the pair E7/E8 both are a divalent moiety according to formula (25) or (26), at least one R7 or R8 is a hydrophilic moiety R9.

The hydrophilic moiety R9 may be R9a, which is an aromatic moiety substituted with at least one acidic group/residue. R9a may be —(CH2)n-aryl, wherein n=0-3, and aryl is C5-10 aryl, wherein 1 or 2 of the carbon atoms may be replaced by N, O or S. The aryl is substituted with 2 or 3 carboxylic acid or sulfonic acid groups/residues, and optionally with 1-2 substituents selected from halogen, methyl, ethyl, propyl, isopropyl, tert-butyl. Suitable counterions for acid residues are for example $Li^+$, $Na^-$, $K^+$, $NH4^+$, $Mg^{2+}$, $Ca^{2+}$ or other cations. Protons, Na and $K^+$ generally are preferred. According to a particular embodiment, hydrophilic moiety R9a is phenyl or benzyl substituted with 2 sulfonic acid groups/residues.

Furthermore, the hydrophilic moiety R9 may be R9b, which is a cationic moiety with a corresponding counterion. R9b may be —(C0-C6 alkylene)-$B^+$(counterion$^-$), wherein —$B^+$ is an aromatic or aliphatic heterocyclic moiety, a quaternary alkyl or aryl ammonium moiety, or a phosphonium moiety.

According to embodiments, —$B^+$ may be an aromatic heterocyclic moiety comprising a quaternary nitrogen, selected from pyrryl, imidazolyl, pyrazolyl, pyridyl, pyrimidinyl, pyrazyl, chinolyl, indolyl, N-alkyl derivatives thereof, and N-alkenyl derivatives thereof. According to a particular embodiment, —$B^+$ may be an aromatic heterocyclic moiety selected from N-methylimidazolyl, N-allylimidazolyl, 2-ethylimidazolyl, and 1,2-dimethylimidazolyl.

According to embodiments, —$B^+$ may be an aliphatic heterocyclic moiety comprising a quaternary nitrogen, selected from pyrrolidinyl, piperidinyl, morpholinyl, N-alkyl derivatives thereof, and N-alkenyl derivatives thereof. According to a particular embodiment, —$B^+$ may be an aliphatic heterocyclic moiety selected from N-methylmorpholinyl, N-ethylmorpholinyl, 1-methylpiperidinyl.

According to embodiments, —$B^+$ may be a quaternary alkyl or aryl ammonium moiety of the formula —N(R10)3, wherein R10 in each occurrence independently is —(CH2)n-phenyl, wherein n=0-3, or (C1-C6)alkyl, wherein alkyl optionally is substituted with up to 3 substituents selected from hydroxy and amino. According to a particular embodiment, —$B^+$ may be a quaternary ammonium moiety, wherein R10 in each occurrence independently is phenyl or benzyl, or (C1-C4)alkyl, wherein alkyl optionally is substituted with up to 3 substituents selected from hydroxy and amino.

According to embodiments, —$B^+$ may be a phosphonium moiety of the formula —P(C1-C6)alkyl, wherein alkyl optionally is substituted with up to 3 substituents selected from hydroxy and amino.

Suitable counterions for charge on $B^+$ are for example halogen ions, sulfate, phosphate, hydrogen phosphate, nitrate, and/or acid residues of organic acids such as oxalate, formate, acetate, citrate, tartrate, malonate, and pyruvate. Chloride, bromide and methylsulfate generally are preferred.

Furthermore, the hydrophilic moiety R9 may be R9c, which is linear, branched or cyclic polyalkoxy or polyamino moiety. The polyalkoxy or polyamino moiety optionally may be substituted for example with carboxy, amino, methyl, ethyl, hydroxy(C0-C4 alkyl), and/or C1-C4 alkoxy. According to a particular embodiment, hydrophilic moiety R9c may be linear or branched polyoxyethylene, polyoxy(iso)propylene or polyoxy(iso)butylene comprising 12-80, in particular 15-40 polyoxyalkylene units optionally substituted with carboxy, amino, methyl, ethyl, hydroxy(C0-4 alkyl), and/or C1-4 alkoxy.

In Formula (26), the linkage of a polyalkoxy or polyamino moiety R9c to Formula (26) may be via 0 or N. In that case, the terminal group of the polyalkoxy or polyamino moiety will be the alkyl portion of the corresponding structural unit. For Formula (25) and optionally in Formula (26), the linkage of a polyalkoxy or polyamino moiety will be via the alkylene part. In that case, the terminal group of the polyalkoxy or polyamino moiety is —OR11, wherein R11 is hydrogen or C1-C6 alkyl optionally substituted with carboxy, amino, methyl, ethyl, hydroxy(C0-C4 alkyl), and/or C1-C4 alkoxy. Typically, R11 will be the alkyl group corresponding to the structural unit of the polyalkoxy or polyamino moiety.

According to a particular embodiment, R9c is a cyclic polyalkoxy or polyamino moiety, which usually are denoted as crown ethers. For example, R9c may be a crown ether selected from 9-crown-3, 12-crown-4, 15-crown-5, 18-crown-6, 21-crown-7, 24-crown-8, and aza-analogues thereof. Other suitable crown ethers are benzo-analogues of the above.

According to an embodiment, both the pair E5/E6 and the pair E7/E8 are a divalent moiety independently selected from formulae (25) and (26). For example, both the pair E5/E6 and the pair E7/E8 are a divalent moiety according to formula (25).

The hydrophilic peri-arylene dyes described above have at least one absorption maximum in the visible spectrum. Typically, they have at least one absorption maximum within the 400-700 nm range. The maximum absorption coefficient at the at least one absorption maximum typically is at least 20,000 L/mol·cm, for example at least 30,000 L/mol·cm, such as at least 50,000 L/mol·cm.

Furthermore, the hydrophilic peri-arylene dyes described above may be photoluminescent. If so, the fluorescence quantum yield may be 15% or higher for absorptions in the range of 560-590 nm. For absorptions in the range of 490-530 nm, the fluorescence quantum yield may be 80% or higher, such as at least 90% or 95%.

4 THE HAIR COLORING COMPOSITION

The hair coloring composition according to the present invention comprises a medium, at least one aromatic dye in the medium and optionally pigment microparticles in mixture with the medium. The aromatic dye is as described above. In particular, the aromatic may be selected from rylene dyes, nitro dyes, aryl and heteroaryl azo dyes, chinon/chinonimine/chinondiimine dyes, methin dyes, azomethine-like hydrazone and imine dyes, and porphyrin dyes. According to embodiments, the dye or an aromatic ring of the dye is substituted with one or more hydrophobic moieties having a linear or non-linear structure. For example, the dye may be a peri-arylene dye as described above which dye comprises a perylene, terrylene or quarterrylene core or higher rylene core. According to embodiments, the dye may be substituted with a reactive moiety R20, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkyl)OSO2(aryl), (C0-C6 alkyl)SO2Cl, (C0-C6 alkyl)Si(O—(C1-C3 alkyl))3, (aryl)SO2Cl, aryl(C0-C4)OH, aryl(C0-C4)NH2, wherein aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, and formula (30),

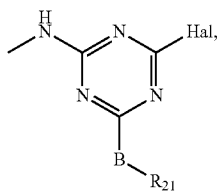

(30)

wherein B is selected from NH and O; Hal is F, Cl or Br; and R21 is linear or branched (C1-C6 alkyl).

In addition, the dye may have an octanol/water partition coefficient (log $P_{ow}$) as described above and/or be soluble in a medium having an octanol/water partition coefficient (log $P_{ow}$) as described above. The dye may be dissolved in the medium.

The one or more hydrophobic moieties with which the dyes may be substituted usually will be long-chain alkyl structures. According to an embodiment, each of the one or more hydrophobic moieties comprises 14-28 carbon atoms, and is selected from:

- —(CH2)m-CH(C3-24 alkyl)2 or —(CH2)m-C(C3-24 alkyl)3, wherein m=0-5, wherein alkyl is linear and is optionally substituted with one or more substituents selected from halogen, C1-C6 alkyl, C1-C6 alkoxy, NH(C1-C6 alkyl), and N(C1-C6 alkyl)2,
- —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and
- —(CH2)o-phenyl, wherein o=1-3 which may be substituted with up to 3 substituents selected from C1-C6 alkyl and C1-C6 alkoxy, in particular isopropyl and/or tert-butyl,
- —(CH2)n-naphthyl, wherein n=0-3 which may be substituted with up to 3 substituents selected from C1-C6 alkyl and C1-C6 alkoxy, in particular isopropyl and/or tert-butyl The moieties may be unsymmetrical in that the alkyl chains have different chain lengths. Alternatively, the moieties may be symmetrical.

4.1 Peri-Arylene Dyes

According to embodiments, the hair coloring composition according to the present invention comprises a medium, and at least one peri-arylene dye in the medium. In particular, the hair coloring composition may comprise at least one peri-arylene dye according to formula (1), described above, in the medium. According to embodiments, the hair coloring composition may comprise at least one peri-arylene dye according to formula (24), described above, in the medium. The peri-arylene dye may be dissolved in the medium in an amount of at least 0.1% by weight, or at least 0.5% by weight, such as at least 1% by weight.

According to embodiments, the hair coloring composition comprises at least one peri-arylene dye according to formula (1)

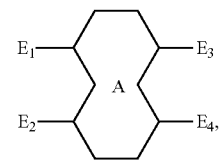

(1)

wherein structure A

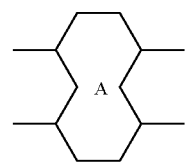

is selected from formulae (2) through (4)

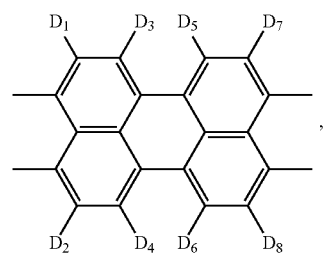

(2)

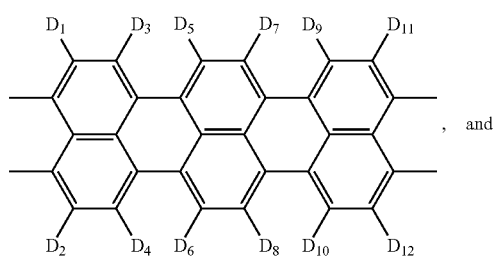

(3), and

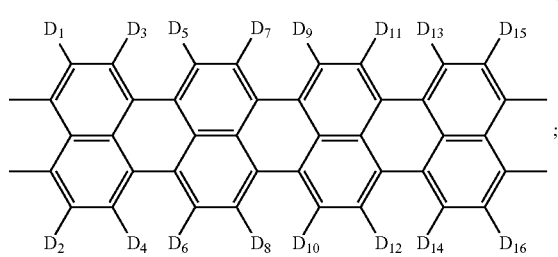

(4);

wherein each of D1 through D16 independently may be selected from hydrogen, C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl.

In addition, an even number of the moieties D1 through D16 may form one or more divalent moieties and/or one or more condensed ring structures.

In particular, one or more of the pairs of D3/D5, D4/D6, D7/D9, D8/D10, D11/D13 and D12/D14 may be a divalent moiety selected from —O—, —S—, -(secondary amine)-, or -(tertiary amine)-. When one of the said pairs forms a divalent moiety being a tertiary amine, an example for such structure is —N(C1-C24 alkyl)-, wherein alkyl optionally may be substituted with one or more substituents selected from C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester.

Furthermore, one or more of the pairs of D3/D5, D4/D6, D7/D9, D8/D10, D11/D13 and D12/D14 may form a condensed ring structure selected from formulae (5) through (8):

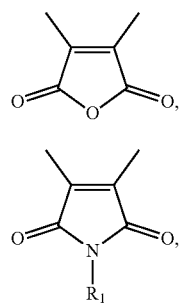
(5)

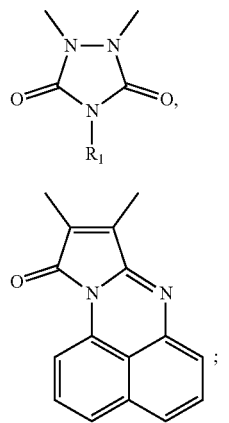
(6)

(7)

(8)

optionally substituted with up to 3 substituents selected from hydroxyl, nitro, halogen, C1-C6 alkyl, C1-C6 alkoxy, NH(C1-C6 alkyl), N(C1-C6 alkyl)2, and a reactive moiety R20.

wherein R1 is hydrogen, linear or branched (C1-C5)alkyl, cyclohexyl, a reactive moiety R20, or —(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2;

According to an embodiment, E1 and E2 in Formula (1) each may be a monovalent moiety independently selected from hydrogen, C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl. If E1 and E2 in Formula (1) are monovalent moieties, the pair of moieties E3/E4 is a divalent moiety according to formula (9) or (10):

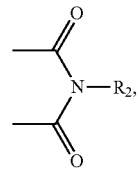
(9)

wherein R2 is a hydrophobic moiety comprising at least 6 carbon atoms, or a reactive moiety R20;

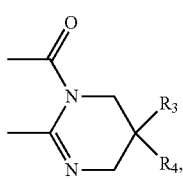
(10)

and
wherein R3 is a hydrophobic moiety comprising at least 3 carbon atoms, or a reactive moiety R20;
and wherein R4 is hydrogen, methyl, ethyl, methoxy, ethoxy, a reactive moiety R20, or a hydrophobic moiety R3.

According to an embodiment, the pair of moieties E1/E2 and the pair of moieties E3/E4 both are a divalent moiety. If both E1/E2 and E3/E4 are divalent moieties, E1/E2 is selected from formulae (11) and (12) and E3/E4 is independently selected from formulae (11) through (15):

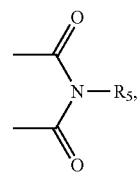
(11)

wherein R5 is hydrogen, linear or branched (C1-C5)alkyl, cyclohexyl, amino, NH(C1-C4 alkyl), N(C1-C4 alkyl)2, a reactive moiety R20, or a hydrophobic moiety R2;

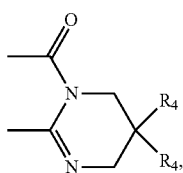
(12)

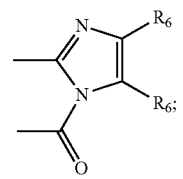
(13)

wherein R6 is hydrogen, methyl, ethyl, methoxy, ethoxy, a reactive moiety R20, or a hydrophobic moiety;

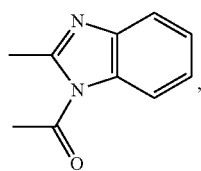 (14)

optionally substituted with up to 3 substituents selected from hydroxyl, nitro, halogen, C1-C6 alkyl, C1-C6 alkoxy, NH(C1-C6 alkyl), N(C1-C6 alkyl)2, a reactive moiety R20; and

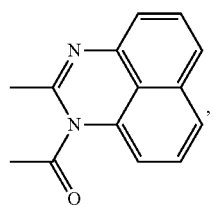 (15)

optionally substituted with up to 3 substituents selected from hydroxyl, nitro, halogen, C1-C6 alkyl, C1-C6 alkoxy, NH(C1-C6 alkyl), N(C1-C6 alkyl)2, a reactive moiety R20.

When the pair E1/E2 is a divalent moiety according to formula (11) or (13) and the pair E3/E4 is a divalent moiety according to formula (11), (12) or (13), at least one R4, R5 or R6 is a hydrophobic moiety. When both pairs E1/E2 and E3/E4 are divalent moieties according to formula (12), all moieties R4 may be hydrogen.

As mentioned above, R2 may be a hydrophobic moiety. According to an embodiment, R2 is a hydrophobic moiety comprising 6-28 carbon atoms. In particular, R2 may be a hydrophobic moiety comprising 6-28 carbon atoms, selected from:
- —(CH2)m-C(R2a)(R2b)(R2b), wherein m=0-5, R2a is linear C3-24 alkyl and each R2b independently is hydrogen or linear C3-24 alkyl, wherein alkyl is optionally substituted with one or more substituents selected from halogen, C1-C6 alkyl, C1-C6 alkoxy, NH(C1-C6 alkyl), and N(C1-C6 alkyl)2,
- —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3 or, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and
- —(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, in particular isopropyl and/or tert-butyl.

According to a particular embodiment, R2 may be a moiety comprising 14-28 carbon atoms, selected from:
- —(CH2)m-CH(C3-24 alkyl)2 or —(CH2)m-C(C3-24 alkyl)3, wherein m=0-5, wherein alkyl is linear and is optionally substituted with one or more substituents selected from halogen, C1-C6 alkyl, C1-C6 alkoxy, NH(C1-C6 alkyl), and N(C1-C6 alkyl)2,
- —(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3 or, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and
- —(CH2)o-phenyl, wherein o=1-3 which may be substituted with up to 3 substituents selected from C1-C6 alkyl and C1-C6 alkoxy, in particular isopropyl and/or tert-butyl, —(CH2)n-naphthyl, wherein n=0-3 which may be substituted with up to 3 substituents selected from C1-C6 alkyl and C1-C6 alkoxy, in particular isopropyl and/or tert-butyl.

According to a further particular embodiment, R2 may be a moiety, in particular a moiety comprising 14-28 carbon atoms, selected from:
- —(CH2)m-CH(C7-16 alkyl)2 or —(CH2)m-C(C7-16 alkyl)3, wherein n=0-3, wherein alkyl is linear and is optionally substituted with one or more substituents selected from halogen, methyl, ethyl, propyl, isopropyl, or
- —(CH2)n-N(C7-C16 alkyl)2 or —(CH2)n-NH—(CH2)n-C(C5-C10 alkyl)3, wherein n=0-3 and alkyl is linear and is optionally substituted with one or more substituents selected from halogen, methyl, ethyl, propyl, isopropyl.

According to a further particular embodiment, R2 may be a moiety, in particular a moiety comprising 14-28 carbon atoms, selected from
- —(CH2)m-CH(C9-16 alkyl)2 or —(CH2)m-C(C9-16 alkyl)3, wherein alkyl is linear, or —N(C8-C16 alkyl)2 or —NH—CH2-C(C6-C8 alkyl)3, wherein alkyl is linear.

In embodiments comprising the moiety R3, R3 may be a hydrophobic moiety —(CH2)m-C(R3a)(R3b)(R3b), wherein m=0-5, R3a is C3-24 alkyl and each R3b independently is hydrogen or C3-24 alkyl, wherein alkyl is linear and is optionally substituted with one or more substituents selected from halogen, C1-C6 alkyl, C1-C6 alkoxy, NH(C1-C6 alkyl), N(C1-C6 alkyl)2. According to a particular embodiment, R3a and at least one R3b may be optionally substituted C3-24 alkyl, for example optionally substituted C6-20 alkyl.

In embodiments comprising the moiety R6, R6 may be a hydrophobic moiety R6a selected from:
- —(CH2)m-C(R6b)(R6c)(R6c), wherein m=0-5, R6b is linear C3-24 alkyl and each R6c independently is hydrogen or linear C3-24 alkyl, wherein alkyl is optionally substituted with one or more substituents selected from halogen, C1-C6 alkyl, C1-C6 alkoxy, NH(C1-C6 alkyl), and N(C1-C6 alkyl)2,
- —(CH2)n-NH(C14-28 alkyl) or —(CH$_2$)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2.

According to a particular embodiment, R6b and at least one R6c may be optionally substituted C3-24 alkyl, for example optionally substituted C6-20 alkyl. According to another embodiment, R6a may be —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted.

According to embodiments, the hair coloring composition may comprise at least one peri-arylene dye according to formula (16), (17), (18) or (19):

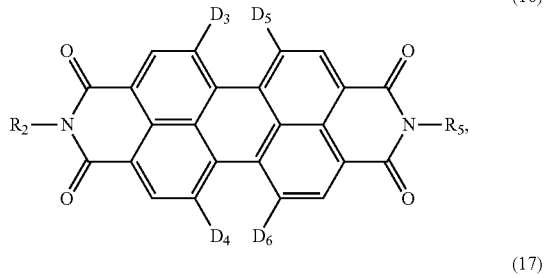

(16)

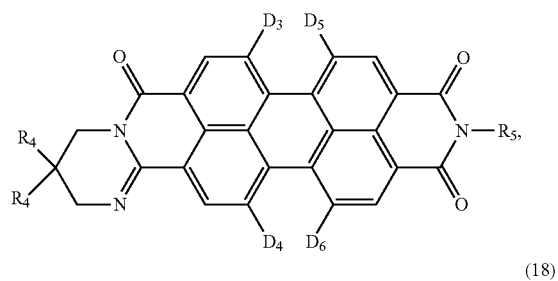

(17)

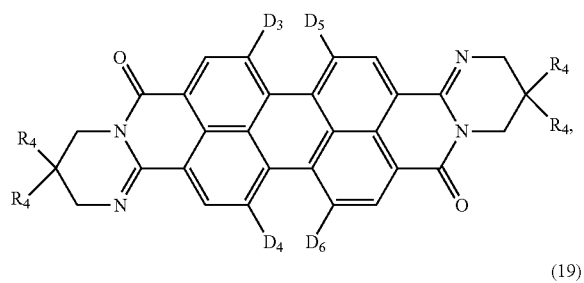

(18)

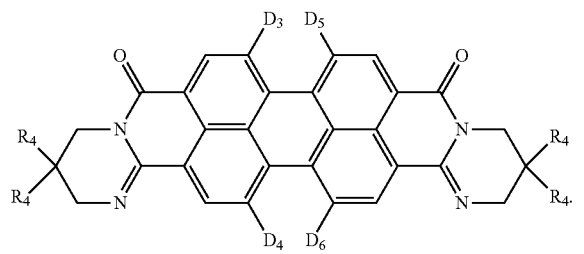

(19)

According to embodiments, the hair coloring composition may comprise at least one peri-arylene dye according to formula (16) to (19), wherein D3 is hydrogen, D5 is selected from hydroxyl, amino, N(C1-C24 alkyl)2, NH(C1-C24 alkyl), nitro and halogen, and the pair D4/D6 is a divalent moiety selected from —O—, —S—, —NH—, or formulae (5) through (8).

According to embodiments, the hair coloring composition may comprise at least one peri-arylene dye according to formula (16) to (19), wherein D3 and D5 each is hydrogen, and the pair D4/D6 is a divalent moiety selected from —O—, —S—, —NH—, or formulae (5) through (8).

According to embodiments, the hair coloring composition may comprise at least one peri-arylene dye according to formula (16) to (19), wherein the pair D4/D6 is a divalent moiety according to formula (5).

According to embodiments, the hair coloring composition may comprise at least one peri-arylene dye according to formula (16) to (19), wherein D3, D4 and D6 each is hydrogen, and D5 is selected from hydroxyl, amino, N(C1-C24 alkyl)2, NH(C1-C24 alkyl), nitro and halogen. According to particular embodiments, the hair coloring composition may comprise at least one peri-arylene dye according to formula (16) to (19), wherein D5 is selected from amino, nitro, N(C1-C6 alkyl)2, and NH(C1-C6 alkyl).

According to embodiments, the hair coloring composition may comprise at least one peri-arylene dye according to formula (16), wherein R5 is amino, NH(C1-C4 alkyl) or N(C1-C4 alkyl)2.

According to embodiments, the hair coloring composition may comprise at least one peri-arylene dye according to formula (16) to (19), wherein each R5 is R2 and wherein each R4 is R3.

The one or more peri-arylene dyes present in the hair coloring composition may comprise at least one hydrophobic moiety. For example, the at least one peri-arylene dye may comprise at least two of said hydrophobic moieties. In another example, all of the peri-arylene dyes present in the hair coloring composition comprise at least two of said hydrophobic moieties.

According to embodiments of the hair coloring composition, the dye may be substituted with at least one reactive moiety R20. For example the dye may be substituted with one reactive moiety R20. According to embodiments, the dye may be free of a reactive moiety R20

The one or more peri-arylene dyes present in the hair coloring composition may have a molecular weight of more than 500 g/mol, in particular more than 760 g/mol. For example the molecular weight may be more than 860 g/mol, such as more than 960 g/mol.

Specific examples of peri-arylene dyes which may be present in the hair coloring composition are the compounds of formulae (20), (21), (22), and/or (23) disclosed above.

Dye Concentration

The hair coloring composition for coloring hair fibers according to the present disclosure comprises one or more dyes. The hair coloring composition may comprise from about 0.005% to about 5%, about 0.01% to about 3%, about 0.1 to about 2%, or about 0.25% to about 1.5% dye(s), by weight of the hair coloring composition. In particular, the hair coloring composition may comprise from about 0.005% to about 5%, about 0.01% to about 3%, about 0.1 to about 2%, or about 0.25% to about 1.5%, by weight of the hair coloring composition, of one or more peri-arylene dyes described above. In particular, the one or more peri-arylene dyes are dyes according to formula (1).

Dye Material

The peri-arylene dye(s) used in the hair coloring composition can include at least two different peri-arylene dyes, or can include at least three peri-arylene dyes. The peri-arylene dyes absorb light within the visible spectrum, resulting in a perceivable color. The one or more peri-arylene dye in the hair coloring composition have at least one absorption maximum in the visible spectrum. According to embodiment, they have at least one absorption maximum within the 400-700 nm range. The maximum absorption coefficient at the at least one absorption maximum typically is at least 20,000 L/mol·cm, for example at least 30,000 L/mol·cm, such as at least 50,000 L/mol·cm. In particular embodiments, the extinction coefficient is greater than 50,000 ore even greater than 60,000 within the visible spectrum such as within the range 400-650 nm.

Optionally, one or more of the peri-arylene dyes are photoluminescent. According to embodiments, at least one peri-arylene dye in the hair coloring composition has a fluorescence emission maximum within the visible spectrum, in particular within the range 400-650 nm. According to embodiments, at least one peri-arylene dye in the hair coloring composition exhibits photoluminescence with a fluorescence quantum yield of at least 30%, in particular 50%, 70% or 80%. For example, the fluorescence quantum yield may be 15% or higher for absorptions in the range of 560-590 nm. For absorptions in the range of 490-530 nm, the fluorescence quantum yield may be 80% or higher, such as at least 90% or 95%.

According to embodiments, none of the peri-arylene dyes in the hair coloring composition is photoluminescent.

Depending on the degree of the change in color that is desired on the keratin fiber, the at least one peri-arylene dye in the hair coloring composition can also be can be used in varying amounts. The more dye that is used, the higher is the extent of the change in color in general.

4.2 Pigments

The hair coloring composition embodiments of the present invention optionally may comprise pigments. According to embodiments, however, the hair coloring composition is free of pigments. The pigment-comprising hair coloring composition embodiments of the present invention make it possible to obtain colored and remanent coatings, without substantially altering the keratin fibers. As used herein, the term "pigment" generally refers to any particle colorant having or containing pigment material that gives hair fibers color including black and white, such as titanium dioxide that give only white to hair fibers. The pigments are substantially water-insoluble. The pigments, to distinguish from dyes presented in molecular from, are also referred to as pigment microparticles. The pigments can be organic, inorganic, or a combination of both.

The at least one pigment that optionally may be used can be chosen from the organic and/or mineral pigments known in the art, such as those described in Kirk-Othmer's Encyclopedia of Chemical Technology and in Ullmann's Encyclopedia of Industrial Chemistry. The pigments comprised in the microparticles comprising at least one pigment which will not substantially diffuse or dissolve into keratin fibers during typical application methods. Instead, the pigment comprised in the microparticles comprising at least one pigment will substantially remain separate from the fibers but will be held in place on the surfaces of the hair strands by the polar functional silicone polymer The at least one pigment can be in the form of powder or of pigmentary paste. It can be surface treated, surface coated or encapsulated.

The material of the pigment microparticles can be inorganic or organic. Inorganic-organic mixed pigments are also possible. It is also possible to use a mixture of different type of pigments to deliver different color effects on the hair. The variety of pigments that can be used in embodiments of the present disclosure makes it possible to obtain a wide range of colors, and also optical effects such as metallic effects or interference effects.

4.3 the Film Formers

According to embodiments, the hair coloring composition comprises a film former, for example carboxylic acid polymer. According to embodiments, a layer of film former may be applied separately from the hair coloring composition. When applied separately, film former typically will be applied as a coating layer substantially covering the micro layer of peri-arylene dye(s).

4.3.1 Carboxylic Acid Polymer Film Former

The carboxylic acid polymer includes homopolymer, copolymer or terpolymer embodiments. These embodiments comprise appropriate monomeric units of olefinic carboxylic acids such as (meth)acrylic acid, as well as olefinic acid esters and amides and neutral olefinic monomers. The homopolymer may include units of olefinic carboxylic acid monomers including (meth)acrylic acid, maleic acid, fumaric acid, itaconic acid, crotonic acid, pentenoic acid and optional olefinic acid monomer derivatives duplicative of these said olefinic carboxylic acid monomers but having at least one of the carboxylic acid groups activated with a leaving group. The homopolymer in this context has a carboxylic acid group or a leaving group acid derivative as a side chain with each monomeric unit. The copolymer and terpolymer may include units of said olefinic carboxylic acid monomers and in addition may include one or more monomeric units of esters of said olefinic carboxylic acid monomers wherein the esterifying alcohol is a linear, branched or cyclic alkyl monoalcohol or diol of 1 to 6 carbons for the linear alkyl group (2 to 6 carbons for the diol), 3 to 6 carbons for the branched alkyl group and 3 to 10 carbons for the cyclic alkyl group, amides of said olefinic carboxylic acid monomers. N-alkyl amides of said olefinic carboxylic acid monomers wherein the alkyl group is a linear, branched or cyclic alkyl group as described for the monoalcohol, N-aminoalkyl amides of said olefinic carboxylic acid monomers wherein the amidating amine is a linear, branched or cyclic alkyl diamine with 2 to 6 carbons in the linear alkyl group, 3 to 6 carbons in the branched alkyl group and 3 to 10 carbons in the cyclic alkyl group, neutral olefinic monomers including those of the formula: $HR^1C=CHR^2$ wherein $R^1$ and $R^2$ are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, $CONH_2$, COOH, $NO_2$, CN, SO3H, $SONH_2$, pyridyl, $O_2CR^3$ wherein $R^3$ is alkyl of 1 to 3 carbons, vinyl and alkyl vinyl having 1 to 3 carbons in the alkyl group. Excluded from this description of the carboxylic acid polymer component of the hair coloring composition according to the present invention are the commercial acrylates copolymer designated as Neocryl 1127 and Neocryl 1125.

The carboxylic acid polymer embodiments may have an acid value ranging from about 0.1 to about 700, preferably about 1 to about 400, more preferably 10 to 190, especially more preferably 25 to 250, most preferably 40 to 200. The weight percentage of carboxylic acid monomer relative to the total weight of the polymer may range from about 0.2 weight percent to 30 weight percent. The molar ratio of carboxylic acid monomer to total monomer may range from 0.2:100 to 30:100, preferably 0.5:100 to 28:100, more preferably 1.0:100 to 26:100 most preferably 2:100 to 25:100. The molar ratio of 100:100 means that all monomeric units are carboxylic acid units.

The weight average molecular weight Mw of the carboxylic acid polymer embodiments may range from about 300 daltons to about 10 MDa. Preferably the Mw may range from about 500 Da to about 1 MDa, more preferably about 750 Da to about 500 kDa, especially more preferably about 1 kDa to about 50 kDa. The polydispersity may range from about 1 to about 10, preferably about 1.1 to about 7, more preferably 1.1 to about 5, most preferably 1.1 to about 3.

The carboxylic acid polymer embodiments are all water soluble while their degree of water solubility depends upon several factors including the Mw, the molar content of carboxylic acid monomer, the pH and temperature. The water solubility of the carboxylic acid polymer embodiments can also be increased by neutralization with a base. The neutralization can be performed with any base. Particularly the base useful for neutralization includes volatile bases, for example ammonia and or volatile organic amines as discussed elsewhere in this disclosure. Volatile refers to a material with a boiling point below 200 C at standard atmospheric pressure. At lower Mw and higher molar content of carboxylic acid monomer, the carboxylic acid polymer without neutralization is water soluble at all pH increments. At higher Mw and lower molar content of carboxylic acid monomer the carboxylic acid polymer without neutralization will be water soluble to a certain moderate extent such as from 5 wt % to 15 wt % relative to the weight of polymer and water. The solubility of these embodiments of the carboxylic acid polymer can be increased by neutralization so that the embodiments of the resulting neutralized carboxylic acid polymer will be fully soluble in water. The concentrations of these embodiments of neutralized high Mw, low carboxylic acid monomer content polymers can range from a minimum of about 5 weight percent of water up to 90 weight percent of water. These weight percentages address the saturation points and depend at least in part upon the neutral olefinic monomer, carboxylic acid ester or amide monomer content, carboxylic acid monomer content and the weight average molecular weight of the polymer. At high percentage of carboxylic acid monomer content of the polymer and low Mw, the saturation point will range up to 90 weight percent or greater. At low percentage of carboxylic acid monomer content of the polymer and high Mw, the saturation point will be at the lower end of the range.

The viscosity of the composition functions to hold the composition on the hair strands prior to removing the medium. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat strands of hair. Appropriate viscosity of the composition is the result of the interaction of the carboxylic acid polymer, its concentration, and as appropriate, an optional viscosity control agent and an optional thickening agent. Generally the viscosity of the composition may range from about 0.1 to about 200 Pa s$^{-1}$, preferably 1 to 100 Pa s$^{-1}$, more preferably 10 to 75 Pa s$^{-1}$. Viscosity measurements are carried out on a controlled stress rheometer e.g. using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec$^{-1}$ shear rate is obtained from the shear stress vs. shear rate curve, and the corresponding viscosity is calculated by dividing the obtained shear stress by 10.

The carboxylic acid polymer may be or become cross linked upon its formation of coating on hair strands. The cross linking may be covalent, non-covalent, hydrogen bonding, electrostatic interaction, ionic interaction or any combination thereof. Covalent crosslinking may be facilitated by inclusion of a minor amount of diol or diamine such as alkylene glycol or diamine of 2 to 6 carbons in the alkylene group. The diol or diamine can combine with carboxylic acid groups of adjacent polymers to form diester or diamide links. Similarly, the diol ester or aminoalkyl amide of a few of the carboxylic acid groups of the polymer can be present and will combine with carboxylic acid groups of adjacent polymer molecules to form diester or diamide links. Alternatively, a few carboxylic acid derivatives with a facile leaving group can be included in the polymer. The derivative will combine with a carboxylic acid group of an adjacent polymer so as to form an anhydride link light cross linking such as 0.1 percent to 2 percent of the available carboxylic acid groups of the polymer may be cross linked in this fashion. The light cross linking will improve resistance of the coating toward removal with dilute soap or shampoo aqueous solutions.

The concentration of the carboxylic acid polymer in the composition may range from about 2% to about 30%, preferably about 4% to about 25%, more preferably about 6% to about 20%, most preferably about 8% to about 15% by weight relative to the total weight of the composition. Specific concentrations include about 2%, about 4%, about 6%, about 8%, about 10%, about 12%, about 14%, about 16%, about 18%, about 20%, about 22% about 24% by weight relative to the total weight of the composition. The determination of the concentration for embodiments of the carboxylic acid polymer will depend in part upon the resulting viscosity, the saturation point of the carboxylic acid polymer in the medium and the interaction, if any, between the carboxylic acid polymer and other components of the composition. As discussed above, the viscosity is managed so that the composition will not run off the surfaces of strands of hair yet will level and flow to substantially coat those surfaces. Development of appropriate viscosity in part by management of the concentration of the carboxylic acid polymer can be experimentally determined by routine methods such as formulation of several samples of differing concentrations of polymer in the composition, coating those samples on a hair swatch and observing the flow, spread and leveling of the composition on the hair strands. The product can be applied to a hair strand using the coloring procedure described herein afterwards. The top of the hair strand, where it is glued together is clamped in a stand such that the hair is aligned vertically downwards. After a 5 minute dwell time it is observed if any and how much product has dripped from the hair tress. The results obtained from the several samples can be plotted against flow time and leveling time to determine an appropriate concentration or range of concentrations of the particular carboxylic acid polymer in the composition. A preferred concentration of the carboxylic acid polymer in the composition ranges from about 5% to about 45%, more preferably about 8% to about 35% and most preferably about 10% to about 30% by weight relative to the total weight of the composition. Examples of the carboxylic acid polymer concentration can be in the approximate range of 15%, 20% or 25% by weight relative to the total weight of the composition. Further examples of the carboxylic acid polymer concentration range from 0.1% to 40% by weight, such as from 0.1% to 30% by weight, for example ranging from 0.5% to 20% by weight, such as from 1% to 20% by weight, for example ranging from 10% to 15% by weight, relative to the total weight of the hair coloring composition.

The carboxylic acid polymer may be formulated and exemplified as a homopolymer of (meth)acrylic acid alone, especially polyacrylic acid. Its Mw may range from about 500 Da to about 500 kDa, preferably about 1 kDa to about 200 kDa, more preferably about 500 Da to about 10 kDa and most preferably about 500 Da to about 5 kDa with a polydispersity in the range of about 1, 2 to about 3, preferably 1.3 to about 2. The poly(meth)acrylic acid is neutralized with a volatile base as described above so that it is completely water soluble. At the foregoing Mw's the un-neutralized poly(meth)acrylic acid will be soluble in water but the concentration of the un-neutralized polymer will not be as high as that of the neutralized polymer.

The carboxylic acid polymer may also be formulated and exemplified as a homopolymer of (meth)acrylic acid alone and a few of the carboxylic groups may be converted to acyl groups bonded to leaving groups that will enable the acyl groups to form anhydrides with carboxylic acid groups. Appropriate leaving groups include imidazolonyl moieties, carbodiimide moieties, t-butyl anhydride moieties and activated ester moieties. Upon formulation of this homopolymer into the medium, the acyl-leaving groups will combine with carboxylic acid groups to form cross link anhydride groups. The number of anhydride groups relative to the total number of carboxyl groups of the homopolymer is small, such as 1% to 5%, preferably 2% to 3% so that the crosslinking is light. This light cross linking enables solubility of the cross linked homopolymer in the medium especially when subsequently neutralized with a volatile base yet provides resistance toward aqueous penetration into the polymer lattice when the polymer is in a solidified state.

The carboxylic acid polymer may also be formulated and exemplified as a copolymer or terpolymer of (meth)acrylic acid and a neutral olefin monomer selected from the group consisting of (meth)acrylate ester wherein the esterifying alcohol is a C1 to C22 monoalcohol, preferably methanol, ethanol, propanol, isopropanol or n-butanol, (meth)acrylamide, styrene, carboxystyrene (i.e. vinylbenzoic acid), carboxyamidostyrene (i.e. vinylbenzamide), vinylpyridine, vinyl oxyalkanoyl (vinyl acetate and homologs of the acetate) and any combination thereof. Preferred olefin monomers include methyl (meth)acrylate, (meth)acrylamide and styrene. Of these preferred olefin monomers, methyl acrylate, acrylamide and styrene are preferred. More preferred olefin monomers are methyl acrylate and acrylamide with methyl acrylate being most preferred. The copolymer may include one or more neutral olefin monomers and preferably only one while the terpolymer may include two or more neutral olefin monomers and preferably two or three. The molar percent of the (meth)acrylic acid monomer relative to the total moles of monomer of the copolymer or terpolymer may range from about 30 mole percent to about 0.2 mole percent, preferably about 28 mole percent to about 0.5 mole percent, more preferably 26 mole percent to about 1 mole percent, most preferably about 25 mole percent to about 2 mole percent. The remaining mole percent is made up of one or more of the neutral olefin monomers. Its Mw may range from about 300 Da to about 10 MDa, preferably about 500 Da to about 1 MDa, more preferably about 750 Da to about 500 kDa and most preferably about 1 kDa to about 50 kDa with a polydispersity in the range of about 1.0 to about 10, preferably 1.1 to about 5. The copolymer or terpolymer is neutralized with a volatile base as described above so that it is completely water soluble. At the foregoing Mw's the un-neutralized copolymer or terpolymer will display some solubility in water but the concentration of the un-neutralized polymer will not be as high as that of the neutralized polymer.

The copolymer and terpolymer may be constructed with random distribution of the different monomer units along the polymer backbone, or may be block copolymers which has blocks of single monomer units, or may be a graft copolymer which has one monomer unit forming the polymer backbone and a different monomer unit forming polymeric side chains. The different constructions of polymer provide differing polymer to polymer binding properties and different macromolecular characteristics. The block copolymer can provide regions of hard and soft polymer characteristics. A block copolymer can display crystalline regions and amorphous regions that can enable development of water soluble and water resistant regions. Blocks of differing electronic and lipophilic character can impart an open repulsive character to the polymer so that tightly fit inter-structures are minimized. A grafted polymer or segmented polymer are capable of intertwined conformation and compact molecular dimension so as to enable tightly fitted inter-structures.

The homopolymer, copolymer and terpolymer may also be constructed to include reactive side chains having terminal hydroxyl or amine groups. These are described above as monomeric (meth)acrylate esters of diols and (meth)acrylamides of diamines. The pendant hydroxyl or amine groups of these monomeric units of the polymer can combine with the carboxyl groups of the (meth)acrylic acid monomeric units of another polymer to provide cross-linking. To provide the combination, the water bi-product of the cross-linking can be removed to drive the thermodynamic equilibrium to completion. In the context of the present invention, this thermodynamic shift can occur during the setting of the hair coloring composition on the strands of hair. The extent of cross-linking may be controlled so that the mechanical and chemical properties of the carboxylic acid polymer as described herein are preserved.

The glass transition temperature of the carboxylic acid polymer in part contributes to the flexibility, strength, hardness and similar qualities of the coating on the keratin fiber surfaces. The glass transition temperature of the polymer embodiments may range in degrees Celsius from about −60° C. to about 90° C., preferably about −50° C. to about 20° C. This glass transition temperature or $T_g$ determines the solid-solid transition of the polymer from a hard glassy material to a soft rubbery material. If the $T_g$ of the polymer is too high, the coating on the keratin fibers will be stiff and inflexible. This is an undesirable result. The coating should be soft, flexible and unnoticeable to touch and sight yet should not flake, break-up or otherwise release from the keratin fiber, and especially from human hair, when stroked by a hand or brushed with a brush. The Tg of a polymer can be measured using ASTM D7426-08.

Examples of the carboxylic acid polymer of the hair coloring composition according to the present invention include Ultrahold Strong® sold by BASF, Luvimer® sold by BASF, Amerhold® sold by Amerchol, Acudyne® Rohm & Haas, and Acrylidone® sold by ISP. All of these commercial polymers contain monomeric units of (meth)acrylic acid and are copolymers containing (meth)acrylate esters, amides and/or neutral olefins.

Other Examples

Acrysol ASE-75 Thickener (Dow), Primal 3208 Emulsion (Dow), Acrysol ASE-95NP Thickner (Dow), Acrysol I-62A (Dow), Acrysol WS-24 Colloidal (Dow), Acrysol WS-50 Colloidal Dispersion (Dow), Plexisol P 550-40 (Kremer), Pemulen TR-1 Polymer (Lubrizol), Pemulen TR-2 Polymer (Lubrizol), FIXATE FREESTYLE POLYMER (Lubrizol), Rovene 6005 (Mallard Creek), Rovene 6017 (Mallard Creek), Rovene 6020 (Mallard Creek), Rovene 6103 (Mallard Creek), Rovene 9410 (Mallard Creek), Silform HYFLEX (Momentive), Mowinyl 6718 (Mowinyl), Mowinyl 6750 (Mowinyl), Mowinyl 67510 (Mowinyl), Mowinyl 6760 (Mowinyl), Mowinyl 6960 (Mowinyl), X-200 (PMC/SEIKO), J-140A (PMC/SEIKO), RE-1075 (PMC/SEIKO), COVACRYL P12 (Sensient), Covacyl E14 WP (Sensient), COVACRYL MT10 (Sensient), WorleeMicromer C20/42 (Worlee), WorleeMicromer C60/42 (Worlee), WorleeMicromer C60/42 NP (Worlee), Avalure AC 120 Polymer (Lubrizol).

4.3.2 (Meth)Acrylate Copolymer Film Former

According to embodiments, the film former is a copolymer comprising repeating units of at least one (meth)acrylate monomer, at least one olefin monomer and (meth)acrylic acid monomer. The (meth)acrylate copolymer includes monomeric units of several (meth)acrylates and olefins. These embodiments comprise the copolymer of one or more repeating monomeric units selected from olefinic ester monomers wherein the ester is a (meth)acrylate, maleate, butenoate, pentenoate and similar olefinic esters and the esterifying alcohol is a linear, branched or cyclic alkyl monoalcohol or diol of 1 to 6 carbons for the linear alkyl group (2 to 6 carbons for the diol), 3 to 6 carbons for the branched alkyl group and 3 to 10 carbons for the cyclic alkyl group. Included also as possible repeating monomeric units of the copolymer are olefinic carboxamide monomers, N-alkyl carboxamide monomers wherein the alkyl group is a linear, branched or cyclic alkyl group as described for the monoalcohol, N-aminoalkyl olefinic carboxamide monomers wherein the amidating amine is a linear, branched or cyclic alkyl diamine with 2 to 6 carbons in the linear alkyl group, 3 to 6 carbons in the branched alkyl group and 3 to 10 carbons in the cyclic alkyl group. Additionally, neutral repeating olefinic monomeric units are possibilities for the copolymer. Monomers providing repeating olefinic monomeric units include those of the formula: $HR^1C=CHR^2$ wherein $R^1$ and $R^2$ are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, $CONH_2$, COOH, $NO_2$, CN, $SO_3H$, $SONH_2$, pyridyl, $O_2CR^3$ wherein $R^3$ is alkyl of 1 to 3 carbons, vinyl and alkyl vinyl having 1 to 3 carbons in the alkyl group. The molar percent amounts of the foregoing monomers making up the monomeric units of the copolymer may range up to substantially close to one hundred molar percent. The copolymer may include monomeric units of olefinic carboxylic acid monomers including (meth)acrylic acid, maleic acid, fumaric acid, itaconic acid, crotonic acid and pentenoic acid. The molar percent amounts of such olefinic carboxylic acid monomeric units of the copolymer constitutes at most a minor molar percent. While the acid number cannot provide an accurate molar percent for the number of olefinic carboxylic acid monomer units in this situation, the copolymer typically and essentially for each embodiment possesses an acid number indicating that a minor molar amount of the olefinic monomeric units of the copolymer is the olefinic carboxylic acid monomeric unit.

The (meth)acrylate copolymer embodiments may have an acid value ranging from about 1 to about 200 preferably about 2 to 125, more preferably about 3 to 100 and most preferably about 4 to 75, or about 30. Preferably the (meth)acrylic acid monomeric units of the copolymer are produced by hydrolysis of the (meth)acrylate ester monomers during polymerization and work up. Alternatively, (meth)acrylic acid monomer can be added to the monomeric mixture to be polymerized and the polymerization and work up processes can be conducted under conditions designed to substantially avoid ester hydrolysis.

The weight average molecular weight Mw of the (meth)acrylate copolymer embodiments may range from about 2 kilo daltons (2 kDa) to about 10 million daltons, (10 MDa). Preferably the Mw may range from about 5 kDa to about 5 MDa, more preferably about 5 kDa to about 1 MDa, especially more preferably about 5 kDa to about 500 kDa. The polydispersity may range from about 1 to about 10, preferably about 1.1 to about 7, more preferably 1.1 to about 5, most preferably 1.1 to about 3.

The (meth)acrylate copolymer embodiments are dispersible or soluble in the medium and their degree of dispersibility or solubility and stability as dispersed or soluble components in the medium depends upon several factors including the Mw, the molar content of carboxylic acid monomer, the pH and temperature. The dispersibility or solubility of the (meth)acrylate copolymer embodiments can also be increased by neutralization with a base. The neutralization can be performed with any base. Particularly the base useful for neutralization includes volatile bases, for example ammonia and or volatile organic amines as discussed elsewhere in this disclosure. Volatile refers to a material with a boiling point below 200° C. at standard atmospheric pressure. At lower Mw and higher molar content of carboxylic acid monomer, the (meth)acrylate copolymer without neutralization is dispersible or soluble at all pH increments and is soluble to some extent in water. At higher Mw and lower molar content of carboxylic acid monomer the (meth)acrylate copolymer without neutralization will be water soluble to a certain low extent such as from 2 wt % to 10 wt % relative to the weight of polymer and water. The solubility of these embodiments of the (meth)acrylate copolymer can be increased by neutralization so that the embodiments of the resulting neutralized (meth)acrylate copolymer exhibit somewhat increased but still low solubility in water. The soluble concentrations of these embodiments of neutralized high Mw, low carboxylic acid monomer content polymers can range from a minimum of about 2 weight percent of water up to 15 weight percent of water. These weight percentages address the saturation points and depend at least in part upon the neutral olefinic monomer, carboxylic acid ester or amide monomer content, carboxylic acid monomer content and the weight average molecular weight of the polymer. At higher percentage of carboxylic acid monomer content of the polymer and low Mw, the saturation point will range up to 20 weight percent or greater. At low percentage of carboxylic acid monomer content of the polymer and high Mw, the saturation point will be at the lower end of the range.

The viscosity of the composition functions to hold the composition on the hair strands while the coating is formed. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat strands of hair. Appropriate viscosity of the composition is the result of the interaction of the (meth)acrylate copolymer, its concentration, and as appropriate, an optional viscosity control agent, and an optional thickening agent. Generally, the viscosity of the composition for use with hair of the scalp, brow and lashes may range from that of water to motor oil, and in quantitative terms about 0.1 to about 200 Pa s$^{-1}$, preferably 1 to 100 Pa s$^{-1}$, more preferably 10 to 75 Pa s'. The viscosity of the composition for use with nails and skin may range from that of motor oil to honey and range from about 140 cps to about 10K cps. The Pas' measurements of water, motor oil and honey can be found in any textbook on viscosity and in Wikipedia. Viscosity measurements are carried out on a controlled stress rheometer e.g.

Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 $sec^{-1}$ shear rate is obtained from the shear stress vs. shear rate curve, and the corresponding viscosity is calculated by dividing the obtained shear stress by 10.

The (meth)acrylate copolymer may be or become cross linked upon its formation of coating on hair strands. The cross linking may be covalent, non-covalent, hydrogen bonding, electrostatic interaction, ionic interaction or any combination thereof. Covalent crosslinking may be facilitated by inclusion of a minor amount of diol or diamine such as alkylene glycol or diamine of 2 to 6 carbons in the alkylene group. The diol or diamine can combine with carboxylic acid groups of adjacent polymers to form diester or diamide links. Similarly, the diol ester or aminoalkyl amide of a few of the carboxylic acid groups of the polymer can be present and will combine with carboxylic acid groups of adjacent polymer molecules to form diester or diamide links. Alternatively, a few carboxylic acid derivatives with a facile leaving group can be included in the polymer. The derivative will combine with a carboxylic acid group of an adjacent polymer so as to form an anhydride link light cross linking such as 0.1 percent to 2 percent of the available carboxylic acid groups of the polymer may be cross linked in this fashion. The light cross linking will improve resistance of the coating toward removal with dilute soap or shampoo aqueous solutions. Cross linking is also preferred for embodiments of the coloring composition to be applied to finger and/or toe nails.

The concentration of the (meth)acrylate copolymer in the composition may range from about 2% to about 30%, preferably about 4% to about 25%, more preferably about 6% to about 20%, most preferably about 8% to about 15% by weight relative to the total weight of the composition. Specific concentrations include about 2%, about 4%, about 6%, about 8%, about 10%, about 12%, about 14%, about 16%, about 18%, about 20%, about 22% about 24% by weight relative to the total weight of the composition. The determination of the concentration for embodiments of the (meth)acrylate copolymer will depend in part upon the resulting viscosity, the saturation point of the (meth)acrylate copolymer in the medium and the interaction, if any, between the (meth)acrylate copolymer and other components of the composition. As discussed above, the viscosity is managed so that the composition will not run off the surfaces of strands of hair yet will level and flow to substantially coat those surfaces. Development of appropriate viscosity in part by management of the concentration of the (meth)acrylate copolymer can be experimentally determined by routine methods such as formulation of several samples of differing concentrations of polymer in the composition, coating those samples on a hair swatch and observing the flow, spread and leveling of the composition on the hair strands. The product can be applied to a hair strand using the coloring procedure described herein afterwards. The top of the hair strand is clamped in a stand such that the hair is aligned vertically downwards. After a 5 minute dwell time it is observed if any and how much product has dripped from the hair tress. The results obtained from the several samples can be plotted against flow time and leveling time to determine an appropriate concentration or range of concentrations of the particular (meth)acrylate copolymer in the composition. A preferred concentration of the (meth)acrylate copolymer in the composition ranges from about 5% to about 45%, more preferably about 8% to about 35% and most preferably about 10% to about 30% by weight relative to the total weight of the composition. Examples of the (meth)acrylate copolymer concentration can be in the approximate range of 15%, 20% or 25% by weight relative to the total weight of the composition. Further examples of the (meth)acrylate copolymer concentration range from 0.1% to 40% by weight, such as from 0.1% to 30% by weight, for example ranging from 0.5% to 20% by weight, such as from 1% to 20% by weight, for example ranging from 10% to 15% by weight, relative to the total weight of the coloring composition.

The (meth)acrylate copolymer may also be formulated and exemplified as a copolymer of a minor amount of (meth)acrylic acid along with (meth)acrylate esters and olefins and a few of the carboxylic groups may be converted to acyl groups bonded to leaving groups that will enable the acyl groups to form anhydrides with carboxylic acid groups. Appropriate leaving groups include imidazolonyl moieties, carbodiimide moieties, t-butyl anhydride moieties and activated ester moieties. Upon formulation of this copolymer into the medium, the acyl-leaving groups will combine with carboxylic acid groups to form cross link anhydride groups. The number of anhydride groups relative to the total number of carboxyl groups of the copolymer is small, such as 1% to 5%, preferably 2% to 3% so that the crosslinking is light. This light cross linking enables solubility of the cross linked copolymer in the medium especially when subsequently neutralized with a volatile base yet provides resistance toward aqueous penetration into the polymer lattice when the polymer is in a solidified state. This aspect is especially preferred when the coloring composition is to be applied to nails of fingers and/or toes.

The (meth)acrylate copolymer may also be formulated and exemplified as a copolymer of a neutral monomer selected from the group consisting of (meth)acrylate ester wherein the esterifying alcohol is a C1 to C22 monoalcohol, preferably methanol, ethanol, propanol, isopropanol or n-butanol, (meth)acrylamide, styrene, carboxystyrene (i.e. vinylbenzoic acid), carboxyamidostyrene (i.e. vinylbenzamide), vinylpyridine, vinyl oxyalkanoyl (vinyl acetate and homologs of the acetate) and any combination thereof. Preferred olefin monomers include methyl (meth)acrylate, (meth)acrylamide and styrene. Of these preferred monomers, methyl acrylate, acrylamide and styrene are preferred. More preferred monomers are methyl, ethyl, propyl, butyl, pentyl, hexyl, ethyl hexyl and lauryl acrylate, styrene and acrylamide. Most preferred is a copolymer produced from the monomers styrene, acrylic acid and one or more acrylate esters with methyl, ethyl, propyl, butyl and lauryl groups. The acid function of the copolymer can be achieved and controlled by partial basic hydrolysis of the (meth)acrylate ester under controlled conditions during the polymer formation. Alternatively, a minor amount of (meth)acrylic acid monomer can be added to the monomer mixture to be polymerized. Following work-up of copolymer isolation, the copolymer may be titrated with a volatile base as described above to neutralize the acid groups present so as to increase solubility and/or dispersibility in the medium.

The copolymer may be constructed with random distribution of the different monomeric units along the polymer backbone, or may be block copolymers which has blocks of single monomer units, or may be a graft copolymer which has one monomer unit forming the polymer backbone and a different monomer unit forming polymeric side chains. The different constructions of polymer provide differing polymer to polymer binding properties and different macromolecular characteristics. The block copolymer can provide regions of hard and soft polymer characteristics. A block copolymer can display crystalline regions and amorphous regions that can enable development of water soluble and water resistant regions. Blocks of differing electronic and lipophilic character can impart an open repulsive character to the polymer so that tightly fit inter-structures are minimized. A grafted polymer or segmented polymer is capable of intertwined conformation and compact molecular dimension so as to enable tightly fitted inter-structures.

The copolymer may also be constructed to include reactive side chains having terminal hydroxyl or amine groups. These are described above as monomeric (meth)acrylate esters of diols and (meth)acrylamides of diamines. The pendant hydroxyl or amine groups of these monomeric units of the polymer can combine with the carboxyl groups of the (meth)acrylic acid monomeric units of another polymer to provide cross-linking. To provide the combination, the water bi-product of the cross-linking can be removed to drive the thermodynamic equilibrium to completion. In the context of the present invention, this thermodynamic shift can occur during the setting of the coloring composition. The extent of cross-linking may be controlled so that the mechanical and chemical properties of the (meth)acrylate copolymer as described herein are preserved.

The glass transition temperature of the (meth)acrylate copolymer in part contributes to the flexibility, strength, toughness and similar qualities of the coating on the keratin fiber surfaces. The glass transition temperature of the polymer embodiments may range in degrees Celsius from about −60° C. to about 30° C., preferably about −50° C. to about 20° C. This glass transition temperature or $T_g$ determines the transition of the polymer from a hard glassy material to a soft rubbery material. If the $T_g$ of the polymer is too high, the coating on the keratin fibers will be stiff and inflexible. This is an undesirable result. The coating should be soft, flexible and unnoticeable to touch and sight yet should not flake, break-up or otherwise release from the keratin fiber, and especially from human hair of the scalp, brow and lashes and skin, when stroked by a hand or brushed with a brush. The $T_g$ of a polymer can be measured using ASTM D7426-08. Thus, for coatings of hair of the scalp, brow and lashes, the copolymer as the coating should be chosen to function significantly above its $T_g$ (e.g., flexible and soft) under all environmental conditions. In contrast, the $T_g$ of the (meth) acrylate copolymer for production of a finger or toe nail coating should enable a hard, glassy material following application to the nail. Consequently, the copolymer in this application should be chosen to function significantly below its $T_g$ (e.g., hard and glassy) in all environmental conditions.

Examples of the (meth)acrylate copolymer of the coloring composition according to the present invention include Rovene 6103® (Mallard Creek), RE-1075 (PMC/SEIKO) product containing monomeric units of (meth)acrylic acid and an acid value from about 0.1 to about 100, preferably about 1 to about 50, more preferably about 30.

4.3.3 Polar Functional Silicone Polymer Film Former

The polar functional silicone polymer which may be incorporated into embodiments of the hair coloring composition according to the invention include an organomodified silicone of the pendant or graft type as Formula I wherein polar functional substituents are incorporated within or onto monovalent organic groups, A1, A2 and A3 and an organic group C which does not contain a polar functional substituent. The polymer may contain in any order and in any number the Siloxane Unit Designations (SUD) II, III, IV V and VI. SUD I terminates the silicone polymer. The dangling valences of SUD's I, II, III, IV, V and VI are the bonds to the next siloxane unit. Multiples of the SUD's bonded together form the silicone polymer. With this arrangement, the polar functional siloxane units SUD III, IV and V may appear anywhere within the polymer and may be interspaced with SUD II which contains only methyl substituents and SUD VI which contains aliphatic, aromatic and heteroaromatic groups as long as they do not contain preferred, more preferred and most preferred polar functional substituents as defined in the Summary. Polar functional siloxane units SUD III, IV and V may contain the same or different polar functional substituents. Each instance of SUD III, IV and V may be interspersed with other SUD units along the silicone chain. Each instance of SUD III, IV and V may be the same or may be different from any other instance of SUD III, IV and V so that polar functional siloxane units of multiple specific identities, of a few different identities or of the same identity may appear throughout the silicone chain. The same dispersion and variation of identity applies to each instance of SUD VI. The substituents A1, A2 and A3 are organic groups with polar functional substituents. The substituent C is an organic group with a neutral substituent or an aliphatic, aromatic or heteroaromatic group without a polar substituent. The variable $B_1$ is an SiC organic group as defined above, and preferably is methyl, OH, an alkyl or an alkoxy group wherein the alkyl or alkoxy group is a linear alkyl or alkoxy group of 1 to 6 carbons, or a branched or cyclic alkyl or alkoxy group of 3 to 6 carbons.

Together, SUD III, IV and V constitute SiA polar functional units. SiA for Formula I expands the kind of unit from only an amine to any polar functional substituent as set forth below. Together, SUD I, II and VI constitute SiC non-functional units. SiC for Formula I narrows the kind of unit included because hydrogen bonding groups and dipolar groups are included within the SiA definition for Formula I.

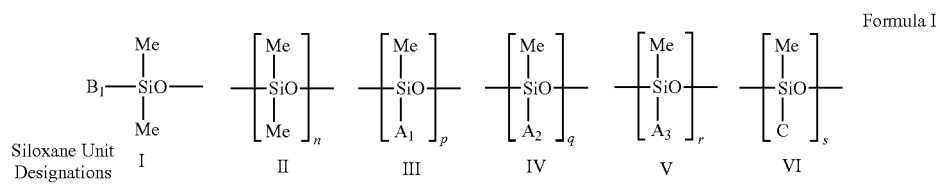

Formula I

The SUD's of Formula I are present according to certain molar amount ranges. The molar amount range n for SUD II is about 50 to 2000. The molar amount range p for SUD III is about 0 to 50. The molar amount range q for SUD IV is about 0 to 50. The molar amount r for SUD V is about 0 to 50, The molar amount s for SUD VI is about 1 to 50. At least one of p, q and r is greater than 0. The sum of p+q+r is the sum of the number of SUD units III, IV and V. This sum provides the number of SiA units carrying polar functional substituents. The sum n+s+2 is the sum of the number of SUD units II, VI and the two termini units SUD I. This sum provides the number of SiC units. Thus, the sum of p+q+r relative to the sum of n+s+2 provides a ratio of siloxane polar functional units (SiA) to non-polar siloxane monomeric units (SiC). The ratio of SiA:SiC for Formula I is from about 1:1000 to about 1:10 (moles of SiA to SiC units), preferably 1:1000 to 1:25, more preferably 1:600 to 1:50, most preferably 1:400 to 1:75 or 1:300 to 1:200.

Also included are the organomodified silicones of the block copolymer type as shown in Formula II wherein these polar functional substituents are incorporated within or onto organic oligomer moieties. The SUD'S I, II and VI as defined above and as repeated multiple times form the silicone portion of the block copolymer while the Organic Oligomer Unit Designations (OOUD) VII, VIII and IX form the organic polymer block units. The OOUD's are blocks so that OOUD VII, VIII or IX may be present alone one or multiple times in the block copolymer or a mixture of OOUD VII, VIII and IX blocks may be present single or multiple times in the block copolymer. Multiples of the SUD units II and VI may be present as unitary blocks or as mixed units in a block and form the silicone blocks of the copolymer. The copolymer is terminated by SUD I. The Org of OOUD VII, VIII and IX may be large or short oligomeric units of polyolefin, polyester, polyamide, polyurethane, polyol, polyurea and similar organic polymeric groups. The oligomeric units are substituted by organic groups $A_1$, $A_2$ and $A_3$ which carry polar functional substituents as defined above. $B_1$ is methyl, OH, an alkyl or an alkoxy group as described above for Formula I.

The SUD's and OOUD's divide into two categories. The polar functional unit category SiA includes the OOUD's while the non-functional unit category includes the SUD's. The sum of p+q+r provides the total molar number of SiA units while the sum of n+s+2 provides the total molar number of SiC units, wherein the number 2 accounts for the two terminal SUD I units. The total molar number of SiA units is greater than or equal to 1 so that at least one of p, q and r is at least 1. The molar number ranges for each of the SiA OOUD's provides p as about 0 to 50, q as about 0 to 50 and r as about 0 to 50. The molar number ranges for SiC SUDII and OOUD VI provides n as about 50 to 4000 and s as about 0 to 50. The molar ratio of SiA units to SiC units is from about 1:1000 to about 1:10, preferably 1:1000 to 1:25, more preferably 1:600 to 1:50, most preferably 1:400 to 1:75 or 1:300 to 1:200. The preferred $B_1$ group for Formula I and Formula II is methyl, hydroxyl and alkoxy. With $B_1$ as methyl, the terminus of the aminosilicone is non-reactive. With $B_1$ as hydroxyl or alkoxy, the terminus of the aminosilicone is reactive so that it will possible that they can couple to form longer chains. This coupling will form macropolymers of the aminosilicone especially as the aminosilicone interacts with hair strands. Although it is not a limitation of the invention, it is believed that the interaction upon macropolymer formation during application of the composition of the invention with at least a portion of this embodiment of the aminosilicone to hair entwines the macropolymer with the hair strand thus increasing the adherence of the composition to the hair.

The foregoing polar functional pendant or block silicones include siloxanes designated as a D group, $Me_2SiO2/1$, i.e, —O—Si(Me)$_2$-O—. These polar functional pendant or block silicones can also incorporate siloxane branching groups and cross linking groups including $MeSiO3/2$, known as silsesquioxane or T groups, and $SiO4/2$, known as Q groups by those skilled in the art. The T groups of two silicone chains can combine to form a cross link such as is depicted by Formula III

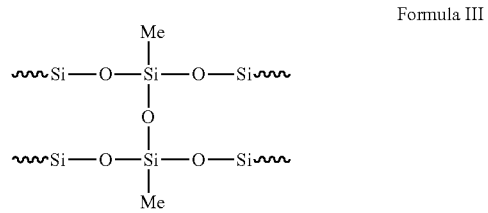

Formula III

If the T and Q groups are formulated with hydroxyls and mixed with water incident with application to hair, the hydroxyls couple as described above to cross-link. The result will be similar to that described above for the macropolymer formation discussed above.

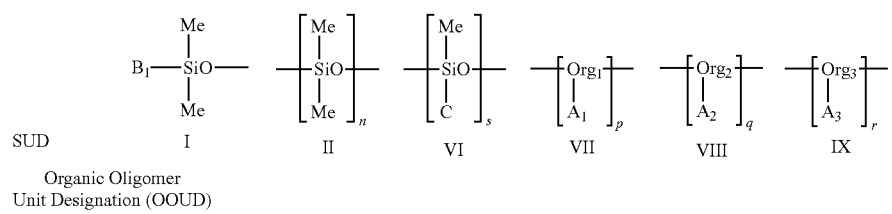

Formula II

SUD: I, II, VI, VII, VIII, IX

Organic Oligomer Unit Designation (OOUD)

Organic groups $A_1$, $A_2$ and $A_3$ may be straight, branched or mono- or polycyclic aliphatic, mono or polyunsaturated alkyl, aryl, heteroalkyl, heteroaliphatic or heteroolefinic moieties or any combination thereof comprising 3 to 150 carbon atoms together with up to 50 heteroatoms and/or heteroatom groups that establish functional polarity of the organic groups. Especially, the heteroatoms and heteroatom groups may include but are not limited to oxygen, nitrogen, sulfur, phosphorus, hydroxyl, carboxamido, sulfonamido, and any combination thereof. The organic group C may be the same organic group as mentioned for $A_1$, $A_2$ and $A_3$ except that C will not have a heteroatom and/or heteroatom groups that confer functional polarity on C. Preferably, the organic groups $A_1$ though $A_3$ are linear, branched or cyclic aliphatic, heteroaliphatic, aromatic, heteroaromatic moieties or any combination thereof comprising 1 to 26 carbons (3 carbons minimum for branched and cyclic moieties) together with the foregoing heteroatoms and heteroatom groups and any combination thereof. Organic group C preferably is the same but without heteroatoms and heteratom groups. More preferably the organic groups $A_1$ though A3 are aliphatic or heteroaliphatic moieties of 1 to 14 carbons with heteroatoms and heteroatom groups and any combination thereof (for branched or cyclic aliphatic and heteroaliphatic moieties, the minimum carbon number is 3). More preferably organic group C is the same but without heteroatoms and heteroatom groups. Especially more preferably, the organic groups $A_1$ though A3 are linear alkyl moieties of 1 to 10 carbons or branched or cyclic alkyl moieties of 3 to 10 carbons with heteroatoms and heteroatom groups, and any combination thereof. Especially more preferably, organic group C is the same but without heteroatoms and heteroatom groups. The organic groups, the preferred organic groups and more preferred organic groups designated as $A_1$ through A3 may have within the carbon chain, one or more ether groups, one or more thioether groups, one or more secondary or tertiary amino groups, one or more hydroxyl groups, one or more carboxamido groups, one or more sulfonamido groups or any combination thereof.

As organic groups with heteroatoms and/or heteroatom groups, the organic groups $A_1$ though A3 incorporate one or more polar substituents selected from electron withdrawing, or electron donating groups with Hammett sigma para values between −1.0 and +1.5. Hammett sigma para values are discussed in Rompp Chemie Lexikon, Georg Thieme Verlag, Stuttgart, N.Y., 9th Edition, 1995 under "Hammett Gleichung". The polar substituents can be non-ionic, zwitterionic, cationic or anionic and can include valence substituents completing the valence requirements of the polar substituents. The valence substituents include aliphatic and/or aromatic groups $R_1$, $R_2$, $R_3$, and $R_4$ as defined below. The polar substituents include S-linked groups such as but not limited to $SO_2H$, $SO_3H$, $SR_1$, $SCN$, $SO_2R_1$, $SO_3R_1$, $SSR_1$, $SOR_1$, $SO_2NR_1R_2$, $SNR_1R_2$, $S(NR_1)R_2$, $S(O)(NR_1)R_2$, $SR_1(NR_1)$, $SONR_1R_2$. The polar substituents include N-linked groups such as but not limited to $NR_1R_2$, $NR_1R_2R_3+$, NC, $NR_1OR_2$, $NR_1SR_2$, NCO, NCS, $NO2$, $N=NR_1$, $N=NOR_1$, $NR_1CN$, $N=C=NR_1$, $NR_1NR_2R3$, $NR_1NR_2NR_3NR_4$, $NR_1N=NR_2$. The polar substituents include carbon-linked groups and miscellaneous groups such as but not limited to COOH, COX, CONS, $CONR_1R_2$, $CONR_1COR_2$, $C(=NR_1)NR_1R_2$, CHO, CHS, CN and NC wherein X is a halogen.

The $R_1$, $R_2$, $R_3$, and $R_4$ groups of the polar substituents may be each independently selected from hydrogen, straight, branched or mono- or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially O, N, S, P. Preferably, $R_1$, $R_2$, $R_3$, and $R_4$ are each independently selected from hydrogen straight, branched or cyclic alkyl groups of 1 to 6 carbons (minimum of 3 for branched and cyclic), more preferably independently selected from hydrogen, methyl, ethyl, propyl or isopropyl, especially more preferably independently selected from hydrogen or methyl.

The weight average molecular weight range of Formulas I and II is from about 10 kDA to about 150 kDa, preferably about 18 kDA to about 135 kDa, more preferably about 22 kDA to about 120 kDa. Almost all of the aminosilicone embodiments of Formulas I and II are liquid at ambient temperature and pressure so that for practical purposes they have no glass transition temperature (Tg). For some higher weight average molecular weight aminosilicone embodiments of Formulas I and II, the glass transition temperature range for Formulas I and II is low, in the neighborhood of −40° C. to 10° C., preferably −30° C. to 0° C.

Preferred polar functional substituents for use in embodiments of the present invention as described include, but are not limited to, polyoxyalkylene (polyether), primary, secondary and tertiary amine, quaternary ammonium, amide, carboxyl, sulfonate, sulfate, carbohydrate, phosphate, and hydroxyl. These preferred polar functional substituents may be incorporated into organic groups $A_1$ through $A_3$ which may be pendantly bonded along the silicone chain as depicted by Formula I or as pendant parts of block organic polymer and/or oligomer groups depicted by Formula II. Additional highly preferable polar functional substituents bonded to any of $A_1$ through $A_3$ are amine moieties and/or polyol-moieties of the formulas -ONY or —$NYR_1$ or

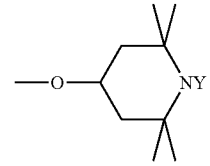

wherein each $R_1$ is independently selected from the group consisting of a hydrogen atom and a group of formula $R_2NY_2$, each Y is independently a hydrogen atom or Y', and each Y' is a group of formula —$CH_2CH(OH)R_2$—OH or —$CH_2CH(OH)R_2$—$NH_2$ wherein $R_2$ is independently hydrogen or a divalent hydrocarbon group having 1 to 10 carbon atoms, and the proviso that every Y is not H. More preferably, Y' is a group of the formula
—$CH_2CH(OH)CH_2OH$ or —$CH_2CH(OH)CH_2NH_2$ and the functionalized silicone is of pendant Formula I, wherein n is from 200 to 500, p is from 20 to 50, q, r and s are equal to zero and $B_1$ is hydroxyl, methyl or methoxy, preferably methyl. In this configuration, SUD II and III may be distributed in any random or regular order along the silicone chain. The functional polar substituent $A_1$ of SUD III in each instance may be the same or different pursuant to the foregoing highly preferred $A_1$-A3 configurations and preferably is the same in all instances.

More preferably, the polar functional silicones of the present invention include, but are not limited to amino silicones of the following Formula IV.

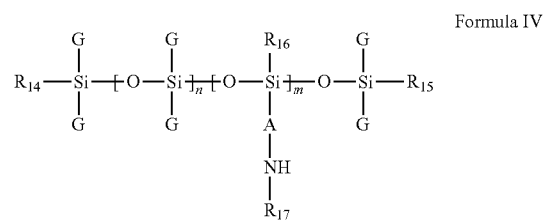

Formula IV

For Formula IV, the designators m and n are associated respectively with SiA moieties and SiC moieties. The SiA moieties of Formula IV are those with -A-NH—$R_{17}$ and the molar number is indicated by the designator m. The SiC moieties of Formula IV are all Si groups except those with -A-NH—$R_{17}$ and the molar number is indicated by n plus two for the two siloxane termini. The designators m and n are numbers with a sum (n+2+m) ranging from 150 to 2200, SiC which is n plus 2 (for the two terminal Si units), is a number ranging from 1 to 2000, and SiA which is m, is a number ranging from 1 to 200. These molar numbers are chosen such that ratio of SiA:SiC is 1:1000 to 1:10, preferably 1:1000 to 1:25, more preferably 1:600 to 1:50, most preferably 1:400 to 1:75 or 1:300 to 1:200 and the sum m+n+2 or SiA+SiC is in the range 150 to 2000, more preferably 250 to 1800, most preferably 300 to 1600. The weight average molecular weight range of Formula IV is from about 10 kDA to about 150 kDa, preferably about 18 kDA to about 135 kDa, more preferably about 22 kDA to about 120 kDa. These molar numbers, SiA and SiC ratios and numbers and weight average molecular weight ranges apply to the hair coloring compositions containing aminosilicone of Formula IV before application to hair. Following application, the silicone can undergo chain extension and cross-linking so that ratios, molar numbers and weights will be capable of change post application. The possibility that post application chain extension and cross linking may produce differences in SiA:SiC ratios, molar number and molecular weight averages and similar variations for polar functional silicones of Formulas I and II may also occur. Consequently, all parameters for Formulas I and II also apply pre-application to hair.

Almost all of the aminosilicone embodiments of Formula IV are liquid at ambient temperature and pressure so that for practical purposes they have no glass transition temperature (Tg). Theoretically the lack of a practical glass transition temperature means that, the glass transition temperature range would be extremely low, in the neighborhood of minus 200 C to minus 72° C.

The groups $R_{14}$, $R_{15}$, $R_{16}$, which may be identical or different, are chosen from a hydroxyl radical, C1-C4 alkoxy radicals and methyl. A is chosen from linear and branched C3-C8 alkyl radicals. $R_{17}$ is chosen from H, phenyl, linear or branched C1-C4 alkyl radical, benzyl or preferably linear or branched alkylamine for example (C2-C8)alkyl-(NH$_2$). $R_{17}$ can also contain amido groups or other hetero atoms. Preferably the group A-NH—$R_{17}$ is chosen from —(CH2)3-NH—(CH2)3NH2, —CH2-CH(CH3)-CH2-NH—(CH2)3NH2, —CH2-CH2-CH2-NH2, —CH2-CH(CH3)-NH2. G is chosen from phenyl, hydroxyl, C1-C8 alkyl, preferably methyl. As discussed above for Formulas I and II, an aminosilicone of formula IV having OH or C1-C4 alkoxy radicals bonded directly to silicon can couple and/or crosslink to form larger and/or crosslinked macromolecules.

These aminosilicones may be of the random or block type in that the silicone monomeric groups SiC and SiA signified by n and m respectively may be randomly distributed along the silicone chain or these monomeric groups may be arranged as oligomeric blocks of the SiC moieties and the SiA moieties. In addition, an SiA moiety can be a terminal polymer group in place of the —Si G$_2$R$_{15}$ group and in this alternative, the SiA moiety preferably would also be present within the silicone polymer, however, an aminosilicone with only and SiA moiety at the two termini of the polymer is also an embodiment of the polar functional silicone component of the hair coloring composition of the invention. Thus, an aminosilicone polymer of Formula IV containing only terminal SiA moieties is included. It will have a low weight average molecular weight so that it meets the SiA:SiC ratio requirement. It will also preferably be capable of crosslinking so that it can form larger molecules when applied to hair strands. Polymers which are then subsequently reacted with a carbinol compound, preferably glycidol, are also included in the description.

Suitable polar functionalsilicones of the present invention include, but are not limited to, organomodified silicones with amine functionality available commercially under the trade names such as:

A) Random pendant (graft) polymers DOWSIL™ AP-8087 Fluid, DOWSIL™ 2-8566, DOWSIL™ 8500, DOWSIL™ CE 8401, DOWSIL™ 2-2078, XIAMETER™ MEM-0939 Emulsion, XIAMETER™ MEM-0949 Emulsion, XIAMETER™ MEM-8177 Emulsion, XIAMETER™ MEM-8194 Emulsion, DOWSIL™ CE-8170 AF Microemulsion, DOWSIL™ 969 Emulsion, BELSIL® ADM 1650, BELSIL® ADM 6057 E, BELSIL® ADM 6102 E, BELSIL® ADM 6300 E, BELSIL® ADM 8105 E, BELSIL® ADM 8301 E, Silsoft* A+, KF-862, KF-861, KF-8625, KF-8005, KF-8004, KF-8675, KF-873, and X-52-2328; and B) Block Copolymers for example DOWSIL™ AP-8104 Fluid, Silsoft™ A+, Silsoft™ A-843, Silsoft* CLX-E.

Silicone Node Building Additive.

In some embodiments of the current disclosure, a further material may be added to the functional silicone polymer to enhance the performance on hair. While not wishing to bound by any specific theory, it believed that they can interact with the polar functional silicone polymer, and alter the rheology of the resulting film making the resulting mixture harder to be removed from the hair surface. Examples of materials include organosiloxanes that are resins in that they contain reactive groups that can bind or interact with substrate groups and/or other polymers. These organosiloxane resins include the following.

Organosiloxane resins which may be included as a silicone node building additive according to the invention comprise combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.5 and R is a methyl group. Silanol or alkoxy functionalities may also be present in the resin structure. The hydroxyl and/or alkoxy groups of these organosiloxane resins are capable of enabling binding reaction with hydroxyls of other polymers and/or proteins.

More preferably, the organosiloxane resins comprise repeating monofunctional $R_3SiO_{1/2}$ "M" units and the quadrafunctional $SiO_2$ "Q" units, otherwise known as "MQ" resins. In this case, the ratio of the "M" to "Q" functional units is advantageously around 0.5 to 0.9 and the value of n is 1.2. Organosiloxane resins such as these are commercially available as SR1000 and SS4230 available from Momentive™ and Wacker 803 from Wacker Silicones.

These resins can hydrogen bond with proteins of the keratin fibers of hair strands and can bind with the Si—OH groups of aminosilicones of formulas I, II and IV. This dual interaction is capable of enabling stronger interaction and adherence of the aminosilicone polymer to the hair strands and can improve the wash resistance of the coloring composition on the hair strands. This resin building additive may be one of the pretreatments discussed above that is an optional coating modification for use with the aminosilicone polymers. Alternatively, the additive may be added within the formulation containing the polar functional silicone.

The polymer coating can have a surface energy between about 20 and about 50 mJ m$^{-2}$. The polymer coating preferably has high transmission, to ensure that it does not interfere with the optics of the hair color. The polymer preferably has a refractive index between 1.4 and 1.6.

While not intending to be bound by theory of hair-composition interaction, it is believed that the addition of polar functionality within the silicone polymer enables an increase in the level of interaction with the cuticles of hair strands. This interaction is believed to be especially useful on sections of hair strands remote from the hair roots because the hair strand surfaces of these sections may have become more polar and hydrophilic making it more difficult to maintain a surface coating thereon.

4.3.4 Multicomponent Composition/Concept (I)

According to embodiments, the film former is a multicomponent composition according to concept (I).

An aspect of the invention concerning a multicomponent composition (I) provides embodiments comprising first and second components, each comprising a functional silicone polymer. The first component comprises a linear and/or branched first silicone polymer with functional groups. The second component comprises a second linear or branched silicone polymer with functional groups. Generally, the first and second silicone polymers may comprise the same linear and/or branched silicone structure or different linear and/or branched silicone structures. The silicone polymers can be conceptualized as being random and/or block portions of linear and/or branched silicone polymer moieties with no functional groups (non-reactive silicone or organosilicone units) with interspersed reactive siloxane monomeric units carrying the functional groups. The functional groups may be attached through connecting units to the backbones of the silicone polymers, to the branch chains of the silicone polymers or to both.

The functional groups of these silicone polymers typically are complementarily reactive and are arranged with the silicone polymers so as to provide complementary reactive pairs. The complementary pairs may be designated as first and second functional groups. In some instances, the first and second functional groups may be the same, such as mercapto and mercapto, so that a reactive pair may be, but not necessarily be, the same functional group (hereinafter a self-reactive functional group). The silicone polymers presenting the complementary reactive pairs of functional groups are first and second silicone polymers. The complementary reactive pairs and the self-reactive functional group can be reactively combined in situ to covalently bond together. Because the complementary reactive pairs and self-reactive functional groups are parts of large molecules having dipolar groups, hydrogen bonding groups and large lipophilic groups, the in situ interaction may also involve electrostatic, ionic, hydrogen bond, coordinate or entanglement interaction. Embodiments of the first and second silicone polymers with different first and second functional groups typically are kept separate until application to substrate material.

Embodiments of the multicomponent composition (I) also provide a third component comprising a base compound. The base compound comprises a small molecule, a dimer, trimer, oligomer or polymer of organic or silicone construction which carries one or more pendant and/or terminal third functional groups which are amine groups, mercapto groups, sulfonate groups, carboxylate groups or carbamate groups. Especially preferred are base compounds with amine groups. The third functional groups of the base compound interact with the first and second functional groups through covalent, ionic, entanglement, dipolar, electronic and/or electrostatic linking or any combination thereof to meld together the first silicone polymer, the second silicone polymer and the base compound. The third component is typically and usually adapted to be combined with the substrate material as a pretreatment prior to sequential, simultaneous or mixed application of the first and second components.

Embodiments of the multicomponent composition (I) also provide a fourth component comprising an agent, such as a catalyst, an accelerator, a curing agent, an enhancer and/or an inorganic complexer, for efficiently and preferably gently facilitating the melding together of the first, second and third components.

First and Second Silicone Polymers

The multicomponent composition (I) comprises first, second and third components with optional fourth component for production of a remanent colored coating on substrate material and especially on keratin material and fibers such as hair. The components interact in situ to provide covalent bonding among the first, second, third components and the substrate material. The third and fourth components are discussed in separate sections below.

The first and second components which form a part of the embodiments of the multicomponent composition (I) include as active constituents linear and/or branched silicone polymers with pendant and/or terminal functional groups that are complementary reactive pairs when different or are self-reactive pairs when the same. The silicone polymers comprise non-reactive organosiloxane monomeric units and reactive siloxane monomeric units to which are bonded the functional groups. The silicone polymers divide into first and second silicone polymers when the reactive siloxane units bear different functional groups as complementary reactive pairs. Embodiments of the silicone polymers that bear a self-reactive functional group can be viewed as a single silicone polymer with a sole functional group that can covalently bind with itself to accomplish the melding together of the compositional substituents. Examples of such self-reactive functional groups include but are not limited to mercapto and mercapto, Si—OH and Si—OH as well as Si—OMe and Si—OMe.

Embodiments of a silicone polymer with a self-reactive functional group can have variations of the structure of the silicone polymer so that fraction of the polymer may be of high $M_n$ or while another fraction may be of low $M_n$. Alternatively, one fraction may be linear while the other fraction may be branched. Other variations are also possible based on these same considerations. Variations of these kinds segment the silicone polymer with a self-reactive functional group into first and second silicone polymers even through only one functional group is present. Nevertheless, although multicomponent composition (I) may be composed of two silicone polymers of differing structure and/or complementary reactive pairs or may be composed of a single silicone polymer with a self-reactive functional group, the silicone polymer components can be addressed as a single entity with functional group and structural variations.

The silicone polymer may be arranged as portions of linear and/or branched silicone polymer moieties with no functional groups (non-reactive silicone or organosiloxane units) interspersed with reactive organosiloxane monomeric units bearing the complementary reactive pairs or the self-reactive pairs. The reactive organosiloxane monomeric units are linked to the functional groups through connecting units which typically are organic bivalent connecting units.

The linear and/or branched silicone polymer comprises polymerized units of a non-reactive organosiloxane monomer and at least two pendant and/or terminal reactive organosiloxane monomer units having functional groups. The functional groups may be complementary reactive pairs which will parse the silicone polymer into first and second silicone polymers or may be a self-reactive functional group. While the complementary reactive pairs and the two of the self-reactive functional group covalently bond together in situ, the melding of the first, second and third components to form a remanent coating also includes ionic, electrostatic, entanglement and/or coordination interactions between the molecules of these components.

The reactive organosiloxane monomeric units are distributed throughout the backbones and branch chains of the silicone polymers. The reactive organosiloxane units carry the functional groups which comprise isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, pentadienyl, azido, Si—OH, Si—OR, Si—O—N=CHR, Si—O—N=CR$_2$, Si—OAc, Si—CH=CH$_2$ or Si—H where is R is C1-C6 alkyl. The functional groups may be selected as first and second functional groups of the silicone polymers according to their action as complementary reactive pairs. A complementary reactive pair means that the pair can react together under ordinary environmental conditions or can react together with the help of a fourth component such as catalyst or substance that will lower the reaction activation energy needed for the reactive pair bonding. If the complementary pair can react together under ordinary environmental conditions without the help of a fourth component such as a catalyst, the pair cannot appear on the same silicone polymer. Complementary reactive groups that can react together under ordinary environmental conditions without help of a fourth component are well-known. Some functional groups are capable of functioning as self-reactive groups such as mercapto, the Si—O functional groups or isocyanato. Such self-reactive groups do not ordinarily react together under ordinary environmental conditions. A fourth component such as a catalyst usually will enable the bonding of such self-reactive groups.

As mentioned above, the arrangement and distribution of functional groups may follow the complementary reactive pair concept or may follow the self-reactive functional group concept. While at a conceptual level, the first and second silicone polymers are simply silicone polymers bearing the complementary reactive pair or bearing the self-reactive functional group, at a functional level, differences in silicone structure separate a silicone polymer with a self-reactive functional group into first and second silicone polymers. With the understanding that first and second silicone polymers may actually be a single silicone polymer under certain circumstances and may be two separate and distinct silicone polymers under other circumstances, the structural details of the silicone polymer with complementary reactive pairs or with self-reactive pairs are described in greater detail in the following passages about the first and second silicone polymers.

The First and Second Silicone Polymers

With appropriate selection of the functional groups from the complementary reactive pair category these functional groups can be designated as X groups. With appropriate selection of the corresponding functional groups from the complementary reactive pair category these functional groups can be designated as Y groups. The groups X and Y can also be a self-reactive functional group. The X and Y groups may be bonded through connector units CU to the silicon of the reactive siloxane monomeric unit. The combination of connector units CU and X as well as CU and Y are designated as CU-X and CU-Y. These reactive siloxane monomer units respectively have Formulas I and II:

Formula I: reactive organosiloxane unit is —(O)$_{(4-d-c)/2}$SiR$^4_c$[CU-X1 or CU-X2]$_d$ Formula II: reactive organosiloxane unit is —(O))$_{(4-d-c)/2}$SiR$^4_c$[CU-Y1 or CU-Y2]$_d$ d is 1 to 3, c is 0 to 2 and d+c is between 1 and 3; R is C1-C6 alkyl or phenyl, Because of the differentiation of the functional groups as complementary reactive pair or a self-reactive functional group, the CU-X units are divided into CU-X1 and CU-X2 and the CU-Y units are divided into CU-Y1 and CU-Y2. The X1 of CU-X1 and Y1 of CU-Y1 are the complementary reactive pair functional groups. The X2 of CU-X2 and Y2 of CU-X2 are the self-reactive functional group.

The functional group of CU-X1, X1, is isocyanato, thioisocyanato, carboxyl, linear, branched or cyclic epoxyalkyl, olefinoyloxy, malonic anhydrido, formyl, mercapto, vinyl, alkynyl. The functional group Y1 of CU-Y1 is hydroxyl, amino, mercapto, furanyl, pentadienyl or azido. X1 and Y1 may both be mercapto or both may also be isocyanato in which instance they may also be a self-reactive functional group.

The CU-X2 and CU-Y2 units of Formulas I and II provide a self-reactive reactive functional group that will covalently link together through silanol/alkoxysilane condensation. The functional group for this embodiment is bonded to the silicone and may be —Si—OH, —Si—OR$^{15}$ with R$^{15}$ being a C1-C6 alkyl group, Si-oxime, Si-acetoxy or Si-vinyl/Si-hydrogen. With CU-X2 and CU-Y2 as the choices for Formulas I and II, these functional groups are bonded to the siloxane moiety [—(O)$_{(4-d-c)/2}$SiR$^4_c$] by the CU organic group or are bonded directly to the siloxane moiety without the CU unit.

Exemplary embodiments of these self-reactive functional groups coupled to CU units either through oxygen or directly have any of the following structures: wherein d is an integer of 1 to 3 and c is 3-d.

-CU-(O)$_{(1/2)}$Si(Me)$_c$(OH)$_d$, -CU-Si(Me)$_c$(OH)$_d$, -CU-(O)$_{(1/2)}$Si(Me)$_c$(OR$^{15}$)$_d$ [which includes -CU-O$_{(1/2)}$Si(OR$^{15}$)$_3$], -CU-Si(Me)$_c$(OR$^{15}$)$_d$, -CU-Si(OR$^{15}$)$_3$, -CU-(O)$_{(1/2)}$Si(Me)$_c$(O—N=CR$^{15}$)$_d$, -CU-Si(Me)$_c$(O—N=CR$^{15}$)$_d$, -CU-(O)$_{(1/2)}$Si(Me)$_c$(OCOMe)$_d$, -CU-Si(Me)$_c$(OCOMe)$_d$, or the couple -CU-SiMe$_2$H/-CU-SiMe$_2$-vinyl.

Exemplary embodiments of these self-reactive functional groups coupled directly to the siloxane moiety [—(O)$_{(4-d-c)/2}$SiR$^4_c$ without the CU unit have any of the following structures: —(O)$_{(1/2)}$Si(Me)$_c$(OH)$_d$, —(O)$_{(1/2)}$Si(Me)$_c$(OR$^{15}$)$_d$, —(O)$_{(1/2)}$Si(Me)$_c$(O—N=CR$^{15}$)$_d$, —(O)$_{(1/2)}$Si(Me)$_c$(OCOMe)$_d$ While the SiH/Si-vinyl couple is not technically a self-reactive group, it is placed in the CU-X2/CU-Y2 category so as to distinguish it from the vinyl—mercapto complementary reactive pair. The SiH/Si-vinyl pair provides a hydrosilation in situ bonding arrangement.

The siloxane moieties of Formulas I and II [—(O)$_{(4-d-c)/2}$SiR$^4_c$] are the silicons of the reactive siloxane units which form part of the backbone and/or the branch chains of the silicone polymer. The silicons of Formulas I and II may be bonded to 1, 2 or 3 CU-X units or CU-Y units as indicated by the designator d (an integer of 1-3). If less than three CU-X/CU-Y units are present on the silicon, the remaining silicon valences may be bonded to an oxygen or to an R$^4$ group when R$^4$ is C1-C6 alkyl or phenyl. When bonded to one oxygen, the reactive siloxane units, Formula I and Formula II, will be terminal reactive siloxane units of a backbone or branch of the silicone polymer, e.g., M units according to the nomenclature MDTQ. When bonded to two oxygens, the reactive siloxane units, Formulas I and Formula II, will be parts of linear portions of the backbone and/or branch of the silicone polymer, D units. When bonded to three oxygens, the reactive siloxane units will be branching groups of the backbone and/or branch of the silicone polymer, T units.

The CU units of Formulas I and II provide the pendant organic chains to which the functional groups are bonded. The CU units are linear and/or branched saturated aliphatic chains or linear and/or branched saturated heteroaliphatic chains of one to forty-eight carbons, preferably one to twenty-four carbons, more preferably one to twelve carbons, or aromatic and/or heteroaromatic groups of one, two or three separate or fused rings, each ring being a 5 or 6 single ring or a bicyclic 10 member ring as described in the Definitions Section. The CU units may also be combinations of the saturated aliphatic and/or heteroaliphatic chains and the aromatic and/or heteroaromatic groups. The aliphatic chains may be linear and/or branched polymethylenyl chains. The CU heteroaliphatic chains may be linear and/or branched polymethylenyl chains in which parts of the polymethylenyl chains are linked together by heteroatom linking groups such as ether, sulfur, amino, carboxyl, amido, urethano, ureido, carbonyl, carbonato and/or imino. The heteroatom linking groups preferably are compatible with the particular X or Y functional group chosen for an embodiment of the silicone polymer. Exemplary aromatic and heteroaromatic rings include phenyl, naphthyl, thiophenyl, pyridinyl, pyrazinyl, quinolinyl, quinazolinyl, imidazolyl, benzimidazolyl, thiazolyl, benzothiazolyl, indolyl, indenyl, indanyl and similar aromatic and heteroaromatic groups.

Preferred Embodiments of CU-X1 and CU-Y1

Some preferred embodiments of the CU-X1 unit and the CU-Y1 unit may have the following Formula III. The selections of the atoms and integer designators for CU-X1 and CU-Y1 according to Formula III are independent. The unattached valence of $O_q$ (oxygen) of Formula III binds oxygen to the silicon of Formula I/II when q is 1. When q is zero, one of the carbons of groups $R^1$ or A or $R^2$ or the heteroatom Z binds to silicon. Selection of $R^1$, Z, A or $R^2$ depends on which of the designators y, p, f, b and t is one and which is zero. The group $[A_bR^3_{3-e}]_t(R^2)_e]$ is structured to show that as many as three functional groups X/Y may be bound to single reactive siloxane monomeric unit, i.e., bound to silicon through the connecting unit CU. The connecting unit description $(O-R^1-Z-R^1-A-R^2)$ is a preferred embodiment of the general foregoing description of CU: linear and/or branched saturated aliphatic chains or heteroaliphatic chains.

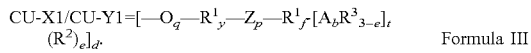

CU-X1/CU-Y1=$[-O_q-R^1_y-Z_p-R^1_f-[A_bR^3_{3-e}]_t(R^2)_e]_d$.    Formula III

The symbols and designations of the preferred embodiments of Formula III are defined as follows.
  i) The designators e and d are integers 1, 2 or 3, with d being the same as given for Formula I.
  ii) The designators q, y, p, f, t and b are zero or the integer 1.
  iii) The symbol $R^1$ for each instance independently is hydrogen or $-(CHR^6)_m$ wherein m is zero or an integer of 1 to 10.
  iv) The symbol $R^2$ is Q-X for CU-X1 and Q-Y for CU-Y1.

v) The symbol $R^3$ is hydrogen or C1-C6 linear or branched alkyl.
  vi) The symbol $R^5$ is hydrogen, C1-C6 alkyl or branched alkyl.
  vii) The symbol $R^6$ is hydrogen or C1-C6 linear or branched alkyl.
  viii) The symbol Z is O, $CHOR^5$, COO, OCONH, OCOO, —S—, $NR^5$; or Z is a bond or hydrogen when the designator p is zero.
  ix) For the symbol A: when b is 1, A is carbon to which is bonded $R^3$ and $R^2$; when b is zero, A is a bond to $R^2$ if $[A_bR^3_{3-e}]$ is present.
  x) When t is 1, the group $[A_bR^3_{3-e}]$ is present.
  xi) When t is zero, the group $[A_bR^3_{3-e}]$ is absent and $R^2$ is bonded to one of 0, either instance of $R^1$ or Z when the designator q, y, p of 0, $R^1$ and Z closest to $R^2$ is 1 and the others are 1 or zero.
  xii) The symbol Q is a bond, a C1-C10 linear or branched alkylenyl or a C1-C10 linear or branched oxyalkyl.
  xii) The symbol X is isocyanato, thioisocyanato, carboxyl, linear, branched or cyclic epoxyalkyl, olefinoyloxy, malonic anhydrido, formyl, mercapto, vinyl or alkynyl;
  xiii) Y is hydroxyl, amino, mercapto, furanyl, pentadienyl or azido or
  xiii) Q and X together are Si—CH=$CH_2$ and Q and Y together are Si—H.

Number and Distribution of Reactive Siloxane Units in Silicone Polymers

The silicone polymers (e.g. first and second silicone polymers) are linear and/or branched silicone polymers with at least two reactive siloxane monomeric units per molecule and a majority of non-reactive siloxane units $(R)_nSi(O_{(4-n)/2}$ wherein R is a C1-C6 alkyl or phenyl and n is zero or an integer of 1 to 3. In terms of the well-understood siloxane nomenclature MDTQ, the nonreactive siloxane units of the silicone polymers can be M units with three organic groups ($R_3SiO_{1/2}$), D units with two organic groups ($R_2SiO_{2/2}$), T units with one organic group ($R_3SiO_{3/2}$) and Q units with no organic groups ($SiO_{4/2}$). The M units are terminal units. The D units are linear chain units. The T units provide preformed branching of the silicone polymer backbone and the T and Q units enable pre-formed cross link and star arrangements of either the silicone polymer backbones. Preferably, very few T and Q units, if any, are present in the silicone polymers to provide preformed cross link connections between the silicone polymer molecules. Several T units may be present to provide branching of the silicone polymers. More preferably, the silicone polymers primarily have linear backbones with optional short silicone chain branching and little or no cross link or star arrangements between polymer molecules of the silicone polymer.

The preferred arrangement of the functional groups in each of the first and second silicone polymers provides that each member of the functional group list individually and separately is present at a minimum number of two per majority of silicone polymer molecules and may be distributed throughout the polymer backbone and/or along the branch chains. In addition, multiple functional groups may be present at a single position on the backbone and especially on branch chains. An example of such a multiplicity would be a branch chain ending with a t-butyl group, the three termini of which have hydroxyl groups. The number of a particular functional group present in a molecule can be assessed by calculating the number average polymer molecular weight divided by the functional group equivalent weight where the equivalent weight refers to the mass of polymer which has one equivalent reactive group. If this calculation gives a value of 2, this shows that the average polymer has two functional groups. The minimum means only that a minimum of two of a single member of the functional group class may be present or there may be present multiples of two of any one or more of the other members of a functional group class. This arrangement provides minimums, without reference to the presence of other functional groups, of two hydroxyl groups, two amine groups, two mercapto groups, two carboxylic or sulfonic acid groups, two vinyl groups and two olefinoyloxy groups. A minimum number of three is preferred individually and separately for each kind of functional group. A minimum number of four is more preferred individually and separately for each kind of functional group. A minimum number of five is most preferred for carboxyl and hydroxyl groups and a minimum number of at least two or three carboxyl groups is preferred in the presence of other functional groups provided that the multiple presence is mutually compatible. Not all silicone polymer molecules will have the same number of functional groups; however, a majority to substantially greater than a majority of the silicone polymer molecules such as from 95 mole percent to 98 mole percent will statistically have the same number of functional groups. Some silicone polymer molecules may have more than the specified number of functional groups; however, statistically this number will be less than a majority and preferably statistically will be significantly less than a majority such as less that a 10 mole percent, more preferably less than a 5 mole percent and most preferably less than a 2 mole percent.

For all versions of the silicone polymer, the portion of the reactive silicone units relative to the total of reactive and non-reactive silicone units present in the silicone polymer may range in mole percent from as little as about 0.05-2 mole percent to as much as 34 mole percent. Said in another fashion, the molar ratio of non-reactive to reactive silicone units may range of about 2000:1 to about 3:1; preferably about 1250:1 to about 3:1, more preferably about 800:1 to about 3:1, most preferably about 500:1 to 3:1, especially most preferably about 250:1 to about 3:1 with especially preferred molar ratios being about 4:1 to about 3:1 or about 20 mole percent to about 30 mole percent of the reactive silicone units.

Examples of CU Units

Some examples of the aliphatic groups as a polymethylenyl chain, the heteroaliphatic group as a heteropolymethylenyl chain and the aromatic/heteroaromatic group of the CU connector unit may comprise but are not limited to any of the following divalent formulas of charts I, II, III and IV. In these charts, the group My represents methylenyl (—$CH_2$—), the group Me represents methyl (—$CH_3$), the group Bz represents phenylenyl (a benzene ring with two free valences), the group Py represents pyridylenyl (a pyridine ring with two free valences), the group Th represents thiophenylenyl with two free valences and the group $B_1$ represents benzimidazolylenyl with two free valences. The left and right valences of these examples of the CU units may be bonded respectively to the silicone and to the X or Y of Formula I or II above. The group $R^{25}$ is a branch polymethylenyl group ending with a methyl group and may have from one to twelve carbons (with one carbon, $R^{25}$ is methyl). The heteroatoms are selected so that they would not interfere with the complementary reactive pairs or the self-reactive groups or with the left valence bond between these CU units and the silicon of the reactive siloxane monomeric unit, Formula I and Formula II.

CHART I

| Saturated Aliphatic CU Units | |
|---|---|
| -My- | -My-My(Me)-My- |
| -My-My- | -My-My-My($R^{25}$)-My-My-My- |
| -My-My-My- | -My-My-My($R^{25}$))-My- |
| -My-My-My-My- | -My-My-My($R^{25}$)-My-My- |
| -My-My-My-My-My- | -My-My(My-My-My-My-Me)My-My-My-My- |
| -My-My-My-My-My-My- | -My-My-My-My-My(Me)My- |

CHART II

| Saturated Heteroaliphatic CU Units | |
|---|---|
| -My-O-My-O-My- | -My-My-My-O-My-My-My-O-My-My-My- |
| -My-My-O-My-My-O-My-My-O-My-My | -My-My-My-CHOH-My-My($R^{25}$)-My-O-My-My-My- |
| -My-My-My-$NR^3$-My-My-O-My-My- | -My-My-MyCHO$R^3$-My-My(My-My-Me)-O-My-My-My- |
| -My-My-My-CHOH-My-My-O-My-My- | -My-CHOH-My-My-My-$NR^3$-My-My-My- |
| -My-My-My-My-CHOH-My-My-My-$NR^3$-My-My-My- | -My-My-My-O-My-O-My- |
| -My-My-My-O-My-My-My-$NR^3$-My-My-My- | -My-My-My-$NR^3$-My-My-My-$NR^3$-My-My-My- |
| -My-My-My-CHOH-My-My-My-O-My-My-My- | -My(Me)-My-O-My(Me)-My-O-My(Me)-My-O-My(Me)-My-O-My(Me)-My- |
| -My-My-My-CHOH-My-My-My- | -My-My-My-My(My-My-My-Me)- |
| -My-My-My-CHOH-My($R^8$)-My-My- | -My-My-My-O-My-My($R^8$)-My-O-My-My-My- |
| -My-My-My-$NR^3$-My($R^8$)-My-My- | -My-My-My-CHOH-My($R^8$)-My-My-O-My-My-My- |
| -My-My-O-My(Me)-My-O-My-My-O-My(Me)-My-O-My-My-O-My(Me)-My-O-My-My- | -My-My(OH)-My-My-O-My-My- |
| -My-My-O-My-My(MyOH)-My-My-O-My-My(Me)-My-My | -My-My(OH)-My-My-$NR^3$-My-My- |

CHART III

| Additional Saturated Heteroaliphatic CU Units | |
|---|---|
| -My-NH-My-O-My- | -My-My-My-CO$_2$-My-My-My-O-My-My-My- |
| -My-My-My-S-My-My-My- | -My-My-My-CHOH-My-My(R$^{25}$)-My-O-My-My-My- |
| -My-My-My-NR$^3$-My-My-CONH-My-My- | -My-My-MyCHOR$^3$-My-My(My-My-Me)-O-My-My-My- |
| -My-My-My-CHOH-My-My-CONH-My-My- | -My-CHOH-My-My-My-NR$^3$-My-My-My- |
| -My-My-My-My-CHOH-My-My-My-NR$^3$-My-My-My- | -My-My-My-CONH-My-O-My- |
| -My-My-My-NHCOO-My-My-My-NR$^3$-My-My-My- | -My-My-My-NR$^3$-My-My-My-CONR$^3$-My-My-My- |
| -My-My-My-CHOH-My-My-My-O-My-My-My- | -My-My-My-My-NHCOO-My-My-My-My-My-My- |
| -My-My-My-NHCOO-My-My-My- | -My-My-My-My(My-My-My-My-Me)-OCONH-My-My-My- |
| -My-My-My-CHOH-My(R$^{25}$)-My-My- | -My-My-My-O-My-My(R$^{25}$)-My-O-My-My- |
| -My-My-My-NR$^3$-My(R$^{25}$)-My-My- | -My-My-My-CHOH-My(R$^{25}$)-My-My-OCONH-My-My-My- |

CHART IV

| Aromatic and Heteroaromatic CU units | |
|---|---|
| -Bz-Bz-O-Bz-Bz-O-My-My-O-My-My | -My-My-Bz-My-My- |
| -Bz-O-My-My- | -My-Bz-My- |
| -Bz- | -My-Py-My- |
| -Py- | -My-My-Py-My-My- |
| -Bz-Py-O-Bz-O-My-My- | -My-O-Bz-O-My- |
| -O-Bz-My- | -O-Py-My- |
| -O-Bz- | -O-Py- |
| -Th- | -Bi- |
| -My-Th-My- | -My-Bi-My- |

Preferred CU's include monomethylenyl, trimethylenyl, hexamethylenyl, methylenyl-[branch dimethylenylmethyl)]-methylenyl and tetramethylenyl-[branch methylenylmethyl]-methylenyl. More preferred CU's include monomethylenyl, trimethylenyl, tetramethylenyl, hexamethylenyl and dimethylenyl-[branch methylenylmethyl]-dimethylenyl, divalent benzylenyl, divalent pyridylenyl, methylenyl-benzylenyl, methylenyl-pyridylenyl, thiophenylenyl, quinolinylenyl, benzimidazolylenyl and dimethylenyl-benzylenyl-dimethylenyl.

Combining the CU units with embodiments of X as isocyanate provides the preferred embodiments of the isocyanate CU-X1 groups for Formula I:
  i) —(CH$_2$)$_3$OCONH—(CH$_2$)$_6$NCO,
  ii) —(CH$_2$)$_3$OCH$_2$C(CH$_2$OCONH—(CH$_2$)$_6$NCO)$_2$(CH$_2$CH$_3$) [two isocyanate groups on branched alkylenyl group],
  iii) —(CH$_2$)$_3$O(CH$_2$)C(CH$_2$OCONH—(CH$_2$)$_6$NCO)$_3$ [three isocyanate groups on branched alkylenyl group],
  iv) —(CH$_2$)$_3$OCH$_2$CH(CH$_3$)$_p$[O(CH$_2$)$_2$OCH$_2$—OCONH—(CH$_2$)$_6$NCO]$_q$ wherein p is zero or 1 and p+q is 2.
  v) —(CH$_2$)$_3$OCONH—(CH$_2$)$_6$—CH$_2$—(CH$_2$)$_6$—NCO.

Preferred embodiments of the epoxy CU-X1 groups for Formula I include:
  i) —(CH$_2$)$_3$OCH$_2$-epoxy,
  ii) —(CH$_2$)$_3$OCH$_2$C(CH$_2$-epoxy)$_2$CH$_2$CH$_3$ [two epoxy groups on branched alkylenyl group],
  iii) —(CH$_2$)$_3$O(CH$_2$)C(CH$_2$-epoxy)3 [three epoxy groups on branched alkylenyl group],
  iv) —(CH$_2$)$_3$OCH$_2$CH(CH$_3$)$_p$[O(CH$_2$)$_2$O—CH$_2$-epoxy]$_q$ [wherein p is zero or 1 and p+q is 2].

Preferred embodiments of olefinoyloxy CU-X1 groups for Formula I include
  i) —(CH$_2$)$_3$OC(O)C(CH$_3$)=CH$_2$, —(CH$_2$)$_3$OC(O)C(H)=CH$_2$,
  ii) —(CH$_2$)$_3$OCH$_2$CH(OH)CH$_2$OC(O)C(CH$_3$)=CH$_2$,
  iii) —(CH$_2$)$_3$OCH$_2$CH(OH)CH$_2$OC(O)C(H)=CH$_2$,
  iv) —(CH$_2$)$_3$[O(CH$_2$)$_2$]$_q$[O(CH$_2$)CH(CH$_3$)]$_r$OC(O)C(CH$_3$)=CH$_2$, where r+q is greater than 1 and less than 10
  v) —(CH$_2$)$_3$[O(CH$_2$)$_2$]$_q$[O(CH$_2$)CH(CH$_3$)]$_r$OC(O)C(H)=CH$_2$, where r+q is greater than 1 and less than 11.

Preferred embodiments of formyl CU-X1 groups for Formula I include:
  i) —(CH$_2$)$_3$CHO,
  ii) —(CH$_2$)$_3$OCH$_2$C(CH$_2$CHO)$_2$(CH$_2$CH$_3$) [two formyl groups on branched alkylenyl group],
  iii) —(CH$_2$)$_3$O(CH$_2$)$_2$C(CH$_2$CHO)$_3$ [three formyl groups on branched alkylenyl group],
  iv) —(CH$_2$)$_3$[O(CH$_2$)$_2$CH(CH$_3$)]$_p$[O(CH$_2$)$_2$]$_q$ OCH$_2$—CHO wherein p+q is greater than 1 and less than 11.

Preferred embodiments of amino CU-Y1 groups for Formula II include:
  i) —(CH$_2$)$_3$NH$_2$,
  ii) —CH$_2$CH(CH$_3$)CH$_2$NH$_2$,
  iii) —(CH$_2$)$_3$NH(CH$_2$)$_2$NH$_2$,
  iv) —CH$_2$CH(CH$_3$)CH$_2$NH(CH$_2$)$_2$NH$_2$,
  v) —(CH$_2$)NH$_2$,
  vi) —(CH$_2$)NH(CH$_2$)$_2$NH$_2$, Preferred embodiments of mercapto CU-Y1 groups for Formula II include:
  i) —(CH$_2$)$_3$SH,
  ii) —CH$_2$CH(CH$_3$)CH$_2$SH.

Preferred embodiments of the hydroxyl CU-Y1 groups for Formula II include:
  i) —(CH$_2$)$_3$OH,
  ii) —(CH$_2$)$_3$O(CH$_2$)$_2$OH,
  iii) —(CH$_2$)$_3$O(CH$_2$)C(CH$_2$OH)$_2$(CH$_2$CH$_3$),
  iv) —(CH$_2$)$_3$[OCH$_2$CH(CH$_3$)]$_p$[O(CH$_2$)$_2$]$_q$ OH, wherein p+q is greater than 1 and less than 11.

In addition to X or Y being a single occurrence on a reactive siloxane unit, the foregoing Formulas and description show that X and Y may be multiple occurrences on a single reactive siloxane unit. For example, a precursor compound with multiple X or Y groups such as multiple isocyanate groups and multiple hydroxyl groups may be used to form CU with multiple functional groups. In this example, a dihydroxy reactive siloxane unit may be prepared by combining trimethylolpropane and dimethyl dichlorosilane to form a precursor reactive siloxane unit. This unit can be combined with a silicone polymer having hydroxyl groups so as to add the chlorosilane moiety to the silanol —(O)$_{(1/2)}$SiMe$_2$OH moiety of the silicone polymer. The result produces a silicone polymer with a pendant hydroxyl functional group:

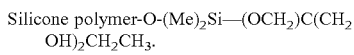

Silicone polymer-O-(Me)$_2$Si—(OCH$_2$)C(CH$_2$OH)$_2$CH$_2$CH$_3$.

Once this unit is combined with the polysiloxane compound, the resulting compound may further be combined with hexamethylene diisocyanate to add one of its isocyanate groups to each of the two remaining hydroxyl groups. The resulting isocyanate reactive siloxane unit bound to the silicone polymer has the formula

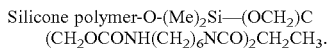

Silicone polymer-O-(Me)$_2$Si—(OCH$_2$)C(CH$_2$OCONH(CH$_2$)$_6$NCO)$_2$CH$_2$CH$_3$.

These two units CU-X1 and CU-Y1 may be combined with an appropriate polysiloxane to provide first and second silicone polymer examples.

Generally, when the third component is present, the weight average polymer molecular weight M$_w$ of the first and second silicone polymers may be in a range from about 1000 Da to about 1 MDa, preferably about 1100 Da to about 500 KDa, more preferably about 1.2 KDa to about 500 KDa, especially more preferably about 1.5 KDa to about 300 KDa, most preferably about 1.5 KDa to about 150 KDa. Preferably one of the silicone polymers may have a minimum M$_w$ of about 150 Da and the other may have a minimum M$_w$ of about 1.5 KDa. These M$_w$ ranges apply to the first and second silicone polymer having all first and second functional groups when the third component with the base compound is included in the multicomponent composition (I).

When the third component is absent and the first and second components alone form the multicomponent composition (I), the weight average molecular weights of the first and second silicone polymers having CU-X1 and CU-Y1 units are in a range from about 1000 Da to about 1 MDa, preferably about 1100 Da to about 500 KDa, more preferably about 1.2 KDa to about 500 KDa, especially more preferably about 1.5 KDa to about 300 KDa, most preferably about 1.5 KDa to about 150 KDa.

When the third component is absent and the first and second silicone polymers have CU-X2 and CU-Y2 units alone or the complementary reactive pair Si—H and Si—CH═CH$_2$, the weight average molecular weights of the first and second silicone polymers are in a range from about 1100 Da to about 150 KDa, preferably a range of 1.5 KDa to 150 KDa, and a polydispersity wherein the molecular weight fraction below 1 KDa of the first and second silicone polymers is less than 5 wt %, preferably less than 1 wt %, more preferably less than 0.1 wt % or virtually indetectable relative to the average molecular weights of the first and second silicone polymers.

In one embodiment, the properties of the coating produced by the combination of the first and second silicone polymers and optionally the amine polymer as the base compound coupled with the reactive pairing of the first and second functional groups produces a coating with a Shore OO Hardness of greater than 10, more preferably greater than 15 even more preferably greater than 20, most preferably greater than 25, as measured using the test method described in the examples section.

As an option, a quantity of non-reactive organosilicone polymer such as up to about 0.1 wt %, or up to about 1 wt %, or up to about 35 wt % or higher such as up to about 60 wt % or 75 wt % relative to the total weight of the first and second silicone polymer can be included with the first and second silicone polymers. The presence of a non-reactive silicone polymer along with the first and second silicone polymers enables dilution of the first and second silicone polymers. The dilution may have an effect upon the in situ melding of the composition. The non-reactive polyorganosilicone of this embodiment has a M$_n$ of at least about 2.5 KDa or preferably at least about 5 KDa. It is recognized that a low M$_n$ silicone may also be present as a medium or as a component of a medium. Decamethylcyclopentasiloxane or d5 is an example of a silicone as a medium. Low M$_n$ silicones of this kind are volatile so that they do not remain with the composition following its application and in situ interaction on the substrate material.

The in situ melding is also affected by the number in situ linkages between and among the components providing the first and second silicone polymers and the base compound delivers primary control of the degree of network and star interconnections among these components. Too many interconnections may tend to increase a degree of inflexibility to the resulting coating. Too few interconnections may tend to decrease the remanence of the resulting coating. In addition to this primary control, dilution of the first and second silicone polymers with a non-reactive silicone polymer can help with coating flexibility and other physical parameters such as elasticity, inter-strand interaction for hair strands and tactile sensation. Modification of primary control may also be established by M$_n$, position of functional groups along the chains of the first and second silicone polymers and ancillary components such as surfactants, diluents, dispersants and other excipients discussed below.

Coordination of First, Second and Third Functional Groups

The first and second functional groups of the first and second components form complementary reactive pairs of functional groups according to the following pairings. The third component containing the base compound also participates in the pairing as one of the functional groups. (The third component is described below). These pairings include:

i) isocyanate or thioisocyanate and hydroxyl, amine or mercapto or any combination of hydroxyl, amine and mercapto;
ii) carboxyl and hydroxyl, amine or mercapto or any combination of hydroxyl, amine and mercapto;
iii) alkylepoxy and hydroxyl, amine or mercapto or any combination of hydroxyl, amine and mercapto;
iv) olefinoyloxy and hydroxyl, amine or mercapto or any combination of hydroxyl, amine and mercapto (an example of olefinoyloxy is acrylyloxy or crotonyloxy);
v) olefinoyloxy and furanyl or pentadienyl or a combination of furanyl and pentdientyl;
vi) malonic anhydrido and hydroxyl, amine or mercapto or any combination of hydroxyl, amine and mercapto;
vii) formyl and amine or mercapto or any combination of amine and mercapto;
viii) vinyl and amine or mercapto or a combination of amine and mercapto;
ix) vinyl and furanyl or pentadienyl or a combination of furanyl and pentdienyl;
x) azido and alkynyl;
xi)) when the functional groups are a self-reactive functional group, mercapto and mercapto to form disulfide;
xii) when the functional groups are a self-reactive functional group, any combination of one silanol groups (SiOH) and/or silylalkoxy groups (SiOR) and/or silyloxime groups (Si—O—N=CHR) and/or silylacetoxy groups (Si—OAc) to form Si—O—Si bonds; and, xiii) when the first functional group is Si-vinyl and the second functional group is Si—H.

The reactive siloxane units of the first and second silicone polymers are coordinated so that the multicomponent composition (I) comprises first and second components having first and second functional group pairings according to the foregoing list.

Preferred reactive pairs of the first and second silicone polymers having reactive organosiloxane monomeric units of Formulas I and II include:

i) isocyanate and hydroxyl, amine or mercapto or any combination of hydroxyl, amine and mercapto;

ii) epoxy and hydroxyl, amine, or mercapto or any combination any two or more of hydroxyl, amine and mercapto;

iii) olefinoyloxy and hydroxyl, amine or mercapto or any combination of any two or more of hydroxyl and amine and mercapto, and a preferred embodiment of the olefinoyloxy group is (meth)acrylyloxy or crotonyloxy;

iii) carboxyl and hydroxyl, amine or mercapto or any combination of any two or more of hydroxyl, amine and mercapto;

iv) any combination of silanol, silanol, silylalkoxy and silylalkoxy.

Especially preferred reactive pairs of the first and second silicone polymers having reactive organosiloxane monomeric units of Formulas I and II include:

i) isocyanate and hydroxyl, amine or mercapto or any combination of hydroxyl, amine and mercapto;

ii) epoxy and hydroxyl, amine or mercapto or any combination of hydroxyl, amine and mercapto;

iii) carboxyl and hydroxyl or amine or a combination of hydroxyl and amine

Most preferred reactive pairs of the first and second silicone polymers respectively having reactive organosiloxane monomeric units of Formulas I and II include:

i) isocyanate and hydroxyl, amine or mercapto or any combination of hydroxyl, amine and mercapto;

ii) epoxy and hydroxyl, amine or mercapto or any combination of hydroxyl, amine and mercapto;

iii) any combination of silanol, silanol, silylalkoxy and silylalkoxy.

In a further embodiment, variations of Formulas I and II can be adapted to form disulfide or urea groups through use of mercapto groups or isocyanate groups as a self-reactive group.

Ratios

Generally, the first and second silicone polymers comprise at least a majority of non-reactive organosiloxane monomeric units. Both silicone polymers may be linear, branched and optionally and to a minor extent networked through interchain linkages through T and Q units. When either or both first and second silicone polymers are branched, and/or have very long linear chains, the reactive first and second siloxane monomeric units of Formulas I and II are preferably positioned along or within the silicone polymer chain so that in situ linkages can be obtained. In other words, the reactive siloxane monomeric units preferably are not sterically hindered. The ratio of non-reactive organosiloxane monomeric units to reactive organosiloxane monomeric units for each silicone polymer bears on the extent to which in situ linking between the silicone polymers and with the base compound can be produced. The amount of reactive siloxane units with the silicone polymers can be calculated as discussed in preceding paragraph 0063.

Embodiments of the multicomponent composition (I) manage the number of functional groups per silicone molecule so as to provide statistically a uniform number of functional groups per molecule throughout the volume of molecules present. Nevertheless, it is possible that not all of the molecules of the silicone polymers will contain precisely the same number of functional groups. The number of functional groups in a silicone polymer may spread at least by ±1 or 2 groups from the average. The spread can be due in part to the variation of molecular weights of the silicone polymers and in part due to the polymerization and coupling methods associated with any chemical reaction. It is preferred that a substantial majority of the silicone polymers, and preferably at least almost all of the silicone polymers such as about 95 to 98 percent of the silicone polymers preferably have at least two reactive pairs, more preferably have at least three reactive pairs, most preferably have at least four reactive pairs and especially most preferably have at least five reactive pairs per molecule. It is especially preferred that at least about 98% of the silicone polymers have statistically uniform numbers of reactive siloxane units per molecule.

An overall range for the molar ratio of non-reactive organosiloxane monomeric units to reactive organosiloxane monomeric units of the first and second silicone polymers runs from as little as about 2000:1 to as much as about 3:1 considering the range of weight average molecular weight for the silicone polymers. Preferably, this range extends from about 1250:1 to about 3:1, more preferably about 800:1 to about 3:1 and most preferably about 500:1 to 3:1 and especially most preferably a range of about 250:1 to 3:1. A typical range in many circumstances is especially most preferably from 5:1 to 1:5.

G Factor Analysis

When the silicone polymers with complementary reactive pairs or with self-reactive functional groups are applied to the hair, they will undergo an in situ covalent linking reaction leading to the formation of new covalent bonds. According to the multicomponent process of the invention, application to the substrate material and especially the hair of the multicomponent composition (I) results in the formation of a solid, flexible silicone coating having a network and/or star three dimensional configuration. Dyes are embedded in the coating. The new in situ formed bonds can change the rheological characteristics of the silicone polymers. Whilst not wishing to be bound to any particular theory, it believed to be advantageous if the silicone polymer components change from having a substantial G" component, the so called loss modulus, and a negligible G' component, the so called storage modulus, prior to application to the hair, to the reverse situation where there is negligible G" component and a substantial G' component. This can also be considered by consider the phase angle φ, where $$\varphi = \arctan\left(\frac{G''}{G'}\right)$$

When the complex shear modulus changing from more the 45 degrees to less than 45 degrees. Both the phase angle of the resulting film or coating, and the complex shear modulus can be optimized for performance. Alternatively, it may be possible to quantify the resulting coating properties in terms of Young's Modulus and elongation at breaking.

The following parameters further help to define the properties of the materials that are particularly useful. Whilst not wishing to be bound by any particular theory, the degree of connectedness, i.e. formation of new in situ connections and the separation between these new connections can impact the performance of the resulting composition on substrate material such as hair. With too many connections and too little separation between the connections the resulting interconnected material can be too stiff, leading to poor performance on hair, both tactile perception and permanence through extended hair washing. This negative performance can also be expressed as having a phase angle φ less than 30 degrees, more particularly less than 15 degrees, even more less than 2 degrees. Conversely if there are insufficient connections and the separation between them is too great, the material is too fluid like leading to sticky feel, a potential for transfer of the color to other surfaces, and lower permanence and resistance to washing. This negative performance can also be expressed as having a phase angle φ greater than 60 degrees, more particularly greater than 75 degrees, even more particularly, greater than 88 degrees.

The average length between new in situ connections can be described as the average in situ link length for a given polymer and is the average distance between successive reactive organosiloxane monomeric units, Formulas I and II (which are OZ of the following mathematical formula) of a molecule, expressed in terms of $Si(R)_2O_{2/2}$ or D units:

$$\text{Cross link length} = \frac{100}{\sum_{n=1}^{n=n} MPC(OZ)_n}$$

for a series of n potential OZ groups (Formulas I and II) within a given polymer and the term MPC is defined as Mole Percent, which is equal to the number of modifications of the given species per 100 Si groups within the silicone material.

The cross linking role for a given species is given by:

$$\text{Cross link role} = \frac{\sum_{n=1}^{n=n} N_n MPC_n DP}{200}$$

For a series of n potential reactive siloxane units (OZ, Formulas I and II) within a given polymer where N is the number of OZ groups for the given functional group that can form cross links with other functional groups, MPC is the mole percent of the given group within the polymer and DP is the number average degree of polymerization of the polymer. When present, silicone polymers which do not have any OZ functionality have a cross link role=0, they will not form any new silicone connections. When the cross link role=1, the first and second silicone polymers only perform the role of chain extension when used by themselves, although those skilled in the art would understand that such chain extension would not necessarily have to occur through terminal ends of the silicone chain. When the cross link role>1 the first and second silicone polymers can perform network building, the higher this number the greater the impact of the network building. The properties of the resulting film or coating will depend on a complex relationship of the in situ link length and the in situ link role and dilution roles of all of the constituents of the composition including but not limited to the first and second silicone polymers and non cross linkable silicone polymers used.

Where more than one functional and non functional silicone polymer is used the following factors need to be considered. For each silicone polymer added, the reduced fraction of the given silicone polymer needs to be calculated.

$$\text{Reduced Fraction} = \frac{\frac{\text{Mass Fraction silicone component}}{DP}}{\int_{n=1}^{n=n} \frac{\text{Mass Fraction silicone component}_n}{DP_n}}$$

Where the mass fraction of the silicone component is the percent of the non-volatile silicone phase. A volatile silicone is one with a boiling point less than 225 C. If present, silicones which do not have an OZ (Formulas I and II) functionality are also included within the calculation to determine the reduced fraction of the total silicone phase. The DP is the number average degree of polymerization, i.e. the number of Si atoms within the polymer. This effectively factors the number of each type of silicone polymer added by the number of individual polymer entities versus just using the weight of the amount of silicone species added. Thus, the effect of a low DP material, e.g. with a DP=10 can produce a larger effect versus the same addition of a higher DP material, e.g. with a DP of 10,000. When added at equal weights, there are 100 times more of the low DP polymer entities versus the high DP polymer chains.

For the mixed system the following terms can be calculated.

Average cross link length =

$$\int_{n=1}^{n=n} \text{Cross linked length}_n \times \text{Reduced Fraction}_n$$

For n silicone polymer materials within the formulation.

$$\text{Average cross link role} = \int_{n=1}^{n=n} \text{Cross linked role}_n \times \text{Reduced Fraction}_n$$

For n silicone polymer materials within the formulation.

Using these terms for the silicone phase, non-limiting material combinations which are preferred include those where the average cross link length is greater than 5, more preferably greater than 10, even more preferably greater than 15, and where the average cross link role is greater than 1.3, more preferably greater than 1.5, even more preferably greater than 1.6. Preferably the average cross link length is less than 400, more preferably less than 350, even more preferably less than 250, and where the average cross link role is less than 6, more preferably less than 4.5, even more preferably less than 4.

The Third Component

The third component is a base compound with third functional groups. The base compound may be a small molecule, a dimer, trimer, tetramer, pentamer, hexamer, oligomer, small or large polymer having pendant and/or terminal third functional groups which may be amine, mercapto, carboxylate, sulfonate or carbamate groups, preferably amine groups. In combination with the first and second functional groups, it is believed that the third functional groups meld together with the first and second functional groups to form a coating having a network and/or star arrangement that is interconnected throughout the first and second silicone polymers and the base compound as well as interconnected with the substrate material. Embodiments of the third component combine with embodiments of the first and second components of the multicomponent composition (I) to meld together (e.g., covalently bond as well as entangle large chains together, blend, combine and unite together as one) these components into a colored coating on substrate material that displays significant remanence. Embodiments of the substantive feature of the third component are the base compound. Embodiments of the base compound incorporate amine groups, carboxylate groups, sulfonate groups, carbamoyl groups and/or mercapto groups and most preferably amine groups into and onto an organic or silicone core or chain.

The base compound preferably has a weight average molecular weight of about 150 Da to about 1 MDa. When the base compound is a polymer, its $M_n$ is preferably about 400 Da to about 500 KDa, more preferably about 400 Da to about 250 KDa, most preferably about 2 KDa to about 100 KDa.

Preferred embodiments of the base compound as an organic core with amine groups may be one or more polymer(s). The amine polymer(s) may comprise one or more amino functional group(s) per polymer chain, wherein the amino functional group(s) are selected from the group consisting of primary, secondary, tertiary amino functional groups and mixtures thereof.

Embodiments of the base compound may be selected from the group consisting of polyethyleneimine, polyallylamine hydrochloride, polydiallyldimethylammonium chloride, polyvinylamine, aminopolysaccharides, aminopolysilicones, copolymers thereof and mixtures thereof. The amine polymer(s) may preferably be selected from the group consisting of polyethyleneimine, polydiallyldimethylammonium chloride, copolymers thereof and mixtures thereof. Additional embodiments of the base compound include tri and tetra mercapto branched alkyl compounds wherein the mercapto groups are the termini and the branches are C3-C10 methylenyl groups on a C3-C10 polymethylenyl backbone.

These embodiments of the base compound may be linear or branched and/or may be random or block copolymers.

As amino polymer(s) such as the embodiments of the base compound described above, exemplary selections include:

a) Linear polyethyleneimine of the formula:

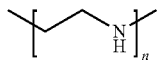

in which n is an integer representing the degree of polymerization, wherein n ranges from 50 to 20,000, alternatively from 100 to 3,500;

b) Branched polyethyleneimine consisting of primary, secondary and tertiary amine groups of the formula:

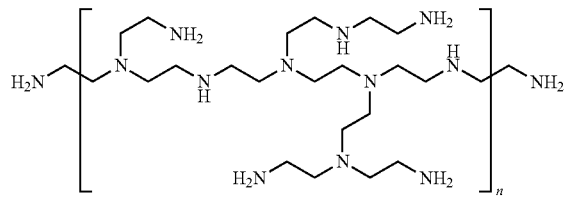

in which n is an integer representing the degree of polymerization, wherein n ranges from 5 to 4,000, alternatively from 50 to 500;

c) Polyallylamine hydrochloride of the formula:

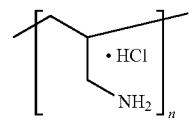

in which n is an integer representing the degree of polymerization, wherein n ranges from 50 to 20,000, alternatively from 150 to 2000;

d) Polydiallyldimethylammonium chloride of the formula:

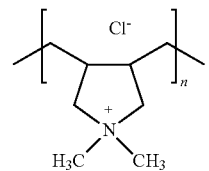

in which n is an integer representing the degree of polymerization, wherein n ranges from 10 to 20,000, alternatively from 150 to 4,000;

copolymers thereof and mixtures thereof.

These embodiments of the base compound, e.g., the amine polymer(s) may have a charge density when fully protonated of at least 0.3, preferably at least 0.6, more preferably at least 0.8, even more preferably at least 1.0 positive charges per monomer unit.

Embodiments of the base compound may also be amino silicone compounds. Embodiments of the amino silicone polymer base compound may comprise any silicone polymer chain that incorporates amine functional groups into the silicone polymer. The amino silicone compounds may also be aminosiloxane compounds or oligomers and aminosilane small molecule (monomeric) compounds such as $Me_3Si$—O—$SiMe_2$-O—$SiMe_2NH_2$ and $(CH_3O)_3Si(CH_2)_3NH_2$, $(CH_3CH_2O)_3Si(CH_2)_3NH_2$, $(CH_3O)_3Si(CH_2)_3NH(CH_2)_2NH_2$, $(CH_3CH_2O)_3Si(CH_2)_3NH(CH_2)_2NH_2$ A preferred amino silicone base compound is one having amine functional groups (hereinafter an aminosilicone polymer). The molar ratio of siloxane monomeric units with at least one pendant organic amine group (hereinafter SiA moieties) to siloxane monomeric units having silicon bonded to a substituent selected from the group consisting of alkyl (C1 to C6) or phenyl (hereinafter SiC moieties) is in the range of from about 1:1000 to 1:10 (ratio of SiA units to SiC units), preferably 1:1000 to 1:25, more preferably 1:600 to 1:35, most preferably 1:400 to 1:35 or 1:300 to 1:40. An SiA moiety may contain more than one amine group in which case it counts as just one SiA moiety. An SiC moiety may contain any number of other pendant groups as long as a primary, secondary, tertiary or quaternary amine group is not present. The aminosilicone polymer may have a weight average molecular weight ranged from about 5 KDa to about 150 KDa, preferably about 6 KDa to about 130 KDa, more preferably about 8 KDa to about 120 KDa.

The amine functional groups of the aminosilicone polymer may be primary, secondary, tertiary amine groups or quaternary ammonium groups or any combination thereof.

The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—Si(R')$_2$—O— wherein each R' is independently selected from a pendant organic amine group and an alkyl group of 1 to 6 carbons and at least one R' group is a pendant organic amine group. The organic amine group may be a linear alkyl group of 1 to 16 carbons or a branched or cyclic alkyl group of 3 to 16 carbons. The alkyl group may contain one or more heteroatoms and/or hetero-groups in the chain including such groups as —NH—, —O—, —S—, —CONH— or —NHCO—, —SO2NH— or —NHSO$_2$—. Typical pendant amine groups include such arrangements as:

—(CH$_2$)$_3$—NH—(CH$_2$)$_3$NH$_2$, —CH$_2$—CH(CH$_3$)—CH$_2$—NH—(CH$_2$)$_3$NH$_2$ (CH$_2$)$_3$—CONH—(CH$_2$)$_3$NH$_2$, —(CH$_2$)$_3$—NHCO—(CH$_2$)$_3$NH$_2$ and single amine groups such as —(CH$_2$)—NH$_2$ wherein n is 1 to 6, preferably 1 or 4 or branched chain versions thereof such as —CH$_2$—CH(CH$_3$)—CH$_2$—NH$_2$.

The amine group or groups may be pendant to the silicone chain at uniform or random locations along and within the silicone chain. The amine functional group may also terminate the ends of the silicone chain but an aminosilcone polymer having terminal amine groups preferably will also have pendant amine groups along the silicone chain.

The silicone chain of the aminosilicone polymer may be linear, branched or crosslinked. In addition to the SiA and SiC moieties, aminosilicone may also include any one or more of MDTQ groups of the formulas A, B, C and D wherein R is a methyl group:

A) —O(R)$_2$Si—O— (known as a D siloxane unit)
B) —O(R)SI(—O—)$_2$ or —O—Si(—O—)$_2$—O— (known as T siloxane unit and Q sesquisilicate unit respectively)
C) (R)$_3$SI—O— (known as M siloxane unit).

For this embodiment of the aminosilicone polymer component of the base compound the A), B), C) and D) groups constitute together the SiC moieties defined above. The A) group provides a linear silicone chain link, the B) group provides a branched or crosslinked silicone chain link, the C and D groups provide a silicone chain termination. The distribution of the SiA moiety and the A), B), C), and D) groups of the SiC moiety follows ordered or random arrangement and the SiA to SiC ratios and weight average molecular weight ranges given above The Fourth Component The fourth component is an agent that catalyzes the in situ covalent reaction of the complementary reactive pairs and self-reactive functional groups. The agent may also be a chemical enhancer for overcoming activation energy of the in situ reaction, an enzyme, a coordination complex or complexing agent for promoting the functional group interaction. Lewis acids, enzymes for ester and amide formation, carbodiimides, Friedel Crafts catalysts, Lewis bases, mixed anhydrides, leaving group donators, and similar chemical entities are examples of such agents. The fourth component is optional and typically is added when the complementary reactive pair or the self-reactive functional group typically does not covalently react under normal environmental conditions. For the silanol/alkoxysilane condensations, a typical activation agent is water.

Substitution of an Organic Polymer for One of the Silicone Polymers

The multicomponent composition (I) is generally characterized as a linear and/or branched silicone polymer having units of a non-reactive organosiloxane monomer and at least two pendant and/or terminal reactive organosiloxane monomer units having functional groups. The reactive siloxane monomeric units are distributed throughout the backbones and branch chains of the silicone polymer and carry functional groups comprising isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, cyclopentadienyl, azido, Si—OH, Si—OR, Si—O—N=CHR. Si—OAc, Si—CH=CH$_2$ or Si—H. The functional groups may be complementary reactive pairs which will parse the silicone polymer into first and second silicone polymers or may be a self-reactive functional group. Hence, the silicone polymer can be segregated into first and second silicone polymers each carrying one part of the complementary reactive pair of the reactive organosilicone units or each carrying a self-reactive organosilicone unit. One of these two segregated silicone polymer may alternatively be an organic polymer. Any organic polymer can be modified to carry half of the complementary reactive pair of functional groups or carry half of the self-reactive functional group combination. The organic polymer also may contain other functional groups as long as these other groups do not reactively interfere with the in situ covalent bonding of the complementary reactive pair or the self-reactive functional group.

Embodiments of the organic polymer can be adapted to have pendant or terminal or pendant and terminal functional groups selected from either part of the complementary reactive pairs of functional groups. One part presents the functional groups of isocyanato, thioisocyanato, carboxyl, linear, branched or cyclic epoxyalkyl, olefinoyloxy, malonic anhydrido, formyl, mercapto, vinyl, alkynyl or Si—CH=CH$_2$. The other part presents the functional groups of hydroxyl, amino, mercapto, furanyl, cyclopentadienyl, azido or Si—H. One part will be bonded to the organic polymer. The other part will be bonded to the silicone polymer as described above. Together the organic polymer and silicone polymer constitute polymers presenting the complementary reactive pairs of functional groups. Alternatively, the organic polymer and the silicone polymer may both be bonded to a self-reactive functional group including Si—OH, Si—OR, Si—O—N=CHR. Si—OAc, mercapto or isocyanate.

Organic compounds serving this role are organic polymers including but not limited to oligomers and polymers of appropriate monomeric units such as but not limited to one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers or of amino acid monomeric units, amino acid units providing peptides, gelatin or biopolymers; carbohydrate monomeric units providing alginates, cellulosic derivatives, cellulose esters, polysaccharides; hydroxylated polyester, acrylate functionalized polyester, polyester polyurethane acrylic copolymer, polyurethane-polyglycol copolymer, polycarbonate diols, styrene-allyl alcohol copolymer, ketone resins; as well as other repeating residues based on carbon or carbon in combination with other atoms such as oxygen and/or nitrogen, and any combination thereof. Additional precursor organic polymers include but are not limited to non-polar olefinic polymers, polar, non-protonic olefinic polymers, vinyl polymers, polyethers, polycondensates, block polymers and any compound with repeating carbon unit residues. Preferably the precursor organic polymers are polyolefins including polyvinyl compounds, polyesters, polyethers, polyurethanes or polyamides or any combination thereof. More preferably, the organic polymers are polyolefins including polyvinyl compounds, polyesters or polyurethanes or any combination thereof. Especially more preferably, the organic polymers are polyolefins, polyvinyl compounds or polyesters.

Organic polymers containing acid groups may be developed from any monomeric unit containing acid groups such as carboxylic acid, sulfonic acid, sufinic acid, phosphoric acid. The acidic units may be combined with non acidic units which are hydrophilic or hydrophobic to provide appropriate precursor organic polymers. Such polymers are described in the following passages.

Organic polymers may include copolymers of (meth)acrylic acid and of at least one linear, branched or cyclic (cycloaliphatic or aromatic) (meth)acrylic acid ester monomer and/or of at least one linear, branched or cyclic (cycloaliphatic or aromatic) mono- or disubstituted (meth)acrylic acid amide monomer.

Included are copolymers such as acrylic acid/ethyl acrylate/N-tert-butylacrylamide terpolymers such as the product sold under the name Ultrahold 8 and that sold under the name Ultrahold Strong by the company BASF; (meth)acrylic acid/tert-butyl (meth)acrylate and/or isobutyl (meth)acrylate/C1-C4 alkyl (meth)acrylate copolymers such as the acrylic acid/tert-butyl acrylate/ethyl acrylate terpolymer sold by the company BASF under the name Luvimer 100P; (meth)acrylic acid/ethyl acrylate/methyl methacrylate terpolymers and tetrapolymers such as the ethyl acrylate/methyl methacrylate/acrylic acid/methacrylic acid copolymer such as the product sold under the name Amerhold DR-25 by the company Amerchol; methyl methacrylate/butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

Additional examples of organic polymers include copolymers of acrylic acid and of C1-C4 alkyl methacrylate and terpolymers of vinylpyrrolidone, of acrylic acid and of C1-C20 alkyl, for example lauryl, methacrylate, such as that sold by the company ISP under the name Acrylidone M and the copolymer of methacrylic acid and of ethyl acrylate sold under the name Luvimer MAEX by the company BASF.

Yet other examples of organic polymers include amphoteric copolymers such as N-octylacrylamide/methyl methacrylate/hydroxypropyl methacrylate/acrylic acid/tert-butylaminoethyl methacrylate copolymers, in particular that sold under the name Amphomer by the company National Starch, or the copolymer Lovocryl L47 sold by the same company.

Additional examples of organic polymer include copolymers of (meth)acrylic acid and of (meth)acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, alpha-methylstyrene or a substituted styrene. Other examples include copolymers of (meth)acrylic acid and of at least one olefinic monomer chosen from vinyl esters such as those mentioned above and containing no (meth)acrylic acid acrylamide or ester monomer. These copolymers may also contain olefinic groups resulting from the copolymerization with styrene, .alpha.-methylstyrene, a substituted styrene and optionally monoethylenic monomers such as ethylene.

Still other examples include copolymers of vinyl monoacid such as crotonic acid and vinylbenzoic acid and/or of allylic monoacid such as allyloxyacetic acid.

Organic polymers include copolymers of crotonic acid containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an alpha- or beta-cyclic carboxylic acid. These copolymers may also contain olefinic groups resulting from the copolymerization with styrene, alpha-methylstyrene, a substituted styrene and optionally monoethylenic monomers such as ethylene.

Organic polymers include vinyl polymers such as vinyl acetate/crotonic acid/polyethylene glycol copolymers such as that sold by the company Hoechst under the name "Aristoflex A"; vinyl acetate/crotonic acid copolymers such as that sold by the company BASF Additional examples of precursor organic polymers include the polyolefins, polyvinyls, polyesters, polyurethanes, polyethers, polycondensates and natural polymers of the following passages.

Additional organic polymers include but are not limited to homopolymers and copolymers of olefins; cycloolefins; butadiene; isoprene; styrene; vinyl ethers, esters, or amides; (meth)acrylic acid esters or amides containing a linear, branched, or cyclic C1-C24 alkyl group, a C6-C24 aryl group or a C2-C24 hydroxyalkyl group. These polymers may be obtained from monomers such as isooctyl(meth)acrylate, isononyl(meth)acrylate, 2-ethylhexyl(meth)acrylate, lauryl(meth)acrylate, isopentyl(meth)acrylate, n-butyl (meth)acrylate, isobutyl(meth)acrylate, ethyl(meth)acrylate, methyl(meth)acrylate, tert-butyl(meth)acrylate, tridecyl (meth)acrylate, stearyl(meth)acrylate, hydroxyethyl(meth)acrylate, 2-hydroxypropyl(meth)acrylate, benzyl acrylate, phenyl acrylate, and mixtures thereof. Amides monomers include but are not limited to (meth)acrylamides, such as N-alkyl(meth)acrylamides, for example of a C2-C12 alkyl, such as N-ethylacrylamide, N-t-butylacrylamide, and N-octylacrylamide; N-di(C1-C4)alkyl (meth)acrylamides and perfluoroalkyl(meth)acrylates.

Organic polymers may also include embodiments based upon attachment of a vinyl group to a diverse number of compounds. Polymerization delivers the polyvinyl compound (e.g., a version of polyolefins) with a large variation of substituent identity. Examples of vinyl monomers for such polymerization include but are not limited to vinyl alkanoate such as vinyl acetate, N-vinylpyrrolidone, vinylcaprolactam, vinyl N—(C1-C6)alkylpyrroles, vinyloxazoles, vinylthiazoles, vinylpyrimidines, vinyl pyridine, vinyl thiophene, and vinylimidazoles, olefins such as ethylene, propylene, butenes, isoprene, and butadienes.

Organic polymers also include but are not limited to, for example, of the alkyl acrylate/cycloalkyl acrylate copolymer, the acrylates/C12-22 alkyl methacrylate copolymer and vinylpyrrolidone copolymers, such as copolymers of a C2-C30 alkene, such as a C3-C22 alkene, and combinations thereof. VP copolymers include but are not limited to VP/vinyl laurate copolymer, the VP/vinyl stearate copolymer, the butylated polyvinylpyrrolidone (PVP) copolymer, the VP/hexadecene copolymer, the VP/eicosene copolymer, the VP/triacontene copolymer or the VP/acrylic acid/lauryl methacrylate copolymer, octylacrylamide/acrylates/butylaminoethyl methacrylate copolymer, acrylates/octylacrylamide copolymer, polymers bearing fluoro groups belonging to one of the classes described in the above text, and the copolymers of alkyl(meth)acrylate and perfluoroalkyl(meth) acrylate. Additional precursor organic polymers include those resulting from the polymerization or copolymerization of an ethylenic monomer, comprising at least one ethylenic bond, which can be, for example, conjugated (or dienes). Precursor organic polymer resulting from the polymerization or copolymerization of an ethylenic monomer, vinyl, acrylic, or methacrylic copolymers are also included without limitation.

Organic polymers as block copolymers are also included, examples of which include but are not limited to a block copolymer comprising at least one block comprising styrene units or styrene derivatives (for example methylstyrene, chlorostyrene, or chloromethylstyrene). The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block of styrene units or styrene derivatives may be a diblock or triblock copolymer, for example of the polystyrene/polyisoprene or polystyrene/polybutadiene type, those of the polystyrene/copoly(ethylene-propylene) type or alternatively of the polystyrene/copoly(ethylene/butylene) type as well as styrene-methacrylate copolymers.

Further embodiments of organic polymers include but are not limited to those chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer chosen from vinyl esters (other than the vinyl ester already present), α-olefins (containing from 8 to 28 carbon atoms), alkyl vinyl ethers (in which the alkyl group contains from 2 to 18 carbon atoms), or allylic or methallylic esters (containing a linear or branched saturated hydrocarbon-based radical of 1 to 19 carbon atoms, bonded to the carbonyl of the ester group).

Further non-limiting examples of the organic polymers include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, vinyl dimethylpropionate/vinyl laurate, vinyl acetate/octadecyl vinyl ether, vinyl acetate/allyl stearate, vinyl acetate/1-octadecene and allyl propionate/allyl stearate. Additional organic polymer precursors include polyalkenes and copolymers of C2-C20 alkenes, for example polybutene, polymers of natural origin, which are optionally modified, chosen from shellac resin, sandarac gum, dammar resins, elemi gums, copal resins, and polysaccharides comprising alkyl (ether or ester) side chains, for example alkylcelluloses containing a linear or branched, saturated, or unsaturated C1-C8 alkyl radical, such as ethylcellulose and propylcellulose.

Organic polymers of natural origin may be chosen, for example, from cellulose-based polymers such as nitrocellulose, cellulose acetate, cellulose acetobutyrate, or cellulose acetopropionate. Non-limiting examples include the ethylcellulose the cellulose acetobutyrate, and the cellulose acetopropionates.

Organic polymers also include but are not limited to polycondensates which include but are not limited to polyurethanes, polyurethane-acrylics, polyurethane-polyvinylpyrrolidones, polyester-polyurethanes, polyether-polyurethanes, polyureas, polyurea-polyurethanes, and mixtures thereof. The precursor polyurethanes may be, for example, a copolymer of aliphatic, cycloaliphatic, or aromatic polyurethane, or of polyurea-polyurethane.

The polyurethanes may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting examples of organic polymer may also include polyesters, polyester amides, fatty-chain polyesters, polyamides, and epoxyester resins. The precursor polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol, and 4,4-N-(1-methylpropylidene)bisphenol may be used as aliphatic diols.

The polyesteramides may be obtained in a manner similar to that for the polyesters, via the polycondensation of diacids with amino alcohols. The polyamides may be obtained in a manner similar to that for the polyesters, via the polycondensation of diacids with diamines. Exemplary precursor polyesters that may be mentioned include aliphatic polyesters containing C4-50 alkyl side chains or polyesters resulting from the condensation of fatty acid dimers, or alternatively polyesters comprising a silicone segment in the form of a terminal block, graft, or group.

Transforming the Precursor Organic Polymer to the Organic Polymer

The organic polymers may be transformed to the organic polymer with a functional group by incorporation of one or more polymerization compatible monomeric units bearing carboxylic acid groups, sulfonic acid groups, sulfinic acid groups, hydroxyl groups, mercapto groups, olefinoyloxy groups, vinyl and/or amine groups. Typically, a copolymerization with appropriate monomeric units some of which will bear the first functional group accomplishes the incorporation and development of the organic polymer of the first component. Typically, the organic polymer of the first component will have an acid number ranging from small to large and optionally a hydroxyl number and/or amine number and/or mercapto number ranging from small to large. Incorporation of monomeric first functional groups into precursor organic polymers which are olefinic polymers is straightforward as the olefinic first functional group monomeric unit will copolymerize with the other olefinic units of such polymers. For condensation polymers, incorporation can be accomplished through use of a starting monomeric unit containing a first functional group which optionally may be protected. For naturally derived polymers, conversion and/or derivatization of a pendant group such as a hydroxyl group or acid group to a first functional group can be accomplished through known organic chemistry transformations. These conversions are described in the scientific literature such as in J. March, "Advanced Organic Chemistry", 4$^{th}$ Ed. John Wiley & Sons, New York, 1992.

Embodiments of the organic polymer of an alternative to one of the silicone polymers comprise one or more of the above described organic polymers coupled with two or more functional groups, especially polyolefins, polyvinyls, polyesters, polyethers, polyamides, polyurethanes and combinations thereof. Especially preferred are polyolefins, polyvinyls, polyesters, polyurethanes and polyethers. More especially preferred are polyolefins, polyvinyls and polyesters.

Embodiments of the organic polymer may be selected from oligomers and polymers produced from monomers or monomeric units of one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units, urea monomeric units, amide units of diacid/diamine monomers or of amino acid monomeric units, amino acid units providing peptides, gelatin or biopolymers; carbohydrate monomeric units providing alginates, cellulosic derivatives or polysaccharides; as well as other repeating residues based on carbon or carbon in combination with other atoms such as oxygen and/or nitrogen, and any combination thereof. The organic polymer may comprise a polyolefin, a polyester, a hydroxylated polyester, an acrylate functionalized polyester, a polycarbonate, a polyallyl alcohol, a ketone resin, a polyether, a polyimine, a polyurethane, a polyurea, a polyglycol, a polyamide, a polypeptide, poly (2-oxazoline) and its derivatives, a carbohydrate compound, a cellulose, a cellulose derivative such as a cellulose ester or a hydroxylated cellulose or a carboxyl cellulose or a hydroxyl cellulose ester or carboxylic acid, an alginate, a gum, a polysaccharide, an amino acid polymer, a gelatin, an oligopeptide, a polypeptide or a protein, a carbohydrate-amino acid such as a glycosylated peptide or a carbohydrate-purine/pyrimidine base such as a polynucleoside, a biopolymer, a (meth) acrylic copolymer, a crotonic copolymer, a polyurethane-polyglycol copolymer, a polycarbonate diol, a styrene-allyl alcohol copolymer, a polyol, a natural gum, polyvinyl acetate, polyvinylpyrrolidone, polynipam, a polymer based on one or more olefin monomers, a polymer based on ester units of diacids/diol monomers, a polymer based on ester units of hydroxy acid monomers, a polymer based on ether monomeric units, a polymer based on thioether monomeric units, a polymer based on polyol monomeric units, a polymer based on alkylene oxide monomeric units, a polymer based on of alkylene imine monomeric units, a polymer based on urethane monomeric units, a polymer based on urea monomeric units, a polymer based on amide units of diacid/diamine monomers, a polymer based on amide units of amino acid monomeric units or other polymer having repeating residues based on carbon or carbon in combination with other atoms such as oxygen and/or nitrogen, and any combination thereof. Preferred organic polymers include polyolefins, polyvinyls, polyesters, polyethers, polyamides, polyurethanes and combinations thereof. Additional preferred organic polymers include polymers and copolymers based on polyurethane, polyacrylate, silicone resins, polyurea/polyurethane silicones, and copolymers based on silicone resin and on dimethiconol which either have first functional groups or are adapted to have first functional groups. Especially preferred organic polymers include polyolefins, polyvinyls, polyesters, polyurethanes and polyethers and combinations thereof. More especially preferred organic polymers include polyolefins, polyvinyls and polyesters and combinations thereof.

The organic polymer may be linear and/or branched and may incorporate along the polymer backbone, as well as along the branches, pendant moieties such as esters, ethers, oxycarbonyls, amides, aliphatic groups, aromatic groups, linear, branched or cyclic alkyl groups or similar groups that are other than polar and protic. Examples of pendant moieties include but are not limited to such moieties as an alkyl carboxyl ester resulting from polymerization of an alkyl (meth)acrylate, or phenyl resulting from polymerization of styrene. The organic polymer may incorporate any of either part of the complementary reactive pairs of functional groups with the silicone polymer incorporating the other part or the organic polymer may incorporate the self-reactive functional group. Formulas I and II above may be employed to add the functional group to the organic polymer and a chloro precursor of the siloxane moiety $[-(O)_{(4-d-c)/2} SiR^4_c]$ as $[ClSiR^4_c\text{-}CU]$ can act as a linker or connecting group. An allyl Grignard compound may be reacted with the chloro silicon compound to add an allyl group to the silicon atom. The resulting allyl silicon compound can be polymerized into an olefinic organic polymer. The allyl group may be epoxidized and opened to provide a hydroxyl group. The hydroxyl may be oxidized to carboxyl and the resulting epoxy and/or hydroxyl and/or carboxyl compounds can be polymerized with appropriate organic polymers to form polyesters, polyamides, polyols and similar organic polymers.

Glass Transition Temperature

Almost all of the first and second silicone polymer embodiments for the first and second components are viscous liquids and/or gels at ambient temperature and pressure but have a glass transition temperature (Tg) at very low temperatures such as about −30° C. to about −150° C. or −200° C. The base compound as well as substitute organic polymers typically will have a somewhat higher glass transition temperature. Because the Tg's of the silicone polymer components are so low, the starting material Tg's will not play a role in the hardness, stiffness, flexibility and softness of the linked multicomponent composition (I) as a coating on the substrate material.

In general, the glass transition temperature or $T_g$ determines the solid-solid transition of a material such as a polymer from a hard glassy material to a soft rubbery material. If the $T_g$ of the material is too high, and the material is a solid, it will be stiff and inflexible at normal temperatures. For coatings with the silicone polymers and base compound this would be an undesirable result. The coating should be soft, flexible and unnoticeable to touch and sight yet should not flake, break-up or otherwise release from the keratin fiber, and especially from human hair, when stroked by a hand or brushed with a brush. Because the Tg of the silicone polymers is so low, coatings prepared from them will usually exhibit the desirable qualities described above. However, if the in situ linked connections of the first and second silicone polymers and the base compound produces a silicone network coating or with the organic polymer produces an organic-silicone network that does not exhibit the foregoing desirable qualities, a plasticizer can be added to lower the Tg of this linked silicone network.

Exemplary Embodiments

Exemplary embodiments of a multicomponent composition (I) may be depicted as first and second components with reactive organosiloxane monomeric units and a third component with an amine base compound. While the examples can be reframed to depict any of the complementary reactive pairs or self-reactive functional groups described above, a first illustration of the first and second silicone polymer in situ reaction incorporates a first silicone polymer with first reactive organosiloxane monomeric units bearing isocyanate as the functional group X and a second silicone polymer with a second reactive organosiloxane monomeric units bearing hydroxyl as the second functional group Y. A second illustration is composed of a first silicone polymer with first reactive organosiloxane monomeric units bearing epoxy as the functional group X and a second silicone polymer with a second reactive organosiloxane monomeric units bearing amine as the second functional group Y. A third illustration is composed of a first silicone polymer with first reactive organosiloxane monomeric units bearing acrylyloxy as the functional group X and a second silicone polymer with a second reactive organosiloxane monomeric units bearing amine as the second functional group Y. In all illustrations, the base compound may be an organic amine polymer, polyethyleneimine or may alternatively be a mercaptosilane such as KBE 803 from Shin Etsu. For the isocyanate version of this composition, the first and second silicone polymers and base compound may be selected as follows:

i) a silicone polymer bearing pendant hydroxyalkyl groups, Silmer OHT C50 and
ii) a silicone polymer bearing pendant isocyanate groups, Silmer NCO Di 50 and
iii) polyethylene imine Epomin P-1050.

For the epoxy silicone version of this composition, an example is i) silicone polymer bearing pendant epoxy groups, Silmer EP C50 from Siltech,
ii) a quasi-reactive amino silicone, for example Silmer NH C50 from Siltech, optionally in the presence of a Lewis acid catalyst such as K-Pure CXC-1613 from King Industries; and,
iii) polyethylene imine Epomin P-1050

The acryloyl version of this embodiment is exemplified by i) a silicone acrylate, for example Silmer OH ACR Di10 from Siltech,
ii) quasi-reactive amino silicone described above, e.g., Formula X, for example, Silmer NH Dib from Siltech

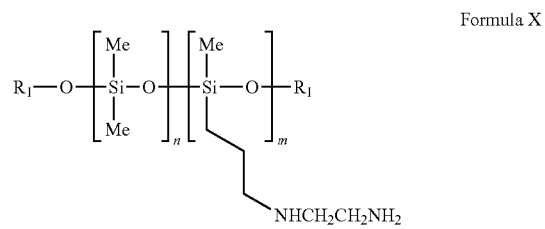

Formula X and iii) polyethylene imine Epomin P-1050.

Such systems can be optimized by selecting the degree of functionality of the isocyanate and hydroxy groups, the epoxy and amine groups or the acrylyloxy and amine groups of the two silicones, the concentration of the amines of the polyethylene imine and the relative ratio among these three starting materials.

Idealized reaction depictions of these three versions of these exemplary embodiments are presented by reaction schemes 20, 30 and 40. The combination of the base compound is omitted. It will react with the isocyanate, the epoxy and the acrylate as depicted for the reactions of these groups with the functional group partner of the complementary reactive pair. For the isocyanate, Scheme 20 the amine base compound will produce urea linking groups in addition to the urethane groups show.

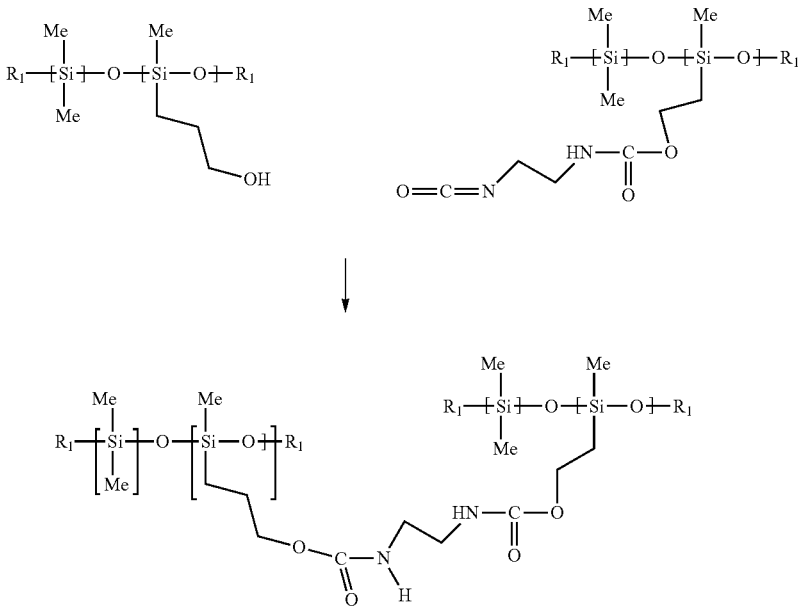

Scheme 20

For Scheme 30, the amine base compound can be considered to be the same aminosilicone used as the second silicone polymer.
Scheme 30
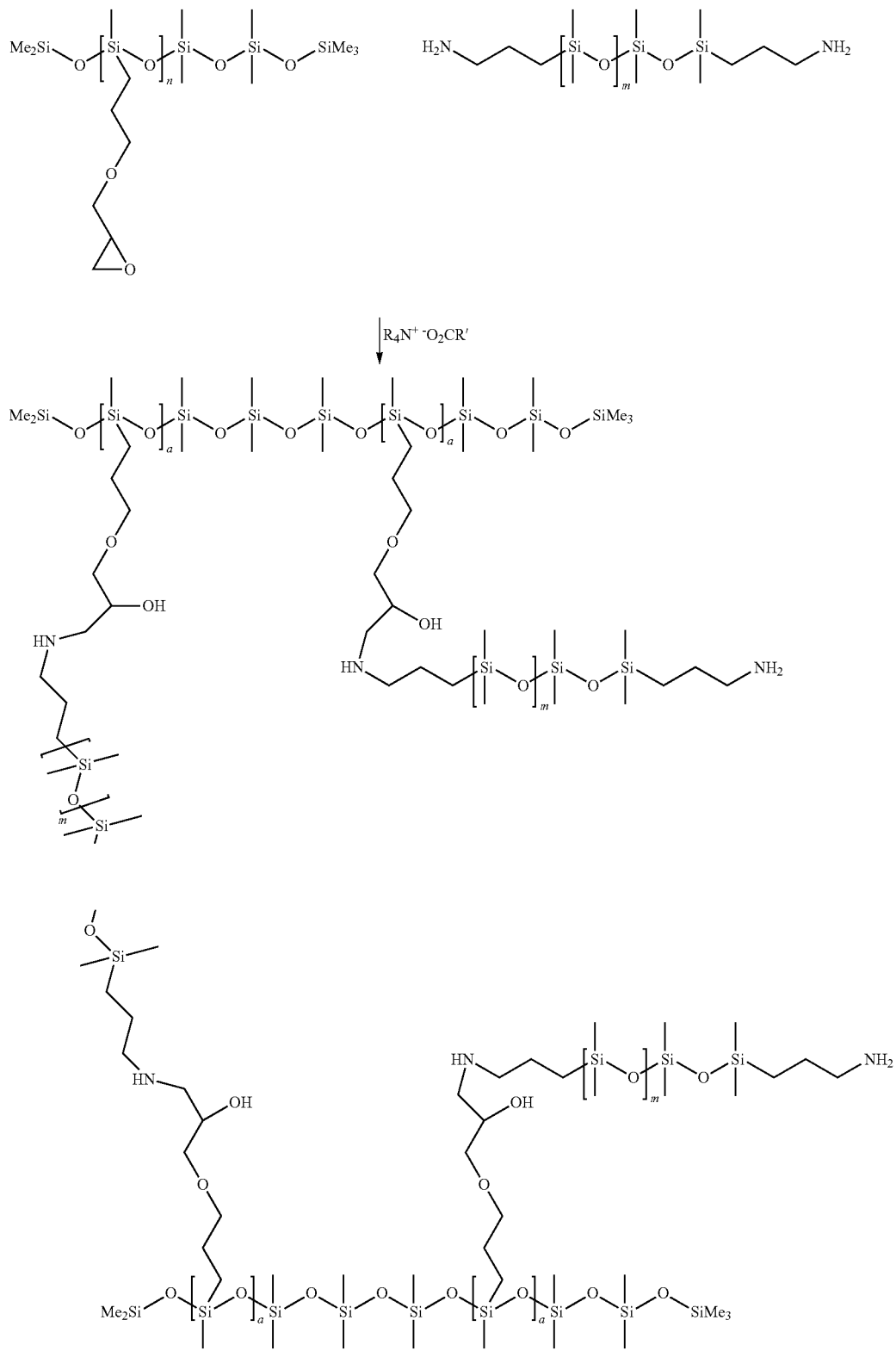

For Scheme 40 an amino base compound such as polyethyleneimine will produce the same Michael addition product shown for addition of the amino silicone to the acryloyl group.
Scheme 40
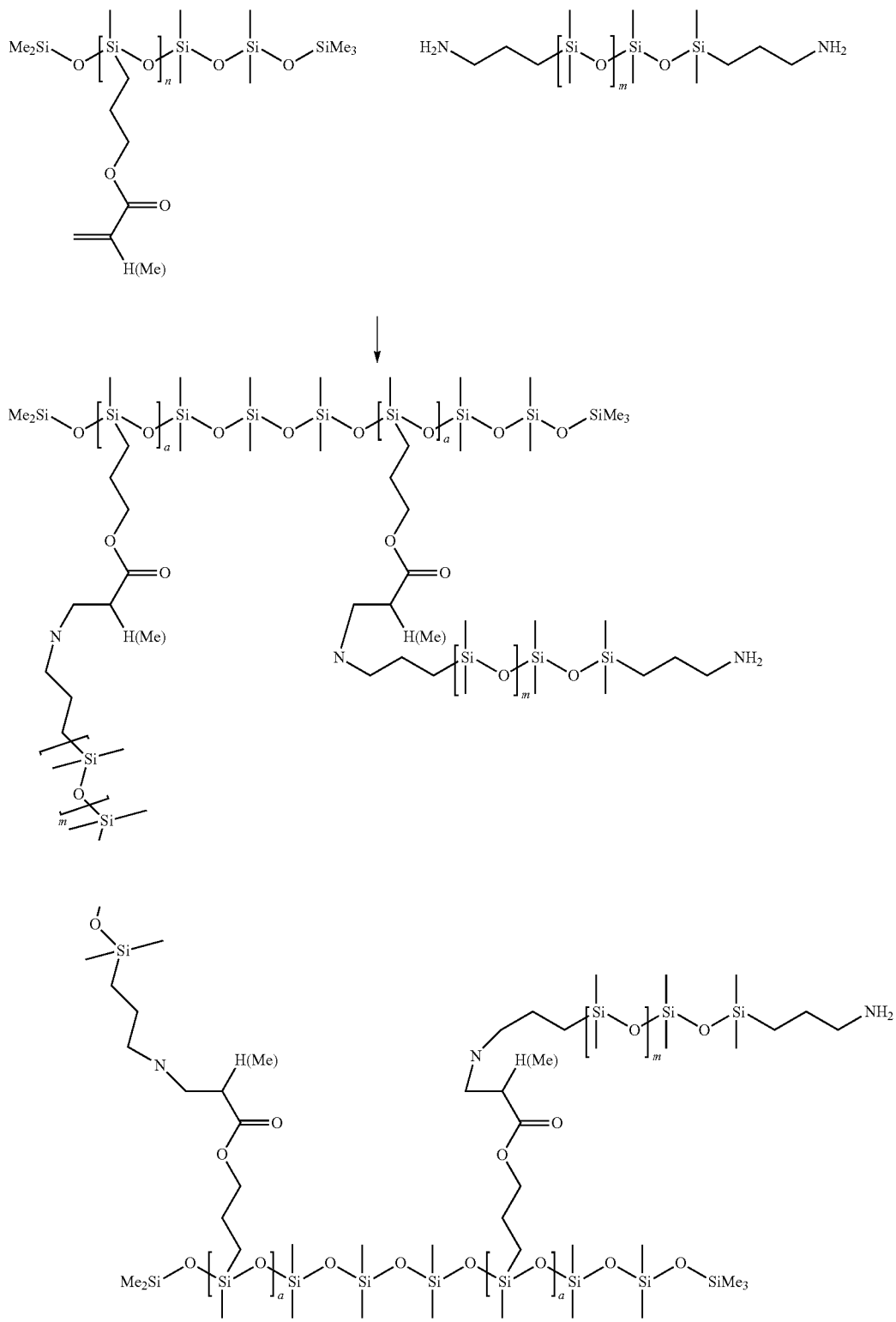

Another Preferred Embodiment

A preferred embodiment of the multicomponent composition (I) comprises a first component containing a first silicone polymer with isocyanate reactive organosiloxane units of foregoing paragraph 0075(i); and a second component containing a second silicone polymer with hydroxyl reactive siloxane units of foregoing paragraph 0081(i) or containing a second silicone polymer with amine reactive siloxane units of foregoing paragraph 0079(i). The third component is polyethyleneimine.

Viscosity, Composition Concentrations

The viscosity of the composition functions to hold the composition in place on the substrate material while the in situ linked coating is formed. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat the substrate material. Appropriate viscosity of the composition is the result of the interaction of the first and second silicone polymers and the base compound, their concentrations, if present pigment microparticles, and as appropriate, an optional viscosity control agent, an optional suspending agent and an optional thickening agent. Generally, the viscosity of the composition may range from about 0.1 to about 200 Pa s$^{-1}$, preferably 1 to 100 Pa s$^{-1}$, more preferably 10 to 75 Pa s$^{-1}$. Viscosity measurements are carried out on a controlled stress rheometer eg. Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec$^{-1}$ shear rate is obtained from the shear stress vs. shear rate curve, and the corresponding viscosity is calculated by dividing the obtained shear stress by 10.

The concentration of each of the first and second silicone polymers in the multicomponent composition with first, second and third components may range from about 0.25% to about 20%, preferably about 0.5% to about 15%, more preferably about 0.75% to about 10% relative to the total weight of the multicomponent composition. A preferred concentration of the combination of the first and second silicone polymers in the multicomponent composition with first, second and third component ranges from about 0.5% to about 35%, more preferably about 1.0% to about 25% and most preferably about 1.5% to about 15% by weight relative to the total weight of the multicomponent composition.

4.3.5 Multicomponent Composition/Concept (II)

According to embodiments, the film former is a multicomponent composition according to concept (II).

First Component: Organic Polymer

The organic polymer of the first component of the multicomponent composition includes linear and/or branched configurations of homopolymer, copolymer, terpolymer and/or multiple monomeric unit polymer embodiments. These embodiments comprise oligomers and polymers of appropriate monomeric units such as but not limited to one or more olefin monomers, ester units of diacids/diol monomers, ester units of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers, amide units of amino acid monomeric units, amino acid units providing peptides, gelatin or biopolymers; carbohydrate monomeric units providing alginates, cellulosic derivatives, polysaccharides; as well as other repeating residues based on carbon or carbon in combination with other atoms such as oxygen and/or nitrogen, and any combination thereof. Preferably the oligomers and polymers are polyolefins, polyesters, polyethers, polyurethanes or polyamides or any combination thereof. More preferably, the oligomers and polymers are polyolefins, polyesters or polyurethanes or any combination thereof. Especially more preferably, the oligomers and polymers are polyolefins or polyesters.

The organic polymer may have non-polar, non-protic pendant moieties such as but not limited to linear, branched or cyclic alkyl groups optionally including oxygen, nitrogen, ester, oxycarbonyl, amide, hydroxyl, thioether, ether, amino, imino, sulfonyl within or along the alkyl groups. These pendant moieties also include aromatic groups, heteroaromatic groups, small to oligomeric repeating carbon units, all with the same optional heteroatoms and heteroatom groups described for the alkyl chains and/or moieties. These pendant moieties may also be oligomeric or polymeric silicone moieties constructed of organosiloxane units.

The first functional groups of the organic polymer differ from the foregoing pendant moieties in that the first functional groups are polar, protic and can react with the second functional groups. The first functional groups may be attached to the forgoing pendant moieties or may be constructed as described below.

The foregoing substitution pattern of the polymer chain of the organic polymer of the first component shows that the organic polymer has two kinds of substituents: the pendant moieties and the first functional groups. Hence, the organic polymer can be conceptualized as a precursor organic polymer with variable substituents in which has been incorporated the first functional groups. Describing the organic polymer in this manner provides a realization of the breadth of the kind of precursor organic polymers that can function as the organic polymer through incorporation of the first functional groups.

Precursor Organic Polymers

Precursor organic polymers can be conceptualized as classes, subclasses and categories of organic polymers without the first functional groups. Such precursor organic polymers include the above described oligomers and polymers minus the first functional groups. These precursor organic polymers include but are not limited to oligomers and polymers of appropriate monomeric units such as but not limited to one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers or of amino acid monomeric units, amino acid units providing peptides, gelatin or biopolymers; carbohydrate monomeric units providing alginates, cellulosic derivatives, cellulose esters, polysaccharides; hydroxylated polyester, acrylate functionalized polyester, polyester polyurethane acrylic copolymer, polyurethane-polyglycol copolymer, polycarbonate diols, styrene-allyl alcohol copolymer, ketone resins;

as well as other repeating residues based on carbon or carbon in combination with other atoms such as oxygen and/or nitrogen, and any combination thereof. Additional precursor organic polymers include but are not limited to non-polar olefinic polymers, polar, non-protonic olefinic polymers, vinyl polymers, polyethers, polycondensates, block polymers and any compound with repeating carbon unit residues. Preferably the precursor organic polymers are polyolefins including polyvinyl compounds, polyesters, polyethers, polyurethanes or polyamides or any combination thereof. More preferably, the organic polymers are polyolefins including polyvinyl compounds, polyesters or polyurethanes or any combination thereof. Especially more preferably, the organic polymers are polyolefins, polyvinyl compounds or polyesters.

Precursor organic polymers containing acid groups may be developed from any monomeric unit containing acid groups such as carboxylic acid, sulfonic acid, sufinic acid, phosphoric acid. The acidic units may be combined with non acidic units which are hydrophilic or hydrophobic to provide appropriate precursor organic polymers. Such polymers are described in the following passages.

Precursor polymers may include copolymers of (meth) acrylic acid and of at least one linear, branched or cyclic (cycloaliphatic or aromatic) (meth)acrylic acid ester monomer and/or of at least one linear, branched or cyclic (cycloaliphatic or aromatic) mono- or disubstituted (meth)acrylic acid amide monomer.

Included are precursor copolymers such as acrylic acid/ ethyl acrylate/N-tert-butylacrylamide terpolymers such as the product sold under the name Ultrahold 8 and that sold under the name Ultrahold Strong by the company BASF; (meth)acrylic acid/tert-butyl (meth)acrylate and/or isobutyl (meth)acrylate/C1-C4 alkyl (meth)acrylate copolymers such as the acrylic acid/tert-butyl acrylate/ethyl acrylate terpolymer sold by the company BASF under the name Luvimer 100P; (meth)acrylic acid/ethyl acrylate/methyl methacrylate terpolymers and tetrapolymers such as the ethyl acrylate/ methyl methacrylate/acrylic acid/methacrylic acid copolymer such as the product sold under the name Amerhold DR-25 by the company Amerchol; methyl methacrylate/ butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

Additional examples of precursor organic polymers include copolymers of acrylic acid and of C1-C4 alkyl methacrylate and terpolymers of vinylpyrrolidone, of acrylic acid and of C1-C20 alkyl, for example lauryl, methacrylate, such as that sold by the company ISP under the name Acrylidone M and the copolymer of methacrylic acid and of ethyl acrylate sold under the name Luvimer MAEX by the company BASF.

Yet other examples of precursor organic polymers include amphoteric copolymers such as N-octylacrylamide/methyl methacrylate/hydroxypropyl methacrylate/acrylic acid/tert-butylaminoethyl methacrylate copolymers, in particular that sold under the name Amphomer by the company National Starch, or the copolymer Lovocryl L47 sold by the same company.

Additional examples of precursor organic polymer include copolymers of (meth)acrylic acid and of (meth) acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, alpha-methylstyrene or a substituted styrene. Other examples include copolymers of (meth)acrylic acid and of at least one olefinic monomer chosen from vinyl esters such as those mentioned above and containing no (meth)acrylic acid acrylamide or ester monomer. These copolymers may also contain olefinic groups resulting from the copolymerization with styrene, .alpha.-methylstyrene, a substituted styrene and optionally monoethylenic monomers such as ethylene.

Still other examples include copolymers of vinyl monoacid such as crotonic acid and vinylbenzoic acid and/or of allylic monoacid such as allyloxyacetic acid.

Precursor organic polymers include copolymers of crotonic acid containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an alpha- or beta-cyclic carboxylic acid. These copolymers may also contain olefinic groups resulting from the copolymerization with styrene, .alpha.-methylstyrene, a substituted styrene and optionally monoethylenic monomers such as ethylene.

Precursor organic polymers include vinyl polymers such as vinyl acetate/crotonic acid/polyethylene glycol copolymers such as that sold by the company Hoechst under the name "Aristoflex A"; vinyl acetate/crotonic acid copolymers such as that sold by the company BASF Additional examples of precursor organic polymers include the polyolefins, polyvinyls, polyesters, polyurethanes, polyethers, polycondensates and natural polymers.

Additional precursor organic polymers include but are not limited to homopolymers and copolymers of olefins; cycloolefins; butadiene; isoprene; styrene; vinyl ethers, esters, or amides; (meth)acrylic acid esters or amides containing a linear, branched, or cyclic C1-C24 alkyl group, a C6-C24 aryl group or a C2-C24 hydroxyalkyl group. These polymers may be obtained from monomers such as isooctyl (meth)acrylate, isononyl(meth)acrylate, 2-ethylhexyl(meth) acrylate, lauryl(meth)acrylate, isopentyl(meth)acrylate, n-butyl(meth)acrylate, isobutyl(meth)acrylate, ethyl(meth) acrylate, methyl(meth)acrylate, tert-butyl(meth)acrylate, tridecyl(meth)acrylate, stearyl(meth)acrylate, hydroxyethyl (meth)acrylate, 2-hydroxypropyl(meth)acrylate, benzyl acrylate, phenyl acrylate, and mixtures thereof. Amides monomers include but are not limited to (meth)acrylamides, such as N-alkyl(meth)acrylamides, for example of a C2-C12 alkyl, such as N-ethylacrylamide, N-t-butylacrylamide, and N-octylacrylamide; N-di(C1-C4)alkyl (meth)acrylamides and perfluoroalkyl(meth)acrylates.

Precursor organic polymers may also include embodiments based upon attachment of a vinyl group to a diverse number of compounds. Polymerization delivers the polyvinyl compound (e.g., a version of polyolefins) with a large variation of substituent identity. Examples of vinyl monomers for such polymerization include but are not limited to vinyl alkanoate such as vinyl acetate, N-vinylpyrrolidone, vinylcaprolactam, vinyl N—(C1-C6)alkylpyrroles, vinyloxazoles, vinylthiazoles, vinylpyrimidines, vinyl pyridine, vinyl thiophene, and vinylimidazoles, olefins such as ethylene, propylene, butenes, isoprene, and butadienes.

Precursor organic polymers also include but are not limited to, for example, of the alkyl acrylate/cycloalkyl acrylate copolymer, the acrylates/C12-22 alkyl methacrylate copolymer and vinylpyrrolidone copolymers, such as copolymers of a C2-C30 alkene, such as a C3-C22 alkene, and combinations thereof. VP copolymers include but are not limited to VP/vinyl laurate copolymer, the VP/vinyl stearate copolymer, the butylated polyvinylpyrrolidone (PVP) copolymer, the VP/hexadecene copolymer, the VP/eicosene copolymer, the VP/triacontene copolymer or the VP/acrylic acid/lauryl methacrylate copolymer, octylacrylamide/acrylates/butylaminoethyl methacrylate copolymer, acrylates/octylacrylamide copolymer, polymers bearing fluoro groups belonging to one of the classes described in the above text, and the copolymers of alkyl(meth)acrylate and perfluoroalkyl(meth)acrylate. Additional precursor organic polymers include those resulting from the polymerization or copolymerization of an ethylenic monomer, comprising at least one ethylenic bond, which can be, for example, conjugated (or dienes). Precursor organic polymer resulting from the polymerization or copolymerization of an ethylenic monomer, vinyl, acrylic, or methacrylic copolymers are also included without limitation.

Precursor organic polymers as block copolymers are also included, examples of which include but are not limited to a block copolymer comprising at least one block comprising styrene units or styrene derivatives (for example methylstyrene, chlorostyrene, or chloromethylstyrene). The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block of styrene units or styrene derivatives may be a diblock or triblock copolymer, for example of the polystyrene/polyisoprene or polystyrene/polybutadiene type, those of the polystyrene/copoly(ethylene-propylene) type or alternatively of the polystyrene/copoly(ethylene/butylene) type as well as styrene-methacrylate copolymers.

Further embodiments of precursor organic polymers include but are not limited to those chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer chosen from vinyl esters (other than the vinyl ester already present), α-olefins (containing from 8 to 28 carbon atoms), alkyl vinyl ethers (in which the alkyl group contains from 2 to 18 carbon atoms), or allylic or methallylic esters (containing a linear or branched saturated hydrocarbon-based radical of 1 to 19 carbon atoms, bonded to the carbonyl of the ester group).

Further non-limiting examples of the precursor organic polymers include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, vinyl dimethylpropionate/vinyl laurate, vinyl acetate/octadecyl vinyl ether, vinyl acetate/allyl stearate, vinyl acetate/1-octadecene and allyl propionate/allyl stearate. Additional organic polymer precursors include polyalkenes and copolymers of C2-C20 alkenes, for example polybutene, polymers of natural origin, which are optionally modified, chosen from shellac resin, sandarac gum, dammar resins, elemi gums, copal resins, and polysaccharides comprising alkyl (ether or ester) side chains, for example alkylcelluloses containing a linear or branched, saturated, or unsaturated C1-C8 alkyl radical, such as ethylcellulose and propylcellulose.

Precursor organic polymers of natural origin may be chosen, for example, from cellulose-based polymers such as nitrocellulose, cellulose acetate, cellulose acetobutyrate, or cellulose acetopropionate. Non-limiting examples include the ethylcellulose the cellulose acetobutyrate, and the cellulose acetopropionates.

Precursor organic polymers also include but are not limited to polycondensates which include but are not limited to polyurethanes, polyurethane-acrylics, polyurethane-polyvinylpyrrolidones, polyester-polyurethanes, polyether-polyurethanes, polyureas, polyurea-polyurethanes, and mixtures thereof. The precursor polyurethanes may be, for example, a copolymer of aliphatic, cycloaliphatic, or aromatic polyurethane, or of polyurea-polyurethane.

The precursor polyurethanes may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting examples of precursor organic polymer may also include polyesters, polyester amides, fatty-chain polyesters, polyamides, and epoxyester resins. The precursor polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol, and 4,4-N-(1-methylpropylidene) bisphenol may be used as aliphatic diols.

The precursor polyesteramides may be obtained in a manner similar to that for the polyesters, via the polycondensation of diacids with amino alcohols. The polyamides may be obtained in a manner similar to that for the polyesters, via the polycondensation of diacids with diamines. Examples of precursor polyesters that may be mentioned include aliphatic polyesters containing C4-50 alkyl side chains or polyesters resulting from the condensation of fatty acid dimers, or alternatively polyesters comprising a silicone segment in the form of a terminal block, graft, or group.

Transforming the Precursor Organic Polymer to the Organic Polymer

The precursor organic polymers may be transformed to the organic polymer by incorporation of one or more polymerization compatible monomeric units bearing carboxylic acid groups, sulfonic acid groups, sulfinic acid groups, hydroxyl groups, mercapto groups, olefinoyloxy groups, vinyl and/or amine groups. Typically, a copolymerization with appropriate monomeric units some of which will bear the first functional group accomplishes the incorporation and development of the organic polymer of the first component. Typically, the organic polymer of the first component will have an acid number ranging from small to large and optionally a hydroxyl number and/or amine number and/or mercapto number ranging from small to large. Incorporation of monomeric first functional groups into precursor organic polymers which are olefinic polymers is straightforward as the olefinic first functional group monomeric unit will copolymerize with the other olefinic units of such polymers. For condensation polymers, incorporation can be accomplished through use of a starting monomeric unit containing a first functional group which optionally may be protected. For naturally derived polymers, conversion and/or derivatization of a pendant group such as a hydroxyl group or acid group to a first functional group can be accomplished through known organic chemistry transformations. These conversions are described in the scientific literature such as in J. March, "Advanced Organic Chemistry", 4$^{th}$ Ed. John Wiley & Sons, New York, 1992.

Embodiments of Classes of the Organic Polymer

Embodiments of the organic polymer of the first component comprise one or more of the above described precursor organic polymers coupled with two or more first functional groups, especially polyolefins, polyvinyls, polyesters, polyethers, polyamides, polyurethanes and combinations thereof. Especially preferred are polyolefins, polyvinyls, polyesters, polyurethanes and polyethers. More especially preferred are polyolefins, polyvinyls and polyesters. The resulting organic polymer may comprise very low to very slight to moderate to substantial water solubility or dispersibility because of the presence of the first functional groups. In some instances, the water solubility or dispersibility may be negligible. Although it is not a limitation of the invention, it is believed that when the organic polymer has negligible water solubility or dispersibility, the melding of the three components to form a remanent coating may not be as efficient as can occur with better water solubility or dispersibility of the organic polymer. It is believed that increased melding can be accomplished by addition of substituents to the organic polymer that will increase the water solubility or dispersibility, preferably up to a limitation indicated by substantial water solubility. The range of solubility may be related to the characteristics of the organic polymer to form an opaque or cloudy dispersion in neutral water and the dispersion becomes less opaque or cloudy or becomes hazy when the pH is increased. Such substituents include but are not limited to acid groups, hydroxyl groups, ether groups, amide groups, ester groups, urethane groups, urea groups and functional groups that can exhibit hydrogen bonding.

Embodiments of the organic polymer may be selected from oligomers and polymers produced from monomers or monomeric units of one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units, urea monomeric units, amide units of diacid/diamine monomers or of amino acid monomeric units, amino acid units providing peptides, gelatin or biopolymers; carbohydrate monomeric units providing alginates, cellulosic derivatives or polysaccharides; as well as other repeating residues based on carbon or carbon in combination with other atoms such as oxygen and/or nitrogen, and any combination thereof. The organic polymer may comprise a polyolefin, a polyester, a hydroxylated polyester, an acrylate functionalized polyester, a polycarbonate, a polyallyl alcohol, a ketone resin, a polyether, a polyimine, a polyurethane, a polyurea, a polyglycol, a polyamide, a polypeptide, poly (2-oxazoline) and its derivatives, a carbohydrate compound, a cellulose, a cellulose derivative such as a cellulose ester or a hydroxylated cellulose or a carboxyl cellulose or a hydroxyl cellulose ester or carboxylic acid, an alginate, a gum, a polysaccharide, an amino acid polymer, a gelatin, an oligopeptide, a polypeptide or a protein, a carbohydrate-amino acid such as a glycosylated peptide or a carbohydrate-purine/pyrimidine base such as a polynucleoside, a biopolymer, a (meth) acrylic copolymer, a crotonic copolymer, a polyurethane-polyglycol copolymer, a polycarbonate diol, a styrene-allyl alcohol copolymer, a polyol, a natural gum, polyvinyl acetate, polyvinylpyrrolidone, polynipam, a polymer based on one or more olefin monomers, a polymer based on ester units of diacids/diol monomers, a polymer based on ester units of hydroxy acid monomers, a polymer based on ether monomeric units, a polymer based on thioether monomeric units, a polymer based on polyol monomeric units, a polymer based on alkylene oxide monomeric units, a polymer based on of alkylene imine monomeric units, a polymer based on urethane monomeric units, a polymer based on urea monomeric units, a polymer based on amide units of diacid/diamine monomers, a polymer based on amide units of amino acid monomeric units or other polymer having repeating residues based on carbon or carbon in combination with other atoms such as oxygen and/or nitrogen, and any combination thereof. Preferred organic polymers include polyolefins, polyvinyls, polyesters, polyethers, polyamides, polyurethanes and combinations thereof. Additional preferred organic polymers include polymers and copolymers based on polyurethane, polyacrylate, silicone resins, polyurea/polyurethane silicones, and copolymers based on silicone resin and on dimethiconol which either have first functional groups or are adapted to have first functional groups. Especially preferred organic polymers include polyolefins, polyvinyls, polyesters, polyurethanes and polyethers and combinations thereof. More especially preferred organic polymers include polyolefins, polyvinyls and polyesters and combinations thereof.

The organic polymer may be linear and/or branched and may incorporate along the polymer backbone, as well as along the branches, pendant moieties such as esters, ethers, oxycarbonyls, amides, aliphatic groups, aromatic groups, linear, branched or cyclic alkyl groups or similar groups that are other than polar and protic. Examples of pendant moieties include but are not limited to such moieties as an alkyl carboxyl ester resulting from polymerization of an alkyl (meth)acrylate, or phenyl resulting from polymerization of styrene.

The first functional groups of the organic polymer differ from the pendant moieties. The first functional groups may be arranged as pendant groups, arranged as terminal groups or may be a combination thereof. The first functional groups may be distributed along the organic polymer backbone, along polymer branches or any combination thereof. The first functional groups may be singly or multiply arranged at a single location of the polymer and in either arrangement may be distributed throughout the backbone and branches. The first functional groups may be polar and/or protic groups including but not limited to carboxylic acid groups, hydroxyl groups, amine groups, mercapto groups (i.e., thiol, —SH), sulfo acid groups (HO$_3$S—), sulfino acid groups (HO$_2$S—), vinyloxycarbonyl, olefinoyloxy including (meth) acrylyloxy or crotonyloxy, alkynyl, Si—OH groups, Si—OR groups, Si—OAc groups, Si—O—N=CHR groups or Si—CH=CH$_2$ groups, or any combination thereof. The number of first functional groups per molecule of organic polymer is at least two and preferably is at least three and more preferably at least four and most preferably at least five. Not all organic polymer molecules may bear the same number of first functional groups.

The first functional groups may be covalently linked to the polymer chain through any manner of linear and/or branched carbon connection arrangements or units. The connection units may covalently bear one or a multiple number of first functional groups. These carbon connection arrangements may be but are not limited to a carbon connection unit comprising a linear, branched or cyclic C1-C24 alkylenyl, oxyalkyenyl, alkylenyloxy or oxyalkylenyloxy unit, a C2-C24 alkanoyl or oxyalkanoyl unit, a C6-C24 aromatic or oxyaromatic unit, a C5-C24 heteroaromatic or oxyheteroaromatic unit having one or two heteroatoms selected from nitrogen, oxygen and sulfur, a $(C_z-O-C_z)_n$ polyether unit wherein z is an integer of 1 to 6 and n is an integer of 2 to 6, a $(C_y-NH-C_y)_m$ polyimino unit wherein y is an integer of 1 to 6 and m is an integer of 2 to 6. The recitation of "oxy" before or after an organic group means that the organic group such as alkylenyl is connected to the polymer chain through an oxygen. For example, an alkylenyl group is connected to the polymer chain by a carbon-carbon bond while an oxyalkylenyl group is connected to the polymer chain by a carbon-oxygen bond.

The first functional groups may also be covalently linked to the organic polymer through linear and/or branched silicon connection units comprising a Si1-Si48 organosiloxane moiety (as $R_2SiO_2$ monomeric residues) having methyl as the organo group with silicon of the connection unit bonded to the first functional group through an alkylenyl group of one to three carbons or through an oxyalkylenyl group of one to three carbons or through an oxyalkylenyloxy group of one to three carbons and combinations thereof.

When the first functional group is Si—OH, Si—OR, Si—OAc, Si—O—N=CHR or Si—CH=CH$_2$ group wherein R is C1-C6 alkyl, this group is bonded to the organic polymer as a moiety of Formula X: —(CH$_2$)$_n$—O$_j$—Si(R$^1$)$_a$(R$^2$)$_{3-a}$. The designator n is an integer of 0 to 6, the designator j is zero or 1, R$^1$ is alkoxy of 1 to 3 carbons or OH or OAc or —O—N=CHR or —CH=CH$_2$, R$^2$ is alkyl of 1 to 3 carbons and a is an integer 1, 2 or 3. Formula X is incorporated into the organic polymer through the valence bond connection to a monomeric group compatible with the monomeric groups of the organic polymer. For example, if the organic polymer is a polyolefin, the open valence of the Formula X is bonded to a vinyl group or to an oxygen of an olefinoyloxy group such as (meth)acryloxy. The vinyl or olefin group is polymerized into the olefinic polymer chain as one of the olefinic monomer groups.

These embodiments of the organic polymer have first functional groups that are compatible with each other and other substituents of the organic polymer.

The Organic Polymer of Hydrophobic and Hydrophilic Monomers

Representative embodiments of some classes of the organic polymer comprise repeating units of a hydrophobic monomer or a hydrophilic monomer or a combination thereof, preferably a combination of the hydrophobic monomer and the hydrophilic monomer.

The hydrophobic monomer of this organic polymer embodiment may be selected from one or more of an olefinic carboxylate ester monomer or an olefinic carboxamide monomer, an olefinic sulfonamide monomer or any combination thereof. The olefinic carboxylate ester comprises an ester of an olefinic carboxylic acid and at least one saturated linear or branched C1 to C24 primary or secondary alcohol or a C4 to C24 cyclic or alkylcyclic alcohol. The olefinic carboxamide monomer comprises an amide of an olefinic carboxylic acid and ammonia or at least one linear or branched C1 to C24 primary amine. The olefinic sulfonamide monomer comprises an amide of an olefinic sulfonic acid and ammonia or at least one linear or branched C1 to C24 primary amine or a cyclic or alkylcyclic C4 to C24 alcohol.

The olefin monomer of this organic polymer embodiment has the formula: H$_2$C=CHR wherein R is selected from hydrogen, linear or branched alkyl of one to twenty four carbons, unsubstituted phenyl or phenyl substituted by one or more linear or branched alkyl of 1 to twenty four carbons, carboxylic ester of an linear or branched C1 to C214 alkanol, carboxamide of ammonia or a linear or branched C1 to C24 primary amine, sulfonamide, sulfinamide, or R is selected from —CR$^2$=CHR$^1$ wherein R$^1$ is hydrogen, methyl, ethyl or phenyl and R$^2$ is hydrogen or methyl.

The hydrophilic olefinic monomer of this embodiment of the organic polymer may be selected from:
(i) a hydroxyl ester of an olefinic carboxylic acid and a linear or branched alkyl diol of 2 to 24 carbons or a cyclic alkyl diol of 5 to 24 carbons;
(ii) an aminoalkyl ester of an olefinic carboxylic acid and a linear or branched C2-C24 aminoalkyl alcohol or a cyclic C5-C24 aminoalkyl alcohol; (ii) a mercaptoalkyl ester of an olefinic carboxylic acid, and a linear or branched C2-C23 mercaptoalkyl alcohol or a cyclic C5-C24 mercaptoalkyl alcohol;
(iii) an olefinic acid;
(iv) vinyl alcohol;
(v) vinyl alcohol ester of an olefinic carboxylic acid wherein the vinyl alcohol ester may be incorporated into an organic polymer through polymerization of a protected vinyl alcohol monomer such as vinyl acetate and exchange of the protecting group with the olefinic carboxylic acid, and within the organic polymer, the olefinic carboxylic acid is a pendant olefinoyloxy group such as but not limited to acrylyloxy or crotonyloxy;
(vi) a polar olefinic compound of the formula H$_2$C=CHC$_6$H$_4$R wherein R is selected from selected from hydroxy, sulfonic acid, sulfinic acid, carboxylic acid, a vinyl group or a polyester polyol group having terminal and/or pendant hydroxyl groups;
(vii) an alkenylalkylalkoxysilane monomeric residue of the formula IV

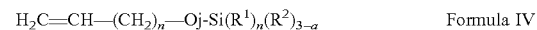

$$H_2C=CH-(CH_2)_n-O_j-Si(R^1)_n(R^2)_{3-a} \qquad \text{Formula IV}$$

wherein n is an integer of 2 to 6, j is zero or 1, R$^1$ is alkoxy of 1 to 6 carbons, hydroxyl, OAc, O—N=CHR or —C=CH$_2$, R$^2$ is alkyl of 1 to 3 carbons and a is an integer 1, 2 or 3;
or,
(viii) any combination of two or more of the hydroxyl ester, the aminoalkyl ester, the mercaptoalkyl ester, the olefinic acid, the vinyl alcohol, the vinyl alcohol ester, the polar olefinic compound or the functional silanyl residue.

The olefinic carboxylic acid of this embodiment of the organic polymer is an alkenoic acid of 3 to 24 carbons or alkendioic acid of 4 to 24 carbons or partially hydrolyzed polyacrylonitile or any combination thereof.

This embodiment of the organic polymer comprises at least two pendant or terminal or pendant and terminal first functional groups which are selected from a hydroxyl group, a carboxylic acid group, a sulfonic acid group, a sulfinic acid group, an amine group, a mercapto group, an olefinoyloxy group, a vinyl group, the silanyl functional groups or a combination thereof. Under typical and usual storage conditions, the various embodiments of the first functional group will not react with each other. Significant activation energy, catalysts and/or coordination agents are typically an important factor enabling linking combinations of complementary reactive pairs of first and second functional groups. Because the first, second, third and fourth components are maintained separately until use, a linked combination among differing functional groups of the organic polymer and the in situ linking material does not occur. For these reasons, all first functional groups are compatible with each other under ordinary and customary environmental conditions.

Additional embodiments of the organic polymer may include polymers of olefinic carboxylic acids such as (meth) acrylic acid, crotonic acid, pentadienoic acid (butadienyl carboxylic acid) optionally combined with olefinic acid esters and amides and neutral olefinic monomers. The organic polymer may include units of olefinic carboxylic acid monomers including (meth)acrylic acid, maleic acid, fumaric acid, itaconic acid, crotonic acid, pentenoic acid pentadienoic acid, isoprenoic acid, partially hydrolyzed polyacrylonitile and optional olefinic acid monomer derivatives that are homologs of these olefinic carboxylic acid monomers. The organic polymer may include units of the foregoing olefinic carboxylic acid monomers and in addition may include one or more monomeric units of esters of olefinic carboxylic acid monomers wherein the esterifying alcohol is a linear, branched or cyclic alkyl monoalcohol or diol of 1 to 12 carbons for the linear alkyl group (2 to 12 carbons for the diol), 3 to 12 carbons for the branched alkyl group and 3 to 12 carbons for the cyclic alkyl group, amides of said olefinic carboxylic acid monomers. N-alkyl amides of the olefinic carboxylic acid monomers wherein the alkyl group is a linear, branched or cyclic alkyl group as described for the monoalcohol, N-aminoalkyl amides of the olefinic carboxylic acid monomers wherein the amidating amine is a linear, branched or cyclic alkyl diamine with 2 to 12 carbons in the linear alkyl group, 3 to 12 carbons in the branched alkyl group and 3 to 12 carbons in the cyclic alkyl group. Neutral olefinic monomers including those of the formula: $HR^1C=CHR^2$ or $HR^1C=CH-CR^3=CHR^4$ wherein $R^1$, $R^2$, R3 and $R^4$ are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, OH, $CONH_2$, COOH, $-(CH_2)_n COOH$, $NO_2$, CN, $SO_3H$, $SONH_2$, pyridyl, $O_2CR'$ wherein R' is alkyl of 1 to 3 carbons, vinyl and alkyl vinyl having 1 to 3 carbons in the alkyl group.

Preferred embodiments of the hydrophilic monomer of the organic polymer include olefinic carboxylic acids and sulfonic acids selected from one or more of (meth)acrylic acid, crotonic acid, pentenoic acid, hexenoic acid, maleic acid, fumaric acid, glutaconic acid, itaconic acid, citraconic acid, mesaconic acid, vinyl sulfonic acid or any combination thereof. More preferred olefinic carboxylic acids include (meth)acrylic acid, crotonic acid, vinyl sulfonic acid, maleic acid, fumaric acid and itaconic acid. Most preferred olefinic carboxylic acids include (meth)acrylic acid, crotonic acid, maleic acid and itaconic acid. Especially preferred olefinic carboxylic acids include (meth)acrylic acid and crotonic acid.

Additional preferred embodiments of the hydrophilic monomer of the organic polymer alone or in combination with preferred olefinic carboxylic and sulfonic acids include the preferred hydroxyalkyl esters of the foregoing preferred acids esterified with a C2-C6 diol including ethylene diol, propylene diol, butylene diol, pentylene diol or cyclohexane diol aminoethanol, aminopropanol and aminobutanol. Especially preferred hydroxyalkyl esters include the more preferred olefinic carboxylic acids esterified with any of these C2-C6 diols. More preferred hydroxyalkyl esters include the most preferred olefinic carboxylic acids with ethylene diol, propylene diol or butylene diol.

Additional preferred embodiments of the hydrophilic monomer of the organic polymer alone or in combination with the preferred olefinic carboxylic and sulfonic acids or in combination with the preferred hydroxyalkyl esters or in combination with the preferred carboxylic and sulfonic acids and the preferred hydroxyalkyl esters includes the aminoalkyl esters of the preferred olefinic carboxylic and sulfonic acids esterified with a C2 C4 amino alcohol including amino ethanol, amino propanol and aminobutanol. More preferred aminoalkyl esters include the more preferred olefinic carboxylic acids esterified with amino ethanol or amino propanol.

Additional preferred embodiments of the hydrophilic monomer of the organic polymer alone or in combination with preferred olefinic carboxylic and sulfonic acids, or in combination with the preferred hydroxyalkyl esters or in combination with the preferred amino alkyl esters and with any combination thereof include the mercapto alky esters of the preferred olefinic carboxylic and sulfonic acids. The preferred mercapto alcohols for these esters include mercaptoethanol, mercaptopropanol and mercaptobutanol. More preferred mercaptoalkyl esters include the more preferred olefinic carboxylic acids esterified with mercaptoethanol.

Additional preferred embodiments of the hydrophilic monomer of the organic polymer alone or in combination with preferred olefinic carboxylic and sulfonic acids, or in combination with the preferred hydroxyalkyl esters or in combination with the preferred amino alkyl esters, or in combination with the preferred mercaptoalkyl esters and with any combination thereof include polar olefinic monomers selected from p-hydroxystyrene, styrene-p-carboxylic acid, o,p-dihydroxystyrene, styrene-p-sulfonic acid and any combination thereof.

Preferred embodiments of the hydrophobic monomer of the organic polymer include the alkyl esters wherein the preferred olefinic carboxylic and sulfonic acids are esterified with a C1 to C8 alcohol including methanol, ethanol, propanol, isopropanol, butanol, isobutanol, pentanol, isopentanol, hexanol, isohexanol, ethylhexanol, cyclohexyl alcohol. More preferred alkyl esters include the more preferred olefinic carboxylic acids esterified with ethanol, propanol, butanol, ethylhexanol or cyclohexyl alcohol. Most preferred alkyl esters include the most preferred olefinic carboxylic acids esterified with ethanol, butanol, ethylhexanol or cyclohexyl alcohol.

Additional preferred embodiments of the hydrophobic monomer of the organic polymer include non-polar olefin monomers selected from styrene, methylstyrene, ethylstyrene, propylstyrene, butadiene, 1-phenylbutadiene, isoprene or any combination thereof.

Yet additional preferred embodiments of an aromatic monomer that may be a hydrophobic monomer or a hydrophilic monomer include styrene, butadiene, phenyl butadiene, isoprene, 4-vinylbenzenecarboxamide, 4-vinyl benzoic acid, ethyl 4-vinyl benzoate, vinyl phenol, 4-vinyl-1-hydroxymethyl benzene, butene, pentene, hexene, divinyl benzene or any combination thereof.

Preferred combinations of the recited species of the hydrophilic monomer and the hydrophobic monomer of the foregoing preferences include any combination of the recited preferred non-polar olefinic monomers, the recited preferred polar olefinic monomers, the recited preferred alkyl esters, the recited preferred hydroxyalkyl esters, the recited preferred aminoalkyl esters, the recited preferred mercapto alkyl esters and the preferred olefinic carboxylic and sulfonic acids. The choice of any combination of these species means selection of the first species of the preferred list of olefinic carboxylic and sulfonic acids, selection of the first species of the preferred list of hydroxy alkyl esters, selection of the first species of the preferred list of amino alkyl esters, selection of the first species of the preferred list of mercapto alkyl esters, selection of the first species of the preferred list of preferred polar olefinic monomers and selection of the first species of the preferred list of non-polar olefinic monomers and combining any two of the selections, any three of the selections, any four of the selections, any five of the selections or combining all six of the selections according to the parameters indicating the amounts of hydrophilic monomer and hydrophobic monomer are to be present in the organic polymer. The choice may also be made in a similar fashion by choosing any species from any preferred list and combining it with any species of any other list or multiple lists to provide all combinations of selections.

The organic polymer embodiments generally may have an acid value ranging from zero or 0.01 to about 700, preferably about 1 to about 500, more preferably 2 to 250, most preferably 7-90 with typical acid numbers below approximately 100. Typical hydroxyl content may average approximately 1 to 20 wt % or may be approximately 3.3 wt %. The organic polymer may have a weight average molecular weight in the range of about 2 KDa to about 2 MDa, preferably about 2 KDa to about 100 KDa, more preferably about 2 KDa to about 25 KDa. The organic polymer may have a glass transition temperature of from about −125° C. to about 90° C.

The preferred arrangement of the first functional groups in the organic polymer provides that each member of the first functional group list individually and separately is present at a minimum number of two per majority of organic polymer molecules and may be distributed throughout the polymer backbone and/or along the branch chains. In addition, multiple first functional groups may be present at a single position on the backbone and especially on branch chains. An example of such a multiplicity would be a branch chain ending with a t-butyl group, the three termini of which have hydroxyl groups. The number of a particular first functional group present in a molecule can be assessed by calculating the number average polymer molecular weight divided by the first functional group equivalent weight. Where the equivalent weight refers to the normal definition of mass of polymer which has one equivalent reactive group, in this case the first functional group. If this gives a value of 2, this shows that the average polymer has two first functional groups. The minimum means only that a minimum of two of a single member of the first functional group may be present or there may be present multiples of two of any one or more of the other members of the first functional group. This arrangement provides minimums, without reference to the presence of other functional groups, of two hydroxyl groups, two amine groups, two mercapto groups, two carboxylic or sulfonic acid groups, two vinyl groups and two olefinoyloxy groups. A minimum number of three is preferred individually and separately for each kind of functional group. A minimum number of four is more preferred individually and separately for each kind of functional group. A minimum number of five is most preferred for carboxyl and hydroxyl groups and a minimum number of at least two or three carboxyl groups is preferred in the presence of other functional groups provided that the multiple presence is mutually compatible. Not all organic polymer molecules will have the same number of functional groups; however, a majority to substantially greater than a majority of the organic polymer molecules such as from 95 mole percent to 98 mole percent will statistically have the same number of functional groups. Some organic polymer molecules may have more than the specified number of functional groups; however, statistically this number will be less than a majority and preferably statistically will be significantly less than a majority such as less that a 10 mole percent, more preferably less than a 5 mole percent and most preferably less than a 2 mole percent.

The organic polymer may be constructed with random distribution of the different monomer units along the polymer backbone and/or branches or may be block copolymers which has blocks of single monomer units or may be a graft copolymer which has one monomer unit forming the polymer backbone and a different monomer unit forming polymeric side chains. The different constructions of polymer provide differing polymer to polymer binding properties and different macromolecular characteristics. The block copolymer can provide regions of hard and soft polymer characteristics. A block copolymer can display crystalline regions and amorphous regions that can enable development of water soluble and water resistant regions. Blocks of differing electronic and lipophilic character can impart an open repulsive character to the polymer so that tightly fit inter-structures are minimized. A graft polymer or segmented polymer is capable of intertwined conformation and compact molecular dimension so as to enable tightly fitted inter-structures.

Additional organic polymer embodiments may comprise one or more monomer unit(s) comprising one or more functional group(s) selected from the group consisting of sulfate, sulfonate, carboxylate, phosphate, phosphonate groups and mixtures thereof as substitutes for the olefinic carboxylic acids of the hydrophilic monomer of the organic polymer. These monomer units may be combined with the other hydrophilic monomers and with the hydrophobic monomers described above to form additional embodiments of the organic polymer. The functional group(s) may preferably be selected from the group consisting of sulfate, sulfonate, carboxylate groups and mixtures thereof. Additionally, anionic polymers of such monomeric units may be combined with the organic polymer embodiments described above to form a mixture of anionic polymer and organic polymer.

The polymeric portions of these substitutes for the acidic hydrophilic units constitute monomers from anionic polymers selected from the group consisting of polystyrene sulfonate salts, k-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The salts may be sodium salts.

Examples of the anionic polymer(s) from which such substitute acidic monomers may be selected may be but are not limited to embodiments including:

a) Polystyrene sulfonate (PSS) sodium salt of the formula:

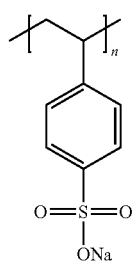

in which n is an integer representing the degree of polymerization, wherein n ranges from 50 to 20,000, alternatively from 150 to 500;

b) Co-polymer of polystyrene sulfonate (PSS) sodium salt and poly(4-styrenesulfonic acid-co-maleic acid) of the formula:

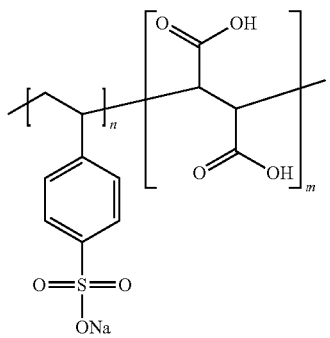

in which n and m are integers representing the degree of polymerization, wherein n+m ranges from 50 to 20,000, alternatively from 150 to 2500;

c) λ-Carrageenan;
d) Dextran sulfate sodium salt;
e) Polyacrylic acid (PAA) of the formula:

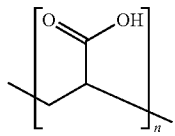

in which n is an integer representing the degree of polymerization, wherein n ranges from 50 to 20,000, alternatively from 150 to 5000;

f) Alginic acid sodium salt;
g) Carboxymethylcellulose sodium salt of the formula:

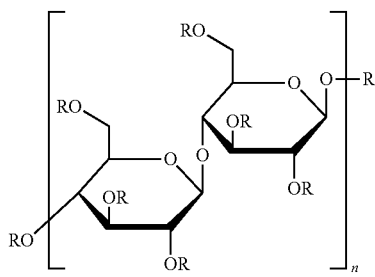

in which: R is H or $(CH_2)_2COONa$ and n is an integer representing the degree of polymerization; copolymers thereof and mixtures thereof.

h) These polymers and copolymer embodiment examples as well as the corresponding monomeric units may be random or block copolymers in combination with the hydrophobic monomers and hydrophilic monomers described above for the organic polymer except that these monomeric units may alternatively be substitutes for the olefinic carboxylic acids of the hydrophilic monomers of the organic polymer.

Second Component, In Situ Linking Material

Embodiments of the in situ linking material may comprise organic small molecules, organic oligomers, organic polymers, siloxanes, polysiloxanes, polyorganosiloxanes or polysilicones. More specifically, embodiments of the in situ linking material may comprise a linear and/or branched organic or silicone core to which is bonded the second functional groups. The organic core may be an organic small molecule including a saturated aliphatic compound or an aromatic compound. The organic core may also be an organic oligomeric compound or an organic polymeric compound designated by the symbol Cpd. The silicone core may be a siloxane, a polysiloxane, a polyorganosiloxane or a polysilicone designated by the symbol Sicpd. The backbone and/or branches of the organic core and the silicone core are bonded to at least two pendant or terminal or pendant and terminal second functional groups. The second functional groups may be distributed throughout the core including the backbone and branches. The second functional groups may be singly or multiply arranged at a single location of the polymer and in either arrangement may be distributed throughout the backbone and branches.

The embodiments of the organic core comprise the small molecule including a saturated aliphatic compound which may be a linear or branched alkyl group of 2 to 24 carbons or a cyclic alkyl group of 5 to 24 carbons. The organic core also comprises an aromatic compound which may be a phenyl, naphthyl, diphenylmethyl, pyridyl, quinolinyl, quinazolinyl or anthracenyl group. The organic core also comprises the polymeric compound Cpd which may be a poly (meth)acrylate with methyl or ethyl ester groups except for the second functional groups, polycrotonate with methyl or ethyl ester groups except for the second functional groups, a polyether, a polyol, a polyurethane, a polyurea, a polyester of a diacid and a diol or of a hydroxy acid, a polymer of one or more monomers of C1-C6 alkyl (meth)acrylate, styrene and a C6-C12 olefin. The polymeric compound Cpd has a weight average molecular weight of from about 0.2 kDa to about 10 kDa.

The embodiments of the silicone core comprise the silicone compound Sicpd including a siloxane, a polysiloxane, a polyorganosiloxane or a polysilicone. Embodiments of Sicpd may be a silane, a di, tri or tetrasilane, an oligosilane, a siloxane, a di, tri or tetrasiloxane, a polysiloxane, a poly organosiloxane, a polyorganosilicone wherein organo groups, if any, are C1-C3 alkyl groups. The Sicpd compound has a weight average molecular weight of from about 0.2 kDa to about 10 kDa.

Each embodiment of the core is bound to at least two second functional groups of the structure of Formula I:

—R—Oq-R'X            Formula I

For Formula I:
(i) the designator q is zero or one.
(ii) R is a C6-C10 aromatic group, a C1-C24 alkylenyl or a C1-C24 oxyalkylenyl residue or a dimethylsiloxanyl chain of 3 to 9-O—Si(Me)$_2$- units and the valence bond of R is attached to directly to the core or attached through an ether oxygen to the organic core, or
(iii) R is a C1-C24 alkylenyl residue, a C1-C24 oxyalkylenyl residue or a C1-C24 carbonylalkenyl residue and the valence bond of R is attached directly or through an ether oxygen —O— to the silicone core, Sicpd.
(iv) R' is a bond or is a linear or branched alkyl or alkanoxyalkyl or alkanaminoalkyl group of Formula III

[—(C1-C6)$_m$-] or [—(C1-C6)$_n$-(CHOH)$_p$(C1-C6)$_r$-Y$_p$—(C1-C6)$_s$—]            Formula III wherein the C1-C6 group is a linear or branched alkyl group of 1 to 6 carbons and the designators m, n, r and s associated with each C1-C6 indicate the total number of carbons possible for the group, the maximum being 24; m is zero or an integer of 1 to 4, n is zero or an integer of 1 to 4, p is zero or one, r is zero or an integer of 1 to 4, s is zero or an integer of 1 to 4, Y is O or N. When all of the designators m, n, p, r, p and s are all zero, R' is a bond.

(v) X is isocyanato, thioisocyanato, linear, branched or cyclic epoxyalkyl, olefinoyloxy such as (meth)acryly-loxy, crotonyloxy, malonic anhydrido, formyl, amino, hydroxyl, mercapto, furanyl, cyclopentadienyl or azide.

A further embodiment of the in situ linking material provides that X of Formula I may be a mono, di, tri or tetra dimethyl siloxane group to which is terminally bonded a reactive silanyl group including silanol group (Si—OH) or an alkoxysilane (Si—OR) with 1 to 6 carbons in the alkoxy group, an SiR$_2$OAc group, an Si—O—N=CHR group, or Si—H group. The in situ linking material of this embodiment may contain two or more of Formula I having the reactive silanyl group. This embodiment presents Si—OH, Si—OR, Si—OAc and Si—O—N=CHR silanyl reactive species which will combine with corresponding reactive silanyl first functional groups of the residue of Formula IV of the organic polymer when the organic polymer has the siloxane monomeric residue of Formula IV as a first functional group. Also, this embodiment presents Si—H reactive species which will combine with the corresponding S—CH=CH$_2$ species of the organic polymer.

The group X in coordination with the chemical and physical properties of the core of the in situ linking material provides in situ linkability with the organic polymer having first functional groups including a hydroxyl, carboxyl, amine, mercapto, vinyl, olefinoyloxy, azide or Si—OH/SiOR/SiOAc/SiONCHR/Sivinyl or any compatible combination thereof. These in situ linkable features enable the in situ linking material to be covalently, ionically, electrostatically, coordination-wise and/or entanglement-wise interactive with the organic polymer and its first functional groups.

Reactive Pairs of Functional Groups

The multicomponent composition presents first and second functional groups disposed within the same class (autoreactive) or on first and second polymer (so as to facilitate bonding of first and second materials via complementary functional groups) that may be arranged so as to constitute reactive pairs. As discussed above, not all members of a functional group class are compatible with each other. For example, the presence of isocyanate and amine or hydroxyl on the same in situ linking material would lead to undesired self-reaction of such an in situ linking material. Other differing members of a functional group class are compatible with each other, such as carboxyl, amine, hydroxyl and mercapto. Although these members of the first functional group have the potential for forming amide, ester and thioester groups, the activation energy needed to cause such as conversion is too high to enable reaction at typical and customary environmental conditions. A catalyst or activation agent is customary in such circumstances. For these reasons, selection of differing members of the first functional group to include within an organic polymer and selection of differing members of the second functional group to include within the in situ linking material will account for the ability or lack of ability of the differing members to undergo undesired combination under ordinary conditions. The choice of first and second functional groups for the organic polymer and the in situ linking material follows the principle of complimentary reactive pairs. These pairs are:

(i) isocyanante or thioisocyanate and hydroxyl, amine or mercapto or any combination of hydroxyl, amine and mercapto;
(ii) carboxyl and hydroxyl, amine or mercapto or any combination of hydroxyl, amine and mercapto in combination with catalyst;
(iii) epoxy and hydroxyl, amine or mercapto or any combination of hydroxyl, amine and mercapto;
(iv) cycloalkylepoxy and hydroxyl, amine or mercapto or any combination of hydroxyl, amine and mercapto;
(v) olefinoyloxy and hydroxyl, amine or mercapto or any combination of hydroxyl, amine and mercapto;
(vi) melonic anhydride and hydroxyl, amine or mercapto or any combination of hydroxyl, amine and mercapto;
(vi) formyl (—CHO) and amine or mercapto or any combination of amine and mercapto;
(vii) azido and alkynyl;
(ix) vinyl and mercapto or amine and any combination of amine and mercapto;
(x) mercapto and mercapto;
(xi) any combination of Si—OH, Si—OR, Si—OAc, Si—O—N=CHR;
(xii) Si—H and Si—CH=CH$_2$.

Preferable reactive pairs of the preceding paragraph include the isocyanate/thioisocyanate and its counterparts, entry (i) above; epoxy and its counterparts, entries (iii and iv) above; olefinoyloxy and its counterparts, entry (v) above; vinyl and mercapto and its counterparts, entry (ix) above; mercapto and mercapto, entry (x) above; and silanol or alkoxysilane and its counterparts, entry (xi) above. More preferred reactive pairs include the isocyanate/thioisocyanate pairs, the epoxy pairs, the mercapto pairs and the silanol/alkoxysilane pairs. Especially more preferred reactive pairs include the isocyanate pairs, the silanol/alkoxysilane pairs and the epoxy pairs. Most preferred reactive pairs include the isocyanate pairs.

Especially preferred embodiments of the in situ linking material include di and tri isocyanates, di and tri epoxides, di and tri olefinoyloxy groups such as acrylyloxy and crotonoxy groups, and silanol and alkoxy silane groups. Exemplary di and tri-isocyanates are formed on polyureido or polyurethane backbones with hexamethylene di and tri isocyanate moieties. Additional isocyanate embodiments include monomeric diisocyanates such as toluene diisocyanate, diphenylmethane diisocyanate, hexamethylene diisocyanate, bis isocyanatocyclohexyl methane, isophorone diisocyanate. Additional isocyanate embodiments include polyisocyanates such as trimethylolpropane triisocyanate, biuret triisocyanate, isocyanurate triisocyanate, uretdione hexamethylene diisocyanate, trimers of the monomeric diisocyanates, and blocked polyisocyanates such as any of the monomeric diisocyanates in which the isocyanates are reacted with any of the blockers: phenol, E-caprolactam, butanone oxime or dimethyl pyrazole. When an alcohol or primary amine is combined with the blocked isocyanate, the alcohol or amine displaces the blocker to form a urethane or urea respectively.

Alternatively, when the organic polymer contains residual unsaturation resulting from polymerization of a diene, an aromatic olefin having a vinyl substituent bonded to the aromatic ring, or an olefinoyloxy group resulting from post-polymerization transformation, the fourth component may be substituted for the second component and the fourth component can be selected to promote coordination or complexation among the residual unsaturation sites of molecules of the organic polymer or can be selected as a free radical initiator to promote free radical coupling of the residual unsaturation sites. In this embodiment, the organic polymer is capable of in situ self-linking.

Also, alternatively, when the organic polymer contains pendant or terminal or pendant and terminal silanol or alkoxysilane groups of Formula IV, the fourth component may be substituted for the third component and second components. The fourth component can be selected to promote condensation between silanol and alkoxysilane groups of the organic polymer. The fourth component is this embodiment is water or a cure catalyst. In this embodiment, the organic polymer is capable of in situ self-linking The Third Component (Base Compound)

Embodiments of the third component may combine with embodiments of the first and second components of the multicomponent composition to meld together (e.g., blend, combine, unite together as one) these components into a colored coating on treated material that displays significant remanence. Embodiments of the substantive feature of the third component are the base compound. Embodiments of the base compound incorporate amine groups into and onto an organic or silicone core or chain. The base compound preferably has a weight average molecular weight of about 150 Da to about 1 MDa. When the base compound is a polymer, preferably about 400 Da to about 500 KDa, more preferably about 400 Da to about 250 KDa, most preferably about 2 KDa to about 100 KDa.

Embodiments of the base compound as an organic core with amine groups may be one or more amine polymer(s). The amine polymer(s) may comprise one or more amino functional group(s) per polymer chain, wherein the amino functional group(s) are selected from the group consisting of primary, secondary and/or tertiary amino functional groups and mixtures thereof, preferably from the group consisting of secondary and tertiary amino functional groups and mixtures thereof.

Embodiments of the base compound may be selected from the group consisting of polyethyleneimine, polyallylamine hydrochloride, polydiallyldimethylammonium chloride, polyvinylamine, aminopolysaccharide, aminosilicones, copolymers thereof and mixtures thereof. The polymer(s) may preferably be selected from the group consisting of polyethyleneimine, aminosilicone, polydiallyldimethylammonium chloride, copolymers thereof and mixtures thereof.

Additional embodiments of the base compound include polymers with carboxylate groups, sulfonate groups, carbamate groups and mercaptan groups. Exemplary base compounds include polymercaptan compounds such as tri-(mercaptoethylenyl) methane, di, tri and poly sulfonate compounds such as tri-(sulfoethylenyl) methane, di, tri and poly carboxylate compounds such as adipic acid, citric acid and polyacrylic acid, and carbamate compounds such as tri-(methylcarbamoylethylenyl) methane.

Preferred base compounds are those carrying amine functionality. These embodiments of the base compound may be linear or branched and/or may be random or block copolymers.

As amine polymer(s) such as the embodiments of the base compound described above, exemplary selections include:

e) Linear polyethyleneimine of the formula:

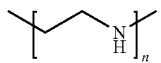

in which n is an integer representing the degree of polymerization, wherein n ranges from 5 to 25,000, alternatively from 11 to 2,500;

f) Branched polyethyleneimine consisting of primary, secondary and tertiary amine groups of the formula:

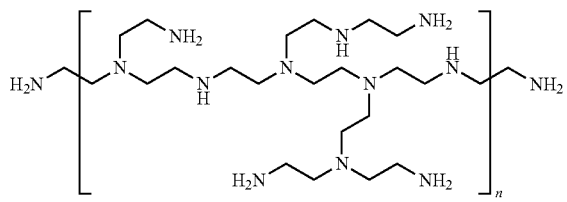

in which n is an integer representing the degree of polymerization, wherein n ranges from 2 to 4,000, alternatively from 5 to 500;

g) Polyallylamine hydrochloride of the formula:

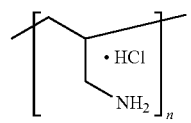

in which n is an integer representing the degree of polymerization, wherein n ranges from 50 to 20,000, alternatively from 5 to 1250;

h) Polydiallyldimethylammonium chloride of the formula:

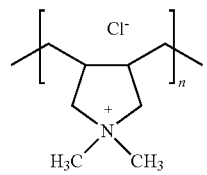

in which n is an integer representing the degree of polymerization, wherein n ranges from 10 to 20,000, alternatively from 150 to 4,000;

copolymers thereof and mixtures thereof.

These embodiments of the base compound, e.g., the amino polymer(s), may have a charge density when fully protonated of at least 0.3, preferably at least 0.6, more preferably at least 0.8, even more preferably at least 1.0 positive charges per monomer unit.

Embodiments of the base compound may also be amino silicone compounds. Embodiments of the amino silicone polymer base compound may comprise any silicone polymer chain that incorporates amine functional groups into the silicone polymer. The amino silicone compounds may also be aminosiloxane compounds or oligomers and aminosilane compounds.

A preferred silicone polymer is one having amine functional groups (hereinafter an aminosilicone polymer). The molar ratio of siloxane monomeric units with at least one pendant organic amine group (hereinafter SiA moieties) to siloxane monomeric units having silicon bonded to a substituent selected from the group consisting of alkyl (C1 to C6) (hereinafter SiC moieties) is in the range of from about 1:1000 to 1:10 (ratio of SiA units to SiC units), preferably 1:1000 to 1:25, more preferably 1:600 to 1:50, most preferably 1:400 to 1:75 or 1:300 to 1:200. An SiA moiety may contain more than one amine group in which case it counts as just one SiA moiety. An SiC moiety may contain any number of other pendant groups as long as a primary, secondary, tertiary or quaternary amine group is not present. The aminosilicone polymer may have a weight average molecular weight ranged from about 10 kDa to about 150 kDa, preferably about 18 kDa to about 130 kDa, more preferably about 22 kDa to about 120 kDa.

The amine functional groups of the aminosilicone polymer may be primary, secondary, tertiary amine groups or quaternary ammonium groups or any combination thereof. The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—Si(R')$_2$—O— wherein each R' is independently selected from a pendant organic amine group and an alkyl group of 1 to 6 carbons and at least one R' group is a pendant organic amine group. The organic amine group may be a linear alkyl group of 1 to 16 carbons or a branched or cyclic alkyl group of 3 to 16 carbons. The alkyl group may contain one or more heteroatoms and/or hetero-groups in the chain including such groups as —NH—, —O—, —S—, —CONH— or —NHCO—, —SO$_2$NH— or —NHSO$_2$—. Typical pendant amine groups include such arrangements as:

—(CH$_2$)$_3$—NH—(CH$_2$)$_3$NH$_2$, —CH$_2$—CH(CH$_3$)—CH$_2$—NH—(CH$_2$)$_3$NH$_2$

—(CH$_2$)$_3$—CONH—(CH$_2$)$_3$NH$_2$, —(CH$_2$)$_3$—NHCO—(CH$_2$)$_3$NH$_2$ and single amine groups such as —(CH$_2$)—NH$_2$ wherein n is 2 to 6, preferably 3 or 4 or branched chain versions thereof such as —CH$_2$—CH$_2$—CH$_2$—NH$_2$, —CH$_2$—CH(CH$_3$)—CH$_2$—NH$_2$.

The amine group or groups may be pendant to the silicone chain at uniform or random locations along and within the silicone chain. The amine functional group may also terminate the ends of the silicone chain but an aminosilcone polymer having terminal amine groups preferably will also have pendant amine groups along the silicone chain. If the aminosilicone polymer contains only terminal amine groups, its weight average molecular weight preferably will be low so that its SiA:SiC ratio will conform to the foregoing values.

The silicone chain of the aminosilicone polymer may be linear, branched or crosslinked. In addition to the SiA and SiC moieties, aminosilicone may also include any one or more of MDTQ groups of the formulas A, B, C and D wherein R is a methyl group:

A) —O(R)$_2$Si—O— (known as a D siloxane unit)
B) —O(R)SI(—O—)$_2$ or —O—Si(—O—)$_2$—O— (known as T siloxane unit and Q sesquisilicate unit respectively)
C) (R)$_3$SI—O— (known as M siloxane unit).

For this embodiment of the aminosilicone polymer component of the base compound the A), B), C) and D) groups constitute together the SiC moieties defined above. The A) group provides a linear silicone chain link, the B) group provides a branched or crosslinked silicone chain link, the C and D groups provide a silicone chain termination. The distribution of the SiA moiety and the A), B), C), and D) groups of the SiC moiety follows ordered or random arrangement and the SiA to SiC ratios and weight average molecular weight ranges given above.

The Fourth Component

The fourth component is an agent that catalyzes the in situ covalent reaction of the complementary reactive pairs and self-reactive functional groups. The agent may also be a chemical enhancer for overcoming activation energy of the in situ reaction, an enzyme, a coordination complex or complexing agent for promoting the functional group interaction. Lewis acids, enzymes for ester and amide formation, carbodiimides, Friedel Crafts catalysts, Lewis bases, mixed anhydrides, leaving group donators, and similar chemical entities are examples of such agents. The fourth component is optional and typically is added when the complementary reactive pair or the self-reactive functional group typically does not covalently react under normal environmental conditions. For the silanol/alkoxysilane condensations, a typical activation agent is water.

Relationships and Preferences for the Components

Embodiments indicating the ratios for combination of the first, second and third components of the multicomponent composition relate to the numbers of functional groups of each of these components. In one embodiment, the organic polymer has at least two or three first functional groups per molecule, the in situ linking material has at least two or three second functional groups per molecule and the base compound has at least two or three third functional groups per molecule. In another embodiment, the organic polymer has at least three or four first functional groups per molecule, the in situ linking material has at least three or four second functional groups per molecule and the base compound has at least three or four third functional groups per molecule. In yet another embodiment, the organic polymer has at least two or three functional groups per molecule, the in situ linking material has at least three to five functional groups per molecule and the base compound has at least two functional groups per molecule so that there is a slight excess of in situ linking material functional groups per molecule relative to the total number of functional groups of the organic polymer and base compound.

Preferred embodiments of the organic polymer follow the preferred relationships described above. An especially preferred embodiment of the organic polymer includes an organic polymer comprising the hydrophilic monomer as (meth)acrylic acid and hydroxyethyl or hydroxypropyl (meth)acrylate, the hydrophobic monomer as methyl or ethyl (meth)acrylate, and no olefin monomer such as styrene or detectable or moderate amount of olefin. An additional especially preferred embodiment of the organic polymer includes an organic polymer comprising the hydrophilic monomer as crotonic acid, hydroxyethyl crotonate or hydroxypropyl crotonate; the hydrophobic monomer as methyl or ethyl crotonate, and the no olefin monomer such as styrene or a detectable amount or a moderate amount of the olefin.

A preferred embodiment of the combination of the first, second and third components of the multicomponent composition includes a combination of a preferred organic polymer embodiment, a preferred in situ linking material embodiment and a preferred base compound embodiment. The preferred organic polymer comprises either of the preferred organic polymers of the foregoing paragraph. Additional preferred organic polymers include those constructed of monomeric units of alkyl (meth)acrylate or alkyl crotonate or a combination thereof with the alkyl group being 1 to 3 carbons; hydroxyalkyl (meth)acrylate or hydroxyalkyl crotonate or a combination thereof with the alkyl group being 1 to 3 carbons; (meth)acrylic acid or crotonic acid or any combination thereof; and optional styrene. The preferred in situ linking material comprises hexamethylene diisocyanate, isophorone diisocyanate, toluene diisocyanate, diphenylmethane diisocyanate, a dimer or trimer of hexamethylene diisocyanate, trimeric isophorone diisocyanate or biuret triisocyanate. The preferred embodiment of the base compound is polyethylene imine.

An especially preferred embodiment of the first, second and third components incorporates an organic polymer comprising monomeric units of alkyl (meth)acrylate, hydroxyalkyl (meth)acrylate and (meth)acrylic acid wherein the hydroxyl content ranges from 1 wt % to about 20 wt % with a preference of from 2 wt % to about 5 wt % and a typical weight percent of about 3.3 wt %. The acid number may be 7-90 with a typical acid number below approximately 100. The especially preferred embodiment also incorporates an in situ linking material comprising a di or tri isocyanate oligomer formed with hexamethylene diisocyanate and a base compound of polyethylene imine.

Yet another especially preferred embodiment of the multicomponent composition includes the combination of first, second and third components. The organic polymer comprises monomeric units selected form C1-C12 alkyl (meth)acrylate, C2-C12 hydroxyalkyl (meth)acrylate or C2-C12 aminoalkyl (meth)acrylate, (meth)acrylic acid and optional styrene. The in situ material is selected from any one of the following compounds: an alkyl core or polymeric compound Cpd containing two or more epoxides, an alkyl core or polymeric compound Cpd containing two or more acryloxyvinyl groups, an alkyl core or polymeric compound Cpd containing two or more amino groups or an alkyl core or polymeric compound Cpd containing two or more isocyanate groups. The third component comprises polyethyleneimine or aminosilicone.

An additional preference for the in situ linking material of the foregoing acrylate combination includes an in situ linking material such as bis (4-isocyanatocyclohexyl) methane or isophorone diisocyanate or hexamethylenediisocyanate, trimethylolpropane coupled with one of the foregoing diisocyanates, biuret of hexamethylene diisocyanate, or isocyanurate of tri hexamethylene diisocyanate.

Another preference for the in situ linking material of the foregoing acrylate combination include an in situ linking material designated as a polymeric compound Cpd which is acryloxyvinyl polymer of alkyl (meth)acrylate and the hydroxyvinyl ester of (meth)acrylate with the (meth)acrylate group being a pendant group.

An especially most preferred embodiment of the combination of the first, second and third components of the multicomponent composition includes the organic polymer as a copolymer of ethyl (meth)acrylate, C2-C6 hydroxyalkyl (meth)acrylate and about 0.1 to about 5 wt % of (meth)acrylic acid relative to the weight of the organic polymer; the in situ material as bis (4-isocyanatocyclohexyl) methane or isophorone diisocyanate or hexamethylenediisocyanate, trimethylolpropane coupled with one of the foregoing diisocyanates, biuret of hexamethylene diisocyanate, or isocyanurate of tri hexamethylene diisocyanate and the base compound as polyethyleneimine; and the fourth component is an agent is a catalyst for the conversion of isocyanate to urethane and/or urea groups.

Another preferred embodiment of the multicomponent composition excludes the second component such that the first component is self-linking. The organic polymer of this self-linking component is repeating units of a hydrophobic monomer and a hydrophilic monomer. The hydrophobic monomer is selected from styrene and one or more of butadiene and isoprene. The hydrophilic olefinic monomer is selected from a hydroxyl ester of an olefinic carboxylic acid and an alkyl diol of 2 to 24 carbons, a C3-C5 olefinic carboxylic acid or a C4-C6 olefinic dicarboxylic acid or a combination thereof. The fourth component is present and is inorganic complexation agent or a catalyst or a free radical initiator. The inorganic complexation agent preferably is zinc or zirconium carbonate which coordinatively complexes with the residual olefinic groups of the organic polymer.

The third component of the foregoing multicomponent composition containing a self-linking organic polymer is an aminopolymer, preferably polyethyleneimine.

An especially preferred embodiment of the multicomponent composition includes a self-linking organic polymer as a copolymer of styrene, butadiene, and itaconic acid so that the copolymer has residual unsaturation. There is no second component. The third component comprises polyethyleneimine. The fourth component comprising a free radical initiator or the second component comprising an inorganic coordination cross-linker agent or mercapto cross-linker optionally combined with the polymer. The first component and the third component are maintained separately or may be combined and the fourth component is maintained separately from the first and third components.

A highly preferred embodiment of the multicomponent composition sets out specifications for the organic polymer, the in situ linking material, the base compound and a relative relationship among the first, second and third functional groups. These first, second and third components include medium.

The organic polymer of this highly preferred embodiment comprises an organic polymer of the combination of hydrophobic monomers and hydrophilic monomers. The hydrophobic monomer comprises a C1-C24 alkyl linear or branched (meth)acrylate monomer or a C1-C24 alkyl linear or branched crotonate monomer or a combination thereof and optional styrene. The styrene may be absent or may be present up to a moderate amount such as up to 20 wt % or up to 50 wt % relative to the total weight of the organic copolymer. The hydrophilic monomer comprises an olefinic acid selected from (meth)acrylic acid or crotonic acid or a combination thereof, and a hydroxyalkyl olefinic ester selected from hydroxymethyl or hydroxyethyl (meth)acrylate or crotonate or any combination thereof. A preferable arrangement of this organic polymer comprises ethyl(meth)acrylate, hydroxyethyl (meth)acrylate and (meth)acrylic acid with optional styrene which may be absent or when present may be present at a weight percentage relative to the total weight of the organic polymer of from zero up to about 30 wt %. The WMW of the organic polymer may be in the range of about 2 KDa to about 25 KDa. The acid number of the organic polymer is in a range of about 7 to about 90. The hydroxyalkyl olefinic ester portion of the organic copolymer is in a range of about 1-5 wt % preferably about 3 to 4 wt % relative to the total weight of the organic copolymer.

The in situ linking material of this highly preferred embodiment comprises a bis (4-isocyanatocyclohexyl) methane or isophorone diisocyanate or hexamethylenediisocyanate, trimethylolpropane coupled with one of the foregoing diisocyanates, biuret of hexamethylene diisocyanate, or isocyanurate of tri hexamethylene diisocyanate. The molar ratio of free isocyanate groups to hydroxyl groups is in a range of about 0.5:2 to 25:1, preferably about 1:1 to about 15:1.

The base compound of this highly preferred embodiment is polyethyleneimine at a concentration of 0.1-5% in an aqueous medium relative to the total weight of the combination of the base compound and the medium. The third component is arranged to be applied to the treated material as a pretreatment before application of the first and second components.

The medium for the organic polymer of this highly preferred embodiment is water. The in situ linking material is neat and is combined with the first component immediately before use. The weight percentage of the organic polymer and the in situ linking material is between 1-10 wt. % of the combined first and second components including the medium and optional pigment.

Another highly preferred embodiment of the multicomponent composition sets out the specifications for a self-linking organic polymer, the base compound and a relative relationship among the first and third functional groups. In this embodiment, the second component is not present as the organic polymer is self-linking. The first and third components include medium.

For this second highly preferred embodiment, the organic polymer comprises repeating units of a hydrophobic monomer and a hydrophilic monomer. The hydrophobic monomer is selected from a non-polar olefinic monomer having the formula $H_2C\!=\!CHR$ wherein R is selected from hydrogen, ethyl, propyl, isopropyl, butyl, phenyl, hydroxyphenyl, nitrile or $-CR^2\!=\!CHR^1$ wherein $R^1$ is hydrogen, methyl, ethyl or phenyl; wherein $R^2$ is H or methyl; or any combination thereof. The hydrophilic olefinic monomer comprises an olefinic carboxylic acid wherein the olefinic carboxylic acid comprises alkendioic acid of 3 to 12 carbons or alkenoic acid of 3 to 12 carbons. A preferred arrangement of this organic polymer comprises a polymer of styrene, butadiene and itaconic or (meth)acrylic acid. The weight percentages of this preferred arrangement respectively are between about 5-50 wt. % of styrene, about 50-95 wt. % butadiene, and about 0-5 wt. % itaconic or (meth) acrylic acid.

The organic polymer is mixed with a medium and the organic polymer constitutes a solids content of about 1 wt % to about 40 wt % relative to the total weight of the first component.

The fourth component of this second highly preferred embodiment comprises a catalyst, coordination agent or free radical initiator for producing covalent, ionic, electrostatic or coordination among the copolymer molecules of the first component. The fourth component preferably is a carbonate salt of a cation selected from an alkali or alkali earth metal or transition metal such as the carbonate salt is zirconium or zinc cation. Alternatively, the fourth component preferably is tri or tetra mercapto or tri or tetra mercapto and a free radical initiator. Alternatively, the fourth component may also be a free radical initiator compound, a peroxide, an azo compound or a photo initiator.

The third component of this second highly preferred embodiment comprises polyethyleneimine at a concentration of 0.1-5% in aqueous medium relative to the total weight of the combination of the base compound and the medium. The third component is arranged to be applied to the treated material as a pretreatment before application of the first and second components.
The preferred parameters for this second highly preferred embodiment include an organic polymer with an acid value of the organic polymer (no acid) to about 100. A glass transition temperature of the organic polymer of from about −60° C. to about 90° C. A weight average molecular weight of the organic polymer in the range of about 2 KDa to about 10 MDa and a weight percentage of the fourth component of from 5-40% of the weight of the polymer when the fourth component is tri or tetramercaptan, or metal carbonate. The weight percentage of the free radical initiator or photo initiator is between 0.1-3 wt. % of the total composition. The organic polymer may also be optionally (at least partially) neutralized with a volatilizable amine compound selected from ammonia and an organic amine.

Viscosity, Composition Concentrations

The viscosity of the composition functions to hold the composition in place on the treated material while the in situ linked coating is formed. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat the treated material. Appropriate viscosity of the composition is the result of the interaction of the organic polymer, the in situ material, the base compound, their concentrations, and as appropriate, an optional viscosity control agent, an optional suspending agent and an optional thickening agent. Generally, the viscosity of the composition may range from about 0.001 to about 2000 Pa s$^{-1}$. Viscosity measurements are carried out on a controlled stress rheometer e.g. Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec$^{-1}$ shear rate is obtained from the shear stress vs. shear rate curve, and the corresponding viscosity is calculated by dividing the obtained shear stress by 10.

The concentration of the organic polymer in the composition may range from about 2% to about 30%, preferably about 4% to about 25%, more preferably about 6% to about 20%, most preferably about 8% to about 15% by weight relative to the total weight of the composition. Specific concentrations include about 2%, about 4%, about 6%, about 8%, about 10%, about 12%, about 14%, about 16%, about 18%, about 20%, about 22% about 24%, about 26%, about 28% or about 30% by weight relative to the total weight of the composition. The determination of the concentration for embodiments of the organic polymer and in situ linking material will depend in part upon the resulting viscosity, the saturation point of the organic polymer in the medium. As discussed above, the viscosity is managed so that the composition will not run off the surfaces of strands of hair yet will level and flow to substantially coat those surfaces. Development of appropriate viscosity in part by management of the concentration of the organic polymer can be experimentally determined by routine methods such as formulation of several samples of differing concentrations of polymer in the composition, coating those samples on a hair tress and observing the flow, spread and leveling of the composition on the hair strands. The product can be applied to a treated material such as a hair tress using the coloring procedure described herein afterwards. The top of the hair strand, where it is glued together is clamped in a stand such that the hair is aligned vertically downwards. After a 5 minute dwell time it is observed if any and how much product has dripped from the hair tress. The results obtained from the several samples can be plotted against flow time and leveling time to determine an appropriate concentration or range of concentrations of the organic polymer in the composition. A preferred concentration of the combination of organic polymer and in situ linking material in the composition ranges from about 1% to about 60%, more preferably about 2% to about 40% and most preferably about 3% to about 30% by weight relative to the total weight of the composition.

The extent of in situ linking between the first, second and third functional groups may be controlled by manipulation of ratios, amounts present and concentrations as well as by physical means as described above so that the mechanical and chemical properties of the coating as described herein are preserved. In connection with hair, these properties include ability to adhere to hair strands, ability to maintain flexibility and free flowing character of the hair, ability to provide remanence, avoidance of stickiness and avoidance of clumping.

The glass transition temperatures of the organic polymer and the in situ linking material and the base compound in part contribute to the flexibility, strength, hardness and similar qualities of the coating on the treated material surfaces. The glass transition temperature of these embodiments may range in degrees Celsius of about −125° C. to about 90° C. This glass transition temperature or $T_g$ determines the solid-solid transition of the polymer from a hard glassy material to a soft rubbery material. If the $T_g$ of the polymer is too high, the coating on the treated material will be stiff and inflexible. This is an undesirable result. The coating should be soft, flexible and unnoticeable to touch and sight yet should not flake, break-up or otherwise release from the keratin fiber, and especially from human hair, when stroked by a hand or brushed with a brush. The Tg of a polymer can be measured using ASTM D7426-08 (2008).

Examples of the organic polymer, in situ linking material and base compound of the multicomponent composition according to the present invention include the following.

Polyols based on polymers of epoxides, polymers of olefinic alcohols, polyacrylates and crotonates carrying pendant hydroxyls, acrylic polyols, polyester-polyacrylates with hydroxyl function including examples such as Aprez Acropol 120 from ACR Coatings; U-2815, D-11, D-217, U-1906AD-5, U-1907S, U-1908R, U-1933R, U-2814-70, U-3100, U-845, U-5200, U-1922, U-2101N, U-2103, U-2108, U-2811S from Add & Poly Resin Industrial; AA-857, AA-911, AA-914, AA-952V, AA-985-70, A-800-50, AA-961-60, AA-988-60, Acrydic 52-666, AA-964-60, AA-966-60, AA-971-70, Acrydic BU-955, Aklate AA-950-50, 11-408, AA-960-60, AA-962-65, AA-976-70, Acrydic GU-1023, Aklate AA-951-50, Aklate AA-952-50, Aklate AA-968-60, D-400-70 from Aekyung Chemical; Akrosyn-301, Akrosyn-302 from Akross Synthetics; Setalux 1196 XX-60, Setalux 1151 XX-51, Setalux 1193 SS-51, Setaqua 6510, Setaqua 6511, Setaqua 6513, Setaqua 6514, Setaqua 6520, Setalux 1184 SS-51, Setalux 1186 SS-60, Setalux 1190 XX-60, Setalux 1903 BA-75, Setalux 1906 BA-75, Setalux 1907 BA-75, Setalux 1908 BA-75, Setalux 1909 BA-75, Setalux 1910 BA-75, Setaqua 6515, Setaqua 6516, Macrynal SM 1009/50BAC, Macrynal SM 2703/80BACX, Macrynal SM 2711/70BAC, Macrynal SM 2727/70X, Macrynal SM 2806/75BAC, Macrynal SM 2855/70BAC, Macrynal SM 2892/65XBAC, Macrynal SM 2930/70BAC, Macrynal SM 510n/65BACX, Macrynal SM 6817w/44WA, Macrynal SM 6826w/43WA, Macrynal VSM 1509/60LG, Macrynal VSM 2155/60EPAC, Macrynal VSM 2702/58XSNA, Setalux 1152 SS-51, Setalux 1152 SS-60, Setalux 1159 SS-55, Setalux 1164 XS-65, Setalux 1179 BA-57, Setalux 1182 SS-55, Setalux 1186 VV-70, Setalux 1187 XX-60, Setalux 1189 SS-60, Setalux 1190 SS-61, Setalux 1192 SS-60, Setalux 1194 SS-51, Setalux 1196 VV-60YA, Setalux 1198 SS-70, Setalux 1199 XS-60, Setalux 1200 XX-55, Setalux 1202 SS-70, Setalux 1204 XS-60, Setalux 1211 BA-65, Setalux 1215 BA-68, Setalux 1251 XX-60, Setalux 1252 SS-65, Setalux 1255 SS-70, Setalux 1263 SS-51, Setalux 1265 XS-60, Setalux 1270 SS-70, Setalux 1271 XS-60, Setalux 1272 SS-70, Setalux 1276 SS-60, Setalux 1385 BX-51, Setalux 17-1015, Setalux 17-1162, Setalux 17-1190, Setalux 17-1196, Setalux 17-1198, Setalux 17-1211, Setalux 17-1215, Setalux 17-1421, Setalux 17-1447, Setalux 17-1608, Setalux 17-1609, Setalux 17-1722, Setalux 17-1745, Setalux 17-1746, Setalux 17-2319, Setalux 1753 SS-70, Setalux 1767 VV-65, Setalux 1769 VV-65, Setalux 1774 SS-70, Setalux 1901 SS-75, Setalux 1905 BA-74, Setalux 1915 BA-75, Setalux 1916 BA-75, Setalux 1917 BA-80, Setalux 1919 BA-74, Setalux 1921 BA-78, Setalux 27-1026, Setalux 27-1316, Setalux 27-1550, Setalux 27-1551, Setalux 27-1597, Setalux 27-1460, Setalux 27-1461, Setalux 57-2500, Setalux 91780 VS-60, Setalux D A 1060 BA, Setalux D A 160 X, Setalux D A 163 X, Setalux D A 170 BA, Setalux D A 265 BA, Setalux D A 365 BA/X, Setalux D A 450 BA, Setalux D A 450 BA/X, Setalux D A 565 X, Setalux D A 575 X, Setalux D A 665 BA, Setalux D A 665 BA/X, Setalux D A 760 BA/X, Setalux D A 960 SN, Setalux D A HS 1170 BA, Setalux D A HS 1375 BA, Setalux D A XP 2285, Setalux D A XP 2588, Setalux HS 1272 BA, Setalux XFS 1027, Setalux 6515, Setalux 6516, Setalux 6522 from Allnex; Joncryl 507, Joncryl 902, Joncryl 903, Joncryl 948, Joncryl 920, Joncryl 934, Joncryl 945, Joncryl 504, Joncryl 963, Joncryl 551, Joncryl 588, Joncryl 906, Joncryl 906-AC, Joncryl 909, Joncryl 910, Joncryl 911, Joncryl 915, Joncryl 918, Joncryl 922, Joncryl 924, Joncryl 942, Joncryl 500, Joncryl 508, Joncryl 510, Joncryl 550, Joncryl 581, Joncryl 582, Joncryl 587, Joncryl 587-AC, Joncryl 804, Joncryl 901, Joncryl 935, Joncryl 960, Joncryl RPD 950-AC/P, Joncryl RPD 950-B, Joncryl RPD 980-B from BASF; Resilac 167, Resilac 162 from C&E; Bayhydrol A 2139/2, Bayhydrol A 145, Bayhydrol A 2290, Bayhydrol A 2845 XP, Bayhydrol A 2846 XP from Covestro; Disvacryl-1015, Disvacryl-1016, Disvacryl-1018, Disvacryl-1019, Disvacryl-1051, Disvacryl-1012, Disvacryl-1013, Disvacryl-1014 from D.S.V. Chemicals; Dailic AC-5120, Dailic AC-5030, Dailic AC-5060, Dailic AC-5101, Dailic AC-5102, Dailic AC-5180, Dailic AC-5500, Dailic AC-5066, Dailic AC-5076, Dailic AC-5085, Dailic AC-5100, Dailic AC-5240, Dailic AC-5285, Dailic AC-5068, Dailic AC-5080, Dailic AC-52855 from Daily Polymer; ESB-1215, ESB-1267, ESB-1270, ESB-1271, ESB-1241 from Dongsheng Chemical; Paraloid AU-608 TBZ Acrylic Polyol, Paraloid AU-830, Paraloid AU-751, Paraloid AU-1033, Paraloid AU-1166, Paraloid AU-608B, Paraloid AU-1453 high-Solids Polyol, Paraloid AU-6085, Paraloid AU-608X, Paraloid AU-685, Paraloid AU-750, Paraloid AU-946 from Dow; Agisyn 670S1-A80, Agisyn 670TH-A80 from DSM-AGI; AC-Eagle OH60-20X55, AC-Eagle OH66-20BA50, AC-Eagle OH100-25BA70, AC-Eagle OH33-45XBA50, AC-Eagle OH66-28X60, AC-Eagle OH90-30X60, AC-Eagle OH92-140X60 from Eagle Chemicals; AC-70601XL, AC-70602SN, AC-70603SN, AC-70604 XL/BA, AC-70604 XL/CA, AC-70605SN, AC-70605XL, AC-70606 XL/BA, AC-70608XL, AC-70609XL, AC-74501XL, AC-74603XSB, HS-70701 XL/SN, HS-70704 XL/CA, HS-74651 XL/BA, HS-74707 BA from Hitech Industries; Acrylic Polyol, PR 407, PR 411 from Keeneyes Industrial; Cryol 911 60%, Cryol 912 60%, Cryol 913 63%, Cryol 940 65%, Cryol 941 50% from Knights Bridge Chemicals; Reactol 175 from Lawter; Polypol 613, Polypol 676, Polypol 693, Polypol 611, Polypol 610, Polypol 615, Polypol 663, Polypol 653 from Polychem Resins; Arolon 5900, Arolon 6473 from Reichhold; Burnock AC 2530, WPU-349 from Sun Chemical.

Cationic Acrylate Polymers useful as organic polymers include, for example; ttopol KX-10; Ottopol KX-99; Ottopol KX-101 from Gellner Industrial; RayCat® 65124 Specialty Polymers; FlOWLEN DOPA-15B; FlOWLEN DOPA-15 BHFS; FlOWLEN DOPA-17 HF; FlOWLEN DOPA-22; FlOWLEN DOPA-35 from Kyoeisha Chemical; MyCroFence AM 215 from Croda; WorléeCryl® 8721 from Worlée.

Polythiols (polymercaptans) include for example; DMDO (1,8-Dimercapto-3,6-dioxaoctane) from Arkema; POLYTHIOL QE-340M from Toray Fine Chemicals Co.

Acrylate polymers useful as organic polymers and precursor organic polymers to which can be added at least two first functional groups such as hydroxyl, amine, mercapto and/or carboxyl include:

Acrylates/Beheneth-25 Methacrylate Copolymer
Acrylates/Beheneth-25 Methacrylate/Steareth-30 Methacrylate Copolymer
Acrylates/C5-8 Alkyl Acrylate Copolymer
Acrylates/C10-30 Alkyl Methacrylate Copolymer
Acrylates/C12-22 Alkyl Methacrylate Copolymer
Acrylates/Ceteth-20 Methacrylate Copolymer
Acrylates/C26-28 Olefin Copolymer
Acrylates/Ethylhexyl Acrylate Copolymer
Acrylates/Hydroxyethyl Acrylate/Lauryl Acrylate Copolymer
Acrylates/Hydroxyethyl Acrylate/Methoxyethyl Acrylate Copolymer
Acrylates/Laureth-25 Methacrylate Copolymer
Acrylates/Lauryl Methacrylate Copolymer
Acrylates/Methoxy PEG-4 Methacrylate Copolymer
Acrylates/Methoxy PEG-15 Methacrylate Copolymer
Acrylates/Methoxy PEG-23 Methacrylate Copolymer
Acrylates/Palmeth-25 Acrylate Copolymer
Acrylates/Steareth-30 Methacrylate Copolymer
Acrylates/Stearyl Methacrylate Copolymer
Acrylic Acid/C12-22 Alkyl Acrylate Copolymer
Acrylic Acid/Stearyl Acrylate Copolymer
Ammonium Acrylates/Ethylhexyl Acrylate Copolymer
Ammonium Acrylates/Methyl Styrene/Styrene Copolymer
Ammonium Styrene/Acrylates/EthylhexylAcrylate/Lauryl Acrylate Copolymer
Behenyl Methacrylate/t-Butyl Methacrylate Copolymer
Butyl Acrylate/Cyclohexyl Methacrylate Copolymer a copolymer of butyl acrylate
and cyclohexyl methacrylate film formers NR
Butyl Acrylate/Ethylhexyl Methacrylate Copolymer a copolymer of butyl acrylate
and 2-ethylhexyl methacrylate monomers film formers;
Butyl Acrylate/Hydroxyethyl Methacrylate Copolymer
Butyl Methacrylate/Acryoyloxy PG Methacrylate Copolymer
C12-22 Alkyl Acrylate/Hydroxyethylacrylate Copolymer
Cyclohexyl Methacrylate/Ethylhexyl Methacrylate Copolymer
Ethylhexyl Acrylate/Methoxy PEG-23 Methacrylate/Vinyl Acetate Copolymer
Ethylhexyl Acrylate/Methyl Methacrylate Copolymer
Glyceryl Acrylate/Acrylic Acid Copolymer
Hydroxyethyl Acrylate/Methoxyethyl Acrylate Copolymer
Methoxy PEG-23 Methacrylate/Glyceryl Diisostearate Methacrylate Copolymer
Poly C10-30 Alkyl Acrylate
Potassium Acrylates Copolymer
Potassium Acrylates/Ethylhexyl Acrylate Copolymer
Sodium Acrylates/Ethylhexyl Acrylate Copolymer
Sodium Acrylate/Vinyl Alcohol Copolymer
Acrylates/Ceteareth-20 Methacrylate Crosspolymer
Acrylates/Ceteareth-20 Methacrylate Crosspolymer-2
Acrylates Crosspolymer-3
Acrylates Crosspolymer-4
Acrylates Crosspolymer-5
Acrylates/Lauryl Methacrylate/Tridecyl Methacrylate Crosspolymer
Acrylates/Methoxy PEG-90 Methacrylate Crosspolymer
Acrylates/VA Crosspolymer
Lauryl Acrylate Crosspolymer
Lauryl Acrylate/VA Crosspolymer
Methyl Methacrylate/PEG/PPG-4/3 Methacrylate Crosspolymer
Polyacrylate-1 Crosspolymer
Potassium Acrylate Crosspolymer
Sodium Acrylates/Beheneth-25 Methacrylate Crosspolymer
Poly(Methoxy PEG-9 Methacrylate)
Polybutyl Acrylate
Polybutyl Methacrylate
Polyethylacrylate
Polyhydroxyethylmethacrylate
Polyisobutyl Methacrylate
Polymethyl Acrylate
Polypropyl Methacrylate
Polystearyl Methacrylate
Sodium Polymethacrylate
Acrylates/C10-30Alkyl Acrylate Crosspolymer
Acrylates/C12-13 Alkyl Methacrylates/Methoxyethyl Acrylate Crosspolymer
Acrylates Crosspolymer
Acrylates/Ethylhexyl Acrylate Crosspolymer
Acrylates/Ethylhexyl Acrylate/Glycidyl Methacrylate Crosspolymer
Acrylates/PEG-4 Dimethacrylate Crosspolymer
Acrylates/Steareth-20 Methacrylate Crosspolymer
Acrylates/Vinyl Isodecanoate Crosspolymer
Acrylates/Vinyl Neodecanoate Crosspolymer
Allyl Methacrylate/Glycol Dimethacrylate Crosspolymer
Allyl Methacrylates Crosspolymer
Butyl Acrylate/Glycol Dimethacrylate Crosspolymer
C8-22 Alkyl Acrylates/Methacrylic Acid Crosspolymer
Glycol Dimethacrylate/Vinyl Alcohol Crosspolymer
Lauryl Methacrylate/Glycol Dimethacrylate Crosspolymer
Lauryl Methacrylate/Sodium Methacrylate Crosspolymer
Methacrylic Acid/PEG-6 Methacrylate/PEG-6 Dimethacrylate Crosspolymer
PEG/PPG-5/2 Methacrylate/Methacrylic Acid Crosspolymer
Potassium Acrylates/C10-30 Alkyl Acrylate Crosspolymer
Sodium Acrylates Crosspolymer-2
Sodium Acrylates/C10-30 Alkyl Acrylate Crosspolymer Sodium Acrylates/Vinyl Isodecanoate Crosspolymer Stearyl/Lauryl Methacrylate Crosspolymer Carboxylated styrene-butadiene polymers serving as organic polymers include Good-rite SB 1168, Good-rite SB 0738, Good-rite SB 1177 Lubrizol; Rovene 4011, Rovene 4019, Rovene 6140, Rovene 4049, Rovene 4310, Rovene 4306, Rovene 4457, Rovene 4041, Rovene 4150, Rovene 4151, Rovene 4176, BarrierPro 4551, Rovene 6140, Rovene 4305, Rovene 5550, Rovene 4487, Rovene 4817, Rovene 4470, Rovene 4475, Rovene 4180, Rovene 4310, Rovene 4402 from Mallard Creek Polymers; Hydro Pliolite 070 from Omnova Solutions; Lipaton SB 5521 from Synthomer Polyisocyanates and isocyanate catalysts serving as the in situ linking material include AH-1075EA, AH-2090BA, AH-2100, AH-3055, AH-1075T/P, AH-2075EA, AH-2200, Burnock from Aekyung Chemical; Macrynal SM 507/53XBAC, Crylcoat 2840-2 from allnex; Unithane 6451 WP 50 from Arkema; Dyranate A201H, Dyranate D101, Dyranate D201 from Asahi Kasei; Basonat TU 75 E, Basonat HI 2000, Basonat HB 475 B/X, Basonat HW 2000, Basonat HW 2100, Basonat HW 1180 PC, Efka SL 3888, Basonat HW 1000, Basonat HB 275 B, Basonat HI 268 B/S, Basonat HI 100, Basonat HB 100, Basonat HI 190 B/S, Basonat HI 290 B, Basonat HB 175 MP/X, Basonat HA 1000, Basonat HA 2000, Basonat HA 3000, Basonat TU 67 MP/X, Basonat HW 3180 B, Efka 3886 from BASF; TexCross AI 45 from Baumeister; Ongronat TR 2010 from BorsodChem; Mondur MRS, Mondur MR Light, Desmodur 44V20L, Mondur MR, Crelan NI-2, Bayhydur XP 2655, Bayhydur XP 2700, Bayhydur BL XP 2706, Desmodur VH 20 N, Bayhydur 401-70, Bayhydur VP LS 2150 BA, Bayhydur VP LS 2306, Bayhydur A145, Bayhydur XP 2451, Desmodur VP LS 2376/1, Desmodur XP 2679, Desmodur XP 2730, Desmodur VL 50, Bayhydur 304, Bayhydur VP LS 2240, Desmodur XP 2406, Bayhydur BL XP 2669, Bayhydur XP 2759, Desmodur E XP 2723, Desmodur E XP 2727, Desmodur VP LS 2078/2, Desmodur VP LS 2114/1, Desmodur VP LS 2371, Baybond XL 7270, Baybond XL 825, Desmodur BL 5375, Bayhydur BL 5335, Crelan UI, Crelan VP LS 2256, Crelan NW-5, Desmodur XP 2580, Desmodur BL XP 2677, Bayhydur 305, Bayhydur VP LS 2310, Bayhydur XP 2487/1, Bayhydur XP 2547, Desmodur VL R 20, Desmodur XP 2565, Desmodur BL 3575 MPA/SN, Desmodur E 22, Desmodur XP 7144, Desmodur E 23A, Bayhydur 3100, Desmodur NZ 1, Desmodur PL 350 MPA/SN, Desmodur IL, Desmodur IL 1351, Desmodur VL, Desmodur VL 2854, Desmodur E XP 2605, Desmodur BL 3175A, Desmodur E 3265, Desmodur E 3265 MPA/SN, Desmodur E 3370, Desmodur IL 1351 51% BA, Desmodur IL 1451, Desmodur IL 1451 BA, Desmodur IL 1451 EA, Desmodur MT, Desmodur VL 50, Desmodur VL 51, Desmodur VP LS 2257, Desmodur XP 2742, Demodur L 75, Bayhydrol XP 2451/1, DesmodurE 1340 PR MPA/X, Desmodur VP LS 2352/1, Bayhydur 302, Bayhydur XP 7165, Desmodur BL 1100, Desmodur BL 1100/1, Desmodur BL 3272 MPA, Desmodur BL 4265 SN, Desmodur E 14, Desmodur E 15, Desmodur E 21, Desmodur E 23A, Desmodur E 743, Desmodur HL BA, Desmodur HL EA, Desmodur IL BA, Desmodur L 67 BA, Desmodur L 67 MPA/X, Desmodur N 100, Desmodur XP 2675, Desmodur XP 2763, Imprafix TRL Solution, Desmodur IL EA, Desmodur BL 3370 MPA, Desmodur E 29, Desmodur L 55 MEK, Desmodur E-28, Desmodur E 1160 MPA/X, Desmodur PL 340 BA/SN, Desmodur eco N 7300, Desmodur BL 1265 MPA/X, Desmodur BL 3175 SN, Desmodur E 1240, Desmodur E 1361 BA, Desmodur E 1361 MPA/X, Desmodur E 1660, Desmodur E 1750 PR, Desmodur E 2190 X, Desmodur E 744, Desmodur HL, Desmodur L 1470, Desmodur N 3900, Desmodur E1160, Desmodur VP LS 2117, Bayhydur eco 7190, Baygal K 166, Baygal K 55, Desmodur I, Desmophen 1920 D, Demophen NH 1220, Hardener OZ, Mondur 582, Desmodur N 3200, Desmodur N 3350 BA, Desmodur N 3368 BA/SN, Desmodur N 3368 SN, Desmodur N 3372 SN, Desmodur N 3375 BA/SN, Desmodur N 3375 MPA, Desmodur N 3386 BA/SN, Desmodur N 3390 BA, Desmodur N 3390 BA/SN, Desmodur N 3390 BA/SN, Desmodur N 3790 BA, Desmodur N 3800, Desmodur N 50 BA/MPA, Desmodur N 60 BA, Desmodur N 75 BA, Desmodur N 75 MPA, Desmodur N 75 MPA/X, Desmodur Z 4470 MPA/X, Desmodur Z 4470 SN, Desmodur Z 4470 SN/BA, Desmodur N 3400, Desmodur Z 4470 BA, Desmodur N 3600, Desmodur N 75 BA/X, Desmodur N 3300 from Covestro; DJF-550/B from Daejin Physics & Chemical; DNW-5500, DNW-6000 from DIC Corporation; Sancure onecan-clear, Sancure DS-7075-D, Sancure DS-7076-G, Sancure DS-7074-P, Sancure DS-7073-K, Sancure DS-7079-F from Dongsan Fine Chemicals; Uradur YB146 Ml, Uradur 1117, Uradur YB147 51 from DSM; Vestanat B 1370, Vestanat EP-B 1042 E, Vestanat T 1890/100, Vestagon EP-BF 1321, Vestanat EP-8 1481 ND, Vestanat EP-DS 1076, Vestanat HB 2640 EX, Vestanat B 1358/100, Vestagon EP-BF 1350, Vestanat B 1186 A, Vestanat EP-B 1358 DINP, Vesttanat EP-B 1581, Vestanat T 1890 E, Vestanat T 1890 L, Vestanat T 1890 M, Vestanat HB 2640 E, Vestanat HB 2640 MX, Vestanat HB 2640/100, Vestanat HB 2640/LV, Vestanat HT 2500 E, Vestanat HT 2500 L, Vestanat HT 2500/100, Vestanat HT 2500/LV from Evonik; Uronal NL 100, Uronal NL 90, Uronal BN 75 from Galstaff Multiresine; Jeffol A-630 from Huntsman; Curing Agent W, Curing Agent W DIL, Curing Agent W3 DIL, Curing Agent W3 from Ichemco; Hiblock BI-175 from KSCNT; Stabio, Takenate D-140N, Takenate D-120N, Takenate D-110N from Mitsui Chemicals; Polurene M 75, Polurgreen ES, Polurene MT 90, Polurene T 70, Polugreen XP AB, Polurene MT 100, Polurgreen HR-01, Polurene MT 90 AB, Polurgreen AD-01, Polurene T 70 AE, Polurgreen AD AB-01, Polurgreen ES.M, Polurgreen ES.P, Polurgreen HR AE-01, Polurgreen OK-01, Polurgreen OK AE-01, Polurgreen OK.S-01 from Sapici; Picassian, Picassian XL-708, Picassian XL-728 from Stahl; Synthalat WA 140, Synthalat A-JB 772, Synthalat A 088 MS, Synthalat A 150, Synthalat A-TS 4399, Synthalat A 156 HS, Synthalat A 150 (A), Synthalat A 150 (B), Synthalat A 1615, Synthalat A 1653 (A), Synthalat A 1653 (B), Synthalat A-HD 6507, Synthalat A-HD 8199, Synthalat A 060, Synthalat A 077 (A), Synthalat A 077 (B), Synthalat A 078, Synthalat A 120 E, Synthalat A 125 HS, Synthalat A 1633 (A), Synthalat A 1633 (B), Synthalat A 1633 (C), Synthalat A-TS-3277, Synthalat A 136, Synthalat A-HD 5667, Synthalat A-TS 1603, Synthalat A-TS 2132, Synthalat A-TS-1664, Synthalat A 055, Synthalat A 090, Synthalat A 087, Synthalat A 191, Synthalat A-TS 1400, Synthalat A 065 (A), Synthalat A 065 (B), Synthalat A 065 (C), Synthalat A 085 (A), Synthalat A 085 (B), Synthalat A 085 (C), Synthalat A 190, Synthalat A 192, Synthalat A 141 HS, Synthalat A 135 N, Synthalat A 150 S from Synthopol; Coronate 2050, Coronate 2030, Coronate 2031, Coronate 2071, Coronate 2074, Coronate 2232, Coronate 2233, Coronate 2255, Coronate 2257, DJF-125/B, Coronate 2014, Coronate 2041, Coronate 2221, Coronate 2222, Coronate 2507, Coronate 2513, Coronate 342, Coronate AP-M, Coronate BI-301, Coronate HX, Coronate HX-T, Coronate 2067, Coronate L, Coronate 2096, Coronate HK, Coronate HL, Coronate HXLV, Coronate HXR, Coronate L-45E, Coronate L-55E from Tosoh; Vanchem HM-4346, Vanchem HM-50 from Vanderbilt Chemicals; Easaqua X D 870, Tolonate HDB, Easaqua WAT-3, Easaqua WAT-4, Tolonate D2, Tolonate HDT, Tolonate HDB 75 BX, Tolonate HDB 75 M, Tolonate HDB 75 MX, Tolonate HDB-LV, Easaqua M 501, Easaqua X D 401, Easaqua X D 803, Tolonate HDB 75 BX, Tolonate HDT 90, Tolonate HDT-LV, Tolonate HDT-LV2, Tolonate IDT 70 B, Tolonate X FD 90 B, Easaqua L 600, Easaqua M 502, Tolonate HDT 90 B, Tolonate X FLO 100 from Vencorex.

Isocyanate catalysts serving to enable in situ linkage of the organic polymer carrying amine, hydroxyl and/or mercapto groups and the in situ linking material carrying isocyanate groups include Dibutyltin dilaurate catalysts for example; Dibutyltin dilaurate, Borchers LH 10 from OMG Borchers; Butaflow BT-71 from Estron Chemical; Dabco T-12 from Evonik; Fomrez SUL-4 catalyst from Galata Chemicals; Fascat 4202 from PMC Group; Tib Kat 218 from TIB Chemicals; Cotin 200 from Vertellus Specialties; Dibutyltin diacetate catalysts for example; Patcat 3003 from Patcham; Fascat 4200 from PMC Group; Tib kat 233 from TIB Chemicals; Dibutyltin oxide catalysts for example; Reaxis C248D, Reaxis C248D from Reaxis; Fascat 9201, Fascat 4201 from PMC Group; Tib kat 248 LC, Tib kat 248 from TIB Chemicals; Bismuth carboxylate catalyst for example; K-Kat 348, K-Kat XC-B221, K-Kat XK-640, K-Kat XK-601, K-Kat XK-628, K-Kat XC-C227 from King Industries; Borchi Kat 0244, Borchi Kat 24 from OMG Borchers; Reaxis C722, Reaxis C716 from Reaxis; Tib Kat 720, Tib Kat 716 from TIB Chemicals; K-Kat 348 from Worlee;

Aluminum chelate catalysts for example; K-Kat 5218 from King Industries.

4.4 Dispersants

It will be apparent to one skilled in the art that careful and selective choice of dispersant can help to maximize performance in terms of maximizing the amount of color produced from an immobilized film, maximizing the remanence or washfastness, and enabling removal of the color.

For example, in the case where the binder polymer is anionic in nature, dispersants which are anionic or nonionic are preferably chosen, rather than cationic, as this avoids undesired precipitation in the formula prior to it forming a colored film on the keratin—i.e. utilizing the principle of avoiding opposing charges.

Likewise, the principle of choosing chemically similar dispersant and binder (for example, a silicone binder paired with a silicone dispersant, can be followed to ensure maximum compatibility.

As well as compatibility as noted above, the other critical criterion in selecting dispersant(s) is their ability to enable optionally present pigment to be dispersed down to the primary particle size, preferably with the minimum amount of input mechanical energy. It will be recognized by someone skilled in the art that the concentration of dispersing agent is also a critical factor. In general it is usually required that there is a minimum amount for dispersing activity and that below this, the system is either not fully dispersed or, worse, that the dispersant acts as a flocculant.

These two considerations together are used to define preferred materials and their respective concentrations.

It may also be the case, depending on the type of binder polymer used, that the binder itself is also a dispersant (see below for discussion of classes of dispersant). In such cases it is possible that no further dispersing additive may be needed.

Overview of Dispersant Kinds, Properties and Chemistry

Dispersants are amphiphilic or amphiphathic meaning that they are chemical compounds possessing both hydrophilic (water-loving, polar) and lipophilic (fat-loving) properties. Dispersants are surface-active polymers that allow the homogeneous distribution and stabilization of solids, such as for example pigments, in a liquid medium (like a binder), by lowering the interfacial tension between the two components. As a result, agglomerates are broken up into primary particles and protected by a protecting dispersant envelope of a re-agglomeration.

The dispersants can be subdivided on the basis of the stabilization mechanism in
1. Dispersants for electrostatic stabilization
    a. Anionic dispersing additives
        i. Polyacrylates
        ii. Polyphosphates
    b. Neutral dispersing additives
    c. Cationic dispersing additives
2. Dispersants for steric stabilization Electrostatic Stabilization The pigment surface is occupied by an additive carrying an ionic charge. All pigment particles are charged the same. The mutual repulsion by the charge is greater than the attractions of the pigment particles. The electrostatic stabilization has its relevance mostly in water-based paint systems.

Polyanionic dispersing additives: polycarboxylates (mostly salts of polyacrylic acids), polyphosphates divided into linear polyphosphates and cyclic metaphosphates, polyacrylates salts of polyacrylic acid, as cations, sodium and ammonium are preferred, these polyacrylates are water-soluble, technical products have molecular weights in the range of 2000 to 20,000 g/mol, optimum is about 8000 g/mol Sodium and ammonium salts of the homo- or copolymers of acrylic acid, methacrylic acid or maleic acid Steric Stabilization The attractive forces between the pigment particles are effective only over relatively small distances of the particles from each other. The approach of two particles to each other can be prevented by molecules that are firmly anchored to the pigment surface and carry groups that extend from the surface and may reduce the potential for the pigments to contact one another. By sufficiently long chain lengths, agglomeration can be prevented.

Water-soluble polymers

Block or graft copolymers, so-called AB block copolymers

Example: AB block polymer of 2-vinylpyridine and methacrylic acid ester

Example: AB block copolymer of polyester (based caprolactam) and triethylenetetramine Typical functional groups for the A segment are carboxyl, amine, sulfate and phosphate for inogenous bonds or polyether and polyamide for hydrogen bonds. B represents the solvated side chain, molecular weights 1000 to 15000 g/mol, e.g. modified polyacrylates or polyhydroxystearates Hydrophilic moieties (e.g., polyethers) and pigment affinic groups (e.g. Groups) containing oligomers or polymers.

The following types are distinguished according to the number of monomer types used in the production:

Homopolymers: only one kind of monomer
Copolymers: two monomers
Terpolymers: three monomers Classification according to distribution of the monomers in the polymer:

Statistical polymers: A and B segments are distributed arbitrarily

Block polymers: the monomers are grouped into blocks

Graft polymers: these consist of a linear homopolymer backbone on which side chains of other monomer blocks are grafted Some examples of dispersants for solvent-based systems are:

oligomeric titanates and silanes for inorganic pigments with OH or carboxy groups.

Oligomeric polymeric carboxylic acids for inorganic pigments (cationic).

Polyamines for inorganic pigments, e.g., cationic polymers.

Salts of long-chain polyamines and polycarboxylic acids for inorganic and organic pigments (electroneutral).

Amine/amide-functional polyesters/polyacrylates for the stabilization of organic pigments.

Polysilicones with and without functional groups including cyclic siloxanes, amine functional cyclic and linear siloxanes, carboxyl functional cyclic and linear siloxanes.

Some examples of dispersants for aqueous systems are:

Inorganic dispersants such as fine-grained CaCO3, Ca3(PO4) 2, polyphosphates, polyphosphoric acids.

Nonionic surfactants such as ethoxlyated fatty alcohol (e.g. Neodol 25-9), ethoxylated oils (e.g. ethoxylated castor oil under the tradename Cremophore RH410)

Block and graft copolymers of the type having distinct hydrophilic and hydrophobic blocks (e.g. ethylene oxide-propylene oxide polymers under the tradename Poloxamer)

Anionic surfactants consisting of the unethoxylated or ethoxylated salts of acids (e.g. sodium ceteth-10-phosphate under the tradename Crodafos).

Examples and classes of nonionic surfactants that can function as dispersants include oligomers (e.g., example, oligomers have up to 20 monomeric units, polymers have at least 20 monomeric units), polymers, and/or a mixture of several thereof, bearing at least one functional group with strong affinity for the surface of pigment microparticles. For example, they can physically or chemically attach to the surface of pigment microparticles. These dispersants also contain at least one functional group that is compatible with or soluble in the continuous medium. For example, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name SOLSPERSE 21,000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof. Similar dispersants will function to disperse the polar functional silicone polymers that are not readily dispersible and/or are not at least partially soluble in aqueous media.

The foregoing dispersant category involving cationic polymers includes polymers such as quaternary ammonium polymers. Examples of quaternary ammonium derivatives of polycondensed fatty acids include, such as for instance, SOLSPERSE 17,000 sold by the company Avecia, and polydimethylsiloxane/oxypropylene mixtures such as those sold by the company Dow Corning under the references DC2-5185 and DC2-5225 C.

The dispersant can be a polyolefin polymer. These dispersants include but are not limited to an olefinic polymer having a molecular weight of about 100 g/mol to about 5,000,000 g/mol, such as about 1,000 g/mol to about 1,000,000 g/mol. Examples of polymers, include, but are not limited to poly(ethylene), poly(propylene), poly(butylene), poly(isobutylene), poly(isoprene), poly(acetal), poly(ethylene glycol), poly(propylene glycol), poly(butylene glycol), poly(methylmethacrylate), poly(dimethylsiloxane), poly(vinylalcohol), poly(styrene), poly(maleic anhydride), poly(ethylmethacrylate), poly(isobutylmethacrylate), poly(methacrylate), poly(butylmethacrylate), poly(n-butylmethacrylate), poly(vinyl butyrate), poly(vinyl chloride), polysiloxane, and mixtures thereof. The polymers can be random, block, or alternating copolymers. In some embodiments, the polymer is a co-polymer that is made from two or more different monomers, such as the monomers that make the polymers described above. Examples of co-polymers include, but are not limited to polyethers, polyesters, polyamides, acrylics, and polystyrenes. The co-polymer can be alternating monomers, random, or block. Examples include a polyether of alternating or block PEO, PPO groups. Examples of acidic groups include, but are not limited to, carboxylic acids, sulfinic acids, sulfonic acids, phosphonic acids, phosphate esters, maleic anhydrides, and succinic anhydride. In some embodiments, the dispersive additive comprises a group selected from phosphonate, phosphate, phosphite, phosphine, and phosphate ester, such as a phosphate, phosphite, and phosphonic acid. In some embodiments, the acidic group has been converted into a salt.

Representative dispersants are also available from a variety of suppliers, and include various nonionic (e.g., ethoxylated) and anionic (e.g., non-ethoxylated salt) forms including agents from Air Products and Chemicals, Inc. (e.g., SURFYNOL™ PSA336); Archer Daniels Midland Co. (e.g., ULTRALEC™ F deoiled lecithin); Ashland Inc. (e.g., NEKAL™ WS-25-I, which is a sodium bis(2,6-dimethyl 4heptyl)sulfosuccinate); BASF (e.g., DISPEX™ AA 4144, DISPEX ULTRA FA 4425 which is a fatty acid-modified emulsifier having a viscosity of 40,000 cps, DISPEX ULTRA FA 4420 which is a fatty acid-modified emulsifier and a dark brown liquid of unspecified viscosity, DISPEX ULTRA FA 4431 which is an aliphatic polyether with acidic groups having a viscosity of 350 cps, DISPEX ULTRA PA 4501 which is a fatty acid modified polymer having a viscosity of 10,000 cps, DISPEX ULTRA PA 4510, EFKA™ PU 4010, EFKA PU 4047 which is a modified polyurethane, EFKA PX 4300, EFKA ULTRA PA 4510 and EFKA ULTRA PA 4530 which are modified polyacrylates, EFKA FA 4620 which is an acidic polyether having a viscosity of 1,400 cps, EFKA FA 4642 which is an unsaturated polyamide and acid ester salt having a viscosity of 2,000 cps, HYDROPALAT™ WE 3135, HYDROPALAT WE 3136 and HYDROPALAT WE 3317 which are difunctional block copolymer surfactants terminating in primary hydroxyl groups and having respective viscosities of 375, 450 and 600 cps, and TETRONIC™ 901 and TERTRONIC 904 which are tetrafunctional block copolymers terminating in primary hydroxyl groups and having respective viscosities of 700 and 320 cps); Borchers (e.g., BORCHI™ Gen 0451 which is a polyurethane oligomer having a viscosity of about 30,000 cps, BORCHI Gen 0652 which is an amine neutralized acrylic acid copolymer having a viscosity of about 75-300 cps, and BORCHI Gen 1252 and BORCHI Gen 1253 which are acrylic ester copolymers having respective viscosities of about 1,500-3,500 and 50-300 cps); Byk-Chemie (e.g., BYK™ 156 which is a solution of an ammonium salt of an acrylate copolymer, DISPERBYK™ which is a solution of an alkyl ammonium salt of a low-molecular-weight polycarboxylic acid polymer, DISPERBYK-102 which is an acidic copolymer, DISPERBYK™-145 which is a phosphoric ester salt of a high molecular copolymer with pigment affinic groups and a liquid of unspecified viscosity, DISPERBYK-190 which is a solution of a high molecular weight block copolymer with pigment affinic groups, DISPERBYK-2013 which is a structured copolymer with pigment affinic groups having a viscosity of 8,600 cps, DISPERBYK-2055 which is a copolymer with pigment affinic groups and a liquid of unspecified viscosity, DISPERBYK-2060 which is a solution of a copolymer with pigment affinic groups having a viscosity of 3,600 cps, DISPERBYK-2061 which is a solution of a copolymer with pigment affinic groups having a viscosity of 491 cps, DISPERBYK-2091, DISPERBYK-2200 which is a high molecular weight copolymer with pigment affinic groups sold in solid form as pastilles and BYKJET™-9152 which is a copolymer with pigment affinic groups having a viscosity of 21,600 cps); Clariant (e.g., DISPERSOGEN™ 1728 which is an aqueous solution of a novolac derivative having a viscosity of 4,000 cps, DISPEROGEN 2774 which is a novolac alkoxylate having a viscosity of 4,000 cps, GENAPOL™ X 1003 and GENAPOL X 1005 which are fatty alcohol ethoxylates having respective viscosities of about 400 cps and 1,300 cps, HOSTAPAL BV concentrate which is a sulfate ester having a viscosity of about 2,700 cps); Cray Valley (e.g., SMA1440H which is an ammonia salt of a styrene maleic anhydride copolymer solution); Dow Chemical Co. (e.g., the TAMOL™ family of dispersants including TAMOL 165A and TAMOL 731A); Elementis (e.g., NUOSPERSE™ FA196 which has a viscosity of 1,200 cps); Lubrizol (e.g., SOLSPERSE™ 27000, SOLSPERSE 28000, SOLSPERSE 32000, SOLSPERSE 39000, SOLSPERSE 64000, SOLSPERSE 65000, SOLSPERSE 66000, SOLSPERSE 71000, SOLSPERSE M387, SOLPLUS™ R700 and SOLPLUS K500); Ethox Chemicals, LLC (e.g., the E-SPERSE™ family of dispersants and ETHOX™ 4658); Evonik (e.g., TEGO™ DISPERS 656, TEGO DISPERS 685, TEGO DISPERS 750W and TEGO DISPERS 757W); Rhodia Solvay Group (e.g., ABEX 2514 and ABEX 2525 which are nonionic surfactants, RHODACAL™ IPAM which is isopropyl amine dodecylbenzene sulfonate having a viscosity of 10,000 cps, RHODAFAC™ RS-710 which is a polyoxyethylene tridecyl phosphate ester, and the RHODOLINE™ family of dispersants including RHODOLINE 4170 and RHODOLINE 4188); Sasol Wax GmbH (e.g., ADSPERSE™ 100, ADSPERSE 500 and ADSPERSE 868) and Stepan Company (e.g., G-3300 which is an isopropyl amine salt of an alkyl aryl sulfonate having a viscosity of about 6000 cps, POLYSTEP™ A-15 which is a sodium dodecylbenzene sulfonate having a viscosity of about 85 cps, POLYSTEP B-11 and POLYSTEP B-23 which are ethoxylated ammonium lauryl ether sulfates respectively containing 4 or 12 moles of ethylene oxide and having respective viscosities of 66 and 42 cps, and POLYSTEP B-24 which is sodium lauryl sulfate having a viscosity of 100 cps).

Commercial dispersant compositions and systems of the synthetic kind described above are sold by several companies who manufacture polymer systems. These include:

BASF
  Water-Based System—
    Dispex® Ultra FA, Dispex® AA, Dispex® CX, Dispex® Ultra PX, Dispex® Ultra PA solvent based system
    Efka® FA, Dispex® Ultra FA, Efka® FA, Efka® PU, Efka® PA, Efka® PX
Clariant
  Dispersogen® 1728, Dispersogen® 2774, Dispersogen® 3169, Dispersogen® AN 100, Dispersogen® AN 200, Dispersogen® ECS, Dispersogen® ECO, Dispersogen® LFS 6, Dispersogen® PCE, Dispersogen® PL 30, Dispersogen® PL 40, Dispersogen® PTS, Dispersogen®, Emulsogen® LCN 217, Emulsogen® TS 200, Dispersogen®, Dispersogen® FN, Dispersogen® FSE, Dispersogen® MT 200, Dispersogen® LFH, Dispersogen® 145, Dispersogen® 4387, Hostapal® BV, Dispersogen® LEC, Dispersogen® PSM, Polyglykol 200 LVC, Polyglykol G500, Polyglykol 300, Polyglykol 400
Lubrizol
  Solsperse™ 3000, Solsperse™, Solsperse™ 8000, Solsperse™, Solsperse™ 120005, Solsperse™ 13300, Solsperse™ 13400, Solsperse™ 13500, Solsperse™ 13650, Solsperse™ 13940, Solsperse™ 16000, Solsperse™ 17000, Solsperse™ 17940, Solsperse™ 17000, Solsperse™ 18000, Solsperse™ 19000, Solsperse™ 20000, Solsperse™ 21000, Solsperse™ 22000, Solsperse™ 24000SC, Solsperse™ 26000, Solsperse™ 27000, Solsperse™ 28000, Solsperse™ 32000, Solsperse™ 32500, Solsperse™ 32600, Solsperse™ 33000, Solsperse™ 35000, Solsperse™ 35100, Solsperse™ 35000, Solsperse™ 36000, Solsperse™ 36600, Solsperse™ 37500, Solsperse™ 38500, Solsperse™ 39000, Solsperse W100.
Byk
  DISPERBYK-102, DISPERBYK-103, DISPERBYK-106, DISPERBYK-107, DISPERBYK-108, DISPERBYK-109, DISPERBYK-110, DISPERBYK-111, DISPERBYK-115, DISPERBYK-118, DISPERBYK-130, DISPERBYK-140, DISPERBYK-142, DISPERBYK-145, DISPERBYK-161, DISPERBYK-162, DISPERBYK-163, DISPERBYK-164, DISPERBYK-166, DISPERBYK-167, DISPERBYK-168, DISPERBYK-170, DISPERBYK-171, DISPERBYK-174, DISPERBYK-180, DISPERBYK-181, DISPERBYK-182, DISPERBYK-184, DISPERBYK-185, DISPERBYK-187, DISPERBYK-190, DISPERBYK-191, DISPERBYK-192, DISPERBYK-193, DISPERBYK-194 N, DISPERBYK-199, DISPERBYK-2000, DISPERBYK-2001, DISPERBYK-2008, DISPERBYK-2009, DISPERBYK-2010, DISPERBYK-2012, DISPERBYK-2013, DISPERBYK-2015, DISPERBYK-2022, DISPERBYK-2023, DISPERBYK-2025, DISPERBYK-2026, DISPERBYK-2050, DISPERBYK-2055, DISPERBYK-2060, DISPERBYK-2061, DISPERBYK-2062, DISPERBYK-2070, DISPERBYK-2080, DISPERBYK-2081, DISPERBYK-2096, DISPERBYK-2117, DISPERBYK-2118, DISPERBYK-2150, DISPERBYK-2151, DISPERBYK-2152, DISPERBYK-2155, DISPERBYK-2157, DISPERBYK-2158, DISPERBYK-2159, DISPERBYK-2163, DISPERBYK-2164, DISPERBYK-2200, DISPERBYK-2205

DOW

TAMOL™ 1124; TAMOL™ 1254; TAMOL™ 165A; TAMOL™ 2002; TAMOL™ 2011; TAMOL™ 681; TAMOL™ 731A; TAMOL™ 851; TAMOL™ 901; TAMOL™ 945; TAMOL™ 960; TAMOL™ 963; TAMOL™

Following the foregoing principles and guidelines, pigment microparticles optionally can be dispersed in the composition with the addition of at least one of a dispersant and a wetting agent. While not wishing to be bound by any specific theory, it is believed that only when pigments are de-aggregated into their primary particles do they deliver the optimum optical performance. For examples, pigments with a primary particle size of 0.02 micron which provide brilliant bright colors, when present as aggregates of around 0.3 micron provide duller colors.

The dispersant serves to protect pigment microparticles against agglomeration or flocculation either in the dry state or in the solvent. Dispersants also serve as wetting agents. In this capacity, dispersants as wetting agents can be low or higher molecular weight monomeric surfactants (for example, anionic, cationic or amphoteric surfactants). Dispersants as wetting agents can be higher molecular weight surface-active or pigment particle affinic polymers (for example, polyelectrolyte dispersants such as maleic acid copolymers, and polyurethanes or polyacrylates containing carboxylic acid, amine or isocyanate pigment affinic anchor groups or polyethylene imines) or other type of polyelectrolytes.

Representative wetting agents include those available from a variety of suppliers including Air Products and Chemicals (e.g., CARBOWET™ GA-210 surfactant which has a viscosity of 80 cps, CARBOWET GA-221 surfactant which has a viscosity of 100 cps, DYNOL™ 607 superwetter which has a viscosity of 205 cps and DYNOL 800 superwetter which has a viscosity of 230 cps); Dow Chemical Co. (e.g., CAPSTONE™ fluorosurfactants FS 31, FS 34, FS 35, FS 61 and FS 64); and Stepan Company (e.g., STEPWET™ DOS-70 surfactant which contains 70% active ingredients and has a viscosity of 200 cps, and STEPWET DOS-70EA surfactant which contains 70% active ingredients and has a viscosity of 220 cps).

4.5 Plasticizer

If the glass transition temperature of the carboxylic acid polymer is too high for the desired use yet the other properties of the polymer are appropriate, such as but not limited to color and wash fastness, one or more plasticizers can be combined with the hair coloring composition embodiments so as to lower the $T_g$ of the carboxylic acid polymer and provide the appropriate feel and visual properties to the coating. The plasticizer can be incorporated directly in the coloring composition or can be applied to the hair before or after the coloring composition. The plasticizer can be chosen from the plasticizers usually used in the field of application.

The plasticizer or plasticizers can have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 40 g/mol.

Thus, the hair coloring composition can also comprise at least one plasticizer. For example, non-limiting mention can be made, alone or as a mixture, of common plasticizers such as: glycols and derivatives thereof, silicones, silicone polyethers, polyesterpolyols; adipic acid esters (such as diisodecyladipate), trimellitic acid esters, sebacic acid esters, azalaeic acid esters; nonlimiting examples of glycol derivatives are diethylene glycol ethyl ether, diethylene glycol methyl ether, diethylene glycol butyl ether or diethylene glycol hexyl ether, ethylene glycol ethyl ether, ethylene glycol butyl ether, or ethylene glycol hexyl ether; polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters; propylene glycol derivatives such as propylene glycol phenyl ether, propylene glycol diacetate, dipropylene glycol ethyl ether, tripropylene glycol methyl ether, diethylene glycol methyl ether, and dipropylene glycol butyl ether. Such compounds are sold by Dow Chemical under the names DOWANOL PPH and DOWANOL DPnB; acid esters, for example esters of carboxylic acids, such as triacids, citrates, phthalates, adipates, carbonates, tartrates, phosphates, and sebacates; esters derived from the reaction of a monocarboxylic acid of formula $R_{11}COOH$ with a diol of formula $HOR_{12}OH$ in which $R_{11}$ and $R_{12}$, which can be identical or different, are chosen from a linear, branched or cyclic, saturated, or unsaturated hydrocarbon-based chain containing, for example, from 3 to 15 carbon atoms for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical; oxyethylenated derivatives, such as oxyethylenated oils, such as plant oils, such as castor oil; mixtures thereof.

Among the esters of tricarboxylic acids mention can be made of the esters of triacids wherein the triacid corresponds to formula

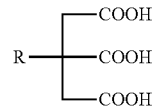

wherein R is a group —H, —OH or —OCOR' wherein R' is an alkyl group containing from 1 to 6 carbon atoms. For example, R can be a group —OCOCH$_3$. The esterifying alcohol for such tricarboxylic acids may be those described above for the monocarboxylic acid esters.

The plasticizer can be present in the composition of the present disclosure in an amount from about 0.01% to 20%.

4.6 Medium

Depending on the dye used, the medium of the hair coloring composition embodiments of the invention may be water alone, water in mixture with a volatile polar protic or aprotic organic solvent, or a non-aqueous solvent or a mixture of non-aqueous solvents with polar protic or aprotic polar organic solvent. In general, the medium is any solvent suitable for dissolving the peri-arylene dyes of the embodiments of the hair coloring composition described herein. A volatile solvent may be present including a volatile polar protic or aprotic organic solvent, or mixtures thereof. Volatile organic solvents of which non-limiting mention may be made include: volatile pyrolidones 1-methylpyrrolidin-2-one, volatile $C_1$-$C_4$ alkanols such as methanol, ethanol or isopropanol; esters of liquid $C_2C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol. Additional solvents include cyclic silicone solvents such as decamethylcyclopentasiloxane, octamethylcyclotetrasiloxane, dowsil polymethyl siloxanes.

According to at least one embodiment of the present disclosure, the organic solvent is chosen from ethanol, isopropanol, butanol, acetone, and isododecane.

As regards the hydrophobic peri-arylene dyes according to formula (1) comprising at least one hydrophobic moiety R2, R3 or R6, the medium may comprise a linear or branched C2-C8 alcohol such as, for example, (iso)propanol and/or (iso)butanol. The medium furthermore may comprise water, preferably in an amount below the solubility limit.

The medium with or without one or more volatile organic solvent may be present in the composition according to the present disclosure in an amount ranging from about 0.1% to about 95% by weight, such as from about 1% to about 70% by weight, for example ranging from 5% to 90% by weight relative to the total weight of the composition.

The ratio of solvent to the peri-arylene dyes can be between about 5:1 to about 10000:1, about 10:1 to about 1000:1 or about 20:1 to about 100:1.

According to embodiments involving a peri-arylene dye according to formula (24) with at least one hydrophilic moiety R8 or R9, the medium may be an aqueous medium.

According to embodiments involving a film former, the medium may be an aqueous medium.

The medium may be present in the composition according to the present disclosure in an amount ranging from about 0.1% to about 95% by weight, such as from about 1% to about 70% by weight, for example ranging from 5% to 90% by weight relative to the total weight of the composition.

4.7 The pH

The hair coloring composition embodiments in accordance with the present disclosure can have a pH ranging from about 3 to about 12, or from about 3 to about 11, preferably about 4 to about 9.6 and in many embodiments 6.8 or higher. For example, the pH can be 8 or higher, 9 or higher or at most 12, or at most 11. In some examples, the hair coloring composition embodiments in accordance with the present invention can have a pH of from about 7 to about 10, about 5 to about 11 or about 6 to about 8.

The pH may range from about 3 to about 8 for polar functional silicone polymers that can form cationic groups, e.g., amines and ranging from about 5 to about 11 for polar functional silicone polymer that can form anionic groups, e.g., carboxylic and sulfonic acids. For silicone polymer with cation forming groups (amines), preferably the pH is about 4 to about 7 and in many embodiments 6.8 or lower.

In some examples, the multicomponent composition embodiments with silicone polymers having cation forming groups in accordance with the present invention can have a pH of from about 3.0 to about 8.0, preferably about 3.5 to about 6.8, more preferably about 4.5 to about 6.8, most preferably about 5.5 to about 6.5.

The hair coloring composition in accordance with the present disclosure can comprise a pH modifier and/or buffering agent. The amount is sufficiently effective to adjust the pH of the composition/formulation. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, such as sodium hydroxide, sodium silicate, sodium meta silicate and ammonium carbonate, and acids such as inorganic and inorganic acids, e.g., phosphoric acid, acetic acid, ascorbic acid, citric acid or tartaric acid, hydrochloric acid, and mixtures thereof.

4.8 the Pretreatment

A pretreatment composition can be applied prior to treating hair with the hair coloring compositions described herein. A pretreatment provides advantages in particular when a carboxylic acid polymer is used as a film former.

A pretreatment composition can be applied to reduce the difference between the root and tip regions of the hair. These two regions have sufficiently different surface properties to make it hard to have a single material which can adhere strongly to both. The pre-treatment composition can be applied to all of the hair, or applied to specific sections as needed to cause the desired result of obtaining even color performance and wash resistance root to tip.

The pretreatment composition may also contribute to improved wetting properties of the keratinous surface such as hair or nails for the film-forming polymer, particularly for the carboxylic acid polymer. The film-forming polymer can wet the keratinous surface such as hair fibers more quickly and more evenly which contributes to an overall more even coloring.

Furthermore, the pretreatment composition also improves the removal properties of the film-forming polymer by application of the trigger formulation.

The pretreatment thus can be considered to form a primer coating of the keratinous surface such as of the hair for improving the wettability, levelling surface properties which would otherwise lead to an uneven wetting, and contributes to the removability of the film-forming polymer.

Aqueous Medium of the Pretreatment Composition

According to embodiments described herein, the aqueous medium of the pretreatment composition comprises water alone, or water in mixture with at least one of polar and protic. In general, the aqueous medium can be any solvent suitable for dissolving the cationic polymer of the embodiments of the pretreatment composition described herein.

Cationic Polymer of the Pretreatment Composition

According to embodiments described herein, the pretreatment composition contains a cationic polymer and an aqueous medium. The pretreatment composition is applied prior to the hair coloring composition, either without or with an intermediate rinsing step to optionally remove excess cationic polymer which has not bound to the hair.

The cationic polymer may be a cationic homopolymer or a cationic heteropolymer. The cationic polymers may be linear or branched.

The cationic polymer may comprise at least one monomer unit, i.e. one or more monomer unit(s), comprising at least one, i.e. one or more, amino functional group(s). The amino functional group(s) may be selected from the group consisting of primary, secondary, tertiary, aromatic amino functional groups and mixtures thereof. Alternatively, the amino functional group may be selected from the group consisting of primary, secondary amino functional groups and mixtures thereof. Alternatively, the amino functional group may be selected from secondary amino functional groups.

According to embodiments described herein, at least 50% of the monomeric units of the cationic polymer contain amino functional group(s), preferably at least 80%, and more preferably at least 90%.

The cationic polymer may have a weight average molecular weight in the range of about 4 kDa to about 450 kDa such as 4 kDa or more to 450 kDa or less, preferably in the range of about 10 kDa to about 200 kDa such as 10 kDa or more to 200 kDa or less, and more preferably in the range of about 10 kDa to about 100 kDa such as 10 kDa or more to 100 kDa or less.

The cationic polymer according to embodiments described herein may be selected from the group consisting of linear polyethyleneimine (linear PEI), branched polyethyleneimine (branched PEI), polyallylamine hydrochloride (PAH), polyallylamin, polyvinylpyridin, and copolymers thereof and mixtures thereof.

According to embodiments described herein, the cationic polymer is selected from linear or branched polyethyleneimines.

Embodiments of the pretreatment composition contain the cationic polymer from 0.1 wt % or more to 5 wt % or less (or 5.0 wt % or less) relative to the total weight of the pretreatment composition, preferably from 0.1 wt % or more to 2 wt % or less (or 2.0 wt % or less) relative to the total weight of the pretreatment composition, more preferably from 0.15 wt % or more to 1.5 wt % or less relative to the total weight of the pretreatment composition, and even more preferably from 0.2 wt % or more to 1 wt % or less (or 1.0 wt % or less) relative to the total weight of the pretreatment composition.

According to embodiments described herein, the cationic polymer is selected from linear or branched polyethyleneimines and contained in the pretreatment composition in the range of from about 0.15 wt % to about 1.5 wt %, such as 0.15 wt % or more to 1.5 wt. % or less, and preferably in the range of from about 0.2 wt % to about 1 wt %, such as 0.2 wt % or more to 1 wt. % (or 1.0 wt %) or less, relative to the total weight of the pretreatment composition.

According to embodiments described herein, the pretreatment composition can contain one or more cationic polymers. Exemplary cationic polymer having a weight average molecular weight in the range of about 4 kDa to about 450 kDa may be:

a) Linear polyethyleneimine of the formula:

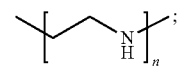

b) Branched polyethyleneimine comprising or consisting of primary, secondary, tertiary amine groups, which may have of the formula:

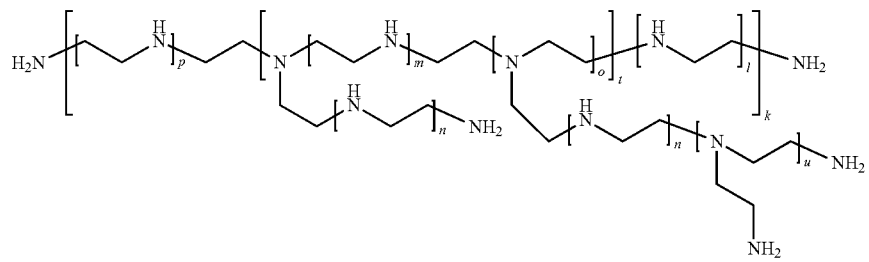

with p, n, m, o, t, l, k, and u being independently selectable, or

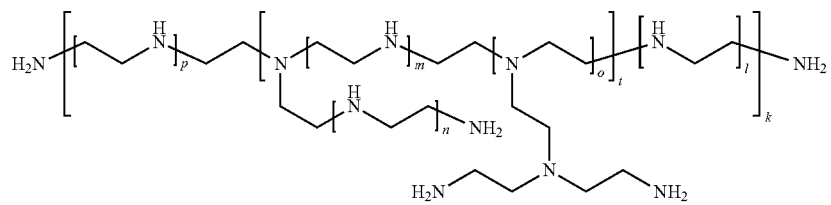

with p, n, m, o, t, l, and k being independently selectable, c) Polyallylamine hydrochloride (PAH) of the formula:

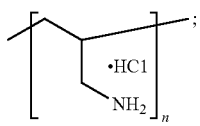

d) Polyallylamine of the formula:

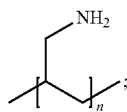

and
e) polyvinylpyridin of the formula:

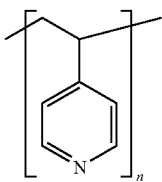

g) copolymers thereof and mixtures thereof.

PH of the Pretreatment Composition

According to embodiments described herein, the pH of the pretreatment composition can be in the range between 7 and 10, preferably in the range between 7.4 and 9.6, more preferably in the range between 7.8 and 9.2, and more preferably in the range between 7.0 and 9.0.

Natural hair has a negative surface charge. Without wishing to be tight by theory, it is believed that a higher pH value renders the cationic polymer of the pretreatment composition less charged resulting in an increased loading of the hair surface with the cationic polymer as the cationic polymer is less charged. The thus formed cationic polymeric base layer can thus be provided with a higher polymer loading. This also improves the binding, and loading, of the subsequently formed polymeric sublayer.

For adjusting the pH, the pretreatment composition can comprise a pH modifier and/or buffering agent such as an alkalizer, an acid, or a combination thereof. PH modifiers and/or buffering agents may be selected from, without being limited to, ammonia, alkanolamines (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol), guanidium salts, alkali metal and ammonium hydroxides and carbonates; and mixtures thereof, sodium hydroxide, ammonium carbonate, acidulents (such as inorganic and inorganic acids including for example phosphoric acid, acetic acid, ascorbic acid, citric acid or tartaric acid, hydrochloric acid); and mixtures thereof.

Thickener

According to embodiments described herein, the pretreatment composition further comprises a thickener in the range of 0.1 wt. % to 3 wt. % (or 3.0 wt. %), preferably in the range between 0.3 wt. % to 2.5 wt. %, more preferably 0.5 wt. % to 2.2 wt. %, and even more preferably 0.5 wt. % to 2.0 wt. % relative to the total weight of the pretreatment composition. Preferably, the thickener is a non-ionic polymer, for example polysaccharides such as cellulose, cellulose gum or xanthan gum, and non-ionic thickeners based on polyether-1 such as commercially available thickener Pure Thix 1442. Specific examples are cellulose at a 0.5 wt. % or polyether-1 based thickener such as Pure Thix 1442 with 2.0 wt. %.

Application of the Pretreatment Composition

According to embodiment described herein, the pretreatment composition is applied to keratin fibers or nails to impart the surface of the fibers or nails with an overall positive charge which subsequently facilitates adsorption of the film-forming polymer of the hair coloring composition, particularly if the film-forming polymer is a carboxylic acid polymer. The cationic polymer of the pretreatment composition may interact with the surface of the keratin fibers through at least one of electrostatic interaction, van-der-Waals interaction and hydrogen bond interaction, or a combination thereof. The initial interaction may be mediated mainly through electrostatic interaction.

After the pretreatment has been applied, and optionally rinsed, the hair coloring composition is applied to the keratin fibers of the hair which have been treated with the pretreatment composition. According to embodiments described herein, the hair coloring or nail coloring composition is applied without a rinsing step between application of the pretreatment composition and the hair or nail coloring composition. Excess liquid of the pretreatment composition may be removed by an absorbing tissue prior to application of the hair or nail coloring composition without drying the keratinous surface. Keeping the keratinous surface wet until application of the hair coloring composition is preferred.

4.9 Optional Components

Optional components of the composition include suspending agents, leveling agents and viscosity control agents. The suspending agents help maintain pigment microparticles, if present, in a dispersed condition and minimize or negate their re-agglomeration. Suspending agents include fatty acid esters of polyols such as polyethylene glycol and polypropylene glycol. These are similar to plasticizers and function in similar fashion to allow pigment microparticles to "slip" by each other without retarding or binding interaction. They act as grease in this fashion. Additionally, suspending agents in part participate in promoting the stable dispersion of pigment microparticles and avoid settling. Pigment microparticles on average are small enough so that Brownian movement participates in maintaining their dispersion. The carboxylic acid polymer also participates through its solubilization or interaction with pigment microparticles and with the medium. The suspending agents provide another factor for maintaining the stable dispersion. They not only provide the "grease" to facilitate Brownian movement but also in part stabilize through interaction as emulsifiers of pigment microparticles in the medium.

Generally, the hair coloring composition embodiments in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

The hair coloring composition embodiments in accordance with the present invention can further optionally contain one or more additives, including, but not limited to, antioxidants (e.g., phenolics, secondary amines, phosphites, thioesters, and combinations thereof), crosslinking agents, reactive diluents (e.g., low molecular weight mono- or di-functional, non-aromatic, (meth)acrylate monomers such as 1,6-hexanediol di(meth)acrylate, tripropylene glycol di(meth)acrylate, isobornyl(meth)acrylate, 2(2-ethoxy-ethoxy)ethyl(meth)acrylate, n-vinyl formamide, tetrahydrofurfuryl(meth)acrylate, polyethylene glycol di(meth)acrylate, tripropylene glycol di(meth)acrylate, neopentyl glycol dialkoxy di(meth)acrylate, polyethyleneglycol di(meth)acrylate, and mixtures thereof), non-reactive diluents (e.g., ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide); dyes, fillers (e.g., silica; carbon black; clay; titanium dioxide; silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide and mixtures thereof), plasticizers (e.g., petroleum oils such as ASTM D2226 aromatic oils; paraffinic and naphthenic oils; polyalkylbenzene oils; organic acid monoesters such as alkyl and alkoxyalkyl oleates and stearates; organic acid diesters such as dialkyl, dialkoxyalkyl, and alkyl aryl phthalates, terephthalates, sebacates, adipates, and glutarates; glycol diesters such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils such as castor, tall, rapeseed, and soybean oils and esters and epoxidized derivatives thereof; esters of dibasic acids (or their anhydrides) with monohydric alcohols such as o-phthalates, adipates and benzoates; and the like and combinations thereof), processing aids, ultraviolet stabilizers (e.g., a hindered amine, an o-hydroxy-phenylbenzotriazole, a 2-hydroxy-4-alkoxybenzophenone, a salicylate, a cyanoacrylate, a nickel chelate, a benzylidene malonate, oxalanilide, and combinations thereof), and combinations thereof.

An additional additive may be a tactile (hair feel) modification agent. These may include, but are not limited to, a softening and/or lubricating and/or anti-static and/or hair alignment and/or anti-frizz benefit and/or impact on the keratin fibres.

4.10 Solids Content

Embodiments of the hair coloring composition include solids and liquids. The solids comprise any substance or material of the hair coloring composition that in a form uncombined with any other material, solvent, liquid or substance is has a solid physical form at ambient conditions. Included at least are the peri-arylene dyes of the hair coloring composition, and, if present, the optional pigment microparticles, and the film former, for example the optional carboxylic acid polymer or optional polar functional silicone polymer, the base compound of the multicomponent composition (I), or the organic polymer and the in situ linking material of the multicomponent composition (II). The medium is a liquid and functions as a solvent and/or a liquid in which solid particles are dispersed. The optional components as well as the plasticizer, surface treatment agent, cross linking agent and other materials added to the medium, if any, are included in the solids content as long as they remain with the composition following application and setting of the hair coloring composition as a coating on strands of human hair. This includes substances that ordinarily would be regarded as liquids because they would remain on strands of hair. The solids content of the hair coloring composition typically may range from about 1 wt % to about 40 wt % relative to the total weight of the composition. A preferred solids content ranges from about 2 wt % to about 30 wt % and another preferred solids content ranges from about 4 wt % to about 20 wt % relative to the total weight of the composition. An especially preferred solids content range is about 4 wt % to about 10 wt % with contents of about 5 wt %, about 6 wt %, about 7 wt %, about 8 wt %, about 9 wt % and about 10 wt % being more especially preferred.

4.11 Testing the Flexibility of a Coating of the Film Former

The coating produced by applying the optional film former to keratin fibers such as human hair must easily expand, contract and flex without flaking, peeling, shedding or detaching. Hair is frequently moving and is highly flexible. The coating needs to mimic these properties of hair. This reduces the chance of the coating from being damaged or cracked which would reduce its wash resistance. From this viewpoint, the coating elongation of the polymer(s) used within the composition is in the range of about 25% to about 1200%, in the range of about 35% to about 1200%, in the range of about 60% to about 1200%, or in the range of about 70% to about 1200%.

Here, the coating elongation of the carboxylic acid polymer is measured as follows. Firstly, the polymer is coated on a polytetrafluoroethylene sheet such that the film thickness after drying becomes 500 µm, dried at normal temperature (20° C.) and at normal pressure (65% RH) for 15 hours, and further dried at 80° C. for 6 hours and at 120° C. for 20 minutes, and then is peeled off from the sheet to form a polymer film. Further, the coating elongation of the obtained film is measured using a tension tester at a measurement temperature of 20° C. and Measurement speed of 200 mm/mm. The measurement of the coating elongation is performed by elongating the film and measuring the length of the coating film elongated before being damaged, and the ratio thereof is represented as the coating elongation as a percentage. In addition, as the tension tester, for example, a tensilon universal tester RTC-1225A (trade name, Orientec Co., Ltd.) or a tester equivalent to the tensilon universal tester can be used.

With the film prepared above, it can also be tested for optical density to check that the polymer film does not itself alter the hair appearance of the hair too significantly.

Further the polymer preferable can have a glass transition point (Tg) as described above so that it is possible to prevent the colored coating from being damaged or cracked and to secure washing and friction fastness.

The polymer coating can have a surface energy between about 20 and about 50 mJ m$^{-2}$. The polymer coating preferably has high transmission, to ensure that it does not interfere with the optics of the hair color. The polymer preferably has a refractive index between 1.4 and 1.6.

4.12 Method for Coloring Hair

The hair coloring composition aspect of the present invention can be applied to keratin fibers to form a micro coating of the dyes and optionally film former such as carboxylic acid polymer. This aspect of the invention concerns a method for coloring keratin fibers and comprises applying embodiments of one or more hair coloring compositions for a time sufficient to deposit an effective color on each keratin fiber. A somewhat to substantially overall distribution of the color on the length and circumference of each fiber is produced.

To accomplish this aspect, embodiments of the hair coloring composition comprising a solution of at least one peri-arylene dye are applied to the hair by brushing, painting, spraying, atomizing, squeezing, printing, rubbing massaging or in some manner coating the hair strands with the embodiments. Optionally, the hair coloring composition may comprise a film former such as carboxylic acid polymer in un-neutralized or neutralized form, and other optional components. Following application of a compositional embodiment to the hair strands, the composition is set or modified to remove the medium. The setting leaves a somewhat to substantially overall color coating containing the dyes and optional additional components such as film former.

The hair coloring compositions in accordance with the present disclosure can have a viscosity that can be controlled to enable the product to be applied to the hair using either a brush and bowl or a bottle, but with sufficient rheology such that it does not drip and run from the hair onto the face or body.

The hair coloring compositions can be utilized in concentrated form or in serial dilutions, to provide for a consistent color results substantially along the entire length of the keratin fibers.

The aspect of coloring mammalian or synthetic keratin fibers with a hair coloring composition as described above includes a method for this coloring. The method comprises applying the above-described hair coloring composition to keratin fibers an effective coloring amount of the composition of medium with peri-arylene dyes, optional carboxylic acid polymer, and optional additional components; and setting the hair coloring composition by removing or otherwise eliminating the medium (e.g., by drying the composition).

As described above, if it is present the setting step converts the salt of the conjugate acid of the volatile base and the conjugate carboxylate polymer to the carboxylic acid polymer (un-neutralized carboxylic acid polymer) and volatile base. If the carboxylic acid polymer is used in an un-neutralized form, or if the conjugate carboxylate polymer contain cross-linking groups, the setting step facilitates the cross-linking also.

During the setting/drying step, color distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm s$^{-1}$ to 50 cm s$^{-1}$ or at a rate between 0.5 cm s$^{-1}$ to 20 cm s$^{-1}$.

The hair coloring composition is applied to the mammalian or synthetic keratin fibers in any suitable way including spraying the hair coloring composition, massaging the keratin fibers by hand, after applying the hair coloring composition to the hand or by combing, brushing or otherwise applying the hair coloring composition throughout the mammalian or synthetic keratin fibers.

Unlike current hair coloring approaches that use dyes, the color with the hair coloring compositions described herein occurs on the surface of the hair strands. Current dye based approaches do provide the head of hair with some color variation, as the strands are not identical, and some of these differences are preserved after coloring. There are also differences root to tip which also helps to provide some variation. Using a surface coloring system such as that of the present invention, the variation of the underlying hair can be substantially removed, leading to a more homogeneous color result. This color result can be a more homogenous application of color. To obtain a somewhat non-homogeneous application of color that tends toward a more natural look, the user can apply the inventive hair coloring composition by any of several techniques.

The methods by which the hair coloring compositions described herein are applied can be modified, such that the user applies the product in one region of the hair, and then apply a diluted version in another region of the hair. The dilution formula is specially chosen to be compatible with the colorant formulation and reduces the coloring strength, while maintaining the longevity of the color result. This can effectively be a "blank" formulation, which contains broadly the same materials as the coloring formulation, but with lower or no dye(s) (and optional pigments) present. When diluted the ratio of the diluent to colorant can be between about 10:1 and about 1:10, about 8:1 and about 1:2 or about 5:1 and about 1:1.

Alternatively, the amount of hair coloring composition applied can be altered in different regions of the hair, for example half the product is applied in the lengths of the hair, leading to a less colorful result. The difference in amounts applied in one region of the hair versus another can be between about 4:1 and about 1:4 or about 2:1 and about 1:2.

Alternatively, a combination of these approaches may be used to deliver the target color variation.

When the foregoing techniques are not possible to be applied, rather than apply a single hair color, it may be possible to apply two or more hair colors to different regions of the hair.

When this is done, the different hair colors preferably provide complimentary colors so as to develop an attractive result. The difference in colors that can be used, based on the end result on hair tresses are as follows. As described within the CIELABCH system:

Color 1 (LCH) versus Color 2 (LCH)
Color 1 L-15<Color 2 L<Color 1 L+15
0 or Color 1 C-10<Color 2 C<Color 1 C+10
Color 1 H-45<Color 2 H<Color 1 H+45

Those skilled in the art of color measurements will know how to interpret difference in hue angles, H, when they extend from low positive values to those near to 360 degrees due to the circular nature of the hue angle.

The method for use of the hair coloring composition in accordance with the present invention can occur during any suitable period. The period of application can be from about 0 to 30 minutes, but in any event a period that is sufficiently long to permit the dye(s) and optional pigments, respectively, to adhere or bind to each separate keratin fiber, substantially along the entire length of each keratin fiber. The resultant is keratin fibers having a color and permanence that is at least equivalent to the color resulting from oxidative hair color, except under much milder conditions.

The hair coloring compositions described herein can be prepared by the manufacturer as a full shade, e.g., one that is ready to apply to the hair, and then shipped as a discrete unit to the user. The user may need to re-blend the hair coloring composition prior to application to ensure that the hair coloring composition delivers the optimum performance. Such re-blending can require shaking the hair coloring composition for about 1 to about 120 seconds or from about 3 to about 60 seconds. Reblending may also be performed by stirring the hair coloring composition prior to use. This may occur for about 1 to about 120 seconds or from about 3 to about 60 seconds. Although the hair coloring compositions according to the present invention are stable, reblending may be desirable. In particular, for hair coloring composition embodiments in accordance with the present invention comprising pigment microparticles, the re-blending to agitate the particles and resuspend them in a substantially uniform distribution is desirable.

Alternatively, the hair coloring composition can be made on demand from a series of discrete formulations and mixed ready for use. Each hair coloring composition would need to be designed such that the combinations of two or more hair coloring compositions produce readily mixable hair coloring compositions with sufficient stability to be used. For example, at least four hair coloring compositions can be made available for blending, at least 5 hair coloring compositions and even at least 6 hair coloring compositions. Additional composition may also be used to impart other signals into the product, for example modifying the rheology, changing the perfume, altering the shine or hair feel properties.

Multiple compositions comprising different dyes can be blended together prior to application to the keratin fibers. Such blending can be done in a manner so as to apply a plurality of complementary surface colors to the keratin fibers.

Another aspect of the present invention is directed to a method for multiple coloring of mammalian or synthetic keratin fibers, the method comprising:

applying a first hair coloring composition in accordance with the foregoing description so that the composition is distributed substantially along the entire length of each keratin fiber for a time sufficient to deposit an effective coloring amount of first dyes/pigment microparticles on the mammalian or synthetic keratin fibers;

applying a second hair coloring composition in accordance with the foregoing description so that the second composition is distributed substantially along the entire length of each keratin fiber for a time sufficient to deposit an effective coloring amount of second dyes/pigment microparticles on the first dyes/pigment microparticles; and setting the hair coloring composition.

The first hair coloring composition can function to enhance the adhesion between the hair and the second hair coloring composition since the first hair coloring composition positioned on the hair more or less functions as "glue" between the hair and the second hair coloring composition. The first hair coloring composition can be applied immediately prior to applying the second hair coloring composition; at least 1 hour prior to applying the second hair coloring composition; at least 24 hours prior to applying the second hair coloring composition; or at least 10 days prior to applying the second hair coloring composition, or at least one month prior to applying the second hair coloring composition. The kinds of pigment microparticles, if present, and color can be varied as can the strength of adherence of the film forming silicone polymers to the hair. The hair coloring compositions can provide for multiple layers, including at least one layer comprising pigment microparticles comprising at least a medium containing a dispersion of at least one dissolved carboxylic acid polymer, or for example, at least one pigment and a polar functional silicone polymer. Optional additional solvents, wetting agents, dispersing agent, and plasticizer may be included.

The coating comprising at least one film former or multicomponent composition, or pigment in a coating of film-forming polymer, can be adhered to the hair utilizing a coating having a total thickness at any given point along the hair fiber of less than about 5 µm, preferably less than about 2 µm as measured using a scanning electron microscope (SEM). To make such measurements, a coated hair sample can be embedded in a suitable resin, and then sectioned root to tip using techniques known to those skilled in the art of scanning electron microscopy. The thickness of the layer on the surface can then be assessed along the line of cuticles over a length of at least 100 µm. The thickness of layer is determined by averaging 10 points evenly spaced over the section of interest.

As described above, application of the hair coloring composition to sections of a hair strand can be varied. In addition to varying the concentration of the peri-arylene dye(s), optional pigment microparticles and optional coloring agent, different shades and/or colors of hair coloring composition can be applied to different sections of a strand of hair or a group of strands of hair. For example, the hair roots, mid sections and tips sometimes or often have different shades of color in their natural condition. This variation can be mimicked, altered or covered through use of differing shades or colors of the hair coloring composition. Roots, for example can be covered with a lighter shade and the tips can be covered with a darker shade to produce a two tone variation of the hair. Application to the hair of the first hair coloring composition followed by stripping the composition from the hair mid sections and ends followed by setting the remaining composition on the hair roots will provide a first hair color micro coating on the roots. The mid-sections and tips can be dipped or brush applied with a second hair coloring composition to complete the two color or two tone treatment. The use of multiple hair coloring compositions to produce multiple micro coatings on the hair can provide overlapping, sequential or coterminous micro coatings on the hair according to typical and routine techniques for applying multiple versions of hair color practiced by professional hair salons.

4.13 Application of Components of Multicomponent Composition

The first, second, third and fourth components of the multicomponent composition may be maintained in separate storage compartments or in separate kit form when the first, second and third functional groups of these components will react if together. Additionally, the substantive constituent of the fourth component is maintained separately if it will catalyze or otherwise cause reaction of such functional groups. A convenient storage means can be utilized such as plastic squeeze tubes, plastic bottles, glass containers, sachets, multi-compartment containers, tooles, spottles syringes and plunger operated dispensing devices. Unit amounts for combination can be formulated so that the entire contents of a unit of the first component can be combined with the entire contents of the second component for application to substrate material, in particular keratin fibers or a keratinous surface. Alternatively, metered or calibrated dispensing containers for providing measured amounts of the components as directed by printed instructions can be provided. With some embodiments, multiple components can be pre-combined for storage and handling as long as a substantive constituent that would cause in situ linking is maintained in a separate compartment.

Use of the foregoing delivery means enables preparation of an embodiment for practice of the method of the present invention. This embodiment may comprise sequential, simultaneous or premixed application of the first and second components to substrate material. This aspect of application provides a layer of combined first and second components on the substrate material that will undergo transformation to a coating in which the first and second functional groups of these components in situ interact to covalently, electrostatically, coordinately, ionically, dipolar-wise, or entanglement-wise connect bond as the completed coating. Preferably the pairs of first and second functional groups are chemically reactive so that covalent bonds are formed between the first and second silicone polymers and the base compound or, respectively, between the organic polymer and the in situ linking material. With this aspect alone, the resulting coating on substrate material, such as but not limited to hair, provides good remanence against repeated shampooing, rinsing and contact with mild detergents, soap and similar wash substances.

Pretreatment with Third Component

Another embodiment of the method according to the present invention may comprise application of the third component to the substrate material as a pretreatment before application of the first and second components as described above. According to this embodiment of the method, the third component containing the base compound is applied on or to at least a portion of the substrate material such as hair, and preferably throughout the substrate material. While it is not a limitation of the invention, it is believed that the pretreatment addition of the third component enables enhancement of adhesion between the hair, and first and second components. It is believed that the amine groups or mercapto groups, preferably amine groups of the third component interact with complementary chemical groups on the substrate material and interact with the first and second silicone polymers. Although it is not a limitation of the invention, it is further believed that the second functional groups also interact with complementary chemical groups of the substrate material. It is believed that these chemical interactions, which are covalent and also are supplemented by coordinate, electrostatic, ionic, dipolar and/or entanglement interactions function to meld together the substrate material, the first and second silicone polymers and the base compound.

Pretreatment with the third component may be carried out prior to application of the first and second components. Pretreatment may be carried out immediately prior to application of the first and second components, or at least 1 hour prior to application of the first and second components, or at least 24 hours prior to application of the first and second components, or at least 10 days prior to application of the first and second components, or at least one month prior to application of the first and second components. Preferably, pretreatment may be carried out immediately prior to or within a few minutes up to an hour before application of the first and second components. Typically, the third component is at least partially dried with optional heating to at least substantially remove or otherwise eliminate the medium of the third component. For example excess medium may be removed by contacting with an abosrbant fabric or surface or the hair may by heated with a hair drier. Preferably, removal of third component medium is accomplished before application of the first and second components.

Application of First and Second Components Following Pretreatment

As described above, first and second components may be applied to the substrate material in combination with the foregoing pretreatment with the third component or may be applied without such pretreatment. In either arrangement, embodiments of the first and second components are maintained separately when the first and second functional groups constitute reactive pairs as described above. Application of the first and second components to pretreated or un-pretreated substrate material may be accomplished by sequential application of the first and second components or simultaneous application of these components to the hair. Typically for sequential application, either of the first and second components may be applied first, preferably the first component is applied first, especially for embodiments including pretreatment with the third component. Alternatively, the first and second components may be mixed together to form a premix immediately before application to the substrate material. Typically, the rate of reaction of the reactive pairs is pre-adjusted through concentration, steric interaction, temperature, and similar factors controlling reaction rate so that a premix preferably will not substantially interact before the premix is applied to the substrate material. The practice of this step with the pre-treatment embodiment initially introduces combined first and second components on top of the pretreatment layer of base compound on the substrate material. Because the first and second components are in a medium, penetration, combination, mixing and/or melding of the first and second components into the pretreatment layer is believed to be accomplished. The penetration is believed to enable the linking among the (organic polymer and the in situ linking material) or (first and second silicone polymers), respectively, the base compound and the substrate material.

Application of the first and second components to pretreated substrate material is preferably carried out after pretreatment. This sequence may be carried out immediately after pretreatment, or at least 1 hour after pretreatment, or at least 24 hours after pretreatment, or at least 10 days after pretreatment, or at least one month after pretreatment.

The sequential, simultaneous or premix application of the first and second components may be applied to at least a portion of the substrate material or may be applied all over the substrate material. The portions of first and second components may be applied sequentially, simultaneously or as a premix in a single application over all the substrate material or may be applied step-by-step to the substrate material. The first and second components may be applied step-by-step, for example, in case the substrate material is damaged. Applying the first and second components in a step-by-step manner as described above, may help to ensure that the treated portions of the substrate material are saturated with the combined first and second components and may therefore provide a better coverage of the substrate material.

Manipulative Techniques for Application

After the pretreatment of the third component has been accomplished, and the pretreated substrate material optionally rinsed, the pretreated substrate material can be dried. The substrate material can be dried using an elevated temperature. The temperature of the substrate material can be increased to elevated temperatures above room temperature such as 40° C. or higher, for example using a hair drier. While the substrate material is being dried, some form of interdigitated implement can be used to help separate portions of the substrate material, and especially separate hair strands from one another. Examples of interdigitated devices include a comb or a brush. The substrate material can be dried with a hair drier while simultaneously being combed or brushed until it is dry to the touch. Alternatively, other means can be employed to dry and separate the substrate material such as hair simultaneously. For example, using a combination of air movement and vibrations will accomplish distribution of the multicomponent composition throughout the strands of hair.

Operational Method for Coating Hair

The performance of operational method aspects of the present invention can be applied to keratin fibers to form a coating of the multicomponent composition. This aspect of the invention concerns a method for coloring substrate material and comprises applying embodiments of one or more multicomponent compositions for a time sufficient to deposit an effective colored coating on the substrate material such as each keratin fiber or hair strand. A somewhat to substantially overall distribution of the coating on the length and circumference of each fiber is produced.

To accomplish this aspect, embodiments of the first, second and third components of multicomponent composition are applied to the substrate material according to the sequences described above by brushing, painting, spraying, atomizing, squeezing, printing, rubbing massaging or in some manner coating the substrate material such as hair strands with the embodiments. Following application of a compositional embodiment to the substrate material such as hair strands, the composition is set, cured, linked, coordinated and/or otherwise melded together preferably by warming with blown warm air from a hair dryer or similarly treated to remove the medium, initiate in situ linking of the (organic polymer and the in situ linking material) or (first and second silicone polymers), respectively, the base compound, the substrate material and if present, remove the volatile base.

The in situ linking of the substantive constituents of first, second and third components during application provides a linked coating that enables it to resist for a time destruction by washing with dilute mixtures of soap and water or shampoo and water. Color fastness (remanence) is developed so that washing with dilute aqueous soap solution or dilute aqueous shampoo will not substantially remove the coating, but the coating can be facilely removed by use of a transformation trigger. The properties of the coating include wash-fastness, flexibility, adhesion, abrasion resistance and remanence which are due at least in part to the linked character of the composition constituents including at least the first and second silicone polymers and the base compound and their intermolecular entwining, ionic and electrostatic intermolecular interaction, covalent and/or non-covalent linking, dipole interaction and lipophilic interaction of neutral moieties of these compositional constituents.

Selection of the substantive constituents of the multicomponent composition can be made on the basis of properties such as a solid lattice formation. Such properties include the flexibility, the hardness, the adhesion, the remanence, the resistance to water or to other chemical compounds, and the abrasion resistance.

The multicomponent compositions in accordance with the present disclosure can have a viscosity that can be controlled to enable the product to be applied to the hair using either a brush and bowl or a bottle, but with sufficient rheology such that it does not drip and run from the hair onto the face or body. Alternatively, low viscosity formulations may be applied to the hair via a suitable application device such that it does not drip and run form the hair onto the face and body.

The multicomponent compositions can be utilized in concentrated form or in serial dilutions, to provide for a consistent color results substantially along the entire length of the keratin fibers.

The aspect of coloring mammalian or synthetic keratin fibers with a multicomponent composition as described above includes a method for this coloring. The method comprises:
(i) applying the above-described multicomponent composition to keratin fibers an effective coloring amount of the first and second silicone polymers, base compound, and optional additional components;
(ii) setting the multicomponent composition by removing or otherwise eliminating the medium (e.g., by drying the composition); and.
(iii) setting the interaction among the first, second and third functional groups of the multicomponent composition by initiating the in situ linking among these groups.

During the setting/drying step, color distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm s$^{-1}$ to 50 cm s$^{-1}$ or at a rate between 0.5 cm s$^{-1}$ to 20 cm s$^{-1}$.

The multicomponent composition is applied to the mammalian or synthetic keratin fibers in any suitable way including spraying the multicomponent composition, massaging the keratin fibers by hand, after applying the multicomponent composition to the hand or by combing, brushing or otherwise applying the multicomponent composition throughout the mammalian or synthetic keratin fibers.

Unlike current hair coloring approaches that use dyes, the color with the multicomponent compositions described herein occurs on the surface of the hair strands. Current dye based approaches do provide the head of hair with some color variation, as the strands are not identical, and some of these differences are preserved after coloring. There are also differences root to tip which also helps to provide some variation. Using a surface coloring system such as that of the present invention, the variation of the underlying hair can be substantially removed, leading to a more homogeneous color result. This color result can be a more homogenous application of color. To obtain a somewhat non-homogeneous application of color that tends toward a more natural look, the user can apply the inventive multicomponent composition by any of several techniques.

The methods by which the multicomponent compositions described herein are applied can be modified, such that the user applies the product in one region of the hair, and then can apply a diluted version in another region of the hair. The dilution formula is specially chosen to be compatible with the colorant formulation and reduces the coloring strength, while maintaining the longevity of the color result. When diluted, the ratio of the diluent to colorant can be between about 10:1 and about 1:10, about 8:1 and about 1:2 or about 5:1 and about 1:1.

Alternatively, the amount of multicomponent composition applied can be altered in different regions of the hair, for example half the product is applied in the lengths of the hair, leading to a less colorful result. The difference in amounts applied in one region of the hair versus another can be between about 4:1 and about 1:4 or about 2:1 and about 1:2.

Alternatively, a combination of this approaches may be used to deliver the target color variation.

When the foregoing techniques are not possible to be applied, rather than apply a single hair color, it may be possible to apply two or more hair colors to different regions of the hair. When this is done, the different in situ hair colors preferably provide complementary colors so as to develop an attractive result. The difference in colors that can be used, based on the end result on hair tresses, such as—natural white hair non pre-bleached are as follows. As described within the CIELCh system:

Color 1 (LCh) versus Color 2 (LCh)
Color 1 L-15<Color 2 L<Color 1 L+15
0 or Color 1 C-10<Color 2 C<Color 1 C+10
Color 1 h-45<Color 2 h<Color 1 h+45

The method for use of the multicomponent composition in accordance with the present invention can occur during any suitable period. The period of application can be from about 0 to 30 minutes, but in any event a period that is sufficiently long to permit the coating to coat and adhere or bind to each separate keratin fiber, substantially along the entire length of each keratin fiber. The resultant is keratin fibers having a color and permanence that is at least equivalent to the color resulting from oxidative in situ hair color, except under much milder conditions.

The multicomponent compositions described herein can be prepared by the manufacturer as a full shade, e.g., one that is ready to apply to the hair, and then shipped as a discrete unit to the user. The user may need to re-blend the multicomponent composition prior to application to ensure that the multicomponent composition delivers the optimum performance. Such re-blending can require shaking the multicomponent composition for about 1 to about 120 seconds or from about 3 to about 60 seconds. Reblending may also be performed by stirring the multicomponent composition prior to use. This may occur for about 1 to about 120 seconds or from about 3 to about 60 seconds. Although the multicomponent compositions according to the present invention are designed to provide stable suspensions, the re-blending is desirable.

Multiple compositions can be blended together prior to application to the keratin fibers. Such blending can be done in a manner so as to apply a plurality of complementary surface colors to the keratin fibers.

The multicomponent compositions can include multiple layers, involving multiple applications of at least the first and second components following the first application of the three components. It may be beneficial also to periodically reapply the third component. The techniques for applying multiple layers follow the techniques described above for application of a single multicomponent composition.

4.14 Post Treatment

A post treatment composition can be applied after treating hair with the hair coloring compositions described herein. This can be applied either directly after the coloring composition without and intermediate drying step, or after the coloring composition has been dried. The post treatment can be either single application or multiple application across time. The post treatment can be used to improve one or more of: feel, resistance to shampoo/conditioner/water washing treatments, and shine of the hair. Nonlimiting examples of materials used to improve the feel are those which impart lubricity to the hair fibers and/or help the hair fibers separate during the drying steps, for example silicones, silicone polyethers, silicone polyglucose, polyisobutene, copolymers of ethylene and propylene oxide, and commonly used cosmetic oils and waxes. Nonlimiting examples of materials used to improve shampoo wash resistance are crosslinking materials (as described herein in the crosslinker section) or materials which act as a 'sacrificial layer' for example polymeric silicones and their copolymers, silicone resins, cosmetics oils and waxes. Nonlimiting examples of materials used to improve the shine of hair (meaning a decrease of the full width at half maximum parameter of the specular reflection curve as measured by a goniophotometer) are those materials which form a smooth film above the previously applied coloring on the hair. In general, any cosmetically known film forming material can be used, but preferred are materials such as polymeric silicones and polycationic materials.

5 REMOVAL OF COLOR

The coloring of the keratin fibers made according to the foregoing aspects of the invention can be removed substantially in total due to at least the non-penetrance of the peri-arylene dye(s) into the keratin fiber. The surface coloration can be removed substantially in total by dissolving the peri-arylene dyes. When the peri-arylene dyes are used together with a film former coating on the exterior surface of the keratin fiber, such as a coating of carboxylic acid polymer, the peri-arylene dyes may be removed while leaving the film former coating essentially intact. Alternatively, the film former may be removed simultaneously with the peri-arylene dyes.

The surface coloration can be removed substantially in total by dissolving the color adhered to the exterior surface of the keratin fiber. This removal is accomplished through use of a de-coloring medium. While dilute mixtures of soap and water or shampoo and water will not readily dissolve the peri-arylene dyes, use of the de-coloring medium will dissolve and thereby remove the peri-arylene dyes to a significant extent.

A de-coloring medium for removing peri-arylene dyes according to the present invention from the exterior surface of keratin fibers may comprise an organic solvent having an octanol/water partition coefficient (log $P_{ow}$) of at least 15, wherein log $P_{ow}$ is calculated based on the GALAS algorithm using ACD/Labs software.

According to embodiments, the de-coloring-medium may have an octanol/water partition coefficient (log $P_{ow}$) of at least 12, wherein log $P_{ow}$ is calculated based on the GALAS algorithm using ACD/Labs software.

Such de-coloring media are in particular suitable for removing peri-arylene dyes having at least one hydrophobic moiety R2, R3 and/or R6 from the exterior surface of keratin fibers.

According to embodiments involving a hydrophobic dye according to the present invention, wherein the dye is substituted with one or more hydrophobic moieties optionally having a non-linear structure and comprising at least 14 carbon atoms, the de-coloring medium comprises natural and/or synthetic fat, wax or oil. For ease of practical use, the de-coloring medium may have a suitable viscosity to enable it being applied to the hair using either a brush and bowl or a bottle, but with sufficient rheology such that it does not drip and run from the hair onto the face or body. The viscosity should be high enough, however, in order to enable satisfactory removal of the de-coloring medium saturated with the peri-arylene dyes. In particular, the de-coloring medium may have a viscosity that ranges from about that of water to that of honey.

Suitable de-coloring medium may comprise oils such as for example cosmetic oils, Ayurvedic oils, therapy oils, massage oils, plant oils, blends of such oils, or blends with other substances, in particular blends with substances presenting a therapeutical benefit, wellness benefit and/or additional fatty or oily substances. According to embodiments, the de-coloring medium may comprise at least 20% by weight, in particular at least 50% by weight of one or more cosmetic oils, Ayurvedic oils, therapy oils, massage oils or plant oils.

When the peri-arylene dyes are present on the exterior surface of keratin fibers within a coating of film former, such as polyacrylic acid, polyacrylate, polar functional silicone polymer or multicomponent composition, the above de-coloring medium may remove the dyes while leaving the film former coating essentially intact.

If it is intended to remove the film former along with the dyes, changing the pH can have a dramatic impact on the properties of the polymer film which is adhered to the surface. A soluble base acting as a trigger agent to neutralize the carboxylic acid groups and enable the conjugate acid to be readily soluble in a mixture of water and organic solvent will facilely remove the coating. Such bases include amino alcohols such as dimethylaminoethanol (dimethylethanolamine, DMEA), dimethylaminopropanol, and similar amino alkanol agents such as monoethanolamine, diethanolamine and triethanolamine and ammonia. Other bases such as NaOH and CaOH can also be used. For amine silicone polymers, a soluble acid can act as a trigger agent to neutralize the amine groups and enable the conjugate base to be readily soluble in a mixture of water and organic solvent.

A warm aqueous solution of the trigger agent is useful in this regard. The concentration of the trigger agent in aqueous solution optionally with an alcohol or ketone organic solvent such as methanol, ethanol, methyl ethyl ketone and the like may range from about 0.1% to about 15% by weight, preferably about 0.5% to about 10% by weight, more preferably about 1% to about 7.5% by weight relative to the total weight of the removal solution. While an aqueous alcoholic solution of an alkali metal hydroxide will also remove the coating, it is too harsh for application to mammalian skin, especially human skin.

The hair coloring removal composition can be applied to the mammalian or synthetic keratin fibers in any suitable way including spraying the hair coloring composition, massaging the keratin fibers by hand, after applying the hair coloring composition to the hand or by combing the hair coloring composition through the mammalian or synthetic keratin fibers. When the product is applied to the hair, the product can be physically distributed to cover all of the hair, and the action of distributing the product around the hair aids in the removal process.

A process that enables the rapid change of hair color requires the following steps. Application of a hair colorant to the hair, with an optional pre-treatment and post treatment. Leaving the color on the hair for one day, preferably for more than one day. Application of a composition to remove the hair color, followed by rinsing and drying the hair. The subsequent application of a hair coloring composition to the hair, with an optional pre-treatment and post treatment will again color the hair with no untoward after effects.

The instant disclosure is not limited in scope by the specific compositions and methods described herein, since these embodiments are intended as illustration of several aspects of the disclosure. Any equivalents are intended to be within the scope of this disclosure. Indeed, various modifications in addition to those shown and described herein can be within the grasp of those with ordinary skill in the art. Such modifications are also intended to fall within the scope of the appended claims.

Also contemplated herein are hair coloring compositions having a given color area defined by color coordinates (a*, b*) in the color space represented by the L*a*b* color system, which can be divided into a plurality of color areas. Each of the plurality of colors obtained from the area surrounding a given set of hair fibers is judged to belong to which color area of the colored area of a certain color. The number of colors judged for each color area is counted, and the color of the color area with the largest number of colors is selected as a representative color of the area surrounding a given set of hair fibers. The compositions are capable of delivering colors on hair (test method herein for fade) such that the results colors lie within the range of about $18<L<about\ 81$, about $-2<a<about\ 45$, and about $-13<b<about\ 70$.

Also contemplated herein are hair coloring compositions that do not change the underlying hair color, but instead change some other feature of the hair including shine (e.g., making it shinier or matte), the thickness of the hair and/or the feel of the hair.

When the color is removed from the hair, the waste water/composition can be treated to remove the pigments, if present, from the waste water effluent system. This can be achieved by filtration, or through cyclone technology, where the density differences are used to force the pigments to the settle, and the water to pass through.

Hair colorants made from surface films consisting essentially of a multicomponent coating that are very resistant to everyday hair treatments (such as washing with shampoo, conditioner etc) can be removed via use of specifically designed "removal formulations." These are specific chemical mixtures, described herein, and are designed to work via one or both of two broad mechanisms. The 'removal formulation' can be made such that it dissolves, weakens or chemically breaks down the binder material.

Changing the pH can have a dramatic impact on the properties of the coating which is adhered to the surface. A soluble base acting as a trigger agent to neutralize acid groups and enable the conjugate base to be readily soluble in a mixture of water and organic solvent will facilely remove the coating. Such bases include amino alcohols such as dimethylaminoethanol (dimethylethanolamine, DMEA), dimethylaminopropanol, and similar amino alkanol agents such as monoethanolamine, diethanolamine and triethanolamine and ammonia. Other bases such as NaOH and $Ca(OH)_2$ can also be used. The concentration of the trigger agent in aqueous solution optionally with an alcohol or ketone organic solvent such as methanol, ethanol, methyl ethyl ketone and the like may range from about 0.1% to about 15% by weight, preferably about 0.5% to about 10% by weight, more preferably about 1% to about 7.5% by weight relative to the total weight of the removal solution.

6 KIT

Also contemplated herein are kits, comprising the hair coloring composition disclosed herein in combination with at least one additional component. According to embodiments, the additional component present in the kit may be a composition comprising a film former as disclosed herein. According to embodiments, the film former may be selected from carboxylic acid polymer(s) and polar functional silicone polymer(s). According to further embodiments, the film former may be selected from a multicomponent composition (I) or a multicomponent composition (II). The film former composition may be intended for mixing with the hair coloring composition, or for separate application. According to embodiments, the additional component present in the kit may be pretreatment composition, in particular a pretreatment composition comprising a cationic polymer. According to embodiments, the additional component present in the kit may be a de-coloring medium. The de-coloring medium may comprise, for example, cosmetic oil, Ayurvedic oil, therapy oil, massage oil, plant oil, or a blend of such oils.

7 COMPOSITION FOR COLORING A KERATINOUS SURFACE

According to a further aspect, the present invention provides a composition for coloring a keratinous surface. The composition comprises a medium, and at least one dye described herein. According to embodiments, the dye may be an aromatic dye selected from rylene dyes, nitro dyes, aryl and heteroaryl azo dyes, chinon/chinonimine/chinondiimine dyes, methin dyes, azomethine-like hydrazone and imine dyes, and porphyrin dyes. The dye or an aromatic ring of the dye may be substituted with one or more hydrophobic moieties having a linear or non-linear structure. The said dye optionally comprises a reactive moiety R20.

According to embodiments, the dye may be a peri-arylene dye as described herein, which peri-arylene dye comprises a perylene, terrylene or quarterrylene core or higher rylene core.

According to embodiments, the peri-arylene dye may be a dye according to formula (1) or formula (24) described herein.

In some embodiments, the composition for coloring a keratinous surface comprises at least one peri-arylene dye substituted with a hydrophobic moiety and/or at least one hydrophilic peri-arylene dye, which peri-arylene dye is substituted with a reactive moiety R20.

In some embodiments of the composition for coloring a keratinous surface, the dye(s) is/are present in an amount of from 0.005% to about 5%, about 0.01% to about 3%, about 0.1 to about 2%, or about 0.25% to about 1.5% by weight of the hair coloring composition.

In some embodiments, the composition for coloring a keratinous surface comprises at least two of said dyes, in particular at least three of said dyes.

In some embodiments of the composition for coloring a keratinous surface, at least one of said dyes is photoluminescent. In some embodiments of the composition for coloring a keratinous surface, none of said dyes is photoluminescent. In some embodiments, the composition for coloring a keratinous surface further comprises a film former.

The keratinous surface may be the surface of a nail, in particular the surface of a human finger or toe nail.

8 METHOD FOR COLORING HAIR USING AN OIL-IN-WATER EMULSION AND REACTIVE DYES

The disclosure below describes a method for coloring mammalian hair using at least one reactive dye. It is to be understood that the reference to mammalian hair includes a reference generally to keratin tissue such as brows, lashes, nails and skin. Accordingly, even though the method is described in the context of mammalian hair, the method generally is applicable to keratinous tissue including natural and/or synthetic keratinous fibers and surfaces.

The at least one direct dye comprises a reactive dye according to the present disclosure, i.e. a reactive dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products. According to embodiments, the reactive dye comprises a reactive moiety R20.

In one aspect, there is provided a method of coloring mammalian hair, the method comprising:
(a) applying, on an external surface of individual hairs of the mammalian hair, an oil-in-water emulsion comprising:
 (A) an aqueous phase containing water; and
 (B) an oil phase containing at least one reactive condensation-curable film-forming amino-silicone pre-polymer that, subsequent to condensation curing, forms an elastomer,
 wherein said oil phase fulfills at least one of the following:
 (i) said at least one reactive condensation-curable film-forming amino-silicone pre-polymer includes at least one reactive condensation-curable film-forming amino-silicone monomer having a molecular weight of at most 1000 g/mole;
 (ii) said oil phase further contains a non-amino cross-linking agent adapted or selected to cure said pre-polymer, said non-amino cross-linking agent having a molecular weight in the range of at most 1000 g/mole;
(b) applying, on said external surface of individual hairs of the mammalian hair, at least one direct dye;
(c) after partial condensation curing of said pre-polymer has occurred so as to form an at least partially cured film on the external surface of the individual hairs, washing the hair with a rinsing liquid to remove any excess of said oil-in-water emulsion.

In some embodiments, a first amino-silicone pre-polymer of the at least one reactive condensation-curable film-forming amino-silicone pre-polymer has at least 3 silanol and/or hydrolysable groups, so as to form a 3-dimensional network.

In some embodiments, a first concentration of the first amino-silicone pre-polymer, within the oil phase, is at least 15%, at least 20%, at least 30%, at least 40%, at least 50%, or at least 60%, by weight, of said oil phase. In some embodiments, the first concentration is at most 95%, at most 90%, at most 85%, at most 80%, at most 75%, or at most 70%. In some embodiments, the first concentration of the first amino-silicone pre-polymer, within the oil phase, is within a range of 20-95%, 20-85%, 30-95%, 30-85%, 40-95%, 40-85%, 40-75%, 45-95%, 45-85%, 50-95%, 50-85%, 55-95%, 55-85%, 55-75%, 60-95%, 60-90%, 60-85%, or 60-80%.

In some embodiments, a combined concentration of the first amino-silicone pre-polymer and the non-amino cross-linking agent, within the oil phase, is within a range of 35-95%, 40-95%, 40-85%, 40-75%, 45-95%, 45-85%, 50-95%, 50-85%, 55-95%, 55-85%, 55-75%, 60-95%, 60-90%, 60-85%, or 60-80%, by weight, of said oil phase.

In some embodiments, a concentration of the non-amino cross-linking agent within the combined concentration is limited by a condition that the oil-in-water emulsion has a surface zeta potential greater than zero (>0), or at least +1 mV, at least +2 mV, at least +3 mV, at least +5 mV, at least +7 mV, or at least +10 mV.

In some embodiments, within the oil phase, a total concentration of the amino-silicone oil, the non-amino-silicone oil and the at least one reactive condensation-curable film-forming amino-silicone pre-polymer, excluding the first amino-silicone pre-polymer, is within a range of 3% to 65%, 3% to 60%, 3% to 55%, 3% to 50%, 3% to 45%, 3% to 40%, 7% to 40%, 10% to 40%, 10% to 50%, 15% to 50%, 15% to 45%, 15% to 40%, 20% to 45%, 25% to 45%, 25% to 50%, 30% to 45%, 30% to 60%, 35% to 50%, or 35% to 60%, by weight. In some embodiments, the total concentration of the afore-said different constituents of the oil phase is subject to the oil phase having a viscosity of no more than 500 mPa·s, as measured at 25° C.

In some embodiments, the concentration of a terminating pre-polymer having a single silanol or hydrolysable group, within the oil phase, is at most 7%, at most 5%, at most 2%, by weight of the oil phase. In some embodiments, the oil phase is devoid of said terminating pre-polymer.

In some embodiments, the total concentration of organic solvents within the oil phase of the emulsion, on a weight basis, is at most 10%, at most 5%, at most 2%, or at most 1%. In some embodiments, the oil phase is devoid of any organic solvent.

In some embodiments, the total concentration of water-miscible co-solvents within the aqueous phase of the emulsion, on a weight basis, is at most 10%, at most 5%, at most 2%, or at most 1%. In some embodiments, the aqueous phase is devoid of any said co-solvent.

In some embodiments, the oil-in-water emulsion further comprises a solid, hydrophobic reactive inorganic filler, said filler disposed or dispersed within the oil phase, said filler selected or adapted to facilitate curing of the condensation-curable film-forming amino-silicone pre-polymer(s). In some embodiments, the reactive filler includes, mainly includes, or consists of, a hydrophobic fumed silica.

In some embodiments, the average particle size (Dv50) of the solid, hydrophobic reactive inorganic filler is within a range of 5 to 500 nm, 5 to 250 nm, 10 to 200 nm, 20 to 200 nm, 40 to 300 nm, 60 to 300 nm, 60 to 250 nm, or 60 to 200 nm.

In some embodiments, the concentration of the solid, hydrophobic reactive inorganic filler disposed or dispersed within the oil phase is within a range of 0.2% to 12%, 0.2 to 10%, 0.2 to 8%, 0.4 to 10%, 0.4 to 8%, 0.6 to 10%, 0.6 to 8%, 0.8 to 8%, or 0.8 to 6%, by weight.

In some embodiments, the concentration of the solid, hydrophobic reactive inorganic filler within the oil-in-water emulsion is within a range of 0.005% to 0.5%, 0.005% to 0.3%, by weight.

In some embodiments, the refractive index of the solid, hydrophobic reactive inorganic filler is within a range of ±10%, ±7%, ±5%, or ±3%, of a refractive index of the oil phase.

In some embodiments, the at least partially cured film is self-terminated on the external surface of the individual hairs.

In some embodiments, the at least one reactive condensation-curable film-forming amino-silicone pre-polymer has a solubility in water of less than 1% by weight at 25° C.

In some embodiments, the at least one reactive condensation-curable film-forming amino-silicone pre-polymer includes a reactive condensation-curable amino-silicone monomer having a solubility in water of less than 1% by weight at 25° C.

In some embodiments, the partial condensation curing is effected or transpires at a temperature of at most 38° C., at most 36° C., at most 34° C., or at most 32° C., and optionally, at least 15° C.

In some embodiments, the washing of the hairs is performed within 30 minutes, within 20 minutes, within 15 minutes, within 10 minutes, within 5 minutes, within 3 minutes, within 2 minutes, or within 1 minute, after the application of the oil-in-water emulsion has been completed.

In some embodiments, following the washing, further curing transpires solely by or substantially solely by humidity or ambient humidity.

In some embodiments, within at least two days, at least three days, at least five days, or at least a week of said washing, all further curing proceeds in the absence of any non-cationic surfactant added to the hair.

In some embodiments, within at least two days, at least three days, at least five days, or at least a week of the washing, treating the hair can be performed with a hair formulation containing a cationic surfactant.

In some embodiments, the said oil-in-water emulsion has a surface zeta potential greater than zero, or at least +1 mV, at least +2 mV, at least +3 mV, at least +5 mV, at least +7 mV, at least +10 mV, at least +15 mV, at least +20 mV, at least +30 mV, at least +40 mV, or at least +60 mV; optionally, at most +100 mV, or at most +80 mV.

In some embodiments, the oil-in-water emulsion has a surface zeta potential greater than zero and below 90 mV, or within a range of 1-50 mV, 1-30 mV, 1-20 mV, 1-15 mV, 2-100 mV, 2-30 mV, 3-100 mV, 3-50 mV, 3-30 mV, 3-20 mV, 5-100 mV, 5-50 mV, 5-30 mV, 5-20 mV, 7-100 mV, 10-80 mV, 15-80 mV, 20-80 mV, or 20-60 mV.

In some embodiments, the surface zeta potential of the oil-in-water emulsion is measured at a pH of 10. In other embodiments, the surface zeta potential is measured at a native pH of said oil-in-water emulsion.

In some embodiments, the rinsing liquid is (i) water, or (ii) a cationic rinsing liquid containing a cationic surfactant, or (iii) a rinsing liquid devoid of non-cationic surfactants, degreasing agents and/or swelling agents, the degreasing and swelling agent respectively able to degrease and swell the at least partially cured film.

In some embodiments, the cationic surfactant is a cosmetically-acceptable primary, secondary, tertiary, or quaternary ammonium compound or polymer.

In some embodiments, the total concentration of reactive condensation-curable amino-silicone components within the oil phase is at least 45%, at least 55%, at least 60%, or at least 65%, by weight. In some embodiments, the total concentration of reactive components within a range of 50-100%, 50-95%, 50-90%, 50-85%, 50-80%, 55-95%, 55-85%, 60-95%, 60-85%, 65-95%, 65-90%, or 70-95%.

In some embodiments, the amino-silicone pre-polymer includes reactive groups selected from the group consisting of alkoxy-silane reactive groups, silanol reactive groups and combinations thereof.

In some embodiments, the oil phase, exclusive of all inorganic content, has no glass transition temperature.

In some embodiments, the at least one reactive condensation-curable film-forming amino-silicone pre-polymer is a liquid at 25° C.

In some embodiments, the viscosity of the at least one reactive condensation-curable film-forming amino-silicone pre-polymer, measured in a suitable rheometer at 25° C., is in a range of 2-1000 milliPascal-second (mPa·s), 2-500 mPa·s, 2-300 mPa-s, 2-200 mPa·s, 5-1000 mPa·s, 5-500 mPa·s, 5-300 mPa·s, 7-500 mPa·s, 7-300 mPa·s, or 7-200 mPa·s.

In some embodiments, the at least one, and optionally all of the at least one reactive condensation-curable film-forming amino-silicone pre-polymers, has an Amine Number or weight average Amine Number in a range of 3-1000, 3-500 or 3-200.

In some embodiments, the solubility in water of the at least one reactive condensation-curable film-forming amino-silicone pre-polymer, by weight, is less than 0.5% or less than 0.25%.

In some embodiments, the total concentration of amino-silicone oil within the oil phase, by weight, is at most 40%, at most 35%, at most 30%, at most 20%, at most 15%, at most 10%, or at most 5%.

In some embodiments, the total concentration of amino-silicone oil within the oil phase, by weight, is within a range of 1% to 40%, 5% to 40%, 10% to 40%, 20% to 40%, 1% to 30%, 5% to 30%, 10% to 30%, 15% to 30%, 20% to 35%, or 20% to 30%.

In some embodiments, the total concentration of non-amino-silicone oil within the oil phase, by weight, is at most 15%, at most 12%, at most 10%, at most 7%, or at most 5%, subject to a surface zeta potential of said oil-in-water emulsion being greater than zero, or at least +1 mV, at least +2 mV, at least +3 mV, at least +5 mV, at least +7 mV, or at least +10 mV.

In some embodiments, the total concentration of non-amino-silicone oil within said oil phase, by weight, is within a range of 1% to 15%, 3% to 15%, 5% to 15%, 8% to 15%, 1% to 12%, 3% to 12%, 5% to 12%, 3% to 10%, 3% to 8%, or 2% to 5%.

In some embodiments, the non-amino cross-linking agent includes, mainly includes, or consists of a reactive condensation-curable film-forming non-amino-silicone monomer.

In some embodiments, the non-amino cross-linking agent includes, mainly includes, or consists of an ethyl silicate, a poly(dimethoxysiloxane), and a poly(diethoxysiloxane).

In some embodiments, the total concentration of the non-amino cross-linking agent within the oil phase is at most 35%, at most 30%, at most 20%, at most 15%, at most 10%, or at most 5%, subject to a surface zeta potential of the oil-in-water emulsion being greater than zero, or at least +1 mV, at least +2 mV, at least +3 mV, at least +5 mV, at least +7 mV, or at least +10 mV.

In some embodiments, the total concentration of the pre-polymer, the non-amino cross-linking agent, the solid, hydrophobic reactive inorganic filler, the amino-silicone oil, the non-amino-silicone oil, and the at least one direct dye, within the oil phase, is at least 90%, at least 93%, at least 95%, at least 97%, at least 98%, or at least 99%, by weight.

In some embodiments, the aqueous phase further contains an oil-in-water emulsifier that is optionally non-ionic, said oil-in-water emulsifier having an HLB number within a range of 12 to 18, 12 to 17, 12 to 16, 12 to 15, or 13 to 16. In some embodiments, the total concentration of the water and any emulsifier, within the aqueous phase, is at least 90%, at least 95%, at least 97% at least 99%, on a weight basis.

In some embodiments, the mammalian hair to which the oil-in-water emulsion is applied is dry or non-wetted mammalian hair, or to pre-dyed hair. In some embodiments, the mammalian hair to which said oil-in-water emulsion is applied is at least one of unpre-degreased, unpre-shampooed, and unpre-bleached.

In some embodiments, the aqueous phase contains, by weight, at most 20%, at most 10%, at most 5%, or at most 2%, of the amount of the at least one direct dye within the oil phase. In some embodiments, the aqueous phase is devoid of said at least one direct dye.

In some embodiments, applying the oil-in-water emulsion according to step (a) and applying the at least one direct dye according to step (b) is carried out simultaneously. When applying the oil-in-water emulsion and the at least one direct dye simultaneously, the at least one direct dye in some embodiments may be applied to said external surface of individual hairs as a component of the oil-in-water emulsion.

In some embodiments, applying the oil-in-water emulsion according to step (a) and applying the at least one direct dye according to step (b) is carried out in separate steps. For example, the oil-in-water emulsion according to step (a) may be applied prior to applying the at least one direct dye according to step (b). When applying the oil-in-water emulsion and the at least one direct dye in separate steps, the at least one direct dye in some embodiments may be applied to said external surface of individual hairs as a component of a further oil-in-water emulsion.

In some embodiments, the at least one direct dye comprises a dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products.

In some embodiments, the at least one direct dye comprises at least one nitro dye. In some embodiments, the at least one direct dye comprises at least one aryl azo dye. In some embodiments, the at least one direct dye comprises at least one heteroaryl azo dye. In some embodiments, the at least one direct dye comprises at least one chinon/chinonimine/chinondiimine dye. In some embodiments, the at least one direct dye comprises at least one methin dye. In some embodiments, the at least one direct dye comprises at least one azomethine-like hydrazone dye. In some embodiments, the at least one direct dye comprises at least one azomethine-like imine dye. In some embodiments, the at least one direct dye comprises at least one porphyrin dye. In some embodiments, the at least one direct dye comprises at least one coupling product.

In some embodiments, the at least one direct dye comprises at least two or at least three dyes selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products.

In some embodiments, the dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products, comprises at least one reactive moiety R20.

In some embodiments, the reactive moiety R20 is attached to an aromatic ring or ring system of the nitro dye, (hetero)aryl azo dye, chinon/chinonimine/chinondiimine dye, methin dye, azomethine-like hydrazone or imine dye, porphyrin dye, or coupling product via a heteroatom selected from nitrogen, phosphorus, oxygen, and sulfur.

In some embodiments, the at least one direct dye comprises at least two or at least three dyes selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products, comprising at least one reactive moiety R20.

The term "coupling product" refers to direct dyes formed by the oxidative coupling reaction of so-called "primaries" and "couplers" described by the Scientific Community of Consumer Safety (SCCS):

http://ec.europa.eu/health/archive/ph_risk/committees/04_sccp/docs/sccp_o_162.pdf An exemplary azo dye comprising a reactive moiety R20 is Basic Blue 41:

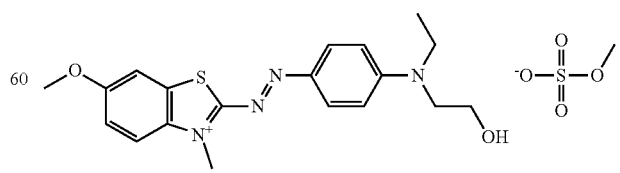

An exemplary chinon/chinonimine/chinondiimine dye comprising a reactive moiety R20 is CI61505:

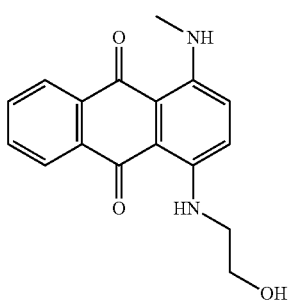 [SMILES: CNc1ccc(NCCO)c2c1C(=O)c1ccccc1C2=O]

An exemplary porphyrin dye comprising a reactive moiety R20 is:

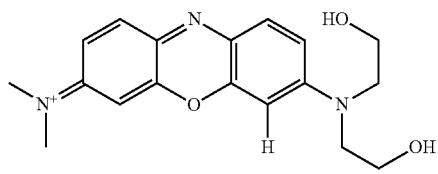 [SMILES: C[N+](C)=c1ccc2nc3ccc(N(CCO)CCO)cc3oc-2c1]

Exemplary coupling products comprising at least one reactive moiety R20 include:

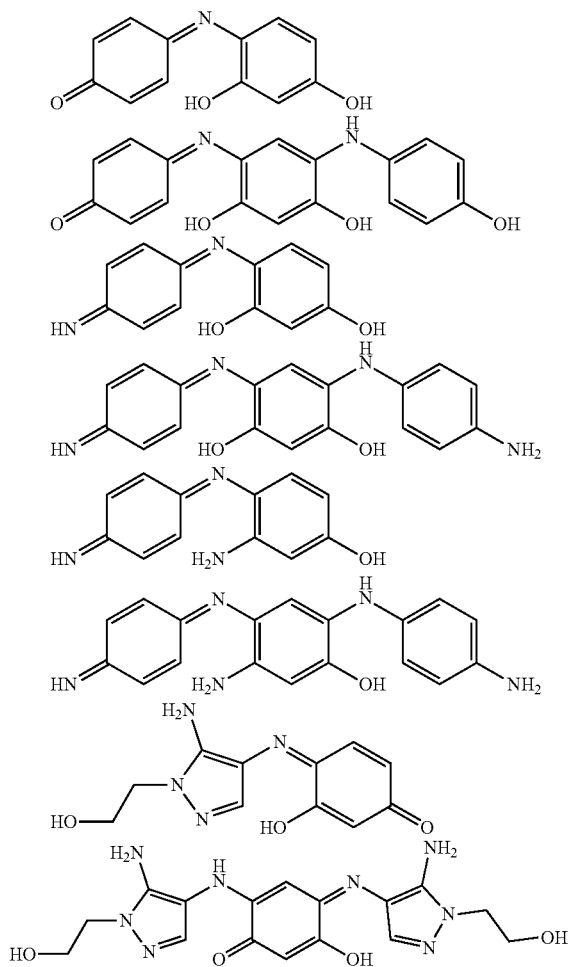

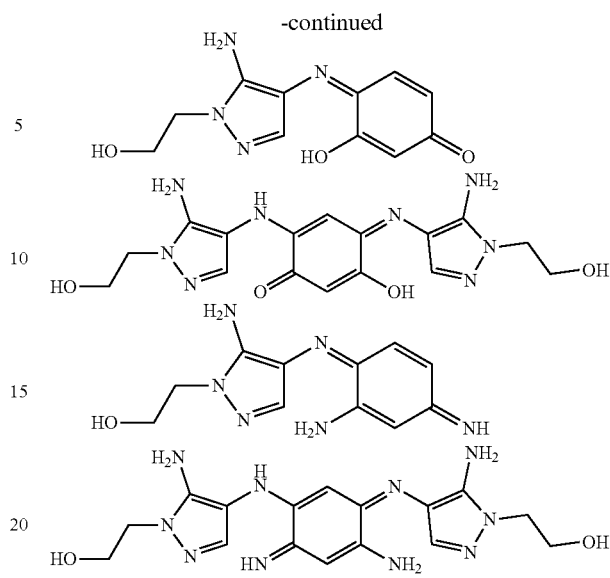

In some embodiments, the at least one direct dye comprises a peri-arylene dye according to the present disclosure, i.e. a peri-arylene dye comprising a perylene, terrylene or quarterrylene core or higher rylene core, wherein the dye optionally is substituted with a hydrophobic moiety having a non-linear structure and comprising at least 13 carbon atoms, and wherein the dye optionally is substituted with a reactive moiety R20.

In some embodiments, the at least one direct dye comprises a peri-arylene dye according to the present disclosure substituted with one or more hydrophobic moieties having a non-linear structure and comprising at least 13 carbon atoms, and optionally substituted with a reactive moiety R20.

In some embodiments, the at least one direct dye comprises a peri-arylene dye according to the present disclosure substituted with at least one reactive moiety R20 and optionally substituted with one or more hydrophobic moieties having a non-linear structure and comprising at least 13 carbon atoms.

In some embodiments, the at least one direct dye comprises a peri-arylene dye according to the present disclosure substituted with one or more hydrophobic moieties having a non-linear structure and comprising at least 13 carbon atoms, and lacking a reactive moiety R20.

In some embodiments, the direct dyes used in the coloring method comprise at least two or at least three different peri-arylene dye according to the present disclosure optionally substituted with one or more hydrophobic moieties having a non-linear structure and comprising at least 13 carbon atoms, and optionally substituted with a reactive moiety R20.

In some embodiments, the direct dyes used in the coloring method comprise at least two or at least three different peri-arylene dyes according to the present disclosure substituted with one or more hydrophobic moieties having a non-linear structure and comprising at least 13 carbon atoms, and optionally substituted with a reactive moiety R20.

In some embodiments, the direct dyes used in the coloring method comprise at least two or at least three different peri-arylene dye according to the present disclosure optionally substituted with one or more hydrophobic moieties having a non-linear structure and comprising at least 13 carbon atoms, and substituted with a reactive moiety R20.

In some embodiments, the at least one direct dye comprises at least one hydrophilic peri-arylene dye according to the present disclosure, optionally substituted with a reactive moiety R20. In some embodiments, the direct dyes used in the coloring method comprise at least two or at least three different hydrophilic peri-arylene dyes according to the present disclosure, optionally substituted with a reactive moiety R20.

In some embodiments, all of the direct dyes used in the coloring method are peri-arylene dyes according to the present disclosure optionally substituted with one or more hydrophobic moieties having a non-linear structure and comprising at least 13 carbon atoms, and optionally substituted with a reactive moiety R20.

In some embodiments, all of the direct dyes used in the coloring method are peri-arylene dyes according to the present disclosure substituted with one or more hydrophobic moieties having a non-linear structure and comprising at least 13 carbon atoms, and optionally substituted with a reactive moiety R20.

In some embodiments, all of the direct dyes used in the coloring method are peri-arylene dyes according to the present disclosure optionally substituted with one or more hydrophobic moieties having a non-linear structure and comprising at least 13 carbon atoms, and substituted with a reactive moiety R20.

In some embodiments, at a relative humidity of 30% to 50%, and at a temperature of 25° C., the at least partially cured film achieves permanence within 24 to 96 hours after the applying of said oil-in-water emulsion on the hair, and optionally, within 24 to 72 hours, within 24 to 48 hours, within 24 to 36 hours, or within 24 to 30 hours.

9 HAIR COLORING COMPOSITION COMPRISING AN OIL-IN-WATER EMULSION AND AT LEAST ONE DIRECT DYE PARTITIONED THEREIN

The present disclosure provides for a hair coloring composition acc comprising an oil-in-water emulsion and at least one direct dye partitioned therein. The at least one direct dye comprises a dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products. In some embodiments, the at least one direct dye optionally comprises a reactive moiety R20.

The oil-in-water emulsion comprises:
(A) an aqueous phase containing water; and
(B) an oil phase containing at least one reactive condensation-curable film-forming amino-silicone pre-polymer that, subsequent to condensation curing, forms an elastomer.

The oil phase fulfills at least one of the following:
(i) said at least one reactive condensation-curable film-forming amino-silicone pre-polymer includes at least one reactive condensation-curable film-forming amino-silicone monomer having a molecular weight of at most 1000 g/mole;
(ii) said oil phase further contains a non-amino cross-linking agent adapted or selected to cure said pre-polymer, said non-amino cross-linking agent having a molecular weight in the range of at most 1000 g/mole;

wherein said at least one reactive condensation-curable film-forming amino-silicone pre-polymer has a solubility in water of less than 1% by weight at 25° C.

In some embodiments, the hair coloring composition comprises a peri-arylene dye according to the present disclosure, i.e. a peri-arylene dye comprising a perylene, terrylene or quarterrylene core or higher rylene core, wherein the dye optionally is substituted with a hydrophobic moiety having a non-linear structure and comprising at least 13 carbon atoms, and wherein the dye optionally is substituted with a reactive moiety R20.

In some embodiments, the hair coloring composition comprises a peri-arylene dye according to the present disclosure optionally substituted with one or more hydrophobic moieties having a non-linear structure and comprising at least 13 carbon atoms, and substituted with a reactive moiety R20.

In some embodiments, the hair coloring composition comprises a peri-arylene dye according to the present disclosure substituted with at least one reactive moiety R20 and substituted with one or more hydrophobic moieties having a non-linear structure and comprising at least 13 carbon atoms.

In some embodiments, the hair coloring composition comprises at least two or at least three different peri-arylene dye according to the present disclosure optionally substituted with one or more hydrophobic moieties having a non-linear structure and comprising at least 13 carbon atoms, and optionally substituted with a reactive moiety R20.

In some embodiments, the hair coloring composition comprises at least two or at least three different peri-arylene dye according to the present disclosure substituted with one or more hydrophobic moieties having a non-linear structure and comprising at least 13 carbon atoms, and optionally substituted with a reactive moiety R20.

In some embodiments, the hair coloring composition comprises at least two or at least three different peri-arylene dye according to the present disclosure optionally substituted with one or more hydrophobic moieties having a non-linear structure and comprising at least 13 carbon atoms, and substituted with a reactive moiety R20.

In some embodiments, the hair coloring composition comprises at least two or at least three different peri-arylene dye according to the present disclosure substituted with one or more hydrophobic moieties having a non-linear structure and comprising at least 13 carbon atoms, and substituted with a reactive moiety R20.

In some embodiments, all of the direct dyes present in the hair coloring composition are peri-arylene dyes according to the present disclosure optionally substituted with one or more hydrophobic moieties having a non-linear structure and comprising at least 13 carbon atoms, and optionally substituted with a reactive moiety R20.

In some embodiments, all of the direct dyes present in the hair coloring composition are peri-arylene dyes according to the present disclosure optionally substituted with one or more hydrophobic moieties having a non-linear structure and comprising at least 13 carbon atoms, and substituted with a reactive moiety R20.

In some embodiments, all of the direct dyes present in the hair coloring composition are peri-arylene dyes according to the present disclosure substituted with one or more hydrophobic moieties having a non-linear structure and comprising at least 13 carbon atoms, and substituted with a reactive moiety R20.

In some embodiments, the dye(s) is/are present in the hair coloring composition in an amount of from 0.005% to about 5%, about 0.01% to about 3%, about 0.1 to about 2%, or about 0.25% to about 1.5% by weight of the hair coloring composition.

In some embodiments, the hair coloring composition comprises at least two dyes, in particular at least three dyes.

In some embodiments, at least one of the dyes present in the hair coloring composition is photoluminescent.

In some embodiments, none of the dyes present in the hair coloring composition is photoluminescent.

In some embodiments, the hair coloring composition further comprises one or more of a plasticizer, wetting agent, water soluble organic dye compound different from said at least one direct dye, thickener, a viscosity control agent or a cationic, anionic, nonionic or amphoteric surfactant.

In some embodiments, the hair coloring composition comprises a linear or branched C2-C8 alcohol. In some embodiments, the alcohol is (iso)propanol and/or (iso)butanol.

10 KIT FOR PRODUCING A REACTIVE COSMETIC COMPOSITION FOR COATING AN EXTERNAL SURFACE OF MAMMALIAN HAIR

According to another aspect, there is provided a kit for producing a reactive cosmetic composition for coating an external surface of mammalian hair, the kit comprising:
(a) a first compartment containing an oil phase including at least one direct dye, at least one of an amino-silicone oil and a non-amino-silicone oil, and optionally, a solid, hydrophobic reactive inorganic filler, disposed within said oil phase;
said at least one direct dye comprising a dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products, wherein said dye optionally comprises a reactive moiety R20;
(b) a second compartment containing a formulation including at least one of:
  (i) at least one reactive condensation-curable film-forming amino-silicone monomer having a molecular weight of at most 1000 g/mole; and
  (ii) a non-amino cross-linking agent; and optionally,
  (iii) at least one of said amino-silicone oil and said non-amino-silicone oil;
(c) a compartment containing at least one reactive condensation-curable film-forming amino-silicone pre-polymer that, subsequent to condensation curing, forms an elastomer, said pre-polymer including at least one of a reactive condensation-curable film-forming amino-silicone polymer and a reactive condensation-curable film-forming amino-silicone oligomer; said filler selected or adapted to facilitate curing of said condensation-curable film-forming amino-silicone pre-polymer, said non-amino cross-linking agent adapted or selected to cure said pre-polymer;
wherein said compartment containing at least one reactive condensation-curable film-forming amino-silicone pre-polymer is one of (A) a third compartment; (B) said second compartment; and, (C) said first compartment, subject to said first compartment being substantially devoid of said solid, hydrophobic reactive inorganic filler.

In some embodiments, the kit is devoid of solid, hydrophobic reactive inorganic filler, and the at least one reactive condensation-curable film-forming amino-silicone pre-polymer is disposed in the first compartment.

In some embodiments, the first compartment further contains solid, hydrophobic reactive inorganic filler, disposed within the oil phase.

In some embodiments, the kit, in particular the first compartment of the kit comprises a peri-arylene dye according to the present disclosure, i.e. a peri-arylene dye comprising a perylene, terrylene or quarterrylene core or higher rylene core, wherein the dye optionally is substituted with a hydrophobic moiety having a non-linear structure and comprising at least 13 carbon atoms, and wherein the dye optionally is substituted with a reactive moiety R20.

In some embodiments, the kit, in particular the first compartment of the kit comprises a peri-arylene dye according to the present disclosure optionally substituted with one or more hydrophobic moieties having a non-linear structure and comprising at least 13 carbon atoms, and substituted with a reactive moiety R20.

In some embodiments, the kit, in particular the first compartment of the kit comprises a peri-arylene dye according to the present disclosure substituted with at least one reactive moiety R20 and substituted with one or more hydrophobic moieties having a non-linear structure and comprising at least 13 carbon atoms.

In some embodiments, the kit, in particular the first compartment of the kit comprises at least two or at least three different peri-arylene dye according to the present disclosure optionally substituted with one or more hydrophobic moieties having a non-linear structure and comprising at least 13 carbon atoms, and optionally substituted with a reactive moiety R20.

In some embodiments, the kit, in particular the first compartment of the kit comprises at least two or at least three different peri-arylene dye according to the present disclosure substituted with one or more hydrophobic moieties having a non-linear structure and comprising at least 13 carbon atoms, and optionally substituted with a reactive moiety R20.

In some embodiments, the kit, in particular the first compartment of the kit comprises at least two or at least three different peri-arylene dye according to the present disclosure optionally substituted with one or more hydrophobic moieties having a non-linear structure and comprising at least 13 carbon atoms, and substituted with a reactive moiety R20.

In some embodiments, the kit, in particular the first compartment of the kit comprises at least two or at least three different peri-arylene dye according to the present disclosure substituted with one or more hydrophobic moieties having a non-linear structure and comprising at least 13 carbon atoms, and substituted with a reactive moiety R20.

In some embodiments, all of the direct dyes present in the kit, in particular in the first compartment of the kit are peri-arylene dyes according to the present disclosure optionally substituted with one or more hydrophobic moieties having a non-linear structure and comprising at least 13 carbon atoms, and optionally substituted with a reactive moiety R20.

In some embodiments, all of the direct dyes present in the kit, in particular in the first compartment of the kit are peri-arylene dyes according to the present disclosure optionally substituted with one or more hydrophobic moieties having a non-linear structure and comprising at least 13 carbon atoms, and substituted with a reactive moiety R20.

In some embodiments, all of the direct dyes present in the kit, in particular in the first compartment of the kit are peri-arylene dyes according to the present disclosure substituted with one or more hydrophobic moieties having a non-linear structure and comprising at least 13 carbon atoms, and substituted with a reactive moiety R20.

In some embodiments, the dye(s) is/are present in the kit, in particular the first compartment of the kit, in an amount of from 0.005% to about 5%, about 0.01% to about 3%, about 0.1 to about 2%, or about 0.25% to about 1.5% by weight.

In some embodiments, wherein a condensation-curable amino-silicone pre-polymer is relatively soluble in water (or becomes so, as a result of hydrolysis), it may be rendered relatively less soluble and even substantially insoluble in water. For instance, a hydrophilic siloxane can be rendered relatively insoluble by reacting it with a different second material (e.g., a hydrophobic silane) capable of modifying its tendency to solubilize in water, the reaction product of the two resulting in a third material being less soluble ("desolubilized") or substantially insoluble ("insolubilized"). This process, which for simplicity may be termed of "desolubilization" or "insolubilization" of a desired reactant, can be carried out prior to the emulsification of the amino-silicone reactant rendered less soluble with the additional constituents of a condensation-curable amino-silicone formulation according to the present teachings. Water-soluble pre-polymers, typically monomers such as silanes, are to be avoided as they would, at low concentrations of relevance to the cost effectiveness of a composition, only form thin monolayers, unable to build-up a coat of sufficient thickness to attach direct dyes in a color meaningful manner. Moreover, water-soluble pre-polymers, even if forming a very thin coat, would readily wash away in a subsequent rinsing step. Such situation is expected if the pre-polymers mainly include (50 wt. % or more) water-soluble pre-polymers. Minor amounts of water-soluble pre-polymers can nevertheless be tolerated, as long as the mixture of all pre-polymers with any additional component of the reactive phase (e.g., silicone oils, amino-silicone oils, non-amino cross-linking agents, reactive fillers, etc.) form a water-insoluble oil blend.

As used herein, the term "solubility" with respect to a component or mixture of components ("component") and a solvent or solvent mixture ("solvent"), is meant to refer to the solubility of the component in the solvent at the native pH, i.e., at the natural pH attained by adding solely the component to the solvent, in the absence of other components and in the absence of any pH modifiers. When the solvent is water, the definition assumes the water has an initial pH of 7.

While at least partially cured pre-polymers can also be non-tacky (e.g., if cross-likers and/or curing accelerators are used), the lack of tackiness to the touch is more generally associated with fully cured polymers. Compositions as used in the present methods, advantageously, are rapidly non-tacky to the touch following their application to the hair fibers, to increase compliance when coloring is performed on a living subject. The problem of tackiness has been differently addressed in the art, for instance, by using in hair care products cross-linked polymers, also known as resins (e.g., silicone resins or polycondensates). While this approach can reduce or prevent an unpleasant touch once dried on hair, it also proscribes reactivity amongst such polymers. Therefore, a layer formed by the deposition of cross-linked polymers cannot have sufficient cohesivity to permit a long lasting attachment to the hair surface nor retention of a direct dye. In such cases, rinsing is typically avoided, as it may readily wash out any loosely attached direct dye.

While some cross-linked polymers can also be purchased under the determination of being possibly only partially cured by their manufacturer, the ability of such commercially available polymers to further cure remains highly hypothetical under typical coloring conditions according to the present teachings. Such condensation reaction, if any, would be very slow at ambient temperature (as suggested by their very long shelf life of almost a year) and would require elevated temperatures to proceed at a fast enough pace (e.g., achieving sufficient curing to maintain coloration in less than a week). However, such elevated temperatures are not practical for living subjects, so that in fact commercially available cross-linked polymers can be considered fully cross-linked were they to be used in methods of the disclosure.

In contrast, by using in the present disclosure reactive materials (or constituents having substantially retained their reactivity), the cross-linking density of the amino-silicone film can be managed by choosing the suitable pre-polymers and cross-linkers, and their respective amounts, allowing the inventors to control the initial viscosity of the composition, the mechanical properties and the thickness of the cured film, the cohesion of the cured film, the feel, and the tackiness of the coated hair etc.

11 TEST METHODS

Coloring Hair Method

Two hair tresses are laid flat within a large plastic weigh boat. 1 g of coloring composition is applied to each gram of hair using a pipette, and the product is brushed into the tress to ensure the coverage is consistent using a Wella Color Brush. After 30 seconds of brushing the tresses are then dried using a hair drier, whist being combed repeatedly. When the hair is dye and the strands individualized the coloring process is complete.

Color Measurement Method

Color is measured using a spectrophotometer, Minolta 2600d. The hair tress is aligned flat on a neutral medium grey background, and five measurements from the top to the bottom of the hair tress using the MAV setting recording the data as SCI, spectral component included. The data points are then averaged to yield the result of the given hair tress within the CIELAB color space using $L^*a^*b$ coordinates.

Wash Fastness Method

The temporary but lasting quality of the hair coloring composition applied to hair and set as the coating on hair can be determined by measurements indicating substantially permanent lastingness. Substantially permanent lastingness generally is indicated when the color of the colored hair fibers changes less than 50%, less than 40%, less than 30%, less than 20%, less than 10% after the colored hair fibers are processed through a 12-cycle rinse study. One cycle is defined as two shampoo treatments followed by a conditioning treatment using Wella Brilliance Shampoo and Conditioner for fine to normal, colored hair. Two hair tresses (Kerling, Natural White special quality) are measured for their initial color and then colored according to the current disclosure. The color of the hair is again measured. For washing, the hair is wetted for 30 seconds, a shampoo is applied (0.1 per gram of hair) and lathered into the hair for 30 seconds, followed by rinsing for 30 seconds, a further dose of shampoo is applied (0.1 g per gram of hair) and lathered for 30 seconds, followed by rinsing for 30 seconds. A conditioner is then applied (0.1 g per gram of hair) for 30 seconds and then rinsed for 30 seconds. The hair is then blow dried for 2 minutes. The water is set to flow at 4 L/min and with a temperature of 37±2° C. This completes one wash cycle which is then repeated as additional 11 times. A final color measurement is performed. The lastingness is calculated as follows. The CIELAB $dE_{76}$(fade) is calculated between the after coloring and after washing. This is assigned as the amount of color lost. The amount of color provided by the given formulation is the CIELAB $dE_{76}$ (color) between the before coloring and after coloring. The amount of fade is then computed as FADE=$dE_{76}$(fade) $dE_{76}$(color)*100. The substantially permanent lastingness is reversed at more than 80%, preferable more than 90% even more preferably close to 100% FADE.

Color Transfer Method

The transfer of the composition from the hair can be assessed using the following method. Hair tresses are colored according to the test method described. A white cotton cloth is used to test the composition transfer. The cloth measuring 15 mm by 75 mm is folded in half so as to create two sides with a size of 15 mm by 37.5 mm. Between the two sides the colored hair tress is inserted and laid flat onto a surface such that the top portion of the tress where it is glued together just protrudes from the folded two sides of cotton. A weight of 0.1 Kg is applied evenly over the top surface of the cotton. The hair tress is then pulled through the cotton cloth over a time until it is removed altogether from the cloth in 1 to 3 seconds. The weight is removed, and the cloth opened to reveal the inner surface. A visual assessment can then be performed on the sample to give it a rating from 0 to 5 for color transfer, with 0 being no transfer and 5 being extremely high transfer. The method can also be used to compare between different prototypes and provide a comparative assessment of better or worse performance.

Hair Damage

The state of the hair can be assessed for example using ATR FT-IR for oxidative damage as described later or through tensile testing methods known to those skilled in the art for assessing hair strength for example using equipment such as those designed and sold by Dia-Stron™.

Damage caused to the hair by application of the hair coloring composition and removal of the resulting coating can be assessed by FT-IR (Fourier Transform Infrared) method, which has been established to be suitable for studying the effects of oxidative treatments on hair (Strassburger, J., J. Soc. Cosmet Chem., 36, 61-74 (1985); Joy, M. & Lewis, D. M., Int. J. Cosmet. Sci., 13, 249-261 (1991); Signori, V. and Lewis, D. M., Int. J. Cosmet. Sci., 19, 1-13 (1997. In general, the oxidation of cystine is thought to be a suitable marker by which to monitor the overall oxidation of the keratinous part of the fiber.

Signori and Lewis (D. M., Int. J. Cosmet. Sci., 19, 1-13 (1997)) have shown that FT-IR using a diamond Attenuated Total Internal Reflection (ATR) cell is a sensitive and reproducible way of measuring the cysteic acid content of single fibers and bundles. A Perkin Elmer Spectrum® 1 Fourier Transform Infrared (FTIR) system equipped with a diamond Attenuated Total Internal Reflection (ATR) cell was used to measure the cysteic acid concentration in mammalian hair. The hair tresses were platted (~1 plait per cm) in order to minimize variations in surface area of contact between readings. Four readings per switch were taken (⅓ and ⅔ down the switch on both sides), and an average calculated. Backgrounds were collected every 4 readings, and an ATR cell pressure of 1 N/m was employed. The cell was cleaned with ethanol between each reading, and a contamination check performed using the monitor ratio mode of the instrument. As prescribed by Signori and Lewis in 1997, a normalized double derivative analysis routine was used. The original spectra were initially converted to absorbance, before being normalized to the 1450 $cm^{-1}$ band (the characteristic and invariant protein $CH_2$ stretch). This normalized absorbance was then twice derivatized using a 13 point averaging. The value of the 1450 $cm^{-1}$ normalized 2nd derivative of the absorbance at 1040 $cm^{-1}$ was taken as the relative concentration of cysteic acid. This figure was multiplied by $-1 \times 10^{-4}$ to recast it into suitable units. It was found that virgin mammalian hair produced a value of around 20 cysteic acid units, and heavily oxidized hair produced values of around 170. The following instrumental conditions were employed:

Spectral Resolution—4 $cm^{-1}$
Data Interval—0.7 $cm^{-1}$
Mirror Scan Speed—0.2 cm $s^{-1}$
Number of Background Scans—20
Number of Sample Scans—20
Scan Range—4000 $cm^{-1}$ to 600 $cm^{-1}$ When the compositions of the current invention can be applied to the hair and then removed there can be a non-significant change to the level of oxidative damage to the hair, whereas with conventional oxidative colorants there can be a large increase in the measured oxidative damage.

Color Fastness

As used herein, the term "color fastness" means substantial color lastingness or color fastness when the color of the colored hair fibers change less than 50%, less than 40%, less than 30%, less than 20%, less than 10% after the colored hair fibers are processed through a multi-cycle rinse study. One kind of protocol for determining color fastness is described in the section below titled "WASH FASTNESS METHOD".

Particle Size

The particle diameter is represented by D10, D50 and/or by D90, which is the median diameter by volume. D10, D50 and D90 is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.01 micron to 2000 micron.

The term "D10," as used herein refers, to the 10th percentile number- or volume-based median particle diameter, which is the diameter below which 10% by number or volume of the particle population is found. The term "D50," as used herein refers, to the 50th percentile number- or volume-based median particle diameter, which is the diameter below which 50% by number or volume of the particle population is found. The term "D90," as used herein refers, to the 90th percentile number- or volume-based median particle diameter, which is the diameter below which 90% by number or volume of the particle population is found. The number or volume measurement is indicated by [num] for number or [vol] for volume. If not indicated otherwise, the particle size is given as D10[vol], D50[vol], and D90[vol], respectively.

Laser diffraction measures particle size distributions by measuring the angular variation in intensity of light scattered as a laser beam passes through a dispersed particulate sample analyzer and the particle size is reported as a volume equivalent sphere diameter. A discussion of calculating D50 is provided in Barber et al, Pharmaceutical Development and Technology, 3(2), 153-161 (1998), which is incorporated herein by reference. Pigment microparticles having a D50[vol] particle diameter of less than 20 nm may enter the cuticles and are therefore difficult to remove. For scattering purposes, Pigment(s) having a D10[vol] particle diameter of at least 60 nm, or at least 80 nm can be used. Pigment(s)

having a D50[vol] particle diameter of more than 1 micron typically do not sufficiently adhere onto hair fibers.

According to an embodiment, the particle size distribution, either relative to the number or volume of the particles, of the pigment microparticles can be at least bi-modal. A bi-modal particle size distribution has two distinct peaks which are spaced relative from, while tri-modal particle size distribution has three distinct peaks. The term "peak" means a local maximum of the distribution curve. The "distance" between two peaks, expressed relative to the particle size, can be at least 0.05 micron, preferably at least 0.1 micron, such as at least 0.2 micron. Providing an at least bi-modal particle size distribution allows to tailor the optical appearance of the colored hair. For example, the scattering properties varies with the particle size so that particles of different size scatter the light into different directions.

The at least bi-modal particle size distribution can be relative to pigment microparticles formed by the same pigment material. In addition to that or alternatively, the at least bi-model particle size distribution can be provided by pigment microparticles of different pigment material.

Viscosity

The $Pas^{-1}$ measurements of water, motor oil and honey can be found in any textbook on viscosity and in Wikipedia. Viscosity measurements are carried out on a controlled stress rheometer e.g. using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 $sec^{-1}$ shear rate is obtained from the shear stress vs. shear rate curve, and the corresponding viscosity is calculated by dividing the obtained shear stress by 10

12 EXAMPLES

Example 1: Perylene Dyes/Polyacrylate or Amino-Functional Siloxane Film Former Method for Coloring Hair Peri-arylene dyes were applied in accordance to the coloring method herein below. The colored hair strands were assessed for color, impact of film former, color fastness and color removal.

The perylene dyes used in the experiments described below are:
  S-9, Red, fluorescent (formula 16, D3=D4=D5=D6=H, R2=R5=—CH(C4H9)2)
  S-17, Red, fluorescent (formula 16, D3=D4=D5=D6=H, R2=R5=—CH(C8H17)2)
  S-19, Red, fluorescent (formula 20)
  S-19-nitro, Red, non-fluorescent (formula 21)
Pretreatment to Apply Cationic Polymer (PEI, Polyethylenimine) on the Hair Fiber Surface:
  1 ml of PEI solution (0.5% aqueous solution of PEI (MW: 75 kDa) is applied on the hair strand.
  The hair strand is dried via blow-dryer, followed by further drying at 40° C. in the oven.

Film Former:
  A 5% aqueous active polyacrylate solution (Acrylic Polymer RE-1075) is prepared as film forming active.
  A 1.25% solution of an amino-functional siloxane polymer (Polymer AP 6087) in isopropanol is prepared as film forming active.
Dyeing Process:
  Version A: 100 mg perylene dye are dissolved in 5 ml n-butanol. 1 ml of this solution is applied directly to the hair fiber and the solvent is evaporated with a blow-dryer. The colored hair strand is then treated with 1 ml of the film former solution followed by 1 min blow dry without combing. Subsequently, further drying with combing is performed until the acrylic polymer or silicone polymer completed all cross link reactions and the hair strand is observed to be dry.
  Version B: 100 mg perylene dye are dissolved in 5 ml n-butanol. 1 ml of this solution is added to 10 g of the polyacrylate film former solution. For siloxane film former, 1% by weight perylene dye, 1.25% by weight Dow Corning AP 6087 and 97.75% by weight isopropanol are combined. A homogeneous emulsion is formed using the Ultra-Turrax for 5-7 min. 1 ml of this emulsion was directly applied to the hair strand, followed by blow drying without combing. Subsequently, further drying with combing is performed until the acrylic polymer or silicone polymer completed all cross link reactions and the hair strand is observed to be dry.
Washing:
  The hair strand is washed with shampoo for the indicated number of cycles and dried at the end of each cycle.
  One cycle is defined as two shampoo treatments followed by a conditioning treatment. For washing, the hair is wetted for 30 seconds, a shampoo is applied (0.1 per gram of hair) and lathered into the hair for 30 seconds, followed by rinsing for 30 seconds, a further dose of shampoo is applied (0.1 g per gram of hair) and lathered for 30 seconds, followed by rinsing for 30 seconds a conditioner is then applied (0.1 g per gram of hair) for 30 seconds and then rinsed for 30 seconds. The hair is then blow dried for 2 minutes. The water is set to flow at 4 L/min and with a temperature of 37±2° C. This completes one wash cycle. The shampoo used is a standard shampoo free of oil and free of quaternary amines.
Color Removal:
  For removing the color, 2 ml plant oil are applied to the hair strand, and rubbed in for 30 seconds. The oil is gently squeezed out, and the hair strand is rinsed with 2 ml of oil. Subsequently, the hair stand is washed with shampoo as above.
Color Data:
  Color data is collected before coloring, after pretreatment, after coloring, after washing for the indicated number of cycles, and after color removal, using a Minolta spectrophotometer CM-2600d.
Controls:
  Perylene dye is applied to PEI-pretreated hair strands following Version A above, but without applying polyacrylate or silicone film former.
Absolute Values

|  | L | a | b |
|---|---|---|---|
| Untreated | 69.25 | 2.54 | 24.83 |
| PEI only | 69.77 | 1.78 | 23.94 |

TABLE 1

Absolute values: S-19 washing test

| # wash | no film former L | no film former a | no film former b | film former: silicones L | film former: silicones a | film former: silicones b | film former: acrylates L | film former: acrylates a | film former: acrylates b |
|---|---|---|---|---|---|---|---|---|---|
| 0 | 25.88 | 49.22 | 44.35 | 32.39 | 50.45 | 51.49 | 30.33 | 58.44 | 44.37 |
| 1 | | | | 28.67 | 49.02 | 48.21 | 33.78 | 51.19 | 52.89 |
| 3 | | | | 40.57 | 41.85 | 17.26 | 33.31 | 48.08 | 49.67 |
| 5 | 54.21 | 27.57 | 22.51 | | | | | | |
| 6 | | | | 47.47 | 42.82 | 24.39 | 36.53 | 52.27 | 55.46 |
| 9 | | | | 43.39 | 38.40 | 25.34 | 38.91 | 52.28 | 54.26 |
| 12 | | | | 50.89 | 35.14 | 23.49 | 38.53 | 53.57 | 55.29 |
| 15 | | | | 50.03 | 31.38 | 19.28 | 38.40 | 54.29 | 55.89 |

TABLE 2

Difference to value after PEI pretreatment: S-19 washing test

| # wash | no film former ΔL | no film former Δa | no film former Δb | film former: silicones ΔL | film former: silicones Δa | film former: silicones Δb | film former: acrylates ΔL | film former: acrylates Δa | film former: acrylates Δb |
|---|---|---|---|---|---|---|---|---|---|
| 0 | 43.89 | 47.44 | 20.41 | 37.38 | 48.67 | 27.55 | 39.44 | 56.66 | 20.43 |
| 1 | | | | 41.1 | 47.24 | 24.27 | 35.99 | 49.41 | 28.95 |
| 3 | | | | 29.2 | 40.07 | −6.68 | 36.46 | 46.3 | 25.73 |
| 5 | 15.56 | 25.79 | −1.43 | | | | | | |
| 6 | | | | 22.3 | 41.04 | 0.45 | 33.24 | 50.49 | 31.52 |
| 9 | | | | 26.38 | 36.62 | 1.4 | 30.86 | 50.5 | 30.32 |
| 12 | | | | 18.88 | 33.36 | −0.45 | 31.24 | 51.79 | 31.35 |
| 15 | | | | 19.74 | 29.6 | −4.66 | 31.37 | 52.51 | 31.95 |

Peri-arylene dye S-19 was applied with film former according to coloring method Version A described above, or without film former. Table 2 above demonstrates the differences between the Lab-values after PEI pretreatment and the Lab-values obtained after the indicated number of wash cycles.

The greatest ΔL is achieved without film former and no washings, but for the treatment without film former, ΔL decreases rapidly and after 5 washings ΔL is smaller than for the embodiments using film former after 15 washings.

Initial coloring performance is similar for silicone polymer film former and acrylate polymer film former, with a ΔL in the range of about 40. Acrylate polymer film former provides for improved color fastness as demonstrated by a ΔL value remaining more constant after an increasing number of wash cycles.

TABLE 3

Absolute values: Perylenes comparison/washing 5 times

| | film former: silicones | | | film former: acrylates | | |
|---|---|---|---|---|---|---|
| | L | a | b | L | a | b |
| S-9 | 49.46 | 39.97 | 26.14 | 42.95 | 51.34 | 45.27 |
| S-17 | 34.54 | 50.37 | 32.05 | 38.45 | 59.48 | 57.37 |
| S-19 | 42.06 | 47.35 | 25.89 | 35.07 | 58.87 | 56.19 |
| S-19-nitro | 25.08 | 47.79 | 43.08 | 24.65 | 51.04 | 42.35 |

TABLE 4

Difference PEI pretreatment: washing 5 times

| | film former: silicones | | | film former: acrylates | | |
|---|---|---|---|---|---|---|
| | ΔL | Δa | Δb | ΔL | Δa | Δb |
| S-9 | 20.31 | 38.19 | 2.2 | 26.82 | 49.56 | 21.33 |
| S-17 | 35.23 | 48.59 | 8.11 | 31.32 | 57.7 | 33.43 |
| S-19 | 27.71 | 45.57 | 1.95 | 34.70 | 57.09 | 32.25 |
| S-19-nitro | 44.69 | 46.01 | 19.14 | 45.12 | 49.26 | 18.41 |

Peri-arylene dyes S9, S-17, S-19 or S-19 nitro were applied according to coloring method Version A described above, either with silicone or acrylate film former. Table 4 above demonstrates the differences between the Lab-values after PEI pretreatment and the Lab-values obtained after 5 wash cycles for each of the dyes.

The ΔL values in Table 4 demonstrate that wash fastness improves with increasing length of the hydrophobic moieties on the perylene core. In addition, wash fastness is more pronounced when the perylene dye is used in combination with acrylate film former as compared to using in combination with silicone film former.

TABLE 5

Absolute values: Perylenes comparison/OFF treatment

| | film former: silicones | | | film former: acrylates | | |
|---|---|---|---|---|---|---|
| | L | a | b | L | a | b |
| S-9 | 66.53 | 3.81 | 14.98 | 52.74 | 18.97 | 19.40 |
| S-17 | 58.97 | 7.17 | 17.77 | 62.19 | 4.76 | 23.55 |
| S-19 | 59.62 | 6.37 | 20.30 | 60.86 | 1.89 | 12.12 |
| S-19-nitro | 56.52 | 6.88 | 17.01 | 63.98 | 3.22 | 18.01 |

TABLE 6

Difference washing 5 times: OFF treatment

| | film former: silicones ΔL | film former: acrylates ΔL |
|---|---|---|
| S-9 | 17.07 | 9.79 |
| S-17 | 24.43 | 23.74 |
| S-19 | 17.56 | 25.79 |
| S-19-nitro | 31.44 | 39.33 |

Peri-arylene dyes S9, S-17, S-19 or S-19 nitro were applied according to coloring method Version A described above, either with silicone or acrylate film former. Table 6 above demonstrates the differences between the Lab-values after 5 times washing and the Lab-values obtained after removal of the dye by oil treatment. Only ΔL values are shown.

The ΔL values in Table 6 demonstrate that the difference between ON treatment (plus 5 times washing) and OFF treatment becomes more pronounced with increasing length of the hydrophobic moieties on the perylene core. This experiment demonstrates higher decoloration is possible for perylene dyes with increasing length of the hydrophobic moieties on the perylene core. In addition, the difference ON/OFF is more pronounced when the perylene dye is used in combination with acrylate film former as compared to using in combination with silicone film former.

FIG. 1 demonstrates the coloring results achieved with the dye S-19. For the naked eye, a perceived color difference between dye S-19 as applied (without washing) and after 5 times washing is negligible. Similarly, as perceived with the naked eye, the hair strand after the color removal treatment exhibits a color rather similar to the untreated control. As is apparent from FIG. 1, the OFF treatment removes the color to an extent that a color hue clearly attributable to the dye S-19 cannot be recognized any longer.

Examples 2A-2C: Azo Dyes/Multicomponent Film Former

Method for Coloring Hair

Azo dyes were applied in accordance to the coloring method herein below. The colored hair strands were assessed for color and color fastness.

The Azo dyes used in the experiments described below are:

Black Azo: 2-[[2-[(E)-[4-[ethyl(2-hydroxyethyl)amino]phenyl]azo]-4-(4-methylpiperazin-1-yl)thiazol-5-yl]methylene]indane-1,3-dione

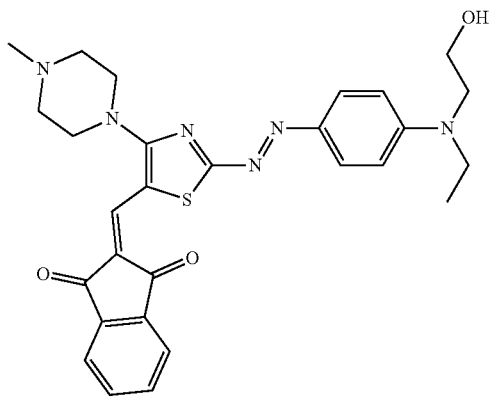 [SMILES: CCN(CCO)c1ccc(/N=N/c2nc(N3CCN(C)CC3)c(C=C3C(=O)c4ccccc4C3=O)s2)cc1]

Blue Azo: 2-{[4-chloro-2-((E)-{4-[ethyl(2-hydroxyethyl)amino]phenyl}diazenyl)-1,3-thiazol-5-yl]methylidene}-1H-indene-1,3(2H)-dione

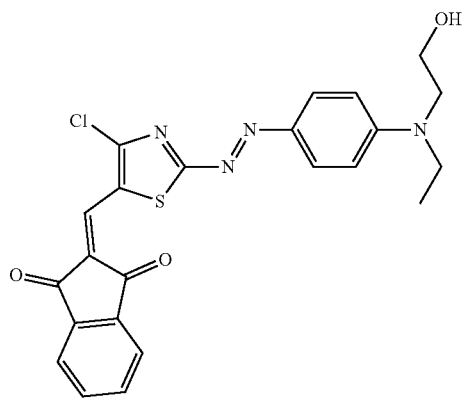 [SMILES: CCN(CCO)c1ccc(/N=N/c2nc(Cl)c(C=C3C(=O)c4ccccc4C3=O)s2)cc1]

Pretreatment to Apply Cationic Polymer (PEI, Polyethylenimine) on the Hair Fiber Surface:

1 ml of PEI solution (0.5% aqueous solution of PEI (MW: 75 kDa) is applied on the hair strand.

The hair strand is dried via blow-dryer, followed by further drying at 40° C. in the oven.

Example 2A: Azo Dye in Multicomponent Kit (Michael Addition)

100 mg azo dye is suspended in 1 g THF, and 8.4 g Isododecane (2,2,4,6,6-pentamethylheptane) solution are added as solvent. Subsequently, 200 mg Silmer OH ACR DI-10 polymer (acrylate derivative) and 300 mg Silamine 2972 is added to the reaction mixture. The mixture is stirred at room temperature for 5 min.

1 g of the above prepared formulation is applied on a pre-treated hair tress (as described above) and the polymers are allowed to react to start forming a film immobilizing the added dye. After removing the excess of the formulation, the film forming reaction is completed as the hair tress is dried via a heat blower.

Color Result:
black azo: dark black shade with slightly violet tone
after 15 washes the color remains to an extent of 30% which complies to a moderate wash fastness observation
blue azo: intense violet tone
after 15 washes the color remains to an extent of 80% which complies to a very good wash fastness observation Example 2B: Azo Dye in Multicomponent Kit (Isocyanates and Alcohol/Amino Group Containing Polymers Back Bone Silicone)

100 mg azo dye are mixed with 300 mg isocyanate polymer (Silmer NCO DI50); 9.4 g 2,2,4,6,6-pentamethylheptane are added and the mixture is well shaked.

Subsequently, 200 mg OH Silicone (Silmer OHT C-50) are added to the reaction mixture. The mixture is stirred at room temperature for 5 min.

1 g of the above prepared formulation is applied on a pre-treated hair tress (as described above) and the polymers are allowed to react to start forming a film immobilizing the added dye. After removing the excess of the formulation, the film forming reaction is completed as the hair tress is dried via a heat blower.

Color Result:
black azo: dark black shade with slightly greenish shine
after 15 washes the color remains to an extent of 50% which complies to a moderate/good wash fastness observation
blue azo: intense greyish blue tone with greenish shine
after 15 washes the color remains to an extent of 90% which complies to an excellent wash fastness observation Example 2C: Azo Dye in Multicomponent Kit (Isocyanates and Alcohol/Amino Group Containing Polymers Back Bone Silicone & Carbon-Hybrid System)

100 mg azo dye are mixed with 400 mg isocyanate polymer (Melio 09-S-11); 9.3 g 1-Methoxy-2-propanol are added and the mixture is well shaked.

Subsequently, 200 mg OH Silicone (Silmer OHT C-50) are added to the reaction mixture. The mixture is stirred at room temperature for 5 min. 1 g of the above prepared formulation is applied on a pre-treated hair tress (as described above) and the polymers are allowed to react to start forming a film immobilizing the added dye. After removing the excess of the formulation, the film forming reaction is completed as the hair tress is dried via a heat blower.

Color Result:
black azo: dark black shade with slightly greenish shine
after 15 washes the color remains to an extent of 80% which complies to a very good wash fastness observation
blue azo: greyish blue tone with greenish shine
after 15 washes the color remains to an extent of 80% which complies to a very good wash fastness observation

13 SUMMARY STATEMENTS

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporate into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

The following first set of statements further describes the present invention.
1. An aromatic dye selected from rylene dyes, nitro dyes, aryl and heteroaryl azo dyes, chinon/chinonimine/chinondiimine dyes, methin dyes, azomethine-like hydrazone and imine dyes, and porphyrin dyes, wherein the dye or an aromatic ring of the dye optionally is substituted with one or more hydrophobic moieties having a linear or non-linear structure, and wherein the dye optionally is substituted with a reactive moiety R20, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkyl)OSO2(aryl), (C0-C6 alkyl)SO2Cl, (C0-C6 alkyl)Si(O—(C1-C3 alkyl))3, (aryl)SO2Cl, aryl(C0-C4)OH, aryl(C0-C4)NH2, wherein aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, and formula (30),

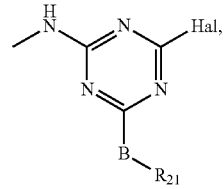

(30)

wherein B is selected from NH and O; Hal is F, Cl or Br; and R21 is linear or branched (C1-C6 alkyl).
2. The dye of statement 1, having an octanol/water partition coefficient (log $P_{ow}$) of at least 20, wherein log $P_{ow}$ is calculated based on the GALAS algorithm using ACD/Labs software.
3. The dye of statement 1 or 2, wherein each of the one or more hydrophobic moieties comprises 14-28 carbon atoms, and is selected from:
—(CH2)m-CH(C3-24 alkyl)2 or —(CH2)m-C(C3-24 alkyl)3, wherein m=0-5, wherein alkyl is linear and is optionally substituted with one or more substituents selected from halogen, C1-C6 alkyl, C1-C6 alkoxy, NH(C1-C6 alkyl), and N(C1-C6 alkyl)2,
—(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and
—(CH2)o-phenyl, wherein o=1-3 which may be substituted with up to 3 substituents selected from C1-C6 alkyl and C1-C6 alkoxy, in particular isopropyl and/or tert-butyl, —(CH2)n-naphthyl, wherein n=0-3 which may be substituted with up to 3 substituents selected from C1-C6 alkyl and C1-C6 alkoxy, in particular isopropyl and/or tert-butyl.
4. A peri-arylene dye comprising a perylene, terrylene or quarterrylene core or higher rylene core, wherein the dye is soluble in a medium having an octanol/water partition coefficient (log $P_{ow}$) of at least 12, wherein log $P_{ow}$ is calculated based on the GALAS algorithm using ACD/Labs software.
5. A peri-arylene dye comprising a perylene, terrylene or quarterrylene core or higher rylene core, having an octanol/water partition coefficient (log $P_{ow}$) of at least 20, wherein log $P_{ow}$ is calculated based on the GALAS algorithm using ACD/Labs software.
6. The peri-arylene dye according to statement 5, having an octanol/water partition coefficient (log $P_{ow}$) of at least 21, in particular at least 22, wherein log $P_{ow}$ is calculated based on the GALAS algorithm using ACD/Labs software.
7. A peri-arylene dye comprising a perylene, terrylene or quarterrylene core or higher rylene core, wherein the dye optionally is substituted with one or more hydrophobic moieties having a non-linear structure and comprising at least 14 carbon atoms, and wherein the dye optionally is substituted with a reactive moiety R20, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkylOSO2(aryl), (C0-C6 alkyl)SO2Cl, (C0-C6 alkyl)Si(O—(C1-C3 alkyl))3, (aryl)SO2Cl, aryl(C0-C4)OH, aryl(C0-C4)NH2, wherein aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, and formula (30),

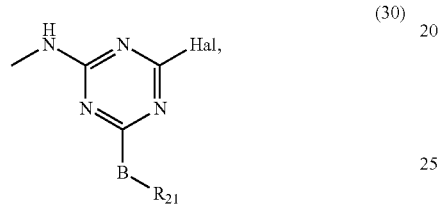
(30)

wherein B is selected from NH and O; Hal is F, Cl or Br; and R21 is linear or branched (C1-C6 alkyl).

8. The peri-arylene dye of any of statements 3-7, wherein the rylene core is substituted at the positions corresponding to positions 3,4 and/or 9,10 of the perylene core with a bridging group.

9. The peri-arylene dye of statement 8, wherein the bridging group at the positions corresponding to positions 3,4 of the perylene core is substituted with a hydrophobic moiety having a non-linear structure and comprising at least 14 carbon atoms.

10. The peri-arylene dye of statement 8 or 9, wherein the bridging group at the positions corresponding to positions 9,10 of the perylene core is substituted with a hydrophobic moiety having a non-linear structure and comprising at least 14 carbon atoms.

11. The dye of any of the preceding statements, substituted with one or more hydrophobic moieties having a non-linear structure and comprising at least 15 carbon atoms.

12. The dye of any of the preceding statements, substituted with one or more hydrophobic moieties having a non-linear structure and comprising at least 17 carbon atoms.

13. The dye of any of the preceding statements, substituted with one or more hydrophobic moieties having a non-linear structure and comprising at least 19 carbon atoms.

14. The dye of any of the preceding statements, substituted with two or more of said hydrophobic moieties.

15. The dye of any of the preceding statements, substituted with at least one reactive moiety R20.

16. The dye of any of the preceding statements, substituted with one reactive moiety R20.

17. The dye of any of statements 1-14, wherein the dye is free of a reactive moiety R20.

18. A peri-arylene dye according to formula (1)

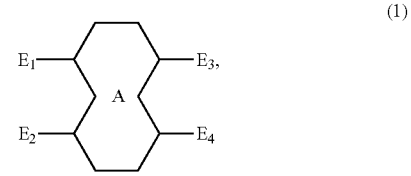
(1)

wherein structure A

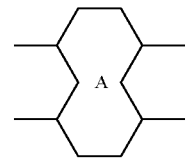

is selected from formulae (2) through (4)

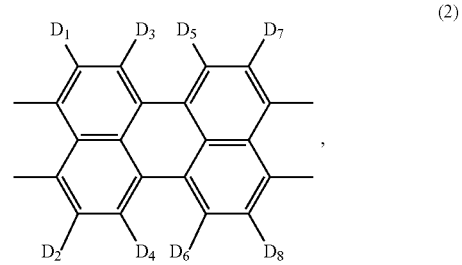
(2)

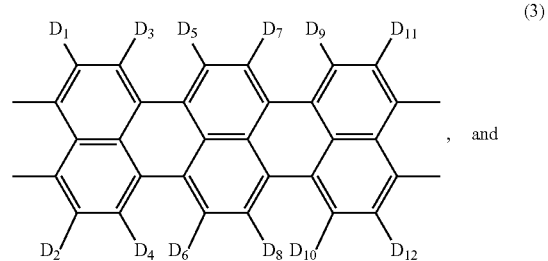
(3)
, and

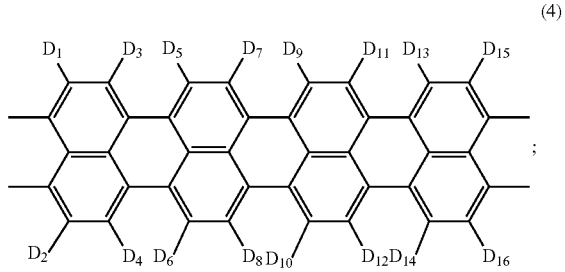
(4)
;

wherein each of D1 through D16 independently is selected from hydrogen, C1-C6 alkyl, (C0-C4 alkyl) hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl, optionally wherein one or more of the pairs of D3/D5, D4/D6, D7/D9, D8/D10, D11/D13 and D12/D14 is a divalent moiety selected from —O—, —S—, —NH—, —N(C1-C24 alkyl)-, optionally wherein one or more of the pairs of D3/D5, D4/D6, D7/D9, D8/D10, D11/D13 and D12/D14 is a condensed ring structure selected from formulae (5) through (8):

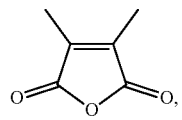
(5)

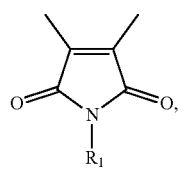
(6)

wherein R1 is hydrogen, linear or branched (C1-C5) alkyl, cyclohexyl, a reactive moiety R20, or —(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2;

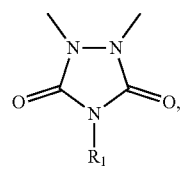
(7)

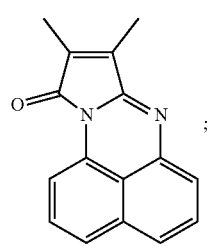
(8)

optionally substituted with up to 3 substituents selected from hydroxyl, nitro, halogen, C1-C6 alkyl, C1-C6 alkoxy, NH(C1-C6 alkyl), N(C1-C6 alkyl)2, and a reactive moiety R20;

wherein (a) E1 and E2 each are a monovalent moiety independently selected from hydrogen, C1-C6 alkyl, (C0-C4 alkyl)hydroxy, C1-C4 alkoxy, amino, N(C1-C24 alkyl)2, —NH(C1-C24 alkyl), nitro, halogen, C1-C3 carboxyl ester, phenoxy optionally substituted with up to 3 (C1-C6)alkyl, and the pair of moieties E3/E4 is a divalent moiety according to formula (9) or (10):

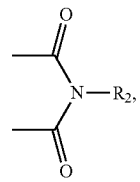
(9)

wherein R2 is a hydrophobic moiety comprising at least 6 carbon atoms, or a reactive moiety R20;

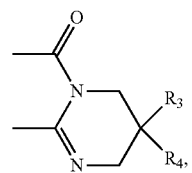
(10)

and
wherein R3 is a hydrophobic moiety comprising at least 3 carbon atoms, or a reactive moiety R20;
and wherein R4 is hydrogen, methyl, ethyl, methoxy, ethoxy, a reactive moiety R20, or a hydrophobic moiety R3;

(b) the pair of moieties E1/E2 and the pair of moieties E3/E4 both are a divalent moiety, wherein E1/E2 is selected from formulae (11) and (12) and E3/E4 is independently selected from formulae (11) through (15):

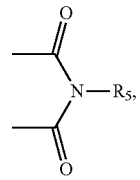
(11)

wherein R5 is hydrogen, linear or branched (C1-C5) alkyl, cyclohexyl, amino, NH(C1-C4 alkyl), N(C1-C4 alkyl)2, a reactive moiety R20, or a hydrophobic moiety R2;

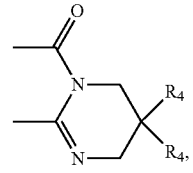
(12)

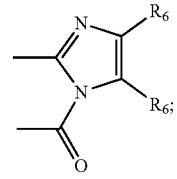
(13)

wherein R6 is hydrogen, methyl, ethyl, methoxy, ethoxy, a reactive moiety R20, or a hydrophobic moiety;

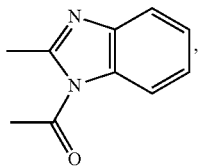
(14)

optionally substituted with up to 3 substituents selected from hydroxyl, nitro, halogen, C1-C6 alkyl, C1-C6 alkoxy, NH(C1-C6 alkyl), N(C1-C6 alkyl)2, a reactive moiety R20; and

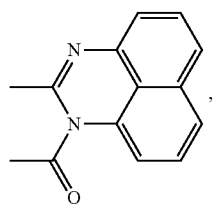
(15)

optionally substituted with up to 3 substituents selected from hydroxyl, nitro, halogen, C1-C6 alkyl, C1-C6 alkoxy, NH(C1-C6 alkyl), N(C1-C6 alkyl)2, a reactive moiety R20;

wherein, when the pair E1/E2 is a divalent moiety according to formula (11) or (13) and the pair E3/E4 is a divalent moiety according to formula (11), (12) or (13), at least one R4, R5 or R6 is a hydrophobic moiety.

19. The peri-arylene dye of statement 18, wherein one of the pairs D3/D5, D7/D9 and D11/D13 is a divalent moiety selected from —O—, —S—, —NH—, —N(C1-C24 alkyl)-, or a condensed ring structure selected from formulae (5) through (8).

20. The peri-arylene dye of statement 19, wherein one of the pairs D4/D6, D8/D10 and D12/D14 is a divalent moiety selected from —O—, —S—, —NH—, —N(C1-C24 alkyl)-, or a condensed ring structure selected from formulae (5) through (8).

21. The peri-arylene dye of statements 18-20, wherein structure A is according to Formula (2).

22. The peri-arylene dye of statements 18-21, wherein R2 is a hydrophobic moiety comprising 6-28 carbon atoms, selected from:
—(CH2)m-C(R2a)(R2b)(R2b), wherein m=0-5, R2a is linear C3-24 alkyl and each R2b independently is hydrogen or linear C3-24 alkyl, wherein alkyl is optionally substituted with one or more substituents selected from halogen, C1-C6 alkyl, C1-C6 alkoxy, NH(C1-C6 alkyl), and N(C1-C6 alkyl)2,
—(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3 or, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and
—(CH2)n-aryl, wherein n=0-3 and aryl is C5-C10 aryl, wherein 1 or 2 of the carbon atoms may be replaced by N, O or S, and wherein aryl optionally is substituted with up to 3 substituents selected from halogen, C1-C6 alkyl, C1-C6 alkoxy, NH(C1-C6 alkyl), N(C1-C6 alkyl)2, in particular isopropyl and/or tert-butyl.

23. The peri-arylene dye of statements 18-22, wherein R3 is a hydrophobic moiety —(CH2)m-C(R3a)(R3b)(R3b), wherein m=0-5, R3a is C3-24 alkyl and each R3b independently is hydrogen or C3-24 alkyl, wherein alkyl is linear and is optionally substituted with one or more substituents selected from halogen, C1-C6 alkyl, C1-C6 alkoxy, NH(C1-C6 alkyl), N(C1-C6 alkyl)2.

24. The peri-arylene dye of statements 18-23, wherein R6 is a hydrophobic moiety R6a selected from:
—(CH2)m-C(R6b)(R6c)(R6c), wherein m=0-5, R6b is linear C3-24 alkyl and each R6c independently is hydrogen or linear C3-24 alkyl, wherein alkyl is optionally substituted with one or more substituents selected from halogen, C1-C6 alkyl, C1-C6 alkoxy, NH(C1-C6 alkyl), and N(C1-C6 alkyl)2,
—(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2.

25. The peri-arylene dye of statements 18-24, wherein R2 is a moiety comprising 14-28 carbon atoms, selected from:
—(CH2)m-CH(C3-24 alkyl)2 or —(CH2)m-C(C3-24 alkyl)3, wherein m=0-5, wherein alkyl is linear and is optionally substituted with one or more substituents selected from halogen, C1-C6 alkyl, C1-C6 alkoxy, NH(C1-C6 alkyl), and N(C1-C6 alkyl)2,
—(CH2)n-NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3 or, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and
—(CH2)o-phenyl, wherein o=1-3 which may be substituted with up to 3 substituents selected from C1-C6 alkyl and C1-C6 alkoxy, in particular isopropyl and/or tert-butyl,
—(CH2)n-naphthyl, wherein n=0-3 which may be substituted with up to 3 substituents selected from C1-C6 alkyl and C1-C6 alkoxy, in particular isopropyl and/or tert-butyl.

26. The peri-arylene dye of statement 25, wherein R2 is:
—(CH2)m-CH(C7-16 alkyl)2 or —(CH2)m-C(C7-16 alkyl)3, wherein n=0-3, wherein alkyl is linear and is optionally substituted with one or more substituents selected from halogen, methyl, ethyl, propyl, isopropyl, or
—(CH2)n-N(C7-C16 alkyl)2 or —(CH2)n-NH—(CH2)n-C(C5-C10 alkyl)3, wherein n=0-3 and alkyl is linear and is optionally substituted with one or more substituents selected from halogen, methyl, ethyl, propyl, isopropyl.

27. The peri-arylene dye of statement 26, wherein R2 is:
—(CH2)m-CH(C9-16 alkyl)2 or —(CH2)m-C(C9-16 alkyl)3, wherein alkyl is linear, or —N(C8-C16 alkyl)2 or —NH—CH2-C(C6-C8 alkyl)3, wherein alkyl is linear.

28. The peri-arylene dye of statements 18-27, wherein the peri-arylene dye is a compound according to formula (16), (17), (18) or (19):

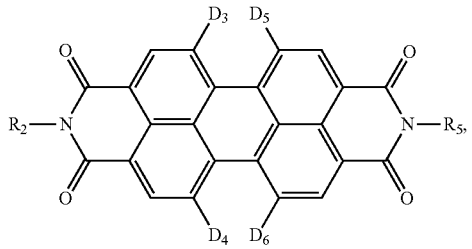
(16)

(17)

(18)

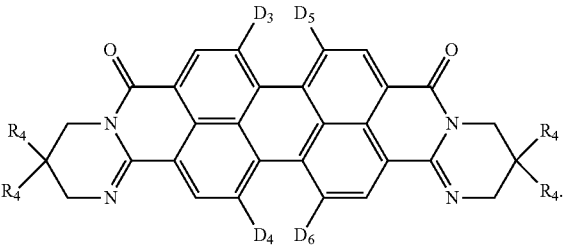
(19)

29. The peri-arylene dye of statement 28, wherein D3 is hydrogen, D5 is selected from hydroxyl, amino, N(C1-C24 alkyl)2, NH(C1-C24 alkyl), nitro and halogen, and the pair D4/D6 is a divalent moiety selected from —O—, —S—, —NH—, or formulae (5) through (8).

30. The peri-arylene dye of statement 28, wherein D3 and D5 each is hydrogen, and the pair D4/D6 is a divalent moiety selected from —O—, —S—, —NH—, or formulae (5) through (8).

31. The peri-arylene dye of any of statements 28-30, wherein the pair D4/D6 is a divalent moiety according to formula (5).

32. The peri-arylene dye of statement 28, wherein D3, D4 and D6 each is hydrogen, and D5 is selected from hydroxyl, amino, N(C1-C24 alkyl)2, NH(C1-C24 alkyl), nitro and halogen.

33. The peri-arylene dye of statement 28, wherein D5 is selected from amino, nitro, N(C1-C6 alkyl)2, and NH(C1-C6 alkyl).

34. The peri-arylene dye of any of statements 28-33, wherein the peri-arylene dye is a compound according to formula (16), and wherein R5 is amino, NH(C1-C4 alkyl) or N(C1-C4 alkyl)2.

35. The peri-arylene dye of any of statements 28-33, wherein each R5 is R2 and wherein each R4 is R3.

36. The peri-arylene dye of any of statements 18-35, comprising at least two of said hydrophobic moieties.

37. The peri-arylene dye of any of statements 18-36, substituted with at least one reactive moiety R20.

38. The peri-arylene dye of any of statements 18-37, substituted with one reactive moiety R20.

39. The peri-arylene dye of any of statements 18-36, wherein the dye is free of a reactive moiety R20.

40. The peri-arylene dye of statements 18-39, having a molecular weight of more than 500 g/mol, in particular more than 760 g/mol, for example more than 860 g/mol, such as more than 960 g/mol.

41. The peri-arylene dye of statement 18, wherein the peri-arylene dye is a compound according to formula (20):
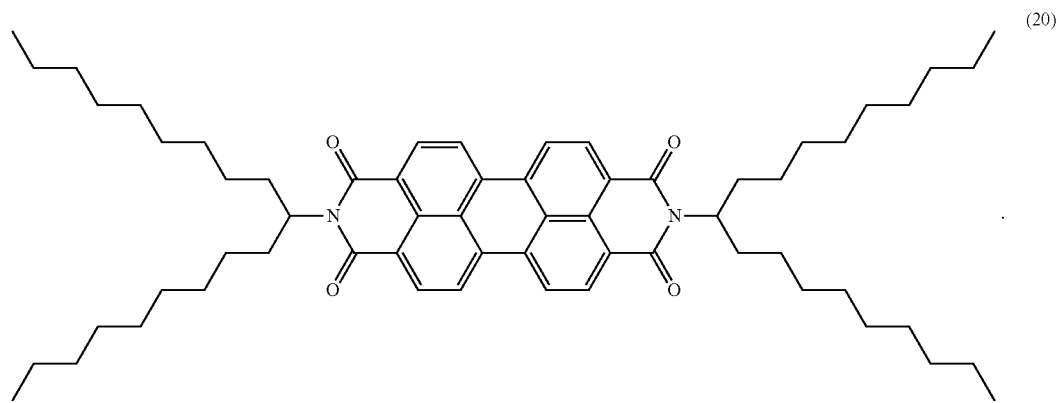 [SMILES: CCCCCCCCCC(CCCCCCCCC)N1C(=O)c2ccc3c4ccc5c6c(ccc(c7ccc(c2c37)C1=O)c64)C(=O)N(C(CCCCCCCCC)CCCCCCCCC)C5=O]
(20)
42. The peri-arylene dye of statement 18, wherein the peri-arylene dye is a compound according to formula (21):
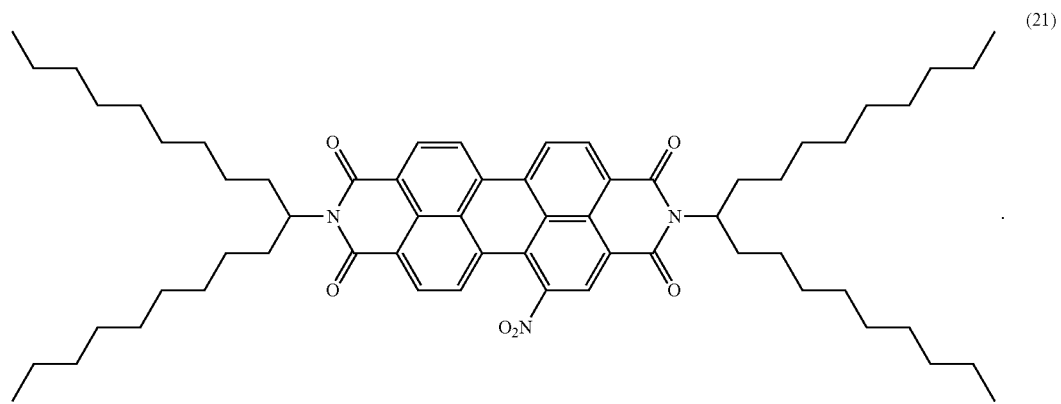
(21)
43. The peri-arylene dye of statement 18, wherein the peri-arylene dye is a compound according to formula (22):
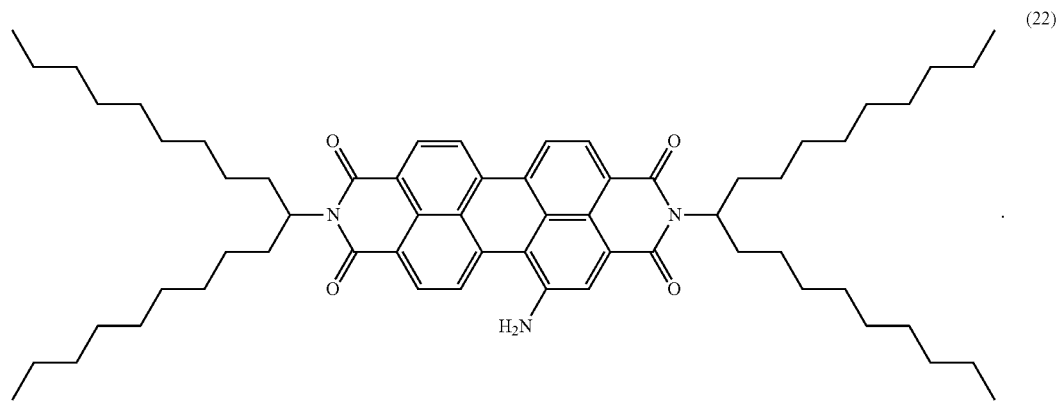 [SMILES: CCCCCCCCCC(CCCCCCCCC)N1C(=O)c2ccc3c4ccc5c6c(cc([N+](=O)[O-])c(c7ccc(c2c37)C1=O)c64)C(=O)N(C(CCCCCCCCC)CCCCCCCCC)C5=O]
(22)

44. The peri-arylene dye of statement 18, wherein the peri-arylene dye is a compound according to formula (23):

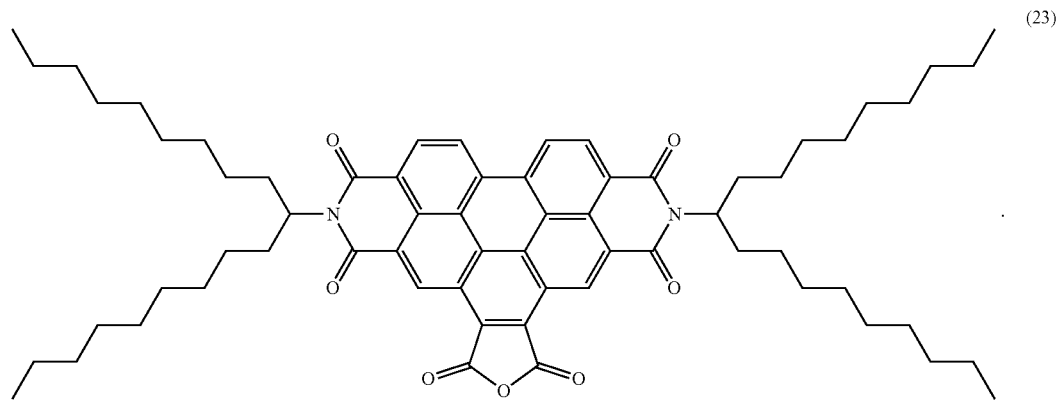 [SMILES: CCCCCCCCCC(CCCCCCCCC)n1c(=O)c2ccc3c4ccc5c(=O)n(C(CCCCCCCCC)CCCCCCCCC)c(=O)c6cc7c8c(=O)oc(=O)c8c8cc(c1=O)c2c3c8c7c4c56]

45. The peri-arylene dye of statement 38, wherein the peri-arylene dye is a compound according to formula (31):

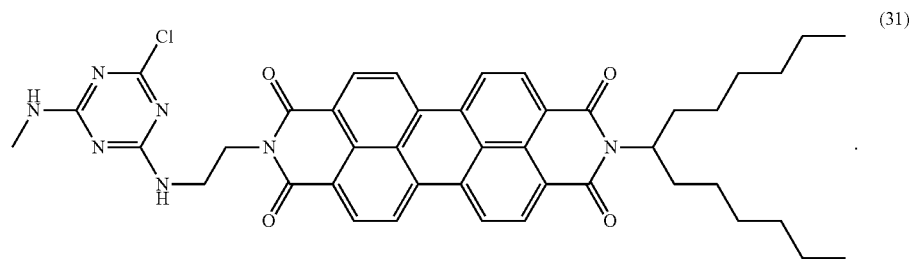 [SMILES: CCCCCCC(CCCCCC)N1C(=O)c2ccc3c4ccc5c6c(ccc(c7ccc(c2c37)C1=O)c64)C(=O)N(CCNc1nc(Cl)nc(NC)n1)C5=O]

46. The peri-arylene dye of statement 38, wherein the peri-arylene dye is a compound according to formula (32):

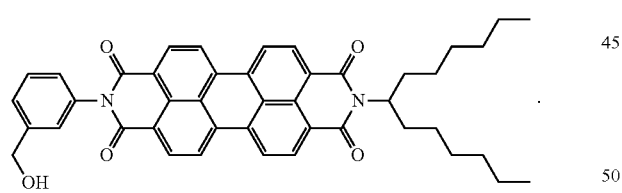

47. The peri-arylene dye of statement 38, wherein the peri-arylene dye is a compound according to formula (33):

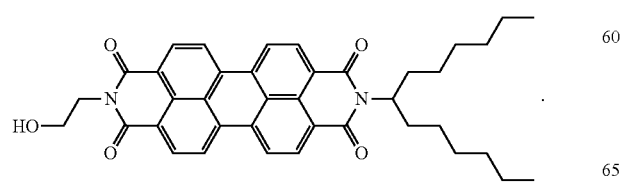

48. The peri-arylene dye of statement 38, wherein the peri-arylene dye is a compound according to formula (34):

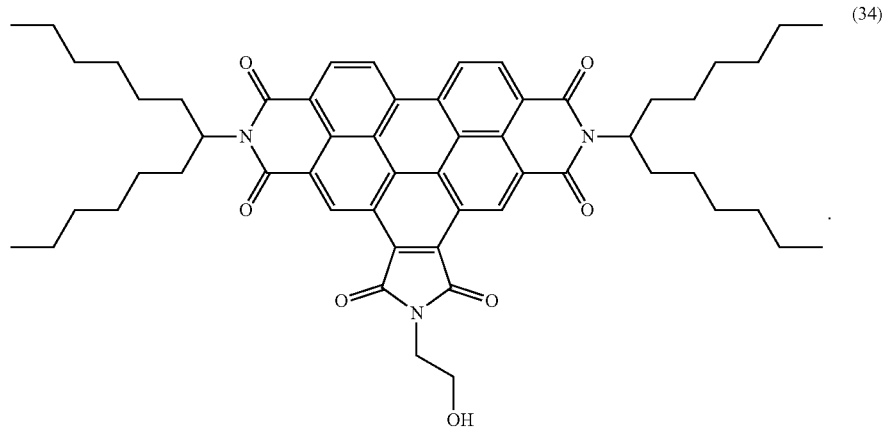 [SMILES: CCCCCCC(CCCCCC)n1c(=O)c2ccc3c4ccc5c(=O)n(C(CCCCCC)CCCCCC)c(=O)c6cc7c8c(=O)n(CCO)c(=O)c8c8cc(c1=O)c2c3c8c7c4c56]

49. The peri-arylene dye of any of statements 18-48, having an absorption maximum within 400-700 nm range, with a maximum absorption coefficient of at least 20,000 L/mol·cm.
50. The peri-arylene dye of any of statements 18-49, having a fluorescence quantum yield of at least 15% for absorptions in the range of 560-590 nm and 80% for absorptions in the range of 490-530 nm.
51. The peri-arylene dye of any of statements 18-50, having an octanol/water partition coefficient ($\log P_{ow}$) of at least 20, wherein $\log P_{ow}$ is calculated based on the GALAS algorithm using ACD/Labs software.
52. The peri-arylene dye of any of statements 18-51, wherein the peri-arylene dye is soluble in a medium having an octanol/water partition coefficient ($\log P_{ow}$) of at least 12, wherein $\log P_{ow}$ is calculated based on the GALAS algorithm using ACD/Labs software.
53. The peri-arylene dye of any of statements 18-52, wherein the peri-arylene dye is soluble in a medium comprising a linear or branched C2-C8 alcohol, and optionally water in an amount below the solubility limit.
54. The peri-arylene dye of statement 53, wherein the medium comprises (iso)propanol and/or butanol.
55. A peri-arylene dye according to formula (24)

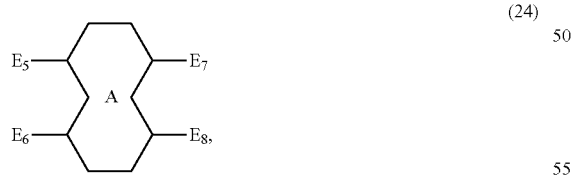

wherein structure A

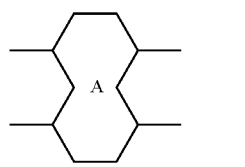

is selected from formulae (2) through (4) as defined in statement 18;
wherein each of D1 through D16 independently is a monovalent moiety as defined in statement 18, optionally wherein one or more of the pairs of D3/D5, D4/D6, D7/D9, D8/D10, D11/D13 and D12/D14 is a divalent moiety as defined in statement 18 or a condensed ring structure selected from formulae (5) through (8) as defined in statement 18;
wherein
(a) E5 and E6 each independently are a monovalent moiety selected from hydrogen, C1-C6 alkyl, (C0-C4 alkyl)hydroxy, C1-C4 alkoxy, amino, N(C1-C24 alkyl)2, —NH(C1-C24 alkyl), carboxylic acid, sulfonic acid, nitro, halogen, C1-C3 carboxyl ester, phenoxy optionally substituted with up to 3 (C1-C6) alkyl, and the pair of moieties E7/E8 is a divalent moiety according to formula (25) or (26), or
(b) the pair of moieties E5/E6 and the pair of moieties E7/E8 both are a divalent moiety independently selected from formulae (25) and (26);
wherein Formula (25) is

wherein R7 is hydrogen or a hydrophilic moiety R9; and
wherein Formula (26) is

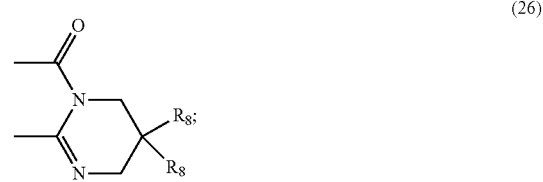

wherein each R8 independently is hydrogen or a hydrophilic moiety R9;

wherein, when E5 and E6 are monovalent moieties or the pair E5/E6 is a divalent moiety according to formula (25), and the pair E7/E8 is a divalent moiety according to formula (25) or (26), at least one R7 or R8 is a hydrophilic moiety R9;

wherein R9 is selected from

R9a: —(CH2)n-aryl, wherein n=0-3, and aryl is C5-10 aryl, wherein 1 or 2 of the carbon atoms may be replaced by N, O or S, wherein aryl is substituted with 2 or 3 carboxylic acid or sulfonic acid groups, and optionally with 1-2 substituents selected from halogen, methyl, ethyl, propyl, iso-propyl, tert-butyl; or R9b: —(C0-C6 alkylene)-13+(counterion), wherein —B⁺ is an aromatic heterocyclic moiety comprising a quaternary nitrogen, selected from pyrryl, imidazolyl, pyrazolyl, pyridyl, pyrimidinyl, pyrazyl, chinolyl, indolyl, N-alkyl derivatives thereof, and N-alkenyl derivatives thereof, an aliphatic heterocyclic moiety comprising a quaternary nitrogen, selected from pyrrolidinyl, piperidinyl, morpholinyl, N-alkyl derivatives thereof, and N-alkenyl derivatives thereof, a quaternary alkyl or aryl ammonium moiety of the formula —N(R10)3, wherein R10 in each occurrence independently is —(CH2)n-phenyl, wherein n=0-3, or (C1-C6)alkyl, wherein alkyl optionally is substituted with up to 3 substituents selected from hydroxy and amino, or a phosphonium moiety of the formula —P(C1-C6)alkyl, wherein alkyl optionally is substituted with up to 3 substituents selected from hydroxy and amino;

R9c: linear, branched or cyclic polyalkoxy or polyamino optionally substituted with carboxy, amino, methyl, ethyl, hydroxy(C0-C4 alkyl), and/or C1-C4 alkoxy.

56. The peri-arylene dye of statement 55, wherein at least one R9 is R9a, and wherein R9a is phenyl or benzyl substituted with 2 sulfonic acid groups.

57. The peri-arylene dye of statement 55, wherein at least one R9 is R9b, and wherein B⁺ is an aromatic heterocyclic moiety selected from N-methylimidazolyl, N-allylimidazolyl, 2-ethylimidazolyl, and 1,2-dimethylimidazolyl.

58. The peri-arylene dye of statement 55, wherein at least one R9 is R9b, and wherein B⁺ is an aliphatic heterocyclic moiety selected from N-methylmorpholinyl, N-ethylmorpholinyl, 1-methylpiperidinyl.

59. The peri-arylene dye of statement 55, wherein at least one R9 is R9b, and wherein B⁺ is a quaternary ammonium moiety, wherein R10 in each occurrence independently is phenyl or benzyl, or (C1-C4)alkyl, wherein alkyl optionally is substituted with up to 3 substituents selected from hydroxy and amino.

60. The peri-arylene dye of statement 55, wherein at least one R9 is R9c, wherein R9c is linear or branched polyoxyethylene, polyoxy(iso)propylene or polyoxy(iso)butylene comprising 12-80, in particular 15-40 polyoxyalkylene units optionally substituted with carboxy, amino, methyl, ethyl, hydroxy(C0-4 alkyl), and/or C1-4 alkoxy, with the terminal group being —OR11, wherein R11 is hydrogen or C1-C6 alkyl optionally substituted with carboxy, amino, methyl, ethyl, hydroxy(C0-C4 alkyl), and/or C1-C4 alkoxy.

61. The peri-arylene dye of statement 55, wherein at least one R9 is R9c, wherein R9c is a crown ether.

62. The peri-arylene dye of statement 61, wherein the crown ether is selected from 9-crown-3, 12-crown-4, 15-crown-5, 18-crown-6, 21-crown-7, 24-crown-8, and aza-analogues thereof.

63. The peri-arylene dye of any one of statement 55-62, wherein the pair E5/E6 and the pair E7/E8 both are a divalent moiety independently selected from formulae (25) and (26).

64. The peri-arylene dye of any one of statement 55-63, wherein the pair E5/E6 and the pair E7/E8 both are a divalent moiety according to formula (25).

65. The peri-arylene dye of any of statements 55-64, having an absorption maximum within 400-700 nm range, with a maximum absorption coefficient at least 20,000 L/mol·cm.

66. The peri-arylene dye of any of statements 55-65, having a fluorescence quantum yield of at least 15% for absorptions in the range of 560-590 nm and 80% for absorptions in the range of 490-530 nm.

67. A hair coloring composition, comprising a medium and at least one dye according to statement 17 or 39 in the medium, the composition optionally further comprising pigment microparticles.

68. The composition of statement 67, wherein the dye(s) is/are present in an amount of from 0.005% to about 5%, about 0.01% to about 3%, about 0.1 to about 2%, or about 0.25% to about 1.5% by weight of the hair coloring composition.

69. The composition of statement 67 or 68, comprising at least two of said dyes, in particular at least three of said dyes.

70. The composition of any of statements 67-69, wherein at least one of said dyes is photoluminescent.

71. The composition of any of statements 67-70, wherein none of said dyes is photoluminescent.

72. The composition of any of statements 67-71, further comprising a film former, wherein the film former is selected from carboxylic acid polymer(s), a copolymer comprising repeating units of at least one (meth)acrylate monomer, at least one olefin monomer and (meth) acrylic acid monomer, polar functional silicone polymer(s), a multicomponent in situ linkable composition.

73. The composition of statement 72, wherein the film former is carboxylic acid polymer, and wherein:

the carboxylic acid polymer comprises a (meth)acrylic acid homopolymer or copolymer or terpolymer;

the homopolymer comprises monomeric units of (meth)acrylic acid and optional carboxyl derivatives thereof;

the copolymer or terpolymer comprises monomeric units of (meth)acrylic acid and monomeric units selected from the groups consisting of one or more (meth)acrylate esters, one or more (meth)acrylamides, carboxyl derivatives of (meth)acrylic acid and monomeric units of neutral olefins and any combination thereof;

the carboxylic acid polymer has an acid value of from about 0.01 to about 700;

the carboxylic acid polymer is optionally at least partially neutralized with a base;

the carboxylic acid polymer has a glass transition temperature in the solid state of from about −60° C. to about 90° C.;

the carboxylic acid polymer has a weight average molecular weight in the range of about 300 Da to about 10 MDa.

74. The composition of statement 73, wherein the carboxylic acid polymer is a Ultrahold Strong®, Luvimer®, Amerhold®, Acudyne®, Acrylidone®, Acrysol ASE-75® Thickener (Dow), Primal 3208® Emulsion (Dow), Acrysol ASE-95NP® Thickener (Dow), Acrysol I-62A® (Dow), Acrysol WS-24® Colloidal (Dow), Acrysol WS-50® Colloidal Dispersion (Dow), Plexisol P 550-40® (Kremer), FIXATE FREESTYLE POLYMER® (Lubrizol), Rovene 6005® (Mallard Creek), Rovene 6017® (Mallard Creek), Rovene 6020® (Mallard Creek), Rovene 6103® (Mallard Creek), Rovene 9410® (Mallard Creek), Silform HYFLEX® (Momentive), Mowinyl 67180 (Mowinyl), Mowinyl 67500 (Mowinyl), Mowinyl 675100 (Mowinyl), Mowinyl 67600 (Mowinyl), Mowinyl 6960® (Mowinyl), X-200® (PMC/SEIKO), J-140A® (PMC/SEIKO), RE-1075 (PMC/SEIKO), COVACRYL P12® (Sensient), Covacyl E14 WP®, (Sensient), COVACRYL MT10® (Sensient), WorleeMicromer C20/42® (Worlee), WorleeMicromer C60/42® (Worlee), WorleeMicromer C60/42 NP® (Worlee), Avalure AC 120® Polymer (Lubrizol), product at least containing monomeric units of (meth)acrylic acid and an acid value from about 0.1 to about 400.

75. The composition of statement 72, wherein the film former is polar functional silicone polymer, and wherein:
   the polar functional silicone polymer comprises dialkylsiloxane units and organosiloxane units with pendant amine groups or organo-oligomer blocks with pendant amine groups or both of the organosiloxane units and the organo-oligomer blocks wherein the ratio of number of organosiloxane units with amine groups or organo-oligomer blocks with amine groups or both to the number of dialkylsiloxane units is in a range of from about 1:1000 to about 1:10;
   the polar functional silicone polymer has a total number of dialkylsiloxane units, if present, organosiloxane units, and, if present, organo-oligomer block units, in a range of from about 150 to about 2200;
   the polar functional silicone polymer has a weight average molecular weight in the range of from about 10 kDa to about 150 kDa.

76. The composition of statement 75, wherein the polar functional silicone polymer is Formula IV Formula IV

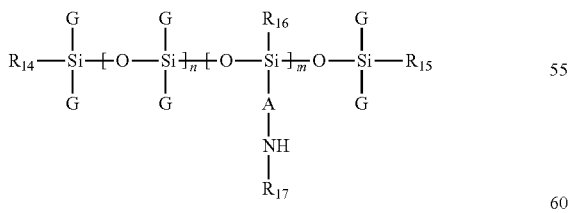

wherein: the siloxane units associated with designators m and n respectively are SiA units and SiC units; the designators m and n+2 are numbers with a sum (n+2+m) ranging from 150 to 2200, n+2 is a number ranging from 1 to 2000 wherein the 2 of n+2 adds the two terminal siloxane units, and m is a number ranging from 1 to 200; and are chosen such that ratio of SiA:SiC is 1:1000 to 1:10;
   $R_{14}$, $R_{15}$, $R_{16}$, which may be identical or different, are chosen from a hydroxyl radical, C1-C4 alkoxy radicals and methyl;
   A is selected from linear and branched C3-C8 alkyl radicals;
   $R_{17}$ is selected from H, phenyl, linear or branched C1-C4 alkyl radical, benzyl or preferably linear or branched alkyl amine of 2 to 8 carbons (C2-C8)$NH_2$; and when $R_{17}$ is phenyl, alkyl benzyl or alkyl amine, $R_{17}$ optionally contains within its carbon chain a group selected from carboxamido, sulfonamide, ether, thioether, secondary or tertiary amino and any combination thereof; and,
   G is selected from phenyl, hydroxyl, C1-C8 alkyl, preferably methyl.

77. The composition of any of statements 67-76, wherein the film former is a multicomponent in situ linkable composition as defined in the second or third set of statements below.

78. The composition of any of statements 67-77, further comprising one or more of a plasticizer, wetting agent, water soluble organic dye compound different from said at least one dye, thickener, a viscosity control agent or a cationic, anionic, nonionic or amphoteric surfactant.

79. The composition of any of statements 67-78, wherein the dye is an aromatic dye according to statement 17, in particular a peri-arylene dye.

80. The composition of any of statements 67-78, wherein the dye is a peri-arylene dye according to statement 39.

81. The composition of statements 79 or 80, wherein the medium comprises an organic solvent having an octanol/water partition coefficient (log $P_{ow}$) of at least 15, wherein log $P_{ow}$ is calculated based on the GALAS algorithm using ACD/Labs software.

82. The composition of any of statements 79-81, wherein the medium has having an octanol/water partition coefficient (log $P_{ow}$) of at least 12, wherein log $P_{ow}$ is calculated based on the GALAS algorithm using ACD/Labs software.

83. The composition of any of statements 79-82, wherein the medium comprises a linear or branched C2-C8 alcohol, and optionally water in an amount below the solubility limit.

84. The composition of any of statements 79-83, wherein the medium comprises (iso)propanol and/or (iso)butanol.

85. The composition of any of statements 67-78, wherein the dye is a peri-arylene dye according to any one of statements 55-66.

86. The composition of any of statements 67-85, wherein the coloring composition further comprises at least one silicone node building additive.

87. The composition of any of statements 67-86, comprising the pigment microparticles.

88. The composition of statement 87, wherein the pigment microparticles are irregularly and/or regularly shaped, comprise at least one pigment color and have at least one dimension of less than one micron;
   the composition has a solids content of about 1 wt % to about 40 wt % relative to the total weight of the composition.

89. The composition of statement 87 or 88, wherein the pigment microparticles are dispersed in the medium.

90. The composition of any of statements 87-89, wherein the pigment microparticles are maintained in the medium dispersion by a suspending agent.
91. A hair coloring composition, comprising an oil-in-water emulsion and at least one direct dye partitioned therein;
   said at least one direct dye comprising a dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products, wherein said direct dye optionally comprises a reactive moiety R20;
   said oil-in-water emulsion comprising:
   (A) an aqueous phase containing water; and
   (B) an oil phase containing at least one reactive condensation-curable film-forming amino-silicone pre-polymer that, subsequent to condensation curing, forms an elastomer,
   wherein said oil phase fulfills at least one of the following:
   (i) said at least one reactive condensation-curable film-forming amino-silicone pre-polymer includes at least one reactive condensation-curable film-forming amino-silicone monomer having a molecular weight of at most 1000 g/mole;
   (ii) said oil phase further contains a non-amino cross-linking agent adapted or selected to cure said pre-polymer, said non-amino cross-linking agent having a molecular weight in the range of at most 1000 g/mole;
   wherein said at least one reactive condensation-curable film-forming amino-silicone pre-polymer has a solubility in water of less than 1% by weight at 25° C.
92. The composition of statement 91, wherein said at least one direct dye comprises a peri-arylene dye according to statement 37 or 38.
93. The composition of statement 91 or 92, wherein said dye(s) is/are present in an amount of from 0.005% to about 5%, about 0.01% to about 3%, about 0.1 to about 2%, or about 0.25% to about 1.5% by weight of the hair coloring composition.
94. The composition of any of statements 91-93, comprising at least two of said dyes, in particular at least three of said dyes.
95. The composition of any of statements 91-94, wherein at least one of said dyes is photoluminescent.
96. The composition of any of statements 91-95, wherein none of said dyes is photoluminescent.
97. The composition of any of statements 91-96, further comprising one or more of a plasticizer, wetting agent, water soluble organic dye compound different from said at least one direct dye, thickener, a viscosity control agent or a cationic, anionic, nonionic or amphoteric surfactant.
98. The composition of any of statements 91-97, comprising a linear or branched C2-C8 alcohol.
99. The composition of statement 98, wherein the alcohol is (iso)propanol and/or (iso)butanol.
100. Colored hair strand comprising hair strand surfaces colored with at least one dye of any of statements 1-66.
101. Colored hair strand of statement 100, wherein the at least one dye is a dye according to any one of statements 1-17, in particular a peri-arylene dye.
102. Colored hair strand of statement 100, wherein the at least one dye is a peri-arylene dye according to any one of statements 18-54.
103. Colored hair strand of statement 100, wherein the at least one dye is a peri-arylene dye according to any one of statements 55-66.
104. Colored hair strand comprising hair strand surfaces colored with the hair coloring composition of any of statements 67-90.
105. Colored hair strand of statement 104, wherein the medium of the composition is removed, in particular wherein the medium has been removed by evaporation.
106. Colored hair strand of any of statements 100-105, comprising hair strand surfaces at least partially coated with a film former selected from carboxylic acid polymer(s) and polar functional silicone polymer(s).
107. Colored hair strand comprising hair strand surfaces colored with the hair coloring composition of any of statements 91-99.
108. Colored hair strand of any of statements 100-107, which is resistant to color fading by repeated washings with shampoo and/or water and soap.
109. Colored hair strand of any of statements 100-108, wherein the color displays color fastness.
110. A method of coloring hair, comprising
   (a) applying the hair coloring composition of any of statements 67-90 to strands of hair, and
   (b) removing the medium.
111. The method of statement 110, wherein the hair coloring composition is the composition of any of statements 72-77.
112. The method of statement 110 or 111, wherein the dye is a peri-arylene dye according to statement 39.
113. The method of any of statements 110-112, further comprising applying a pre-treatment composition to the hair strands, prior to applying the hair coloring composition.
114. The method of statement 113, wherein the pretreatment composition comprises a cationic polymer and an aqueous medium.
115. The method of any of statement 110-114, further comprising applying a composition comprising a film former selected from carboxylic acid polymer(s) and polar functional silicone polymer(s).
116. The method of statement 115, wherein the composition comprising a film former is applied after step (a) and prior to step (b).
117. The method of statement 115 or 116, wherein the film former is a carboxylic acid polymer.
118. A method of coating mammalian hair, the method comprising:
   (a) applying, on an external surface of individual hairs of the mammalian hair, an oil-in-water emulsion comprising:
      (A) an aqueous phase containing water; and
      (B) an oil phase containing at least one reactive condensation-curable film-forming amino-silicone pre-polymer that, subsequent to condensation curing, forms an elastomer,
      wherein said oil phase fulfills at least one of the following:
      (i) said at least one reactive condensation-curable film-forming amino-silicone pre-polymer includes at least one reactive condensation-curable film-forming amino-silicone monomer having a molecular weight of at most 1000 g/mole;
      (ii) said oil phase further contains a non-amino cross-linking agent adapted or selected to cure said pre-polymer, said non-amino cross-linking agent having a molecular weight in the range of at most 1000 g/mole;
wherein said at least one reactive condensation-curable film-forming amino-silicone pre-polymer has a solubility in water of less than 1% by weight at 25° C.;
(b) applying, on said external surface of individual hairs of the mammalian hair, at least one direct dye;
(c) after partial condensation curing of said pre-polymer has occurred so as to form an at least partially cured film on the external surface of the individual hairs, washing the hair with a rinsing liquid to remove any excess of said oil-in-water emulsion.

119. The method according to statement 118, wherein a first amino-silicone pre-polymer of said at least one reactive condensation-curable film-forming amino-silicone pre-polymer has at least 3 silanol and/or hydrolysable groups, so as to form a 3-dimensional network.

120. The method according to statement 119, wherein a first concentration of said first amino-silicone pre-polymer, within said oil phase, is at least 15%, at least 20%, at least 30%, at least 40%, at least 50%, or at least 60%, by weight, of said oil phase.

121. The method according to statement 120, wherein said first concentration is at most 95%, at most 90%, at most 85%, at most 80%, at most 75%, or at most 70%.

122. The method according to statement 120, wherein said first concentration is within a range of 20-95%, 20-85%, 30-95%, 30-85%, 40-95%, 40-85%, 40-75%, 45-95%, 45-85%, 50-95%, 50-85%, 55-95%, 55-85%, 55-75%, 60-95%, 60-90%, 60-85%, or 60-80%.

123. The method according to statement 119, wherein a combined concentration of said first amino-silicone pre-polymer and said non-amino cross-linking agent, within said oil phase, is within a range of 35-95%, 40-95%, 40-85%, 40-75%, 45-95%, 45-85%, 50-95%, 50-85%, 55-95%, 55-85%, 55-75%, 60-95%, 60-90%, 60-85%, or 60-80%, by weight, of said oil phase.

124. The method according to statement 123, wherein a concentration of said non-amino cross-linking agent within said combined concentration is limited by a condition that said oil-in-water emulsion has a surface zeta potential greater than zero (>0), or at least +1 mV, at least +2 mV, at least +3 mV, at least +5 mV, at least +7 mV, or at least +10 mV.

125. The method according to statement 123, wherein within said oil phase, a total concentration of said amino-silicone oil, said non-amino-silicone oil, and said at least one reactive condensation-curable film-forming amino-silicone pre-polymer, excluding said first amino-silicone pre-polymer, is within a range of 3% to 65%, 3% to 60%, 3% to 55%, 3% to 50%, 3% to 45%, 3% to 40%, 7% to 40%, 10% to 40%, 10% to 50%, 15% to 50%, 15% to 45%, 15% to 40%, 20% to 45%, 25% to 45%, 25% to 50%, 30% to 45%, 30% to 60%, 35% to 50%, or 35% to 60%, by weight; and optionally subject to said oil phase having a viscosity of no more than 500 mPa·s, as measured at 25° C.

126. The method according to any of statements 118-125, wherein a concentration of a terminating pre-polymer having a single silanol or hydrolysable group, within said oil phase, is at most 7%, at most 5%, at most 2%, by weight of the oil phase, or wherein said oil phase is devoid of said terminating pre-polymer.

127. The method according to any of statements 118-126, wherein a total concentration of organic solvent within said oil phase, on a weight basis, is at most 10%, at most 5%, at most 2%, or at most 1%, or wherein said oil phase is devoid of any organic solvent.

128. The method according to any of statements 118-127, wherein a total concentration of co-solvent within said aqueous phase, on a weight basis, is at most 10%, at most 5%, at most 2%, or at most 1%, or wherein said aqueous phase is devoid of any said co-solvent.

129. The method according to any of statements 118-128, said oil-in-water emulsion further comprising a solid, hydrophobic reactive inorganic filler, said filler disposed or dispersed within said oil phase, said filler selected or adapted to facilitate curing of said condensation-curable film-forming amino-silicone pre-polymer.

130. The method according to statement 129, wherein said reactive filler includes, mainly includes, or consists of, a hydrophobic fumed silica.

131. The method according to statement 129 or 130, wherein an average particle size (Dv50) of said solid, hydrophobic reactive inorganic filler is within a range of 5 to 500 nm, 5 to 250 nm, 20 to 200 nm, 40 to 300 nm, 60 to 300 nm, 60 to 250 nm, or 60 to 200 nm.

132. The method according to any one of statements 129-131, wherein a concentration of said solid, hydrophobic reactive inorganic filler disposed or dispersed within said oil phase is within a range of 0.2% to 12%, 0.2 to 10%, 0.2 to 8%, 0.4 to 10%, 0.4 to 8%, 0.6 to 10%, 0.6 to 8%, 0.8 to 8%, or 0.8 to 6%, by weight.

133. The method according to statement 132, wherein a concentration of said solid, hydrophobic reactive inorganic filler within said oil-in-water emulsion is within a range of 0.005% to 0.5%, 0.005% to 0.3%, by weight.

134. The method according to any one of statements 129-133, wherein a refractive index of said solid, hydrophobic reactive inorganic filler is within a range of ±10%, ±7%, ±5%, or ±3%, of a refractive index of said oil phase.

135. The method according to any of statements 118-134, wherein said at least partially cured film is self-terminated on the external surface of the individual hairs.

136. The method according to any of statements 118-135, wherein said at least one reactive condensation-curable film-forming amino-silicone pre-polymer includes an reactive condensation-curable amino-silicone monomer having a solubility in water of less than 1% by weight at 25° C.

137. The method according to any of statements 118-136, wherein said partial condensation curing is effected at a temperature of at most 38° C., at most 36° C., at most 34° C., or at most 32° C., and optionally, at least 15° C.

138. The method according to any of statements 118-137, wherein said washing is performed within 30 minutes, within 20 minutes, within 15 minutes, within 10 minutes, within 5 minutes, within 3 minutes, within 2 minutes, or within 1 minute, after said applying of said oil-in-water emulsion has been completed.

139. The method according to any of statements 118-138, wherein following said washing, further curing transpires solely by or substantially solely by humidity or ambient humidity.

140. The method according to any of statements 118-139, wherein within at least two days, at least three days, at least five days, or at least a week of said washing, all further curing proceeds in the absence of any non-cationic surfactant added to the hair.

141. The method according to any of statements 118-140, further comprising, within at least two days, at least three days, at least five days, or at least a week of said washing, treating the hair with a hair formulation containing a cationic surfactant.

142. The method according to any of statements 118-141, wherein said oil-in-water emulsion has a surface zeta potential greater than zero, or at least +1 mV, at least +2 mV, at least +3 mV, at least +5 mV, at least +7 mV, at least +10 mV, at least +15 mV, at least +20 mV, at least +30 mV, at least +40 mV, or at least +60 mV; optionally, at most +100 mV, or at most +80 mV.

143. The method according to any one of statements 118-142, wherein said oil-in-water emulsion has a surface zeta potential greater than zero and below 90 mV, or within a range of 1-50 mV, 1-30 mV, 1-20 mV, 1-15 mV, 2-100 mV, 2-30 mV, 3-100 mV, 3-50 mV, 3-30 mV, 3-20 mV, 5-100 mV, 5-50 mV, 5-30 mV, 5-20 mV, 7-100 mV, 10-80 mV, 15-80 mV, 20-80 mV, or 20-60 mV.

144. The method according to any one of statements 118-143, wherein said surface zeta potential is measured at a pH of 10.

145. The method according to any of statements 118-144, wherein said surface zeta potential is measured at a native pH of said oil-in-water emulsion.

146. The method according to any of statements 118-145, wherein said rinsing liquid is (i) water, or (ii) a cationic rinsing liquid containing a cationic surfactant, or (iii) a rinsing liquid devoid of non-cationic surfactants, degreasing agents and/or swelling agents, the degreasing and swelling agent respectively able to degrease and swell the at least partially cured film.

147. The method according to statement 141 or 146, wherein said cationic surfactant is a cosmetically-acceptable primary, secondary, tertiary, or quaternary ammonium compound or polymer.

148. The method according to any of statements 118-147, wherein a total concentration of reactive condensation-curable amino-silicone components within said oil phase is at least 45%, at least 55%, at least 60%, or at least 65%, by weight, and optionally, within a range of 50-100%, 50-95%, 50-90%, 50-85%, 50-80%, 55-95%, 55-85%, 60-95%, 60-85%, 65-95%, 65-90%, or 70-95%.

149. The method according to any of statements 118-148, wherein said pre-polymer includes reactive groups selected from the group consisting of alkoxy-silane reactive groups, silanol reactive groups and combinations thereof.

150. The method according to any of statements 118-149, wherein said oil phase has no glass transition temperature.

151. The method according to any of statements 118-150, wherein said at least one reactive condensation-curable film-forming amino-silicone pre-polymer is a liquid at 25° C.

152. The method according to any of statements 118-151, wherein a viscosity of said at least one reactive condensation-curable film-forming amino-silicone pre-polymer, measured in a suitable rheometer at 25° C., is in a range of 2-1000 milliPascal·second (mPa·s), 2-500 mPa·s, 2-300 mPa s, 2-200 mPa·s, 5-1000 mPa·s, 5-500 mPa·s, 5-300 mPa·s, 7-500 mPa·s, 7-300 mPa·s, or 7-200 mPa·s.

153. The method according to any of statements 118-152, wherein at least one of, and optionally all of said at least one reactive condensation-curable film-forming amino-silicone pre-polymer, has an Amine Number or weight average Amine Number in a range of 3-1000, 3-500 or 3-200.

154. The method according to any of statements 118-153, wherein said solubility in water of said at least one reactive condensation-curable film-forming amino-silicone pre-polymer, by weight, is less than 0.5% or less than 0.25%.

155. The method according to any of statements 118-154, wherein a total concentration of amino-silicone oil within said oil phase, by weight, is at most 40%, at most 35%, at most 30%, at most 20%, at most 15%, at most 10%, or at most 5%.

156. The method according to any one of statements 118-155, wherein a total concentration of amino-silicone oil within said oil phase, by weight, is within a range of 1% to 40%, 5% to 40%, 10% to 40%, 20% to 40%, 1% to 30%, 5% to 30%, 10% to 30%, 15% to 30%, 20% to 35%, or 20% to 30%.

157. The method according to any of statements 118-156, wherein a total concentration of non-amino-silicone oil within said oil phase, by weight, is at most 15%, at most 12%, at most 10%, at most 7%, or at most 5%, subject to a surface zeta potential of said oil-in-water emulsion being greater than zero, or at least +1 mV, at least +2 mV, at least +3 mV, at least +5 mV, at least +7 mV, or at least +10 mV.

158. The method according to any one of statements 118-157, wherein a total concentration of non-amino-silicone oil within said oil phase, by weight, is within a range of 1% to 15%, 3% to 15%, 5% to 15%, 8% to 15%, 1% to 12%, 3% to 12%, 5% to 12%, 3% to 10%, 3% to 8%, or 2% to 5%.

159. The method according to any of statements 118-158, wherein said non-amino cross-linking agent includes, mainly includes, or consists of a reactive condensation-curable film-forming non-amino-silicone monomer.

160. The method according to any of statements 118-159, wherein said non-amino cross-linking agent includes, mainly includes, or consists of an ethyl silicate, a poly(dimethoxysiloxane), and a poly(diethoxysiloxane).

161. The method according to any of statements 118-160, wherein a total concentration of said non-amino cross-linking agent within said oil phase is at most 35%, at most 30%, at most 20%, at most 15%, at most 10%, or at most 5%, subject to a surface zeta potential of said oil-in-water emulsion being greater than zero, or at least +1 mV, at least +2 mV, at least +3 mV, at least +5 mV, at least +7 mV, or at least +10 mV.

162. The method according to any of statements 118-161, wherein a total concentration of said pre-polymer, said non-amino cross-linking agent, said solid, hydrophobic reactive inorganic filler, said amino-silicone oil, said non-amino-silicone oil, and said at least one direct dye, within said oil phase, is at least 90%, at least 93%, at least 95%, at least 97%, at least 98%, or at least 95%, by weight.

163. The method according to any of statements 118-162, said aqueous phase further containing an oil-in-water emulsifier that is optionally non-ionic, said oil-in-water emulsifier having an HLB number within a range of 12 to 18, 12 to 17, 12 to 16, 12 to 15, or 13 to 16.

164. The method according to any of statements 118-163, wherein a total concentration of said water and any emulsifier, within said aqueous phase, is at least 90%, at least 95%, at least 97% at least 99%, on a weight basis.

165. The method according to any of statements 118-164, wherein the mammalian hair to which said oil-in-water emulsion is applied is dry or non-wetted mammalian hair, or to pre-dyed hair.

166. The method according to any of statements 118-165, wherein the mammalian hair to which said oil-in-water emulsion is applied is at least one of unpre-degreased, unpre-shampooed, and unpre-bleached.

167. The method according to any of statements 118-166, wherein said aqueous phase contains, by weight, at most 20%, at most 10%, at most 5%, or at most 2%, of the amount of said at least one direct dye within said oil phase, or wherein said aqueous phase is devoid of said at least one direct dye.

168. The method according to any of statements 118-167, wherein applying said oil-in-water emulsion according to step (a) and applying said at least one direct dye according to step (b) is carried out simultaneously.

169. The method according to statement 168, wherein said at least one direct dye is applied to said external surface of individual hairs as a component of said oil-in-water emulsion.

170. The method according to any of statements 118-167, wherein applying said oil-in-water emulsion according to step (a) and applying said at least one direct dye according to step (b) is carried out in separate steps.

171. The method according to statement 170, wherein said at least one direct dye is applied to said external surface of individual hairs as a component of an oil-in-water emulsion.

172. The method according to any of statements 118-171, wherein said at least one direct dye comprises a dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products, wherein said dye optionally comprises a reactive moiety R20.

173. The method according to any of statements 170-172, wherein said at least one direct dye comprises a peri-arylene dye according to any one of statements 37-38 or 45-48 substituted with a reactive moiety R20.

174. The method according to any of statements 118-173, wherein said at least one direct dye comprises a peri-arylene dye according to statement 39 lacking a reactive moiety R20.

175. A method according to any one of statements 118-174, wherein, at a relative humidity of 30% to 50%, and at a temperature of 25° C., said at least partially cured film achieves permanence within 24 to 96 hours after said applying of said oil-in-water emulsion on the hair, and optionally, within 24 to 72 hours, within 24 to 48 hours, within 24 to 36 hours, or within 24 to 30 hours.

176. A de-coloring medium for removing dye(s) of statement 17 or 39 from strands of hair.

177. The de-coloring medium of statement 176, wherein the dye(s) is/are is peri-arylene dye(s) according to statement 39.

178. A de-coloring medium for removing dye(s) from strands of hair colored with the hair coloring composition of statement 79 or 80.

179. The de-coloring-medium of any of statements 176-178, comprising an organic solvent having an octanol/water partition coefficient (log $P_{ow}$) of at least 15, wherein log $P_{ow}$ is calculated based on the GALAS algorithm using ACD/Labs software.

180. The de-coloring-medium of any of statements 176-179, having an octanol/water partition coefficient (log $P_{ow}$) of at least 12, wherein log $P_{ow}$ is calculated based on the GALAS algorithm using ACD/Labs software.

181. The de-coloring medium of any of statements 176-180, comprising natural and/or synthetic fat, wax or oil.

182. The de-coloring medium of any of statements 176-181, having a viscosity in the range of about 0.05 to about 1000 Pa s$^{-1}$, in particular about 0.1 to about 200 Pa s$^{-1}$, for example 1 to 100 Pa s$^{-1}$, such as 10 to 75 Pa s$^{-1}$.

183. The de-coloring medium of any of statements 176-182, comprising at least 50% by weight plant oil.

184. A method of removing dye(s) of any of statement 17 or 39 from strands of hair, the method comprising applying the de-coloring medium of any of statements 176-173 to the strands of hair.

185. The method of statement 184, wherein the dye(s) is/are peri-arylene dye(s) according to statement 39.

186. Kit, comprising in separate containers the hair coloring composition of any of statements 67-90, and at least one of
(1) a composition comprising a film former selected from carboxylic acid polymer(s) and polar functional silicone polymer(s),
(2) a pretreatment composition comprising a cationic polymer, and
(3) a de-coloring medium.

187. A kit for producing a reactive cosmetic composition for coating an external surface of mammalian hair, the kit comprising:
(a) a first compartment containing an oil phase including at least one direct dye, at least one of an amino-silicone oil and a non-amino-silicone oil, and optionally, a solid, hydrophobic reactive inorganic filler, disposed within said oil phase;
said at least one direct dye comprising a dye selected from rylene dyes, nitro dyes, aryl and heteroaryl azo dyes, chinon/chinonimine/chinondiimine dyes, methin dyes, azomethine-like hydrazone and imine dyes, porphyrin dyes, and coupling products, wherein said dye optionally comprises a reactive moiety R20;
(b) a second compartment containing a formulation including at least one of:
(i) at least one reactive condensation-curable film-forming amino-silicone monomer having a molecular weight of at most 1000 g/mole; and
(ii) a non-amino cross-linking agent; and optionally,
(iii) at least one of said amino-silicone oil and said non-amino-silicone oil;
(c) a compartment containing at least one reactive condensation-curable film-forming amino-silicone pre-polymer that, subsequent to condensation curing, forms an elastomer, said pre-polymer including at least one of a reactive condensation-curable film-forming amino-silicone polymer and a reactive condensation-curable film-forming amino-silicone oligomer; said filler selected or adapted to facilitate curing of said condensation-curable film-forming amino-silicone pre-polymer, said non-amino cross-linking agent adapted or selected to cure said pre-polymer;
wherein said compartment containing at least one reactive condensation-curable film-forming amino-silicone pre-polymer is one of (A) a third compartment; (B) said second compartment; and, (C) said first compartment, subject to said first compartment being substantially devoid of said solid, hydrophobic reactive inorganic filler.

188. A kit according to statement 187, wherein said at least one direct dye comprises a peri-arylene dye according to any one of statements 37-38 or 45-48 substituted with a reactive moiety R20.

189. A kit according to statement 187 or 188, wherein said first compartment further contains solid, hydrophobic reactive inorganic filler, disposed within said oil phase.

190. A kit according to any of statements 187-189, the kit being devoid of said solid, hydrophobic reactive inorganic filler, and wherein said at least one reactive condensation-curable film-forming amino-silicone pre-polymer is disposed in said first compartment.

191. Use of at least one dye of any of statements 1-66 for dyeing hair.

192. The use of statement 191, wherein the dye(s) is/are dye(s) according to any one of statements 1-54.

193. Use of oil for removing at least one dye of statement 17 or 39 from hair.

194. Use of oil for removing dyes of an artificial hair coloration, wherein the artificial hair coloration comprises a dye of statement 17 or 39, and wherein the dye is present in a film former selected from carboxylic acid polymer(s) and polar functional silicone polymer(s).

195. Use of an O/W or W/O emulsion for removing an artificial hair coloration, wherein the artificial hair coloration comprises at least a film former and dyes within the film former, wherein the emulsion comprises an oil phase and an aqueous trigger phase, wherein the artificial coloration comprises a dye of any of statements 1-66, and wherein the film former is selected from carboxylic acid polymer(s) and polar functional silicone polymer(s).

196. Use of an aqueous trigger formulation for removing an artificial hair coloration, wherein the artificial hair coloration comprises at least a film former and dyes within the film former, wherein the artificial coloration comprises a dye of any of statements 1-66, and wherein the film former is selected from carboxylic acid polymer(s) and polar functional silicone polymer(s).

197. The use of statement 195 or 196, wherein the dye(s) is/are dye(s) according to any one of statements 1-54.

198. The use of any of statements 191-197, wherein the dye(s) is/are peri-arylene dye(s) according to any one of statements 18-54.

199. A composition for coloring a keratinous surface, comprising a medium and at least one dye according to any of statements 1-66 in the medium, the composition optionally further comprising pigment microparticles.

200. The composition of statement 199, wherein the dye(s) is/are present in an amount of from 0.005% to about 5%, about 0.01% to about 3%, about 0.1 to about 2%, or about 0.25% to about 1.5% by weight of the hair coloring composition.

201. The composition of statement 199 or 200, comprising at least two of said dyes, in particular at least three of said dyes.

202. The composition of any of statements 199-201, wherein at least one of said dyes is photoluminescent.

203. The composition of any of statements 199-202, wherein none of said dyes is photoluminescent.

204. The composition of any of statements 199-203, further comprising a film former.

205. The composition of any of statements 199-204, wherein the keratinous surface is the surface of a nail.

206. The composition of statement 205, wherein the nail is a human finger or toe nail.

207. A keratinous surface colored with at least one dye of any of statements 1-66.

208. A keratinous surface colored with the composition of any of statements 199-204.

209. The keratinous surface of statement 207 or 208, wherein the keratinous surface is the surface of a nail.

210. The keratinous surface of statement 209, wherein the nail is a human finger or toe nail.

211. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one nitro dye optionally comprising a reactive moiety R20.

212. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one aryl azo dye optionally comprising a reactive moiety R20.

213. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one heteroaryl azo dye optionally comprising a reactive moiety R20.

214. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one chinon/chinonimine/chinondiimine dye optionally comprising a reactive moiety R20.

215. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one methin dye optionally comprising a reactive moiety R20.

216. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one azomethine-like hydrazone dye optionally comprising a reactive moiety R20.

217. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one azomethine-like imine dye optionally comprising a reactive moiety R20.

218. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one porphyrin dye optionally comprising a reactive moiety R20.

219. The method of statement 172, the hair coloring composition of any of statements 91-99, the kit of any of statements 187-190, the colored hair strand of any of statements 107-109, the composition for coloring a keratinous surface of any of statements 199-206, or the colored keratinous surface of any of statements 207-210, wherein said at least one direct dye comprises at least one coupling product.

220. Use of a Peri-arylene dye according to any of the statements 7-39 in combination with an oil phase (B) according to any of the statements 118-175, to dye human hair.

The following second set of statements further describes the present invention.

1. A multicomponent in situ linkable composition for coloring substrate material, comprising
    a first component comprising a first silicone polymer having first functional groups;
    a second component comprising a second silicone polymer having second functional groups;
    a third component comprising a base compound having third functional groups;
    an aromatic dye according to the present disclosure in one or more of the first and/or second and/or third components;
    one or more of the first, second and third components comprising a medium.

2. A multicomponent composition of statement 1 further comprising a fourth component comprising a catalyst or curing accelerator or curing inhibitor capable of promoting the covalent, ionic, electrostatic, entanglement or coordination in situ linkage among any two or more of the first, second and third functional groups.

3. A multicomponent composition of a linear and/or branched silicone polymer comprising non-reactive organosiloxane monomer units and reactive organosiloxane monomer units, the reactive organosiloxane monomer units having functional groups which are arranged to be complementary reactive pairs or a self-reactive functional group, the functional groups comprising isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, pentadienyl, azido, Si—OH, Si—OR, Si—O—N=CHR. Si—OAc, Si—CH=CH$_2$ or Si—H where R is C1-C6 alkyl.

4. A multicomponent composition of statement 3 comprising first and second components wherein each component comprises a silicone polymer having reactive organosiloxane monomers with functional groups that comprise one half of the complementary reactive pairs of functional groups or the first and second components comprise a silicone polymer having reactive organosiloxane monomers with a self-reactive functional group.

5. A multicomponent composition of statement 4 further comprising a third component comprising a base compound having amine, mercapto, sulfonate, carboxylate or carbamate groups.

6. a multicomponent composition of statement 5 wherein the base compound has amine groups.

7. A multicomponent composition of statement 4 wherein the first component comprises a first silicone polymer and the second component comprise a second silicone polymer;
    Wherein:
    the first silicone polymer and second silicone polymer respectively comprise reactive organosiloxane monomeric units of Formulas I and II, wherein X1 and Y1 are complementary reactive pairs of functional groups, X2 and Y2 are self-reactive functional groups, CU is a divalent organic connecting unit and $R^4$ is oxygen, a C1-C6 alkyl or phenyl:
    Formula I: reactive organosiloxane monomeric unit is —(O)$_{(4-d-c)/2}$SiR$^4_c$[CU-X1 or CU-X2]$_d$
    Formula II: reactive organosiloxane monomeric unit is —(O)$_{(4-d-c)/2}$SiR$^4_c$[CU-Y1 or CU-Y2]$_d$
    d is 1 to 3, c is 0 to 2 and d+c is between 1 and 3,
    X1 comprises isocyanato, thioisocyanato, carboxyl, linear, branched or cyclic epoxyalkyl, olefinoyloxy, malonic anhydrido, formyl, mercapto, vinyl, alkynyl;
    Y1 comprises hydroxyl, amino, mercapto, furanyl, cyclopentadienyl or azido;
    X2 and Y2 each comprise mercapto or isocyanate; or Si(OR)$_3$ or
    X2 and Y2 each comprise OH, oxime, acetoxy, hydrogen or OR$^{15}$ with R$^{15}$ being a C1-C6 alkyl group wherein X2 and Y2 are covalently bonded to CU or bonded directly to silicon and CU is absent.

8. A multicomponent composition of statement 7 wherein the first and second silicone polymers comprise a majority of non-reactive siloxane units (R)$_n$Si(O)$_{(4-n/2)}$ forming backbone and branch chains with R is a C1-C6 alkyl or phenyl and n is zero or an integer of 1 to 3 and the first silicone polymer comprises at least two reactive organosiloxane units of Formula I and the second silicone polymer comprises at least two reactive organosiloxane units of Formula II.

9. A multicomponent composition of any of statements 7 and 8 wherein the divalent organic connecting unit CU comprises a linear and/or branched and/or cyclic saturated C1-C48 aliphatic chain, a linear and/or branched and/or cyclic C1-C48 heteroaliphatic chain or an aromatic and/or heteroaromatic group of one, two or three separate or fused rings, each ring being a 5 or 6 member single ring or a bicyclic 10 member ring; wherein the aliphatic chain comprises a linear and/or branched and/or cyclic C1-C48 polymethylenyl chain and the heteroaliphatic chain comprises a linear and/or branched and/or cyclic C1-C48 polymethylenyl chain wherein portions of the chain are linked together by heteroatom linking groups selected from ether, sulfur, amino, carboxyl, amido, urethano, ureido, carbonyl, carbonato and/or imino.

10. A multicomponent composition of any of the preceding statements, wherein the first, second and third functional groups form reactive pairs of functional groups wherein the reactive pairs are isocyanate and hydroxyl, amine or mercapto or any combination of hydroxyl, amine and mercapto; carboxyl and hydroxyl, amine or mercapto or any combination of hydroxyl, amine and mercapto; alkylepoxy and hydroxyl, amine or mercapto or any combination of hydroxyl, amine and mercapto; olefinoyloxy and hydroxyl, amine, mercapto, furanyl or pentadienyl or any combination of hydroxyl, amine, mercapto, furanyl or pentadienyl; malonic anhydrido and hydroxyl, amine or mercapto or any combination of hydroxyl, amine and mercapto; formyl and amine or mercapto or any combination of amine and mercapto; vinyl and amine or mercapto or a combination of amine and mercapto; vinyl and furanyl or cyclopentadienyl or a combination of furanyl and cyclopentadieny or azido and alkynyl.

11. A multicomponent composition of any of the preceding statements wherein the functional groups are a self-reactive functional group and comprise any combination of Si—OH, Si—OR, Si—O—N=CHR. Si—OAc or comprise mercapto and mercapto, or comprise isocyanate and isocyanate.

12. A multicomponent composition of any of the preceding statements wherein the first and second functional groups are a reactive pair of vinyl and H and the reactive organosiloxane units have silicon as Si-vinyl and Si—H.

13. A multicomponent composition of any of the preceding statements wherein the reactive pairs are isocyanate and hydroxyl, amine or mercapto or any combination of hydroxyl, amine and mercapto; epoxy and hydroxyl, amine, or mercapto or any combination any two or more of hydroxyl, amine and mercapto; olefinoyloxy and hydroxyl, amine or mercapto or any combination of any two or more of hydroxyl and amine and mercapto; carboxyl and hydroxyl, amine or mercapto or any combination of any two or more of hydroxyl, amine and mercapto.

14. A multicomponent composition of any of the preceding statements wherein the reactive pairs are isocyanate and hydroxyl, amine or mercapto or any combination of hydroxyl, amine and mercapto; epoxy and hydroxyl, amine or mercapto or any combination of hydroxyl, amine and mercapto; carboxyl and hydroxyl or amine or a combination of hydroxyl and amine.

15. A multicomponent composition of any of the preceding statements wherein the reactive pair is isocyanate and hydroxyl, amine or mercapto or any combination of hydroxyl, amine and mercapto.

16. A multicomponent composition of any of the preceding statements wherein the reactive pair is any combination of silanol, acetoxy, oxime and alkoxy.

17. A multicomponent composition of any of the preceding statements wherein the reactive pair is epoxy and hydroxyl, amine or mercapto or any combination of hydroxyl, amine and mercapto.

18. A multicomponent composition of any of the preceding statements wherein the reactive pair is carboxyl and hydroxyl or amine or a combination of hydroxyl and amine and the fourth component is a carbodiimide.

19. A multicomponent composition of any of the preceding statements wherein the reactive pair is olefinoyloxy and hydroxyl, amine or mercapto or any combination of hydroxyl, amine and mercapto.

20. A multicomponent composition of preceding statements wherein the olefinoyloxy group is (meth)acryloxy or crotonyloxy.

21. A multicomponent composition of any of the preceding statements wherein the reactive pair is isocyanate and isocyanate.

22. A multicomponent composition of any of the preceding statements wherein the reactive pair is mercapto and mercapto.

23. A multicomponent combination of any of the preceding statements wherein the third component further comprises a dye that is the same as or different from the dye(s) of the first component and/or second component.

24. A multicomponent composition of any of the preceding statements wherein the concentration of each the first and second silicone polymers and base compound in the multicomponent composition ranges from about 0.25 wt % to about 20 wt %, preferably about 0.5 wt % to about 15 w5%, more preferably about 0.75 wt % to about 10 wt % relative to the total weight of the multicomponent composition and the combined concentration of first and second silicone polymers and the base compound is in a range of about 0.5 wt % to about 35 wt %.

25. A multicomponent composition of any of the preceding statements wherein the first functional groups of the first silicone polymer are isocyanate groups and the second functional groups of the second silicone polymer are hydroxyl groups and the base compound is polyethyleneimine.

26. A multicomponent composition of any of the preceding statements wherein the first, second and third functional groups are capable of producing at least one or more of urethane linkages, urea linkages and/or thiourethane linkages.

27. A multicomponent composition of any of the preceding statements wherein a third component is present and one of the first and second silicone polymer has an average molecular weight in a range of 1.5 KDa to 150 KDa and the other silicone polymer has an average molecular weight in a range of 150 Da to 150 KDa.

28. A multicomponent composition of any of the preceding statements wherein a third component is absent and the first and second silicone polymers independently have an average molecular weight in a range of 1.5 KDa to 150 KDa, and a polydispersity wherein the molecular weight fraction below 1 KDa of the first and second silicone polymers is less than 5 wt %, preferably less than 1 wt %, more preferably less than 0.1 wt % or virtually indetectable relative to the average molecular weights of the first and second silicone polymers.

29. The multicomponent composition of any of the preceding statements, wherein at least one dye aromatic dye selected from rylene dyes, nitro dyes, aryl and heteroaryl azo dyes, chinon/chinonimine/chinondiimine dyes, methin dyes, azomethine-like hydrazone and imine dyes, and porphyrin dyes, wherein the dye or an aromatic ring of the dye optionally is substituted with one or more hydrophobic moieties having a linear or non-linear structure, and wherein the dye optionally is substituted with a reactive moiety R20.

30. The multicomponent composition of any of the preceding statements, wherein the at least one dye is a peri-arylene dye comprising a perylene, terrylene or quarterrylene core or higher rylene core, wherein the dye optionally is substituted with one or more hydrophobic moieties having a non-linear structure and comprising at least 14 carbon atoms, and wherein the dye optionally is substituted with a reactive moiety R20.
31. The multicomponent composition of any of the preceding statements, wherein the at least one dye is a peri-arylene dye according to formula (1), (16), (17), (18) or (19).
32. A multicomponent composition of any of the preceding statements any combination thereof further comprising one or more of a plasticizer, a dispersant, wetting agent, anti-agglomeration agent, preservative, fragrance, an organic dye compound, a feel-modification agent, or a thickening agent; the dispersant, anti-agglomeration agent, the plasticizer and thickener capable of providing viscosity parameters to enable flow and hold of the composition on the keratin fibers.
33. A multicomponent composition of any of the preceding statements and any combination thereof, wherein the composition has a viscosity of from about 0.001 to about 2000 Pa s-1.
34. A multicomponent composition of any of the preceding statements wherein the composition has the physical character of a foam.
35. A multicomponent composition of any of the preceding composition statements further comprising a medium wherein the medium comprises at least one liquid selected from the group consisting of water, protic organic medium, protic organic non-aqueous medium, an aprotic, non-aqueous organic medium, a silicone medium and any compatible combination thereof.
36. A multicomponent composition of any of the preceding statements wherein the medium is water or a non-aqueous organic medium.
37. A multicomponent composition of any of the preceding statements wherein the medium is an aprotic non-aqueous organic or silicone medium that has a boiling point at standard pressure at a temperature of from ambient to about 250° C.
38. A multicomponent composition of any of the preceding statements wherein the medium is a nonpolar, aprotic organic medium selected from decane, isodecane, isododecane, a liquid silicone, cyclomethicone, glyme or decamethyl cyclopentasiloxane.
39. A multicomponent composition according to any of the preceding statements, further comprising an excipient selected from a dispersing agent, a preservative, a fragrance, a surfactant, a tactile-modification agent, and a thickening agent or a combination thereof.
40. A multicomponent composition of any of the preceding statements wherein the excipient includes at least a dispersing agent and the concentration of the dispersing agent is in an amount able to generate a positive or negative zeta potential in the composition.
41. A multicomponent composition of any of the preceding statements wherein the dispersing agent is a surfactant selected from silicone based surfactants, ethoxylated aliphatic alcohol, polyoxyethylene glycol, esters of fatty acids and glycerol, polyethylene glycol esters of fatty acids, anhydrosorbitol esters, polyethoxylated sorbitol esters, polysorbates, poloxamer, nonoxynol, fatty alcohol, tritan, tween, alkoxylated, hydrogenated castor oil.
43. A method of any of previous method statements wherein the high energy dispersing technique includes ultra-high speed, high energy mixing.
44. A composition according to the preceding composition statements including the third component wherein the first component is maintained in a first compartment, the second component is maintained in a second compartment and the third component is maintained in a third compartment.
45. A kit comprising the first, second and third compartments with first, second and third components according to claim 44.
46. A composition according to the preceding composition statements not including the third component wherein the first component is maintained in a first compartment, the second component is maintained in a second compartment.
47. A composition according to statement 44 comprising a preapplication formulation prepared by mixing together the first and second components.
48. A method for coloring substrate material comprising applying first to the substrate material the third component of statement 44 to form pretreated substrate material.
49. A method of statement 48 further comprising optionally or at least partially drying the third component on the substrate material.
50. A method of statement 48 or 49 further comprising combining the first and second components of statement 44 to form to form an in situ coloring mixture, applying the in situ coloring mixture to the pretreated substrate material and causing the in situ coloring mixture to form a colored coating on the substrate material.
51. A method of statement 54 further comprising drying the colored coating on the substrate material while mechanically separating the fibers in the substrate material.
52. A method for coloring substrate material comprising combining the first and second components of preceding composition statements to form a color formulation and applying the color formulation to the substrate material to form a coated substrate material and causing the coated substrate material to form a colored coating on the substrate material.
53. A colored coating for hair strands produced according to the method of statements 48-52.
54. A colored coating for hair strands according to statement 58 wherein the composition forms a solid, flexible elastic film on each individualized hair fibre.
55. A colored coating for hair strands according to statement 54 wherein the film has the microscopic appearance of a semicontinuous or continuous coating.
56. A colored coating for hair strands according to statements 54 which are resistant to color fading by repeated washings according to a standard wash procedure.
57. A colored coating for hair strands according to statement 56 wherein the repeated washings number 5 to 15.
58. A colored coating for hair strands according to statement 57 wherein the repeated washing number 15 or more.
59. A color removal composition for applying to color coated hair strands of statement 53 comprising applying one or more of surfactant, solvent, acid, base, polymer, polyelectrolyte, salt sources of fluorine, ionic liquids to remove the color coating.
60. A color removal composition of statement 59 comprising a source of fluorine.
61. A color removal composition comprising a medium with a Hansen solubility parameter according to the ranges $12<\delta d<22$ and $0<\delta p<7$ and $0<\delta h<9$.

62. A method of removing the colored coating of statement 53 comprising combining the colored hair strands with an aqueous-organic mixture of a fluorine source, agitating the mixture on the hair and washing with a basic aqueous solution of detergent with optional brushing.
63. A method of removing the colored coating of the preceding statements by combining the removal composition with either heat, electromagnetism, mechanical energy, or cooling.
64. A method of selecting the removal composition to chemically break down covalent bonds in the in situ linked multicomponent composition.
65. A multicomponent composition of a linear and/or branched silicone polymer and a linear and/or branched organic polymer comprising a silicone polymer of non-reactive organosiloxane monomer units and reactive organosiloxane monomer units and an organic polymer having reactive organic monomeric units, the reactive organosiloxane monomer units and the reactive organic monomeric units having functional groups which are arranged to be complementary reactive pairs or a self-reactive functional group, the functional groups comprising isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, pentadienyl, azido, Si—OH, Si—OR, Si—O—N=CHR. Si—OAc, Si—CH=CH$_2$ or Si—H where R is C1-C6 alkyl; the complementary reactive pairs being arranged so that a functional group of one half of the complementary reactive pair is present with the reactive organosiloxane monomeric unit and a functional group of the other half of the complementary reactive pair is present with the reactive organic monomeric unit; or the reactive organic monomeric unit and the reactive organic monomeric unit both have the same self-reactive functional group.

The following third set of statements further describes the present invention.

1. A multicomponent in situ linkable composition for coloring treated material, comprising:
    a first component comprising an organic polymer having pendant or terminal or pendant and terminal first functional groups;
    a second component comprising an in situ linking material having second functional groups;
    a third component comprising a base compound having third functional groups;
    an aromatic dye according to the present disclosure in one or more or all of the first, second and third components;
    the first second and third functional groups being compatible reaction pairs and being capable of covalent, ionic, entanglement, electrostatic or coordination in situ linkage or a combination thereof; among each other;
        the first, second and third components being separate.
2. A multicomponent composition of statement 1 further comprising
    a fourth component comprising a catalyst agent, an accelerator agent or an inorganic complexation agent, the agent being capable of promoting the among the first, second and third functional groups or any combination thereof, or the inorganic complexation agent capable of forming coordination linkages for the first component.
3. A multicomponent composition of statements 1 and 2 further comprising a medium in any one or more of the first, second, third and fourth components
4. A multicomponent composition according to any of statements 1 or 131-134 wherein
    the organic polymer comprises a polyolefin, a polyester, a hydroxylated polyester, an acrylate functionalized polyester, a polycarbonate, a polyallyl alcohol, a ketone resin, a polyether, a polyimine, a polyurethane, a polyurea, a polyglycol, a polyamide, a polypeptide, a carbohydrate compound, a cellulose, a cellulose derivative, a cellulose ester, a hydroxylated cellulose, a carboxyl cellulose, a hydroxyl cellulose ester, a hydroxy cellulose carboxylic acid, an alginate, a gum, a polysaccharide, an amino acid polymer, a gelatin, an oligopeptide, a polypeptide, a protein, a carbohydrate-amino acid such as a glycosylated peptide, a carbohydrate-purine/pyrimidine base, a polynucleoside, a biopolymer, a (meth) acrylic copolymer, a crotonic copolymer, a polyurethane-polyglycol copolymer, a polycarbonate diol, a styrene-allyl alcohol copolymer, a polyol, a natural gum, polyvinyl acetate, polyvinylpyrrolidone, polynipam, a polymer based on one or more olefin monomers, a polymer based on ester units of diacids/diol monomers, a polymer based on ester units of hydroxy acid monomers, a polymer based on ether monomeric units, a polymer based on thioether monomeric units, a polymer based on polyol monomeric units, a polymer based on alkylene oxide monomeric units, a polymer based on of alkylene imine monomeric units, a polymer based on urethane monomeric units, a polymer based on urea monomeric units, a polymer based on amide units of diacid/diamine monomers, a polymer based on amide units of amino acid monomeric units or a polymer having repeating residues based on carbon or carbon in combination with other atoms comprising oxygen and/or nitrogen and/or sulfur, and any combination thereof;
    the first functional group comprises a hydroxyl group, a carboxylic acid group, an amine group, a mercapto group, a sulfonic acid group, a sulfinic acid group, a vinyl group, a vinyloxycarbonyl group, an olefinoyloxy group, an alkynyl group, or a combination thereof,
    the first functional group is covalently linked to the organic polymer through a carbon connection unit comprising a linear, branched or cyclic C1-C24 alkyl or alkoxy unit, a C2-C24 alkanoyl unit, a C6-C24 aromatic unit, a C5-C24 heteroaromatic unit having one or two heteroatoms selected from nitrogen, oxygen and sulfur, a $(C_z—O—C_z)_n$ polyether unit wherein z is an integer of 1 to 6 and n is an integer of 2 to 6, a $(C_y—NH—C_y)_m$ polyimino unit wherein y is an integer of 1 to 6 and m is an integer of 2 to 6; or
    the first functional group is covalently linked to the organic polymer through a silicon connection unit comprising a Si1-Si48 organosiloxane unit having methyl as the organo group with silicon of the connection unit bonded to the first functional group through an alkylenyl group of one to three carbons or through an oxyalkylenyl group of one to three carbons;

or the first functional group is an alkylenylalkoxysilane monomeric residue of the formula $—(CH_2)_n—O_j—Si(R^1)_a(R^2)_{3-a}$,
wherein n is an integer of 0 to 6, j is zero of 1, $R^1$ is alkoxy of 1 to 6 carbons or OH, an —OAc group, a —O—N=CHR$^1$ group or a —CH=CH$_2$ group, $R^2$ is alkyl of 1 to 3 carbons and a is an integer 1, 2 or 3;
wherein the selected the first functional groups are compatible with each other if not the same;
the in situ linking material comprises an organic core comprising a saturated aliphatic compound, aromatic compound, polymeric compound designated as Cpd or a silicone core comprising a siloxane, a polysiloxane, a polyorganosiloxane or a polysilicone designated as Sicpd,
wherein the organic core or the silicone core has at least two pendant or terminal or pendant and terminal second functional groups, and
wherein the saturated aliphatic compound comprises a linear or branched alkyl group of 2 to 24 carbons or is a cyclic alkyl group of 5 to 24 carbons; the aromatic compound comprises a phenyl, naphthyl, diphenylmethyl, pyridyl, quinolinyl, quinazolinyl or anthracenyl group; the polymeric compound Cpd comprises a poly (meth)acrylate with methyl or ethyl ester groups except for the second functional groups, polycrotonate with methyl or ethyl ester groups except for the second functional groups, a polyether, a polyol, a polyurethane, a polyurea, a polyester of a diacid and a diol or of a hydroxy acid, a polymer of one or more monomers of C1-C6 alkyl (meth)acrylate, styrene and a C6-C12 olefin; the polymeric compound Cpd has a weight average molecular weight of from about 0.2 kDa to about 10 kDa;
the silicone core, Sicpd comprises a silane, a di, tri or tetrasilane, an oligosilane, a siloxane, a di, tri or tetrasiloxane, a polysiloxane, a poly organosiloxane, a polyorganosilicone wherein organo groups, if any, are C1-C3 alkyl groups, the Sicpd compound having a weight average molecular weight of from about 0.2 kDa to about 10 kDa; and
wherein each second functional group independently has the structure of Formula I

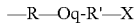 Formula I wherein (i) the designator q is zero or one;
(ii) R is a C6-C10 aromatic group, a C1-C24 alkyl or a C1-C24 oxyalkyl residue or a dimethylsiloxanyl chain of 3 to 9-O—Si(Me)$_2$- units and the valence bond of R is attached to directly to the organic core or attached through an ether oxygen to the organic core, or
(iii) R is a C1-C24 alkylenyl residue, a C1-C24 oxyalkylenyl residue or a C1-C24 carbonylalkenyl residue and the valence bond of R is attached directly or through an ether oxygen —O— to the silicone core, Sicpd;
and,
(iv) R' is a linear or branched alkyl or alkanoxyalkyl or alkanaminoalkyl group of the Formula III or is a bond when all designators m, n, p, r, z and s are zero;

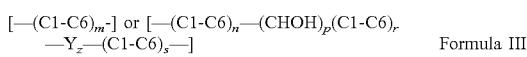 Formula III wherein the C1-C6 group is a linear or branched alkyl group of 1 to 6 carbons and the designators m, n, r and s associated with each C1-C6 indicates the total number of carbons possible for the group, the maximum being 24; m is zero or an integer of 1 to 4, n is zero or an integer of 1 to 4, p is zero or one, r is zero or an integer of 1 to 4, z is zero or 1, s is zero or an integer of 1 to 4, Y is O or N;
X is isocyanato, thioisocyanato, linear, branched or cyclic epoxyalkyl, olefinoyloxy, malonic anhydrido, formyl, amino, hydroxyl, mercapto, furanyl, cyclopentadienyl or azido;
or
X of Formula I is a mono, di, tri or tetra dimethyl siloxane group to which is terminally bonded —Si(R$^1$)$_a$(R$^2$)$_{3-a}$ wherein R$^1$ is alkoxy of 1 to 6 carbons or OH, an —OAc group, a —O—N=CHR$^1$ group, or hydrogen, R$^2$ is alkyl of 1 to 3 carbons and a is an integer 1, 2 or 3.

5. A multicomponent composition comprising first, second and third components:
the first component comprises an organic polymer comprising repeating units of a hydrophobic monomer or a hydrophilic monomer or a combination thereof, preferably a combination of the hydrophilic monomer and the hydrophobic monomer;
the hydrophobic monomer is selected from one or more of an olefinic carboxylate ester monomer or one or more of a non-polar olefinic monomer or any combination thereof;
the olefinic carboxylate ester comprises an ester of an olefinic carboxylic acid and at least one saturated linear or branched C1 to C24 primary or secondary alcohol or a C4 to C24 cyclic alcohol;
the non-polar olefin monomer has the formula

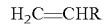

wherein R is selected from hydrogen, linear or branched alkyl of one to twenty four carbons, unsubstituted phenyl or phenyl substituted by one or more linear or branched alkyl of 1 to twenty four carbons, a vinyl group or a polyester polyol group having terminal and/or pendant hydroxyl groups, or R is selected from —CR$^2$=CHR$^1$ wherein R$^1$ is hydrogen, methyl, ethyl or phenyl and R$^2$ is hydrogen or methyl;
the hydrophilic olefinic monomer is selected from a hydroxyl ester of an olefinic carboxylic acid and a linear or branched alkyl diol of 2 to 24 carbons or a cyclic alkyl diol of 5 to 24 carbons; or an aminoalkyl ester of an olefinic carboxylic acid and a linear or branched aminoalkyl alcohol of 2 to 24 carbon or a cyclic aminoalkyl alcohol of 5 to 24 carbons; or a thioalkyl ester of an olefinic carboxylic acid, and a linear or branched thioalkyl alcohol of 2 to 24 carbons or a cyclic thioalkyl alcohol of 5 to 24 carbons, an olefinic acid, vinyl alcohol, or a polar styrene compound selected from hydroxy styrene, carboxy styrene, carboxamido styrene or styrene sulfonate; or is any combination of two or more of the hydroxyl ester, the aminoalkyl ester, the thioalkylester, the olefinic acid or the polar styrene compound;
the olefinic carboxylic acid is an alkenoic acid of 3 to 24 carbons or alkendioic acid of 4 to 24 carbons or partially hydrolyzed polyacrylonitile or any combination thereof;
the organic polymer comprises at least two pendant or terminal or pendant and terminal first functional groups which are selected from a hydroxyl group, a carboxylic acid group, an amine group, a mercapto group, a sulfonic acid group, a sulfinic acid group, a vinyl group, an olefinoxyoyl group, alkynyl group or a combination thereof;

or the first functional group is the residue of a polymerized alkenylalkylalkoxysilane monomer of the formula

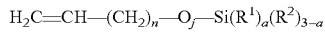

wherein n is an integer of 0 to 6, j is zero of 1, $R^1$ is alkoxy of 1 to 3 carbons, OH, an —OAc group, a —O—N=$CHR^1$ group or a —CH=$CH_2$ group, $R^2$ is alkyl of 1 to 3 carbons and a is an integer 1, 2 or 3; wherein the selected first functional groups are compatible with each other if not the same;

the second component comprises an in situ linking material comprising an organic core comprising a saturated aliphatic compound, aromatic compound, polymeric compound designated as Cpd or a silicone core comprising a siloxane, a polysiloxane, a polyorganosiloxane or a polysilicone designated as Sicpd, wherein the organic core or the silicone core has at least two pendant or terminal or pendant and terminal second functional groups, and wherein the saturated aliphatic compound comprises a linear or branched alkyl group of 2 to 24 carbons or is a cyclic alkyl group of 5 to 24 carbons; the aromatic compound comprises a phenyl, naphthyl, diphenylmethyl, pyridyl, quinolinyl, quinazolinyl or anthracenyl group; the polymeric compound Cpd comprises a poly(meth)acrylate with methyl or ethyl ester groups except for the second functional groups, polycrotonate with methyl or ethyl ester groups except for the second functional groups, a polyether, a polyol, a polyurethane, a polyurea, a polyester of a diacid and a diol or of a hydroxy acid, a polymer of one or more monomers of C1-C6 alkyl (meth)acrylate, styrene and a C6-C12 olefin; the polymeric compound Cpd has a weight average molecular weight of from about 0.2 kDa to about 10 kDa;

the silicone core, Sicpd comprises a silane, a di, tri or tetrasilane, an oligosilane, a siloxane, a di, tri or tetrasiloxane, a polysiloxane, a poly organosiloxane, a polyorganosilicone wherein organo groups, if any, are C1-C3 alkyl groups, the Sicpd compound having a weight average molecular weight of from about 0.2 kDa to about 10 kDa; and wherein each second functional group independently has the structure of Formula I —R—Oq-R'—X        Formula I wherein (i) the designator q is zero or one;
(ii) R is a C6-C10 aromatic group, a C1-C24 alkyl or a C1-C24 oxyalkyl residue or a dimethylsiloxanyl chain of 3 to 9-O—Si$(Me)_2$- units and the valence bond of R is attached to directly to the organic core or attached through an ether oxygen to the organic core, or
(iii) R is a C1-C24 alkylenyl residue, a C1-C24 oxyalkylenyl residue or a C1-C24 carbonylalkenyl residue and the valence bond of R is attached directly or through an ether oxygen —O— to the silicone core, Sicpd;

and, (iv) R' is a linear or branched alkyl or alkanoxyalkyl or alkanaminoalkyl group of the Formula III or is a bond when all designators m, n, p, r, z and s are zero;

[—(C1-C6)$_m$-] or [—(C1-C6)$_n$-(CHOH)$_p$(C1-C6)$_r$-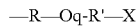(C1-C6)$_s$—]      Formula III wherein the C1-C6 group is a linear or branched alkyl group of 1 to 6 carbons and the designators m, n, r and s associated with each C1-C6 indicates the total number of carbons possible for the group, the maximum being 24; m is zero or an integer of 1 to 4, n is zero or an integer of 1 to 4, p is zero or one, r is zero or an integer of 1 to 4, z is zero or 1, s is zero or an integer of 1 to 4, Y is O or N;

X is isocyanato, thioisocyanato, linear, branched or cyclic epoxy, olefinoyloxy, malonic anhydrido, formyl, amino, hydroxyl, mercapto, furanyl, cyclopentadienyl or azido;

or

X of Formula I is a mono, di, tri or tetra dimethyl siloxane group to which is terminally bonded —Si$(R^1)_a(R^2)_{3-a}$ wherein $R^1$ is alkoxy of 1 to 6 carbons or OH, an —OAc group, a —O—N=$CHR^1$ group, or hydrogen, $R^2$ is alkyl of 1 to 3 carbons and a is an integer 1, 2 or 3;

the third component comprises a base compound comprising an amine compound or a mercapto compound having a weight average molecular weight of about 150 Da to about 1 MDa and the amine compound is selected from aminosilane, aminosiloxane, aminosilicone, aminopolysaccharide or a linear or branched polymer comprising linear polyethyleneimine, branched polyethylene imine, a copolymer of aminoethyl (meth)acrylate and ethyl (meth)acrylate, polyallylamine hydrochloride, polydiallyldimethyl ammonium chloride, polyvinylamine, (vinylamine-styrene) copolymer, poly(omega-aminoalkyl(meth)acrylate), polyvinylpyrrolidone poly (2-oxazoline) and random or block copolymers thereof and mixtures thereof.

6. A multicomponent composition of any of the preceding statements wherein the organic polymer comprises a film forming polymer chosen from polymers and copolymers based on polyurethane, polyacrylate, silicone resins, polyurea/polyurethane silicones and copolymers based on silicone resin and on dimethiconol.

7. A multicomponent composition of claim 6 wherein the polymers and copolymers include or are adapted to include the first functional group.

8. A multicomponent composition of any of the preceding statements wherein the first and second functional groups are complementary reactive pairs.

9. A multicomponent composition of statement 8 wherein the reactive pairs are isocyanate/thioisocyanate and hydroxyl, amine or mercapto or any combination of hydroxyl, amine and mercapto; carboxyl and hydroxyl, amine or mercapto or any combination of hydroxyl, amine and mercapto; epoxy and hydroxyl, amine or mercapto or any combination of hydroxyl, amine and mercapto; cyclohexylepoxy and hydroxyl, amine or mercapto or any combination of hydroxyl, amine and mercapto; (meth)acryloxy and hydroxyl, amine or mercapto or any combination of hydroxyl, amine and mercapto; melonic anhydride and hydroxyl, amine or mercapto or any combination of hydroxyl, amine and mercapto; formyl and amine or mercapto or any combination of amine and mercapto; azido and alkynyl; vinyl and mercapto; mercapto and mercapto; any combination of —Si$(R^1)_a(R^2)_{3-a}$ wherein $R^1$ is alkoxy of 1 to 6 carbons or OH, an —OAc group, or a —O—N=$CHR^1$ group, $R^2$ is alkyl of 1 to 3 carbons and a is an integer 1, 2 or 3; or SiH$R^2$ and —Si$R^2$—CH=$CH_2$.

10. A multicomponent composition of statement 9 wherein the reactive pairs are isocyanate and hydroxyl, amine or mercapto or any combination of hydroxyl, amine and mercapto; epoxy and hydroxyl or amine, or mercapto or a combination any two or more of hydroxyl and amine and mercapto; (meth)acryloxy and hydroxyl, amine or mercapto or a combination of any two or more of hydroxyl and amine and mercapto; mercapto and mercapto; or Si—OH and Si—OR or Si—OH and Si—OH or Si—OR and Si—OR wherein R is methyl or ethyl.

11. A multicomponent composition of statement 9 wherein the reactive pairs are isocyanate and hydroxyl, amine or mercapto or any combination of hydroxyl, amine and mercapto; epoxy and hydroxyl, amine or mercapto or any combination of hydroxyl, amine and mercapto; or Si—OH and Si—OR or Si—OH and Si—OH or Si—OR and Si—OR wherein R is methyl or ethyl.

12. A multicomponent composition of statement 9 wherein the reactive pair is isocyanate and hydroxyl, amine or mercapto or any combination of hydroxyl, amine and mercapto.

13. A multicomponent composition of statement 9 wherein the reactive pair is or Si—OH and Si—OR or Si—OH and Si—OH or Si—OR and Si—OR.

14. A multicomponent composition of statement 9 wherein the reactive pair is epoxy and hydroxyl, amine or mercapto or any combination of hydroxyl, amine and mercapto.

15. A multicomponent composition of statement 9 wherein the reactive pair is carboxyl and hydroxyl or amine or a combination of hydroxyl and amine and the agent is a carbodiimide.

16 A multicomponent composition of statement 8 wherein the reactive pair is (meth)acrylyloxy or crotonyloxy and hydroxyl, amine or mercapto or any combination of hydroxyl, amine and mercapto.

17. A multicomponent composition of any of the preceding statements wherein the agent of the fourth component is a catalyst or accelerator for the first and second functional group reactive pairs.

18. A composition according to any of the preceding statements wherein
the organic polymer includes alkylalkoxysilane monomeric residues of the formula —$(CH_2)_n$—$O_j$—Si$(R^1)_a(R^2)_{3-a}$
wherein n is an integer of 0 to 6, j is zero of 1, $R^1$ is alkoxy of 1 to 3 carbons or OH, $R^2$ is alkyl of 1 to 3 carbons and a is an integer 1, 2 or 3;
the in situ linking material is present or absent and when present is the polymer Cpd with at least two second functional groups of Formula I wherein R is the dimethylsilanoxy chain, the designator q is zero, R' is a bond and X is a mono, di, tri or tetra dimethyl siloxane group to which is terminally bonded a silanol group (Si—OH) or an alkoxysilane (Si—OR) with 1 to 3 carbons in the alkoxy group.

19. A multicomponent composition of statement 18 wherein the in situ linking material is present.

20. A multicomponent composition of statement 18 wherein the in situ linking material is absent, the fourth component is present, is water and the organic polymer is capable of in situ self-linking.

21. A multicomponent composition of any of the preceding statements wherein a medium is compatible with any of the first, second and third functional groups.

22. A composition according to any of the preceding statements wherein the olefinic carboxylic acid is selected from one or more of (meth)acrylic acid, crotonic acid, pentenoic acid, hexenoic acid, maleic acid, fumaric acid, glutaconic acid, itaconic acid, citraconic acid, mesaconic acid or any combination thereof.

23. A composition according to preceding statements wherein the ester alcohol is a C1-C6 linear, branched or cyclic primary or secondary alcohol, a ester amino alcohol is amino ethanol, amino propanol or aminobutanol, the ester diol is ethylene diol, propylene diol, butylene diol, pentylene diol or cyclohexane diol; and the ester mercapto alcohol is mercaptoethanol, mercaptopropanol or mercapto butanol.

24. A composition according to any of the preceding statements wherein the olefinic carboxylic acid is (meth)acrylic acid, crotonic acid, maleic acid, fumaric acid, itaconic acid or a combination thereof.

25. A composition according to any of the preceding statements wherein the ester alcohol is methanol, ethanol, ethylhexyl alcohol, butyl alcohol or propyl alcohol; the ester amino alcohol is amino ethanol; the ester diol is ethylene diol or propylene diol and the ester mercaptoalcohol is mercaptoethanol.

26. A composition according to any of the preceding statements wherein the organic polymer is essentially free to completely free of the non-polar olefinic monomer.

27. A composition according to any of preceding statements 1-25 wherein the non-polar olefinic monomer is present.

28. A composition of any of the preceding composition statements wherein
the weight percentage of hydrophobic monomer is about 99.9% to about 50%, and the weight percentage of the hydrophilic olefinic monomer is about 0.1% to about 50%, the weight percentages being relative to the total weight of the organic polymer, 29. A composition of any of the preceding statements including the third component wherein the base compound of the third component has a weight average molecular weight of about 150 Da to about 1 MDa and the base compound is selected from aminosilane, aminosiloxane, aminosilicone or a linear or branched polymer comprising linear polyethyleneimine, branched polyethylene imine, aminopolysaccharide, a copolymer of aminoethyl (meth)acrylate and ethyl (meth)acrylate, polyallylamine hydrochloride, polydiallyldimethyl ammonium chloride, polyvinylamine, (vinylamine-styrene) copolymer, poly(omega-aminoalkyl(meth)acrylate), polyvinylpyrrolidone poly (2-oxazoline) and random or block copolymers thereof and mixtures thereof.

30. A composition according to any of the preceding statements wherein the in situ linking material is a linear, branched or cyclic alkylenyl or aromatic diisocyanate or triisocyanate having an alkyleny chain of from 4 to 24 carbons, and the organic polymer is a copolymer of hydrophobic monomer of alkyl (meth) acrylate and optional styrene at a weight percent of about 50% to about 97 wt % and hydrophilic monomer of hydroxyalkyl (meth)acrylate and (meth)acrylic acid at a weight percent of about 3 wt % to about 50 wt % wherein all weight percentages are relative to the total weight of the organic polymer.

31. A multicomponent composition of any of the preceding statements wherein the in situ linking material is toluene diisocyanate, diphenylmethane diisocyanate, hexamethylene diisocyanate, bis isocyanatocyclohexyl methane, isophorone diisocyanate, trimethylolpropane tri-hexamethylene diisocyanate adduct, biuret triisocyanate, isocyanurate triisocyanate, uretdione hexamethylene diisocyanate, trimers of hexamethylene diisocyanate, or a blocked polyisocyanate of hexamethylene diisocyanate and a phenol, E-caprolactam, butanone oxime or dimethyl pyrazole blocker.

32. A composition according to any of statements 1-29 wherein the in situ linking material contains amine groups as the second functional group, the organic polymer is a copolymer of alkyl (meth)acrylate, hydroxyalkyl (meth)acrylate, optional styrene, from 2 to 10 mole percent (meth)acrylic acid, the base compound is polyethyleneimine and the fourth component is an aliphatic carbodiimide.

33. A composition of any of the preceding statements wherein the substantial majority of the organic polymer molecules has at least two hydroxyl groups per molecule when the organic polymer contains hydroxyalkyl ester monomeric units.

34. A composition of any of the preceding statements wherein the substantial majority of the organic polymer molecules has at least about three hydroxyl groups per molecule.

35. A composition of any of the preceding statements wherein the substantial majority of the organic polymer molecules has at least about four hydroxyl groups per molecule.

36. A composition of any of the preceding statements wherein the substantial majority of the organic polymer molecules has at least two amine groups per molecule when the organic polymer contains aminoalkyl ester monomeric units.

37. A composition of any of the preceding statements wherein the substantial majority of the organic polymer molecules has at least about three amine groups per molecule.

38. A composition of any of the preceding statements wherein the substantial majority of the organic polymer molecules has at least about four amine groups per molecule.

39. A composition of any of the preceding statements wherein the substantial majority of the organic polymer molecules has at least two mercapto groups per molecule when the organic polymer contains mercaptoester monomeric units.

40. A composition of the preceding statements wherein the substantial majority of the organic polymer molecules has at least about three mercapto groups per molecule.

41. A composition of the preceding statements wherein the substantial majority of the organic polymer molecules has at least about four mercapto groups per molecule.

42. A composition of any of preceding statements wherein the substantial majority of the organic polymer molecules has at least two carboxyl groups per molecule when the organic polymer has olefinic acid monomeric units.

43. A composition of preceding statements wherein the substantial majority of the organic polymer molecules has at least about three carboxyl groups.

44. A composition of preceding statements wherein the substantial majority of the organic polymer molecules has at least about four carboxyl groups per molecule.

45. A multicomponent composition according to any of the preceding statements wherein the organic polymer has at least two or three first functional groups per molecule, the in situ linking material has at least two or three second functional groups per molecule and the base compound has at least two or three third functional groups per molecule.

46. A multicomponent composition of any of the preceding statements wherein the organic polymer has at least three or four first functional groups per molecule, the in situ linking material has at least three or four second functional groups per molecule and the base compound has at least three or four third functional groups per molecule.

47. A multicomponent composition of any of the preceding statements wherein
the organic polymer in water has a pH of from about 3 to about 12;
the organic polymer has an acid value of from about 1 to about 500, preferably about 2 to 250, more preferably about 7 to 90; the copolymer of the organic polymer has a glass transition temperature of from about −125° C. to about 90° C. and the organic polymer has a weight average molecular weight in the range of about 2 KDa to about 2 MDa, the organic polymer has a polydispersity in a range from 2 to 10.

48. A composition according to any of the preceding statements wherein the organic polymer comprises a random distribution of monomer residues or a block arrangement of monomeric residues, each block comprising monomeric residues of similar hydrophilic or hydrophobic properties.

49. A composition according to statement 48 comprising incorporation of the organic polymer as blocks of a block polymer, which block polymer further comprises blocks of an organosilicone polymer.

50. A composition according to any of the preceding statements wherein the organic polymer comprises the hydrophilic monomer as (meth)acrylic acid at about 0.3% to about 10% by weight, and hydroxyethyl or hydroxypropyl (meth)acrylate at about 1% to about 20% by weight, the hydrophobic monomer as methyl or ethyl (meth)acrylate at about 10% to about 80% by weight, and the olefin monomer at zero percent or detectable amount up to about 80% by weight, preferred about 35% to about 45%, more preferably about 38% to about 43%, most preferably about 40% by weight wherein all weights are relative to the total weight of the polymer.

51. A composition according to any of the preceding statements wherein the organic polymer comprises the hydrophilic monomer as crotonic acid at about 1% to about 10% by weight, hydroxyethyl crotonate or hydroxypropyl crotonate at about 1% to about 20% by weight; the hydrophobic monomer as methyl or ethyl crotonate % to about 80% by weight, and the olefin monomer as styrene at about zero percent or detectable amount up to about 80% by weight. preferred about 35% to about 45%, more preferably about 38% to about 43%, most preferably about 40% by weight wherein all weights are relative to the total weight of the polymer.

52. A composition according to any of the preceding statements wherein the organic polymer comprises monomeric units of alkyl (meth)acrylate or alkyl crotonate or a combination thereof with the alkyl group being 1 to 3 carbons; hydroxyalkyl (meth)acrylate or hydroxyalkyl crotonate or a combination thereof with the alkyl group being 1 to 3 carbons; (meth)acrylic acid or crotonic acid or any combination thereof; and optional styrene; the in situ linking material comprises toluene diisocyanate, diphenylmethane diisocyanate, hexamethylene diisocyanate, bis isocyanatocyclohexyl methane, isophorone diisocyanate, trimethylolpropane tri-hexamethylene diisocyanate adduct, biuret triisocyanate, isocyanurate triisocyanate, uretdione hexamethylene diisocyanate, trimers of hexamethylene diisocyanate, or a blocked polyisocyanate of hexamethylene diisocyanate and a phenol, E-caprolactam, butanone oxime or dimethyl pyrazole blocker, an oligomer of ethylhexyl diisocyanate and 1,6 hexane diol with terminal isocyanate groups, oligomeric urethane triisocyanate or any combination thereof; or any combination thereof; and the base compound comprises polyethylene imine.

53. A composition according to any of the preceding statements wherein the organic polymer comprises monomeric units of alkyl (meth)acrylate, hydroxyalkyl (meth)acrylate and (meth)acrylic acid; the hydroxyl number of the polymer is from 0.1 to 5 wt % and the acid number of the polymer is from 7 to 90.

54. A composition according to any of the preceding statements wherein the organic polymer comprises a copolymer of methyl or ethyl (meth)acrylate, hydroxyethyl or hydroxypropyl (meth)acrylate and (meth)acrylic acid.

55. A multicomponent composition of any of the preceding statements wherein:
    the organic polymer comprises C1-C12 alkyl (meth)acrylate, C2-C12 hydroxyalkyl (meth)acrylate or C2-C12 aminoalkyl (meth)acrylate, (meth)acrylic acid and optional styrene;
    the in situ material comprises a polymeric compound Cpd containing two or more epoxides, a polymeric compound Cpd containing two or more acryloxyvinyl groups, a polymeric compound Cpd containing two or more amino groups or a polymeric compound Cpd containing two or more isocyanate groups; and,
    the third component comprises polyethyleneimine or aminosilane or mercaptosilane.

56. A multicomponent composition of any of the preceding statements wherein the polymeric compound Cpd is a polymeric isocyanate comprising bis (4-isocyanatocyclohexyl) methane or isophorone diisocyanate or hexamethylenediisocyanate or a di or tri-isocyanato polymeric urethane of (hexamethylene diol-hexamethylene disocyanate/triisocyanate) or toluene diisocyanate or napthalene diisocyanate or triisocyanate or bis (4-isocyanaatophenyl) methane.

57. A multicomponent composition of any of the preceding statements wherein the in situ material is a polymeric acryloxyvinyl polymer of alkyl (meth)acrylate and the hydroxyvinyl ester of (meth)acrylate with the (meth)acrylate group being a pendant group.

58. A multicomponent composition of any of the preceding statements wherein the in situ material is a copolymer of alkyl (meth) acrylate and aminoalkyl (meth) acrylate, the alkyl group having from 1 to 6 carbons and the second compound is a carbodiimide.

59. A multicomponent composition of any of the preceding statements wherein:
    the organic polymer is a copolymer of ethyl (meth)acrylate, C2-C6 hydroxyalkyl (meth)acrylate and about 0.1 to about 5 wt % of (meth)acrylic acid relative to the weight of the organic polymer;
    the in situ material comprises toluene diisocyanate, diphenylmethane diisocyanate, hexamethylene diisocyanate, bis isocyanatocyclohexyl methane, isophorone diisocyanate, trimethylolpropane tri-hexamethylene diisocyanate adduct, biuret triisocyanate, isocyanurate triisocyanate, uretdione hexamethylene diisocyanate, trimers of hexamethylene diisocyanate, or a blocked polyisocyanate of hexamethylene diisocyanate and a phenol, E-caprolactam, butanone oxime or dimethyl pyrazole blocker or a polymeric and/or oligomeric urethano/urea backbone with multiple pendant or terminal or pendant and terminal isocyanate groups; the base compound comprises polyethyleneimine;
    the agent is a catalyst for the conversion of isocyanate to urethane and/or urea groups.

60. A composition according to any of the preceding statements wherein the olefinic monomer comprises styrene, butadiene, phenyl butadiene, isoprene, 4-vinylbenzenecarboxamide, 4-vinyl benzoic acid, ethyl 4-vinyl benzoate, vinyl phenol, 4-vinyl-1-hydroxymethyl benzene, butene, pentene, hexene, divinyl benzene or any combination thereof.

61. A multicomponent composition according to any of the preceding statements comprising:
    an organic polymer comprising repeating units of a hydrophobic monomer and a hydrophilic monomer, wherein;
    the hydrophobic monomer is a selected from styrene and one or more of butadiene and isoprene;
    the hydrophilic olefinic monomer is selected from a hydroxyl ester of an olefinic carboxylic acid and an alkyl diol of 2 to 24 carbons, a C3-C5 olefinic carboxylic acid or a C4-C6 olefinic dicarboxylic acid or a combination thereof.

62. A multicomponent composition any of the preceding statements wherein the fourth component is present and comprises an inorganic complexation agent.

63. A multicomponent composition of any of the preceding statements wherein the fourth component comprises an inorganic complexation agent which is capable of forming coordination complexes with more than one organic polymer.

64. A multicomponent composition of any of the preceding statements further comprising the third component, the base compound being an amino polymer.

65. A multicomponent composition of any of the preceding statements wherein the aminopolymer is polyethyleneimine.

66. A multicomponent composition of preceding statements wherein the organic polymer comprises repeating units of the hydrophobic monomer and the hydrophilic monomer with up to 10 wt % of the hydrophilic monomer relative to the total weight of the organic polymer.

67. A multicomponent composition of any of the preceding statements wherein the in situ material is absent and the organic polymer contains residual unsaturated and in situ links with itself in the presence of a free radical initiator.

68. A multicomponent composition of any of the preceding statements wherein
the organic polymer comprises a copolymer of styrene, butadiene, and itaconic acid;
the second component comprises the copolymer of the first component;
the third component comprises polyethyleneimine;
a fourth component comprising a free radical initiator or the inorganic coordination cross-linker agent or mercapto cross-linker optionally combined with the polymer; the first component and the third component being separate or combined. and the fourth component being separate from the first, second and third components.

69. A multicomponent composition of any of the preceding statements wherein an aromatic dye according to the present disclosure is incorporated in any one of the first, second and third components, in any two of the components or in all three of the components.

70. A multicomponent composition comprising:
a first component of an organic polymer;
a second component comprising an in situ linking material; the first and second components being separate,
an aromatic dye according to the present disclosure in the first or second component or in both of the first and second components; wherein,
the organic polymer comprises a copolymer of a hydrophobic monomer and hydrophilic monomer, the hydrophobic monomer comprising a C1-C24 alkyl linear or branched (meth)acrylate monomer or a C1-C24 alkyl linear or branched crotonate monomer and styrene or a combination thereof wherein the styrene is present at a weight percentage amount of from none up to about 50 wt % relative to the total weight of the organic copolymer; and the hydrophilic monomer comprising an olefinic acid selected from (meth)acrylic acid or crotonic acid or a combination thereof, and a hydroxyalkyl olefinic ester selected from hydroxymethyl or hydroxyethyl (meth)acrylate or crotonate or any combination thereof;
the in situ linking material comprises toluene diisocyanate, diphenylmethane diisocyanate, hexamethylene diisocyanate, bis isocyanatocyclohexyl methane, isophorone diisocyanate, trimethylolpropane tri-hexamethylene diisocyanate adduct, biuret triisocyanate, isocyanurate triisocyanate, uretdione hexamethylene diisocyanate, trimers of hexamethylene diisocyanate, or a blocked polyisocyanate of hexamethylene diisocyanate and a phenol, E-caprolactom, butanone oxime or dimethyl pyrazole blocker;
the acid number of the organic copolymer is in a range of about 7 to about 90;
the hydroxyalkyl olefinic ester portion of the organic copolymer is in a range of about 1-5 wt % relative to the total weight of the organic copolymer;
the molar ratio of free isocyanate groups to hydroxyl groups is in a range of about 0.5:2 to 25:1, preferably about 1:1 to about 15:1.

71. A multicomponent composition of statement 70 further comprising a third component of a base compound and a medium, wherein the base compound is polyethyleneimine at a concentration of 0.1-5% in medium relative to the total weight of the combination of the base compound and the medium.

72. A multicomponent composition of statement 70 wherein the weight percentage of the organic polymer and the in situ linking material is between 1-20 wt. %, preferably about 1-10 wt %, more preferably 2-8 wt % of the combined first and second components.

73. A multicomponent composition of statement 70 wherein the organic copolymer comprises, styrene at a weight percentage relative to the total weight of the organic copolymer of from none up to about 30 wt %, ethyl (meth)acrylate, hydroxyethyl (meth)acrylate and (meth)acrylic acid.

74. A multicomponent composition of statement 73 wherein the organic copolymer is completely free of styrene.

75. A multicomponent composition comprising:
a first component of a medium and an organic copolymer comprising repeating units of a first hydrophobic monomer and a first hydrophilic monomer; wherein
the first hydrophobic monomer is selected from a non-polar olefinic monomer having the formula $$H_2C=CHR$$

wherein R is selected from hydrogen, ethyl, propyl, isopropyl, butyl, phenyl, hydroxyphenyl, nitrile or $-CR^2=CHR^1$ wherein $R^1$ is hydrogen, methyl, ethyl or phenyl; wherein $R^2$ is H or methyl; or any combination thereof;
the first hydrophilic olefinic monomer comprises an olefinic carboxylic acid wherein the olefinic carboxylic acid comprises alkendioic acid of 3 to 12 carbons or alkenoic acid of 3 to 12 carbons;
a fourth component comprising a catalyst, coordination agent or free radical initiator for producing covalent, ionic, electrostatic or coordination among the copolymer molecules of the first component;
an aromatic dye according to the present disclosure in the first or fourth component or in both of the first and fourth components;
the first component being separate from the fourth component.

76. A multicomponent composition of statement 75 wherein the polymer component of the first component has a weight percentage of about 1 wt % to about 40 wt % relative to the total weight of the first component.

77. A multicomponent composition of statement 75 comprising a third component comprising a base compound in medium, the third component being separate from the first and second components.

78. A multicomponent composition of statement 75-77 wherein the organic copolymer comprises a polymer of styrene, butadiene and itaconic or (meth)acrylic acid wherein the weight percentages respectively are between about 5-50 wt. % of styrene, about 50-95 wt. % butadiene, and about 0-5 wt. % itaconic or (meth)acrylic acid.

79. A multicomponent composition of statement 75 wherein the fourth component is a carbonate salt of a cation selected from an alkali or alkali earth metal or transition metal.

80. A multicomponent composition of statement 75 wherein the cation of the carbonate salt is zirconium or zinc cation.

81. A multicomponent composition of statement 75 wherein the second component is tri or tetra mercapto or a combination of the second component which is tri or tetramercapton and a fourth component which is a free radical initiator.

82. A multicomponent composition of statement 75 wherein the fourth component is a free radical initiator compound.
83. A multicomponent composition of statement 75 wherein the free radical initiator is peroxide or azo or a photo initiator.
84. A multicomponent composition of any of statements 75-83 wherein
the first component comprises a first copolymer of styrene, butadiene and itaconic acid;
the fourth component comprises a free radical initiator;
the third component comprises polyethyleneimine.
85. A multicomponent composition of any of statements 75-84 wherein
the first component of the composition has a pH of from about 3 to about 12 in water;
the first component has an acid value of from zero (no acid) to about 100, preferably 0.1-100, more preferably about 7-90;
the copolymer of the first component has a glass transition temperature of from about −120° C. to about 90° C.;
the copolymer of the first component has a weight average molecular weight in the range of about 2 KDa to about 2 MDa;
the weight percentage of the fourth component is from 5-40% of the weight of the polymer when the fourth component is polymercaptan, or metal carbonate;
the weight percentage of the free radical initiator or photo initiator is between 0.1-3 wt. % of the total composition.
86. A multicomponent composition of any of statements 75-85 wherein the organic copolymer is neutralized with volatilizable amine compound selected from ammonia or an organic amine.
87. The composition of the preceding statements, wherein the aromatic dye is selected from rylene dyes, nitro dyes, aryl and heteroaryl azo dyes, chinon/chinonimine/chinondiimine dyes, methin dyes, azomethine-like hydrazone and imine dyes, and porphyrin dyes, wherein the dye or an aromatic ring of the dye optionally is substituted with one or more hydrophobic moieties having a linear or non-linear structure, and wherein the dye optionally is substituted with a reactive moiety R20.
88. The composition of the preceding statements, wherein the aromatic dye is a peri-arylene dye comprising a perylene, terrylene or quarterrylene core or higher rylene core, wherein the dye optionally is substituted with one or more hydrophobic moieties having a non-linear structure and comprising at least 14 carbon atoms, and wherein the dye optionally is substituted with a reactive moiety R20.
89. The composition of the preceding statements, wherein aromatic dye is a peri-arylene dye according to formula (16), (17), (18) or (19).
90. The composition of the preceding statements, wherein the composition comprises at least one pigment microparticle in one or more of the first, second or third component.
91. The composition of the preceding statements, wherein the composition comprises at least one pigment microparticle that has a flake morphology
92. The composition of the preceding statements and any combination thereof further comprising metallic microplatelets or microparticles which impart reflection to the colored human hair strands.
93. A composition of the preceding statements wherein the flake factor is greater than 10.
94. A composition of any of the preceding statements any combination thereof further comprising one or more of a plasticizer, a dispersant, wetting agent, anti-agglomeration agent, preservative, fragrance, an organic dye compound, a feel modification agent or a thickening agent; the dispersant, anti-agglomeration agent, the plasticizer and thickener capable of providing viscosity parameters to enable flow and hold of the composition on the keratin fibers.
95. A composition of the preceding statements and any combination thereof, wherein the composition has a viscosity of from about 0.001 to about 2000 Pa s$^{-1}$.
96. A composition of any of the preceding statements and any combination thereof, wherein the composition has a viscosity of from about 0.1 to about 200 Pa s$^{-1}$.
97. A composition of the preceding statements, wherein the composition has a viscosity of from about 10 to about 75 Pa s$^{-1}$.
98. A composition of the preceding statements wherein the composition has the physical character of a foam.
99. A composition the preceding composition statements wherein the medium for at least one of the components comprises at least one liquid selected from the group consisting of water, protic organic medium, protic organic non-aqueous medium, an aprotic, non-aqueous organic medium and any compatible combination thereof.
100. A composition of statement 99 wherein the medium is water or a non-aqueous organic medium.
101. A composition of 99 wherein the medium is an aprotic non-aqueous organic medium that has a boiling point at standard pressure at a temperature of from ambient to about 200° C.
102. A composition of statement 99 wherein the medium is a protic organic medium.
103. A composition of statement 99 wherein the medium is a nonpolar, aprotic organic medium selected from decane, isodecane, isododecane, a liquid silicone, cyclomethicone, glyme or decamethyl cyclopentasiloxane.
104. A composition of statement 99 wherein the second component is free of a medium.
105. A composition of statement 100 wherein the medium is water.
106. A composition of the preceding statements, further comprising an excipient selected from a preservative, a fragrance, a feel modification agent or a combination thereof.
107. A composition according to the preceding statements, further comprising an excipient selected from a dispersing agent, a surfactant, a thickening agent or a combination thereof.
108. A composition of statement 107 wherein the excipient includes at least a dispersing agent and the concentration of the dispersing agent is in an amount able to generate a positive or negative zeta potential in the composition.
109. A composition of statement 108 wherein the dispersing agent is a nonionic surfactant selected from ethoxylated aliphatic alcohol, polyoxyethylene glycol, esters of fatty acids and glycerol, polyethylene glycol esters of fatty acids, anhydrosorbitol esters, polyethoxylated sorbitol esters, polysorbates, poloxamer, nonoxynol, fatty alcohol, tritan, tween, alkoxylated, hydrogenated castor oil.

110. A composition of statement 107-109 wherein the excipient includes at least a thickening agent and the concentration of the thickening agent is sufficient to maintain a suspension of metallic flakes or pigments in the composition.

111. A kit comprising a multicompartment container, each container comprising one of the first, second and third components of the multicomponent composition of statement 2.

112. A composition according to statement 1 or 2 comprising a pre-application formulation prepared by mixing together the first and second components.

113. A composition according to the preceding composition statements including the third component wherein the first component is maintained in a first compartment, the second component is maintained in a second compartment and the third component is maintained in a third compartment.

114. A composition according to the preceding composition statements not including the third component wherein the first component is maintained in a first compartment, the second component is maintained in a second compartment.

115. A composition according to statement 113 or 114 comprising a preapplication formulation prepared by mixing together the first and second components to form coloring mixture.

116. A method for coloring keratin material comprising applying first to the keratin material the third component of statement 111 to form pretreated keratin material.

117. A method of statement 116 further comprising optionally or at least partially drying the third component on the keratin material.

118. A method of statement 116 further comprising combining the first and second components of statement 114 to form to form an in situ coloring mixture, applying the in situ coloring mixture to the pretreated keratin material and causing the in situ coloring mixture to form a colored coating on the keratin material.

119. A method of statement 118 further comprising drying the colored coating on the keratin material.

120. A method for coloring keratin material comprising combining the first and second components of statement 114 to form a color formulation and applying the color formulation to the keratin material to form a coated keratin material and causing the coated keratin material to form a colored coating on the keratin material.

121. A colored coating for hair strands produced according to the method of statement 118 or 120.

122. A colored coating for hair strands according to statement 121 wherein the composition forms a solid, flexible elastic film on each individualized hair fibre.

123. A colored coating for hair strands according to statement 122 wherein the film has the microscopic appearance of a semicontinuous or continuous coating 124. A colored coating for hair strands according to statements 115-123 which are resistant to color fading by repeated washings according to a standard wash procedure.

125. A colored coating for hair strands according to statement 124 wherein the repeated washings number 5 to 15.

126. A colored coating for hair strands according to statement 125 wherein the repeated washing number 15 or more.

127. A color removal composition for applying to color coated hair strands comprising applying one or more of surfactant, solvent, acid, base, polymer, polyelectrolyte, salt sources of fluorine, ionic liquids to remove the color coating.

128. A method for removing color from a colored coating of any of claims 121-126 comprising applying one or more of surfactant, solvent, acid, base, polymer, polyelectrolyte, source of fluorine, salt source of fluorine and/or an ionic liquid to remove the color coating.

129. A color removal composition of claim 128 comprising a source of fluoride.

130. A color removal composition comprising a medium with a Hansen solubility parameter of $\delta d+\delta p+\delta h$.

131. A method according to claim 128, comprising combining the colored hair strands with an aqueous-organic mixture of a fluorine source, agitating the mixture on the hair and washing with a basic aqueous solution of detergent with optional brushing.

132. A method according to claim 131 comprising adding one of heat, electromagnetism, mechanical energy, or cooling to the method of claim 131.

133. A method of selecting the removal composition to chemically break down covalent bonds in the in situ cross linked multicomponent composition.

134. A multicomponent in situ linkable composition for coloring treated material, comprising:
a first component comprising an organic polymer having pendant or terminal or pendant and terminal first functional groups;
a second component comprising an in situ linking material having second functional groups;
an aromatic dye according to the present disclosure in one of the first and second components or in both of the first and second components;
the first and second functional groups being complementary reaction pairs that are capable of forming with each other covalent, coordinate, entanglement, ionic or electrostatic linkages in situ or any combination thereof;
the first and second components being separate.

135. A multicomponent in situ linkable composition according to statement 134 further comprising:
a third component comprising a base compound having third functional groups capable of forming covalent, coordinate, entanglement, ionic or electrostatic linkages or combination thereof with the first functional groups of the organic polymer, the second functional groups of the in situ linking material, the treated material or any combination thereof;
the third component being separate from the first and second components 136. A multicomponent composition of any of statement 142-143 further comprising
a fourth component comprising a catalyst agent, an accelerator agent or an inorganic complexation agent, the agent being capable of promoting the covalent, ionic, entanglement, electrostatic or coordination in situ linkage or combination thereof among the first, second and third functional groups or any combination thereof, or the inorganic complexation agent capable of forming coordination linkages for the first component.

137. A multicomponent composition of any of statement 134-136 further comprising a medium in any one or more of the first, second, third and fourth components.

What is claimed is:

1. A hair coloring composition, comprising a medium and at least one aromatic dye in the medium, the composition optionally further comprising pigment microparticles, wherein the aromatic dye is selected from a member of the aromatic dye group consisting of a rylene dye, a nitro dye, an aryl azo dye, a heteroaryl azo dye, a chinon dye, a chinonimine dye, a chinondiimine dye, a methin dye, an azomethine hydrazone dye, an azomethine imine dye, and a porphyrin dye, wherein the selected member of the aromatic dye group optionally is substituted with one or more hydrophobic moieties having a linear or non-linear structure, and wherein the selected member of the aromatic dye group is substituted with a reactive moiety R20, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkyl)OSO2(aryl), (C0-C6 alkyl) SO2Cl, (C0-C6 alkyl)Si(O—(C1-C3 alkyl))3, (aryl) SO2Cl, aryl(C0-C4)OH, aryl(C0-C4)NH2, wherein the aryl is a C5-C10 aryl, wherein 1 or 2 of the carbon atoms of the C5-C10 aryl may be replaced by N, O or S, and wherein the C5-C10 aryl optionally is substituted with up to 3 substituents selected from the group consisting of halogen, C1-C6 alkyl, C1-C6 alkoxy, -NH(C1-C6 alkyl), —N(C1-C6 alkyl)2, and formula (30),

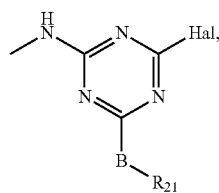

(30)

wherein B is NH or O; Hal is F, Cl or Br; and R21 is linear or branched (C1-C6 alkyl).

2. The hair coloring composition of claim 1, wherein each of the one or more hydrophobic moieties is —(CH2)m-CH (C3-24 alkyl(A))2 or —(CH2)m-C(C3-24 alkyl(A))3, wherein m=0-5, wherein the alkyl(A) is linear and is optionally substituted with one or more substituents selected from the group consisting of halogen, C1-C6 alkyl(B), C1-C6 alkoxy, —NH(C1-C6 alkyl(B)), —N(C1-C6 alkyl(B))2, —(CH2)n-NH(C14-28 alkyl(B)), —(CH2)n-N(C6-C20-alkyl(B))2, —(CH2)n-NH—(CH2)n-CH(C6-C20 alkyl(B))2, and —(CH2)n-NH—(CH2)n-C(C4-C10 alkyl(B))3, wherein n=0-3 and alkyl(B) is linear and is optionally substituted with one or more substituents selected from the group consisting of halogen, C1-C6 alkyl, C1-C6 alkoxy, —NH(C1-C6 alkyl), —N(C1-C6 alkyl)2, and —(CH2)o-phenyl, wherein o=1-3 and which phenyl of —(CH2)o-phenyl may be substituted with up to 3 substituents selected from C1-C6 alkyl and C1-C6 alkoxy.

3. A hair coloring composition, comprising a medium and at least one peri-arylene dye in the medium, the composition optionally further comprising pigment microparticles, wherein the peri-arylene dye is a compound according to formula (1)

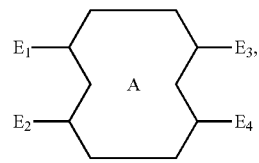

(1)

wherein structure A

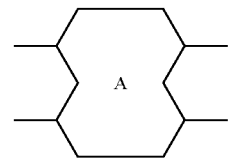

is selected from the group consisting of formulae (2) through (4)

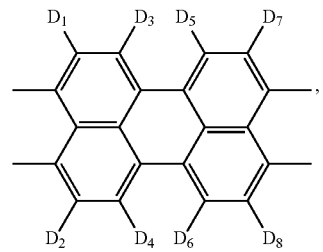

(2)

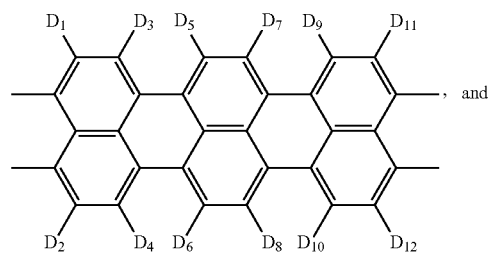

(3)

, and

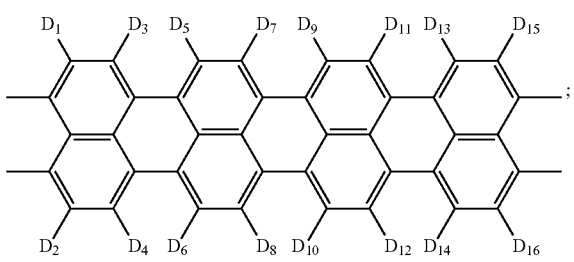

(4)

;

wherein each of D1 through D16 independently is selected from the group consisting of hydrogen, C1-C6 alkyl, (C0-C4 alkyl)hydroxy, C1-C4 alkoxy, amino, —N(C1-C24 alkyl)2, —NH(C1-C24 alkyl), nitro, halogen, C1-C3 carboxyl ester, and phenoxy optionally substituted with up to 3 (C1-C6)alkyl, or wherein one or more of the pairs of D3/D5, D4/D6, D7/D9, D8/D10, D11/D13 and D12/D14 is a divalent moiety selected from the group consisting of —O—, —S—, —NH—, —N(C1-C24 alkyl)-, or wherein one or more of the pairs of D3/D5, D4/D6, D7/D9, D8/D10, D11/D13 and D12/D14 is a condensed ring structure selected from the group consisting of formulae (5) through (8):

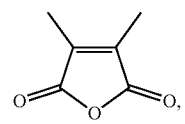
(5)

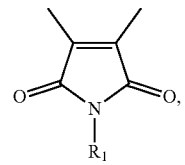
(6)

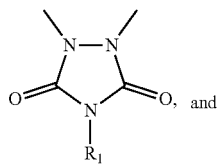
(7)

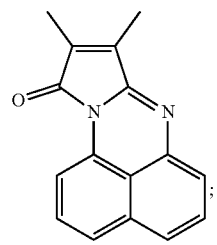
(8)

wherein R1 is hydrogen, linear or branched (C1-C5)alkyl, cyclohexyl, a reactive moiety R20, or —(CH2)n-aryl, wherein n=0-3, wherein the reactive moiety R20 is selected from (C0-C6 alkyl)OH, (C0-C6 alkyl)NH2, (C0-C6 alkyl)Cl, (C0-C6 alkyl)Br, (C0-C6 alkyl)I, (C0-C6 alkyl)OSO2(C0-C3 alkyl), (C0-C6 alkyl)OSO2(aryl), (C0-C6 alkyl)SO2Cl, (C0-C6 alkyl)Si(O—(C1-C3 alkyl))3, (aryl)SO2Cl, aryl(C0-C4)OH, aryl(C0-C4)NH2, the aryl is a C5-C10 aryl, wherein 1 or 2 of the carbon atoms of the C5-C10 aryl may be replaced by N, O or S, and wherein the C5-C10 aryl optionally is substituted with up to 3 substituents selected from the group consisting of halogen, C1-C6 alkyl, C1-C6 alkoxy, —NH(C1-C6 alkyl), —N(C1-C6 alkyl)2;

wherein moiety (8) is optionally substituted with up to 3 substituents selected from the group consisting of hydroxyl, nitro, halogen, C1-C6 alkyl, C1-C6 alkoxy, —NH(C1-C6 alkyl), and —N(C1-C6 alkyl)2;

wherein (a) E1 and E2 each independently are a monovalent moiety selected from the group consisting of hydrogen, C1-C6 alkyl, (C0-C4 alkyl)hydroxy, C1-C4 alkoxy, amino, —NC1-C24 alkyl)2, —NH(C1-C24 alkyl), nitro, halogen, C1-C3 carboxyl ester, and phenoxy which phenoxy is optionally substituted with up to 3 (C1-C6)alkyl, and the pair of moieties E3/E4 is a divalent moiety according to formula (9) or (10):

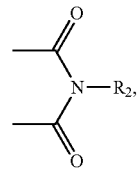
(9)

wherein R2 is a hydrophobic moiety comprising at least 6 carbon atoms, or the reactive moiety R20;

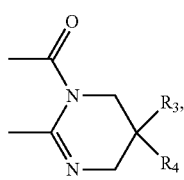
(10)

and wherein R3 is a hydrophobic moiety comprising at least 3 carbon atoms, or the reactive moiety R20;

and wherein R4 is hydrogen, methyl, ethyl, methoxy, ethoxy, the reactive moiety R20, or a hydrophobic moiety R3; or (b) the pair of moieties E1/E2 and the pair of moieties E3/E4 both are a divalent moiety, wherein E1/E2 is formulae (11) or formula (12) and E3/E4 is independently selected from the group consisting of formulae (11) through (15):

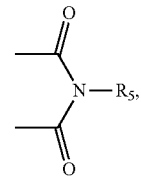
(11)

wherein R5 is hydrogen, linear or branched (C1-C5) alkyl, cyclohexyl, amino, —NH(C1-C4 alkyl), —N(C1-C4 alkyl)2, the reactive moiety R20, or a hydrophobic moiety R2;

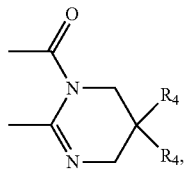
(12)

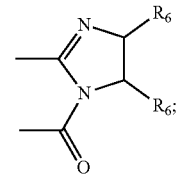
(13)

wherein R6 is hydrogen, methyl, ethyl, methoxy, ethoxy, the reactive moiety R20, or a hydrophobic moiety comprising at least 3 carbons;

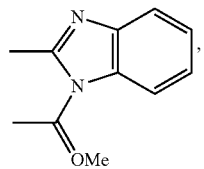
(14)

optionally substituted with up to 3 substituents selected from the group consisting of hydroxyl, nitro, halogen, C1-C6 alkyl, C1-C6 alkoxy, NH(C1-C6 alkyl), N(C1-C6 alkyl)2, the reactive moiety R20; and

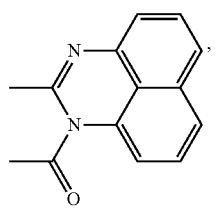
(15)

optionally substituted with up to 3 substituents selected from hydroxyl, nitro, halogen, C1-C6 alkyl, C1-C6 alkoxy, NH(C1-C6 alkyl), N(C1-C6 alkyl)2, the reactive moiety R20;

wherein, when the pair E1/E2 is a divalent moiety according to formula (11) or (13) and the pair E3/E4 is a divalent moiety according to formula (11), (12) or (13), at least one R4, R5 or R6 is the hydrophobic moiety; and wherein at least one peri-arylene dye is substituted with at least one reactive moiety R20.

4. The hair coloring composition of claim 3, wherein R2 is a hydrophobic moiety of the formula
—(CH2)m-C(R2a)(R2b)(R2b), wherein m=0-5, R2a is linear C3-24 alkyl and each R2b independently is hydrogen or linear C3-24 alkyl, wherein each alkyl is optionally and independently substituted with one or more substituents selected from the group consisting of halogen, C1-C6 alkyl, C1-C6 alkoxy, —NH(C1-C6 alkyl), —N(C1-C6 alkyl)2, —(CH2)n-NH(C14-28 alkyl), —(CH2)n-N(C6-C20 alkyl)2, —(CH2)n-NH—(CH2)n-CH(C6-C20 alkyl)2, and —(CH2)n-NH—(CH2)n-C(C4-C10 alkyl)3, wherein n=0-3 and alkyl is linear and is optionally substituted with one or more substituents selected from halogen, C1-C6 alkyl, C1-C6 alkoxy, NH(C1-C6 alkyl), N(C1-C6 alkyl)2, and —(CH2)n-aryl, wherein n=0-3 and wherein aryl is C5-C10 aryl, wherein 1 or 2 of the carbon atoms of the C5-C10 aryl may be replaced by N, O or S, and wherein the C5-C10 aryl optionally is substituted with up to 3 substituents selected from halogen, C1-C6 alkyl, C1-C6 alkoxy, NH(C1-C6 alkyl), N(C1-C6 alkyl)2.

5. The hair coloring composition of claim 3, wherein R3 is a hydrophobic moiety of the formula —(CH2)m-C(R3a)(R3b)(R3b), wherein m=0-5, R3a is C3-24 alkyl and each R3b independently is hydrogen or C3-24 alkyl, wherein each alkyl is linear and is optionally and independently substituted with one or more substituents selected from halogen, C1-C6 alkyl, C1-C6 alkoxy, NH(C1-C6 alkyl), N(C1-C6 alkyl)2.

6. The hair coloring composition of claim 3, wherein R6 is a hydrophobic moiety R6a of the formula
—(CH2)m-C(R6b)(R6c)(R6c), wherein m=0-5, R6b is linear C3-24 alkyl and each R6c independently is hydrogen or linear C3-24 alkyl, wherein each alkyl is optionally and independently substituted with one or more substituents selected from halogen, C1-C6 alkyl, C1-C6 alkoxy, NH(C1-C6 alkyl), and N(C1-C6 alkyl)2,
—(CH2)n—NH(C14-28 alkyl) or —(CH2)n-N(C6-C20 alkyl)2 or —(CH2)n-NH—(CH2)n-CH(C6-C20 alkyl)2 or —(CH2)n-NH—(CH2)n-C(C4-C10 alkyl)3, wherein n=0-3 and each alkyl is linear and is optionally and independently substituted with one or more substituents selected from halogen, C1-C6 alkyl, C1-C6 alkoxy, NH(C1-C6 alkyl), N(C1-C6 alkyl)2.

7. The composition of claim 3, wherein the peri-arylene dye is present in an amount of from 0.005% to about 5%, about 0.01% to about 3%, about 0.1 to about 2%, or about 0.25% to about 1.5% by weight of the hair coloring composition.

8. The composition of claim 3, further comprising a film former, wherein the film former is selected from carboxylic acid polymer(s), (meth)acrylate copolymers, and polar functional silicone polymer(s).

9. The composition of claim 8, wherein the film former is carboxylic acid polymer, and wherein:
the carboxylic acid polymer comprises a (meth)acrylic acid homopolymer or copolymer or terpolymer;
the homopolymer comprises monomeric units of (meth) acrylic acid and optional carboxyl derivatives thereof;
the copolymer or terpolymer comprises monomeric units of (meth)acrylic acid and monomeric units selected from the groups consisting of one or more (meth) acrylate esters, one or more (meth)acrylamides, carboxyl derivatives of (meth)acrylic acid and monomeric units of neutral olefins and any combination thereof;
the carboxylic acid polymer has an acid value of from about 0.01 to about 700;
the carboxylic acid polymer is optionally at least partially neutralized with a base;
the carboxylic acid polymer has a glass transition temperature in the solid state of from about −60° C. to about 90° C.;
the carboxylic acid polymer has a weight average molecular weight in the range of about 300 Da to about 10 MDa.

10. A method of coloring hair, comprising
(a) applying the hair coloring composition of claim 1 to strands of hair, and
(b) removing the medium.

11. The method of claim 10, further comprising applying a pre-treatment composition to the hair strands, prior to applying the hair coloring composition.

12. The method of claim 10 wherein the hair coloring composition comprises a film former selected from a carboxylic acid polymer.

13. The method of claim 11 wherein the hair coloring composition comprises a film former selected from a carboxylic acid polymer.

14. The method of claim 11, wherein the hair coloring composition comprises a film former, wherein the film former comprises:

a first component comprising a first silicone polymer having first functional groups; and a second component comprising a second silicone polymer having second functional groups;

wherein the pre-treatment composition comprises a third component comprising a base compound having third functional groups;

one or more of the first, second and third components comprising a medium.

15. The method of claim 11, wherein the hair coloring composition comprises a film former, wherein the film former comprises:

a first component comprising an organic polymer having pendant or terminal or pendant and terminal first functional groups; and a second component comprising an in situ linking material having second functional groups;

wherein the pre-treatment composition comprises a third component comprising a base compound having third functional groups;

the first second and third functional groups being compatible reaction pairs and being capable of covalent, ionic, entanglement, electrostatic or coordination in situ linkage or a combination thereof among each other.

* * * * *